(12) United States Patent
Alfano et al.

(10) Patent No.: US 8,716,460 B2
(45) Date of Patent: May 6, 2014

(54) PSEUDOMONAS AVR AND HOP PROTEINS, THEIR ENCODING NUCLEIC ACIDS, AND USE THEREOF

(75) Inventors: James R. Alfano, Lincoln, NE (US); Alan Collmer, Ithaca, NY (US); Samuel W. Cartinhour, Ithaca, NY (US); David J. Schneider, Trumansburg, NY (US); Xiaoyan Tang, Manhattan, KS (US)

(73) Assignees: Kansas State University Research Foundation, Manhattan, KS (US); The Board of Regents of the University of Nebraska, Lincoln, NE (US); Cornell Research Foundation, Inc., Ithaca, NY (US); The United States of America as Represented by the Secretary of Agriculture, Washington, DC (US)

( * ) Notice: Subject to any disclaimer, the term of this patent is extended or adjusted under 35 U.S.C. 154(b) by 943 days.

(21) Appl. No.: 11/616,609

(22) Filed: Dec. 27, 2006

(65) Prior Publication Data

US 2007/0162994 A1 Jul. 12, 2007

Related U.S. Application Data

(62) Division of application No. 10/365,742, filed on Feb. 12, 2003, now Pat. No. 7,220,583.

(60) Provisional application No. 60/380,185, filed on May 10, 2002, provisional application No. 60/356,408, filed on Feb. 12, 2002.

(51) Int. Cl.
*C12N 5/10* (2006.01)
*C12N 5/14* (2006.01)
*C12N 15/85* (2006.01)
*C07H 21/04* (2006.01)
*A01H 5/00* (2006.01)

(52) U.S. Cl.
USPC .......... 536/23.7; 435/468; 435/410; 435/430; 424/93.2; 424/93.21; 800/279; 800/301

(58) Field of Classification Search
None
See application file for complete search history.

(56) References Cited

U.S. PATENT DOCUMENTS

| | | | | |
|---|---|---|---|---|
| 5,920,000 A * | 7/1999 | Jones et al. | ................... | 800/301 |
| 6,342,654 B1 | 1/2002 | Li et al. | | |
| 2003/0176653 A1* | 9/2003 | Mason et al. | ................. | 530/350 |
| 2008/0028487 A1* | 1/2008 | Alfano et al. | ................. | 800/278 |

FOREIGN PATENT DOCUMENTS

WO    WO 99/07207    2/1999

OTHER PUBLICATIONS

Collmer et al., "*Pseudomonas syringae* Hrp Type III Secretion System and Effector Proteins," *PNAS* 97(16):8770-8777 (2000).
Alfano et al., "The *Pseudomonas syringae* Hrp Pathogenicity Island has a Tripartite Mosaic Structure Composed of a Cluster of Type III Secretion Genes Bounded by Exchangeable Effector and Conserved Effector Loci That Contribute to Parasitic Fitness and Pathogenicity in Plants," *PNAS* 97(9):4856-4861 (2000).
Fouts et al., "Genomewide Identification of *Pseudomonas syringae* pv. Tomato DC3000 Promoters Controlled by the HrpL Alternative Sigma Factor," *PNAS* 99(4):2275-2280 (2002), with supplemental material available online at www.pnas.org.
Petnicki-Ocwieja et al., "Genomewide Identification of Proteins Secreted by the Hrp Type III Protein Secretion System of *Pseudomonas syringae* pv. Tomato DC3000," *PNAS* 99(11):7652-7657 (2002), with supplemental material available online at www. pnas.org.
Zwiesler-Vollick et al., "Identification of Novel *hrp*-regulated Genes through Functional Genomic Analysis of the *Pseudomonas syringae* pv. *Tomato* DC3000 Genome," *Molecular Microbiology* 45(5):1207-1218 (2002).
Guttman et al., "A Functional Screen for the Type III (hrp) Secretome of the Plant Pathogen *Pseudomonas syringae*," *Science*, 295(5560):1722-1726 (2002).
Vinatzer et al., GenBank Accession No. AF458398, (2002).
Seffernick et al., "Melamine Deaminase and Atrazine Chlorohydrolase: 98 Percent Identical but Functionally Different," *J. Bacteriol.* 183(8):2405-2410 (2001).
Houslay et al., "Cell-type Specific Integration of Cross-talk Between Extracellular Signal-regulated Kinase and cAMP Signaling," *Mol. Pharmacol.* 58(4):659-668 (2000).
Whisstock et al., "Prediction of Protein Function from Protein Sequence and Structure," *Q. Rev. Biophys.* 36(3):307-340 (2003).

* cited by examiner

*Primary Examiner* — Shubo (Joe) Zhou
*Assistant Examiner* — Jeffrey Bolland
(74) *Attorney, Agent, or Firm* — LeClairRyan, a Professional Corporation

(57) ABSTRACT

One aspect of the present invention relates to isolated nucleic acid molecules encoding avirulence proteins or polypeptides of *Pseudomonas syringae* pv. *syringae* DC 3000, or nucleic acid molecules which are complementary thereto. Expression vectors, host cells, and transgenic plants which include the DNA molecules of the present invention are also disclosed. Another aspect relates to the isolated proteins or polypeptides and compositions containing the same. The various nucleic acid molecules and proteins of the present invention can be used to impart disease resistance to a plant, make a plant hypersusceptible to colonization by nonpathogenic bacteria, modify a metabolic pathway in a cell, cause eukaryotic cell death and treat a cancerous condition, as well as inhibit programmed cell death.

24 Claims, 7 Drawing Sheets

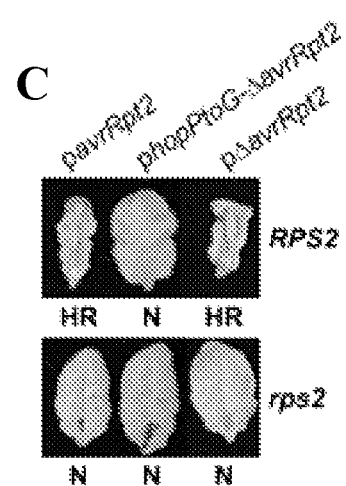
Figures 1A-C

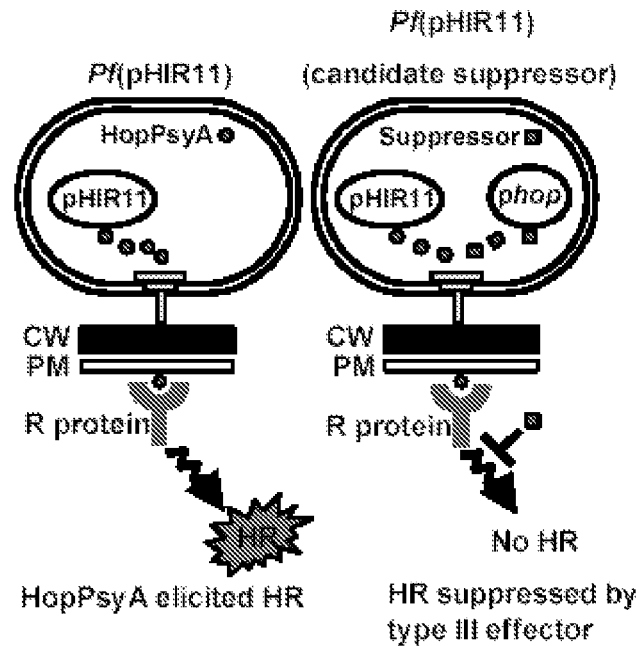
Figure 2A
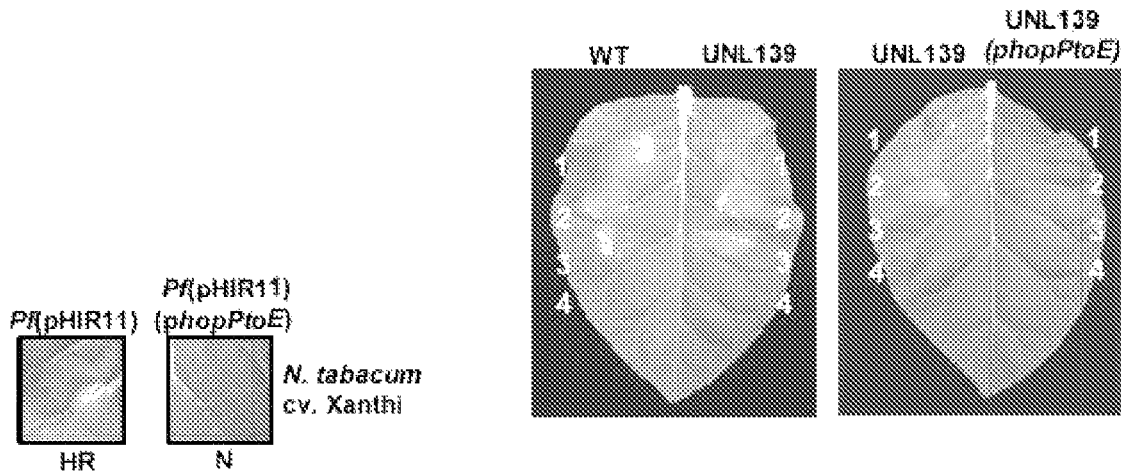
Figure 2B
Figure 2C

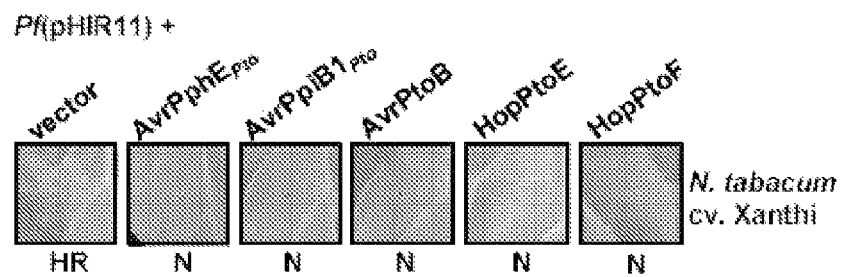
Figure 4A
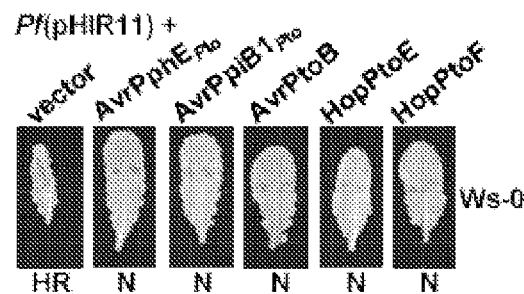
Figure 4B
Figure 4C

SEQUENCE LISTING

<160> NUMBER OF SEQ ID NOS: 209

<210> SEQ ID NO 1
<211> LENGTH: 1899
<212> TYPE: DNA
<213> ORGANISM: Pseudomonas syringae pv. tomato DC3000

<400> SEQUENCE: 1

```
atgcttatcg ggcacagctt gcatcacatg cgacccactg ctgtggattc tagcctacca      60
acttccgcaa ctagccagac tatcagcaat accaaaagtc ggctggatcc gcatcgtgtc     120
cgtgaactta cattcatcgg agtgggtagt agtgttgcct acctactcaa tgagcttaat     180
ggtcgctttg ccgatagcgg ggtaacaacg ccgttttag gaaaagtcag tattgtaggc      240
aaggacgact cttgggccga gaatgttcgt gggaaaggtt atattaacca ccagactgaa     300
attataagcc aatgggacca acaggttcca aaatatgatc ctaactatgc tgctcgtgcc     360
gaattttctg cgagtaaccg aagacagttg acgcgaacag tggagttagg cgcagaacat     420
ttgaaagcac aggtaacagg catttcgcga ttggatgacg ttgttttcg aataaatctg      480
gacaatggcc agattttgca agccgacag attgtactgg ggactggtgc cggacccat      540
accagtatct ggaacagcgt tacatcacac actcaagcag aaaaacgact ggacaacatc     600
aaattgcatg agcagaaagc cttgcgtggc aaggtgctgg acctggatga gtttatgcga     660
gcgagtgatg cctctcccca gacgtttgct ggaaaaacgg tggtgataca tggaccaaat     720
gcaggcattg atgcagctga acgtgccggg gagcttgggg caaatgcggt ttggttacc      780
cgcagtacga atccggtatt gctggatggc aatcaactaa aattcgcgcc agagctggcc     840
aaaagcgcta tacataaagt tgacaaatta gatattcgcc caacaaaact agagaatggt     900
ttcgcattgc gactacatta cagttcgcta ggacaagact cacggagcc aaagaaggtg      960
ctagatgcgg actattatgt gtacgccatg ggtcaagata ttcataagcc gggtagcgca    1020
gcggccatac taggcagtct tctttgacca ctagaaccta tatatgacta cgatcaagtc    1080
tatagcgacc agccttttcaa gacagtaata ggcttgcaaa gtcgcggctc caatagcgat    1140
aatggtttaa ttattgtcgg ggcggcagtt gctcagctgg ccactaatgt tcagcatagc    1200
tataaggacc acgcgttgga tcgtatactt gaggaaatga ccaggctccc cgaaaagcaa    1260
acagaaaagc tatcacaaat gctgttagaa ggtgcgccat cagtacagat ccagacatat    1320
ctaaaaacct ggcagttaga tagcggtcaa ccgccagata acaggtact gcagaatcaa     1380
gtagaaaact atctggcggc ccgagactac ttccagcggc aaaccaacga acaaagggc     1440
aacctggacg gggttgccgc agaggtaaaa aatcaaaccct taaccgaggt tgcatcggtc    1500
atcgtgtcac cacagttagg cacgatcaag gcctccgctg cagcattgtc gggacttatg    1560
ccagcatatg tggctaacgg cgaaaataac tttaccaccg ataatcgaac tatgctccgt    1620
gccggcattg cagcaagata tccgaatata ggtaacgctg aagccagtgc atttatcgat    1680
gaagtagtaa ctttgcgtca ccttaatagt cagcgtttta ttgagaaggt agcaggcgaa    1740
atgatggaca aaggagctca accactggtg tcgttacgcc ccccggtcct aggtgtcccg    1800
gcgtcggtca ggactgctta tgaggcttac ttgcacgcgc tgaattctgg agcgcacgat    1860
ggtacgccgt taagtcagcg ctggctgccc aaaaaatag                           1899
```

<210> SEQ ID NO 2
<211> LENGTH: 632
<212> TYPE: PRT

<213> ORGANISM: Pseudomonas syringae pv. tomato DC3000

<400> SEQUENCE: 2

```
Met Leu Ile Gly His Ser Leu His His Met Arg Pro Thr Ala Val Asp
 1               5                  10                  15

Ser Ser Leu Pro Thr Ser Ala Thr Ser Gln Thr Ile Ser Asn Thr Lys
             20                  25                  30

Ser Arg Leu Asp Pro His Arg Val Arg Glu Leu Thr Phe Ile Gly Val
         35                  40                  45

Gly Ser Ser Val Ala Tyr Leu Leu Asn Glu Leu Asn Gly Arg Phe Ala
     50                  55                  60

Asp Ser Gly Val Thr Thr Pro Phe Leu Gly Lys Val Ser Ile Val Gly
 65                  70                  75                  80

Lys Asp Asp Ser Trp Ala Glu Asn Val Arg Gly Lys Gly Tyr Ile Asn
                 85                  90                  95

His Gln Thr Glu Ile Ile Ser Gln Trp Asp Gln Val Pro Lys Tyr
            100                 105                 110

Asp Pro Asn Tyr Ala Ala Arg Ala Glu Phe Ser Ala Ser Asn Arg Arg
            115                 120                 125

Gln Leu Thr Arg Thr Val Glu Leu Gly Ala Glu His Leu Lys Ala Gln
        130                 135                 140

Val Thr Gly Ile Ser Arg Leu Asp Asp Gly Cys Phe Arg Ile Asn Leu
145                 150                 155                 160

Asp Asn Gly Gln Ile Leu Gln Ser Arg Gln Ile Val Leu Gly Thr Gly
                165                 170                 175

Ala Gly Pro His Thr Ser Ile Trp Asn Ser Val Thr Ser His Thr Gln
            180                 185                 190

Ala Glu Lys Arg Leu Asp Asn Ile Lys Leu His Glu Gln Lys Ala Leu
        195                 200                 205

Arg Gly Lys Val Leu Asp Leu Asp Glu Phe Met Arg Ala Ser Asp Ala
    210                 215                 220

Ser Pro Gln Thr Phe Ala Gly Lys Thr Val Val Ile His Gly Pro Asn
225                 230                 235                 240

Ala Gly Ile Asp Ala Ala Glu Arg Ala Gly Glu Leu Gly Ala Asn Ala
                245                 250                 255

Val Trp Phe Thr Arg Ser Thr Asn Pro Val Leu Leu Asp Gly Asn Gln
            260                 265                 270

Leu Lys Phe Ala Pro Glu Leu Ala Lys Ser Ala Ile His Lys Val Asp
        275                 280                 285

Lys Leu Asp Ile Arg Pro Thr Lys Leu Glu Asn Gly Phe Ala Leu Arg
    290                 295                 300

Leu His Tyr Ser Ser Leu Gly Gln Asp Ser Arg Glu Pro Lys Lys Val
305                 310                 315                 320

Leu Asp Ala Asp Tyr Tyr Val Tyr Ala Met Gly Gln Asp Ile His Lys
                325                 330                 335

Pro Gly Ser Ala Ala Ala Ile Leu Gly Ser Leu Leu Asp His Leu Glu
            340                 345                 350

Pro Ile Tyr Asp Tyr Asp Gln Val Tyr Ser Asp Gln Pro Phe Lys Thr
        355                 360                 365

Val Ile Gly Leu Gln Ser Arg Gly Ser Asn Ser Asp Asn Gly Leu Ile
    370                 375                 380

Ile Val Gly Ala Ala Val Ala Gln Leu Ala Thr Asn Val Gln His Ser
385                 390                 395                 400

Tyr Lys Asp His Ala Leu Asp Arg Ile Leu Glu Glu Met Thr Arg Leu
```

```
                405            410              415
Pro Glu Lys Gln Thr Glu Lys Leu Ser Gln Met Leu Leu Glu Gly Ala
            420                 425                 430
Pro Ser Val Gln Ile Gln Thr Tyr Leu Lys Thr Trp Gln Leu Asp Ser
        435                 440                 445
Gly Gln Pro Pro Asp Lys Gln Val Leu Gln Asn Gln Val Glu Asn Tyr
    450                 455                 460
Leu Ala Ala Arg Asp Tyr Phe Gln Arg Gln Thr Asn Glu Gln Lys Gly
465                 470                 475                 480
Asn Leu Asp Gly Val Ala Ala Glu Val Lys Asn Gln Thr Leu Thr Glu
                485                 490                 495
Val Ala Ser Val Ile Val Ser Pro Gln Leu Gly Thr Ile Lys Ala Ser
            500                 505                 510
Ala Ala Ala Leu Ser Gly Leu Met Pro Ala Tyr Val Ala Asn Gly Glu
        515                 520                 525
Asn Asn Phe Thr Thr Asp Asn Arg Thr Met Leu Arg Ala Gly Ile Ala
    530                 535                 540
Ala Arg Tyr Pro Asn Ile Gly Asn Ala Glu Ala Ser Ala Phe Ile Asp
545                 550                 555                 560
Glu Val Val Thr Leu Arg His Leu Asn Ser Gln Arg Phe Ile Glu Lys
                565                 570                 575
Val Ala Gly Glu Met Met Asp Lys Gly Ala Gln Pro Leu Val Ser Leu
            580                 585                 590
Arg Pro Pro Val Leu Gly Val Pro Ala Ser Val Arg Thr Ala Tyr Glu
        595                 600                 605
Ala Tyr Leu His Ala Leu Asn Ser Gly Ala His Asp Gly Thr Pro Leu
    610                 615                 620
Ser Gln Arg Trp Leu Pro Lys Lys
625                 630

<210> SEQ ID NO 3
<211> LENGTH: 657
<212> TYPE: DNA
<213> ORGANISM: Pseudomonas syringae pv. tomato DC3000

<400> SEQUENCE: 3
atgatcactc cgtctcgata tccaggcatc tatatcgccc ccctcagtaa cgaaccgaca      60
gcagctcaca catttaaaga acaagcagag gaagcacttg accatatcag cgccgcaccc     120
tctggcgata agctattgcg aaaaatatcc actcttgcca gtcaaaaaga tagaaaagtc     180
acgctaaaag agattgaaat aaataaccag tgttataccg aagctgttct gagcagragg     240
caactggaaa agtacgaacc agaaaacttt aacgagaacc ggcacattgc atcacagcta     300
tcacgaaagg ggacctttac caaaggtgaa ggaagcaacg cgattattgg ctggtcacca     360
gacaaagcaa gcatacgctt aaatcagaat ggctcaccgt tacaccttgg aatggataac     420
gacgacaaaa tcacgaccct agctcatgag ctcgttcatg ctcgacatgt gttaggtggc     480
agctccttag cggatggcgg agatcgctat aatccacgta cgggatctgg caaagaggaa     540
cttagggccg ttggattaga taagtaccgc tattcactta caaaaaaacc gtcagagaac     600
tccatccgag ctgaacacgg cctgcctctg cgcatgaagt acagggcaca tcaatag       657

<210> SEQ ID NO 4
<211> LENGTH: 218
<212> TYPE: PRT
<213> ORGANISM: Pseudomonas syringae pv. tomato DC3000
```

```
<400> SEQUENCE: 4

Met Ile Thr Pro Ser Arg Tyr Pro Gly Ile Tyr Ile Ala Pro Leu Ser
 1               5                  10                  15

Asn Glu Pro Thr Ala Ala His Thr Phe Lys Glu Gln Ala Glu Ala
             20                  25                  30

Leu Asp His Ile Ser Ala Ala Pro Ser Gly Asp Lys Leu Leu Arg Lys
             35                  40                  45

Ile Ser Thr Leu Ala Ser Gln Lys Asp Arg Lys Val Thr Leu Lys Glu
 50                  55                  60

Ile Glu Ile Asn Asn Gln Cys Tyr Thr Glu Ala Val Leu Ser Arg Arg
 65                  70                  75                  80

Gln Leu Glu Lys Tyr Glu Pro Glu Asn Phe Asn Glu Asn Arg His Ile
                 85                  90                  95

Ala Ser Gln Leu Ser Arg Lys Gly Thr Phe Thr Lys Gly Glu Gly Ser
             100                 105                 110

Asn Ala Ile Ile Gly Trp Ser Pro Asp Lys Ala Ser Ile Arg Leu Asn
             115                 120                 125

Gln Asn Gly Ser Pro Leu His Leu Gly Met Asp Asn Asp Lys Ile
 130                 135                 140

Thr Thr Leu Ala His Glu Leu Val His Ala Arg His Val Leu Gly Gly
145                 150                 155                 160

Ser Ser Leu Ala Asp Gly Gly Asp Arg Tyr Asn Pro Arg Thr Gly Ser
                 165                 170                 175

Gly Lys Glu Glu Leu Arg Ala Val Gly Leu Asp Lys Tyr Arg Tyr Ser
             180                 185                 190

Leu Thr Lys Lys Pro Ser Glu Asn Ser Ile Arg Ala Glu His Gly Leu
             195                 200                 205

Pro Leu Arg Met Lys Tyr Arg Ala His Gln
             210                 215

<210> SEQ ID NO 5
<211> LENGTH: 636
<212> TYPE: DNA
<213> ORGANISM: Pseudomonas syringae pv. tomato DC3000

<400> SEQUENCE: 5
atgaatagag tttccggtag ctcgtcagcg acttggcagg cagtcaacga tcttgtggag      60
caagtaagcg agagaaccac gttgtctacg acaggttatc agacggcaat gggccgcttg     120
aacaaaccgg aaaaatcaga tgcggatgcg ctgatgacta tgaggagggc gcaacagtac     180
acggatagcg cgaagcgaac ttatatttcg gaaacgctga tgaatctggc agatttgcag     240
caaaggaaaa tctatcgcac caacagcggg aacttgcgtg gcgcgattga gatgacgcct     300
acgcaactca cagattgcgt tacagaagtg cgcgaagagg ggttctccaa ttgtgacata     360
caggcgctgg aaatcggctt gcaccttcga cataagttag gaatctcaga tttcaccatc     420
tacagcaacc gtaagttaag ccataactat gtggtcatcc accccagcaa tgcatttccg     480
aaaggagcga ttgtagactc ttggacggga caggcgtgg tggagctgga cttcaagacc     540
cgattgaaat tcaagcaccg ggaagagaac tacgcagtga cgccaatat gcacgagtgg     600 atcgagagat acggccaagc gcatgtgatt gactga                              636

<210> SEQ ID NO 6
<211> LENGTH: 211
<212> TYPE: PRT
<213> ORGANISM: Pseudomonas syringae pv. tomato DC3000
```

<400> SEQUENCE: 6

```
Met Asn Arg Val Ser Gly Ser Ser Ala Thr Trp Gln Ala Val Asn
 1               5                  10                  15

Asp Leu Val Glu Gln Val Ser Glu Arg Thr Thr Leu Ser Thr Thr Gly
             20                  25                  30

Tyr Gln Thr Ala Met Gly Arg Leu Asn Lys Pro Glu Lys Ser Asp Ala
         35                  40                  45

Asp Ala Leu Met Thr Met Arg Arg Ala Gln Gln Tyr Thr Asp Ser Ala
     50                  55                  60

Lys Arg Thr Tyr Ile Ser Glu Thr Leu Met Asn Leu Ala Asp Leu Gln
 65                  70                  75                  80

Gln Arg Lys Ile Tyr Arg Thr Asn Ser Gly Asn Leu Arg Gly Ala Ile
                 85                  90                  95

Glu Met Thr Pro Thr Gln Leu Thr Asp Cys Val Gln Lys Cys Arg Glu
            100                 105                 110

Glu Gly Phe Ser Asn Cys Asp Ile Gln Ala Leu Glu Ile Gly Leu His
        115                 120                 125

Leu Arg His Lys Leu Gly Ile Ser Asp Phe Thr Ile Tyr Ser Asn Arg
    130                 135                 140

Lys Leu Ser His Asn Tyr Val Val Ile His Pro Ser Asn Ala Phe Pro
145                 150                 155                 160

Lys Gly Ala Ile Val Asp Ser Trp Thr Gly Gln Gly Val Val Glu Leu
                165                 170                 175

Asp Phe Lys Thr Arg Leu Lys Phe Lys His Arg Glu Glu Asn Tyr Ala
            180                 185                 190

Val Asn Ala Asn Met His Glu Trp Ile Glu Arg Tyr Gly Gln Ala His
        195                 200                 205

Val Ile Asp
    210
```

<210> SEQ ID NO 7
<211> LENGTH: 1482
<212> TYPE: DNA
<213> ORGANISM: Pseudomonas syringae pv. tomato DC3000

<400> SEQUENCE: 7

```
atgcaaataa agaacagtca tctctattca gcttcaagaa tggtgcagaa tacttttaat      60
gcctcgccta agatggaagt aactaatgca atagcaaaaa ataatgaacc tgctgcgctg     120
agcgctacgc aaactgcaaa gacacacgaa ggcgattcaa aaggccaatc cagcaataac     180
tctaaattgc ccttccgcgc catgaggtac gctgcatacc ttgcaggcag cgcctacctc     240
tacgataaaa ctgccaataa tttttttctt tctaccactt ctctgcatga tggcaaaggt     300
ggttttacca gcgatgccag gcttaacgat gcacaagata aagcgcgaaa gcgctaccaa     360
aacaaccata gcagcactct tgaaaataaa aactcgcttt taagcccgct taggctttgc     420
ggagagaatc agttcttaac gatgattgat tatcgtgcag caactaagat ttacctctcc     480
gacctagttg acacggagca agcgcacaca tcaattctga gaatattat gtgcctgaaa     540
ggtgagctta ccaatgaaga ggcaataaaa aaactcaacc cggaaaaaac accaaaagac     600
tatgacctta caaatagcga agcctatata agcaagaaca atattctttt gaccggcgtt     660
aaaaatgagg agacgggatc tactggttat acatctcgtt ctatcacaaa gccatttgtg     720
gaaaaaggcc tgaaacactt tataaaagcg actcatggcg aaaaagctct cacgcccaag     780
cagtgtatgg aaactcttga taacttactt cgaaaaagta tcacgctcaa cagtgattcc     840
```

```
caattcgcag caggccaggc acttttggtt ttcagacagg tctatgcggg tgaagacgct    900 tgggggatg cggaacgggt catattgaaa agccattata atcggggcac tgtactccaa    960
gatgaagctg ataaaataga actaagtagg ccgttctcag agcaagattt agcaaagaac   1020
atgtttaaga ggaataccag cattgcaggg ccagtgctct accacgcata tatttatata   1080
caagaaaaaa tcttcaagct accccccgac aaaatagaag atttgaaaca taaatcaatg   1140
gcagacttga aaaacctgcc tttgactcat gttaagctta gcaattccgg tgtgggattt   1200
gaagacgcct cagggttagg agactcgttt acagctctca acgcgacgtc ctgtgttaat   1260
cacgcaagaa taatgagtgg tgagcctccc ttgtcaaaag atgatgttgt gattctgata   1320
ggttgcctca acgccgtata cgacaattcg agcggaataa ggcattctct ccgcgaaatt   1380
gcacgagggt gctttgtggg tgctggtttt acggtccagg acggtgacga cttctacaaa   1440
cagatctgca aaaacgcctc taagcagttt tacaacggct aa                     1482
```

<210> SEQ ID NO 8
<211> LENGTH: 493
<212> TYPE: PRT
<213> ORGANISM: Pseudomonas syringae pv. tomato DC3000

<400> SEQUENCE: 8

```
Met Gln Ile Lys Asn Ser His Leu Tyr Ser Ala Ser Arg Met Val Gln
  1               5                  10                  15

Asn Thr Phe Asn Ala Ser Pro Lys Met Glu Val Thr Asn Ala Ile Ala
                 20                  25                  30

Lys Asn Asn Glu Pro Ala Ala Leu Ser Ala Thr Gln Thr Ala Lys Thr
             35                  40                  45

His Glu Gly Asp Ser Lys Gly Gln Ser Ser Asn Asn Ser Lys Leu Pro
         50                  55                  60

Phe Arg Ala Met Arg Tyr Ala Ala Tyr Leu Ala Gly Ser Ala Tyr Leu
 65                  70                  75                  80

Tyr Asp Lys Thr Ala Asn Asn Phe Phe Leu Ser Thr Thr Ser Leu His
                 85                  90                  95

Asp Gly Lys Gly Gly Phe Thr Ser Asp Ala Arg Leu Asn Asp Ala Gln
            100                 105                 110

Asp Lys Ala Arg Lys Arg Tyr Gln Asn Asn His Ser Ser Thr Leu Glu
        115                 120                 125

Asn Lys Asn Ser Leu Leu Ser Pro Leu Arg Leu Cys Gly Glu Asn Gln
    130                 135                 140

Phe Leu Thr Met Ile Asp Tyr Arg Ala Ala Thr Lys Ile Tyr Leu Ser
145                 150                 155                 160

Asp Leu Val Asp Thr Glu Gln Ala His Thr Ser Ile Leu Lys Asn Ile
                165                 170                 175

Met Cys Leu Lys Gly Glu Leu Thr Asn Glu Glu Ala Ile Lys Lys Leu
            180                 185                 190

Asn Pro Glu Lys Thr Pro Lys Asp Tyr Asp Leu Thr Asn Ser Glu Ala
        195                 200                 205

Tyr Ile Ser Lys Asn Lys Tyr Ser Leu Thr Gly Val Lys Asn Glu Glu
    210                 215                 220

Thr Gly Ser Thr Gly Tyr Thr Ser Arg Ser Ile Thr Lys Pro Phe Val
225                 230                 235                 240

Glu Lys Gly Leu Lys His Phe Ile Lys Ala Thr His Gly Lys Ala
                245                 250                 255

Leu Thr Pro Lys Gln Cys Met Glu Thr Leu Asp Asn Leu Leu Arg Lys
            260                 265                 270
```

Ser Ile Thr Leu Asn Ser Asp Ser Gln Phe Ala Ala Gly Gln Ala Leu
            275                 280                 285

Leu Val Phe Arg Gln Val Tyr Ala Gly Glu Asp Ala Trp Gly Asp Ala
        290                 295                 300

Glu Arg Val Ile Leu Lys Ser His Tyr Asn Arg Gly Thr Val Leu Gln
305                 310                 315                 320

Asp Glu Ala Asp Lys Ile Glu Leu Ser Arg Pro Phe Ser Glu Gln Asp
                325                 330                 335

Leu Ala Lys Asn Met Phe Lys Arg Asn Thr Ser Ile Ala Gly Pro Val
            340                 345                 350

Leu Tyr His Ala Tyr Ile Tyr Ile Gln Glu Lys Ile Phe Lys Leu Pro
        355                 360                 365

Pro Asp Lys Ile Glu Asp Leu Lys His Lys Ser Met Ala Asp Leu Lys
370                 375                 380

Asn Leu Pro Leu Thr His Val Lys Leu Ser Asn Ser Gly Val Gly Phe
385                 390                 395                 400

Glu Asp Ala Ser Gly Leu Gly Asp Ser Phe Thr Ala Leu Asn Ala Thr
                405                 410                 415

Ser Cys Val Asn His Ala Arg Ile Met Ser Gly Glu Pro Leu Ser
            420                 425                 430

Lys Asp Asp Val Val Ile Leu Ile Gly Cys Leu Asn Ala Val Tyr Asp
        435                 440                 445

Asn Ser Ser Gly Ile Arg His Ser Leu Arg Glu Ile Ala Arg Gly Cys
450                 455                 460

Phe Val Gly Ala Gly Phe Thr Val Gln Asp Gly Asp Asp Phe Tyr Lys
465                 470                 475                 480

Gln Ile Cys Lys Asn Ala Ser Lys Gln Phe Tyr Asn Gly
            485                 490

<210> SEQ ID NO 9
<211> LENGTH: 852
<212> TYPE: DNA
<213> ORGANISM: Pseudomonas syringae pv. tomato DC3000

<400> SEQUENCE: 9
atgggtaata tttgtggtac ttctggctcc aatcatgtgt atagtccgcc tattagccct      60
caacatgcat ctggttcgtc cacaccagtg cccagtgctt ctgggacgat gctttctctc     120
agtcatgaac aaatattaag ccagaactat gctagcaata taaggggaa atatcgcacg     180 aaccccgaa aaggaccatc tcctaggctt tctgatacgc tgatgaagca ggcgctgtct     240
tcagtgatca cacaagagaa aaagcgactt aaaagtcaac caaagtcaat agcccaagat     300
attcagcctc caaacagcat gatcaaaaat gcacttgatg aaaaagacag ccacccttt      360 ggtgattgct tttcagacga tgaatttctt gcgatccatc tctatacgag ttgtctttac     420
agaccgatca accatcatct gcggtatgcc ccgaaaaatg atgtcgcgcc tgttgtcgag     480
gcaatgaata gcggtttggc caaacttgct caatacctg attatcaggt gtctggtcag     540
ctgcatagag gcatcaagca aaagatggat gatggtgaag ttatgagtcg cttcaagccg     600
ggtaatactt atcgtgatga cgcgttcatg agcacatcga ctagaatgga tgttacagaa     660
gaatttactt ccgatgtcac gttacatctg cagtcctcat cagccgtcaa tataggtccc     720
ttttcaaaaa acccatacga ggacgaagcg ctcatcccgc ccctgacgcc tttcaaagta     780
accggtctgc acaagcagga cgataggtgg cacgtccact tgaacgagat cgcagagagc     840
tctgacgagt ga                                                        852

<210> SEQ ID NO 10
<211> LENGTH: 283
<212> TYPE: PRT
<213> ORGANISM: Pseudomonas syringae pv. tomato DC3000

<400> SEQUENCE: 10

```
Met Gly Asn Ile Cys Gly Thr Ser Gly Ser Asn His Val Tyr Ser Pro
 1               5                  10                  15
Pro Ile Ser Pro Gln His Ala Ser Gly Ser Ser Thr Pro Val Pro Ser
            20                  25                  30
Ala Ser Gly Thr Met Leu Ser Leu Ser His Glu Gln Ile Leu Ser Gln
        35                  40                  45
Asn Tyr Ala Ser Asn Ile Lys Gly Lys Tyr Arg Thr Asn Pro Arg Lys
    50                  55                  60
Gly Pro Ser Pro Arg Leu Ser Asp Thr Leu Met Lys Gln Ala Leu Ser
65                  70                  75                  80
Ser Val Ile Thr Gln Glu Lys Lys Arg Leu Lys Ser Gln Pro Lys Ser
                85                  90                  95
Ile Ala Gln Asp Ile Gln Pro Pro Asn Ser Met Ile Lys Asn Ala Leu
            100                 105                 110
Asp Glu Lys Asp Ser His Pro Phe Gly Asp Cys Phe Ser Asp Glu
        115                 120                 125
Phe Leu Ala Ile His Leu Tyr Thr Ser Cys Leu Tyr Arg Pro Ile Asn
    130                 135                 140
His His Leu Arg Tyr Ala Pro Lys Asn Asp Val Ala Pro Val Val Glu
145                 150                 155                 160
Ala Met Asn Ser Gly Leu Ala Lys Leu Ala Gln Tyr Pro Asp Tyr Gln
                165                 170                 175
Val Ser Gly Gln Leu His Arg Gly Ile Lys Gln Lys Met Asp Asp Gly
            180                 185                 190
Glu Val Met Ser Arg Phe Lys Pro Gly Asn Thr Tyr Arg Asp Asp Ala
        195                 200                 205
Phe Met Ser Thr Ser Thr Arg Met Asp Val Thr Glu Glu Phe Thr Ser
    210                 215                 220
Asp Val Thr Leu His Leu Gln Ser Ser Ser Ala Val Asn Ile Gly Pro
225                 230                 235                 240
Phe Ser Lys Asn Pro Tyr Glu Asp Glu Ala Leu Ile Pro Pro Leu Thr
                245                 250                 255
Pro Phe Lys Val Thr Gly Leu His Lys Gln Asp Asp Arg Trp His Val
            260                 265                 270
His Leu Asn Glu Ile Ala Glu Ser Ser Asp Glu
        275                 280
```

<210> SEQ ID NO 11
<211> LENGTH: 393
<212> TYPE: DNA
<213> ORGANISM: Pseudomonas syringae pv. tomato DC3000

<400> SEQUENCE: 11

| | | |
|---|---|---|
| atgagcttat cgccgacgct gcaaaagcta actaatatat tgggcccgac aaaaaatgcc | 60 |
| aagcctgtca cagaggctat ccagtggcag gaaggcatgg atataacgct gcatgtcagc | 120 |
| ggcgacagcc ttaccttact agctaaaatc atagaactgc gtacagaccc taaagacgac | 180 |
| attttattgc gcaagctgct tacccatacg tttccgggcc tgcgtctgcg ccgtggcgcg | 240 |
| cttaccatca accctgatga aagtgccctg gttttctctt atgaacacga ttttcacctt | 300 |

```
ctggacaaag cccgttttga gagcctgctg gccaactttg ctgaaacggc gcaggagctt    360
cgagacacag cgacacattt tcgttttaac tga                                 393
```

<210> SEQ ID NO 12
<211> LENGTH: 130
<212> TYPE: PRT
<213> ORGANISM: Pseudomonas syringae pv. tomato DC3000

<400> SEQUENCE: 12

```
Met Ser Leu Ser Pro Thr Leu Gln Lys Leu Thr Asn Ile Leu Gly Pro
 1               5                   10                  15

Thr Lys Asn Ala Lys Pro Val Thr Glu Ala Ile Gln Trp Gln Glu Gly
                20                  25                  30

Met Asp Ile Thr Leu His Val Ser Gly Asp Ser Leu Thr Leu Leu Ala
            35                  40                  45

Lys Ile Ile Glu Leu Arg Thr Asp Pro Lys Asp Ile Leu Leu Arg
     50                  55                  60

Lys Leu Leu Thr His Thr Phe Pro Gly Leu Arg Leu Arg Arg Gly Ala
 65                  70                  75                  80

Leu Thr Ile Asn Pro Asp Glu Ser Ala Leu Val Phe Ser Tyr Glu His
                 85                  90                  95

Asp Phe His Leu Leu Asp Lys Ala Arg Phe Glu Ser Leu Leu Ala Asn
            100                 105                 110

Phe Ala Glu Thr Ala Gln Glu Leu Arg Asp Thr Ala Thr His Phe Arg
        115                 120                 125

Phe Asn
    130
```

<210> SEQ ID NO 13
<211> LENGTH: 387
<212> TYPE: DNA
<213> ORGANISM: Pseudomonas syringae pv. tomato DC3000

<400> SEQUENCE: 13

```
atgaaacaac gagcgacagt catctgcaaa cgtgacggcc aggtgcttta cgtacgcaaa    60
ccaaaatccc gctgggcttt gccaggtggc aagattgaag ccggggaaac gccttttccag   120 gctgccgtgc gcgagctttg cgaagaaacc ggtctggaaa atctcgatct gttgtacctg    180
gcggtgtacg agaaaggtga ggtcacgcac tacgtgttca ccactcaggt tcctgcctac    240
agcgagcctt cgccccagaa cgagatttct gcctgcaaat ggcttgcgcc caaaaatctt    300 ggcgaccta aggccagcag cgcgaccaag gctatcgtca agtcgtatgg ccgccaggct    360
gaagacggtt tactcagcgc taactag                                        387
```

<210> SEQ ID NO 14
<211> LENGTH: 128
<212> TYPE: PRT
<213> ORGANISM: Pseudomonas syringae pv. tomato DC3000

<400> SEQUENCE: 14

```
Met Lys Gln Arg Ala Thr Val Ile Cys Lys Arg Asp Gly Gln Val Leu
 1               5                   10                  15

Tyr Val Arg Lys Pro Lys Ser Arg Trp Ala Leu Pro Gly Gly Lys Ile
                20                  25                  30

Glu Ala Gly Glu Thr Pro Phe Gln Ala Ala Val Arg Glu Leu Cys Glu
            35                  40                  45

Glu Thr Gly Leu Glu Asn Leu Asp Leu Leu Tyr Leu Ala Val Tyr Glu
```

```
                50                  55                  60
Lys Gly Glu Val Thr His Tyr Val Phe Thr Thr Gln Val Pro Ala Tyr
 65                  70                  75                  80

Ser Glu Pro Ser Pro Gln Asn Glu Ile Ser Ala Cys Lys Trp Leu Ala
                 85                  90                  95

Pro Lys Asn Leu Gly Asp Leu Lys Ala Ser Ser Ala Thr Lys Ala Ile
            100                 105                 110

Val Lys Ser Tyr Gly Arg Gln Ala Glu Asp Gly Leu Leu Ser Ala Asn
        115                 120                 125

<210> SEQ ID NO 15
<211> LENGTH: 1014
<212> TYPE: DNA
<213> ORGANISM: Pseudomonas syringae pv. tomato DC3000

<400> SEQUENCE: 15
gtgctcgctt tgcatacgt cagcctgatt agagagcaga aattggacat caaaaaacgt       60
tggccttcca gtgagcagga gttggtagaa gtccgacggt ttaacaaaac cctcgcccgg     120
ctgccgcgtt tccaggttcg caatcgcctc acgcccgct tgattcaggc gctgctgcgg      180
gcggctcaga ttggtcgcgc gttgaaaccg gtcaaacatg acctgcggat tgaaacaacc    240
atcgtcagca ccgtaacgt ccctgtttca gtgcgaatca taaggcccaa aggcaaaccc     300
aaaggcgtgg tgtttgatat tcacggcggc ggttgggtga tcggcaacgc ccagatgaac    360
gatgacctca atatcggtat cgttaacgcg tgcaacgtgg cggtcgtgtc cgttgattac    420
agattggctt tatcgacccc cgtcgaaggg ctgatggatg actgctttc tgccgcatgc     480 tggctgctgg gtagcgactg taaggagttt gccggcctgc cggttattgt cgtcggtgag    540
tccgcgggcg ggcatcttgc cgcagccact ttgctcaaat tgaaagccag gcccgacttg    600
ctcaagcgcg tagtcggcac ggttctgtat tacggcgtgt acgacctgac cgggacaaaa    660
agcgttcgta ccgcaggccc ggaaacgctg gtgctcgacg gcccgggcat ggtcggcgca    720
atgcgcttgc tcgccccgga cagaaccgac gagaagcgcc gcgagccgcc gttatcgccc    780
ttgtatggcg acctcacgga tctgccgccc gccctgatgt ttgtcggcga actcgacccg    840
ctgctggacg cacgctgga aatggccgag cgatggaaaa actcggcaga cgttgaaatg    900
catcttctgc ccgagtctcc acatgggttc atccacttcc cgactgcctt ggcgcgcaag   960
gtacttgcgc gcagccacga gtggataaac gcgaggatgg aaggacggcc ttaa          1014

<210> SEQ ID NO 16
<211> LENGTH: 337
<212> TYPE: PRT
<213> ORGANISM: Pseudomonas syringae pv. tomato DC3000

<400> SEQUENCE: 16

Val Leu Ala Phe Ala Tyr Val Ser Leu Ile Arg Glu Gln Lys Leu Asp
  1                   5                  10                  15

Ile Lys Lys Arg Trp Pro Ser Ser Glu Gln Glu Leu Val Glu Val Arg
                 20                  25                  30

Arg Phe Asn Lys Thr Leu Ala Arg Leu Pro Arg Phe Gln Val Arg Asn
             35                  40                  45

Arg Leu Thr Pro Arg Leu Ile Gln Ala Leu Leu Arg Ala Ala Gln Ile
         50                  55                  60

Gly Arg Ala Leu Lys Pro Val Lys His Asp Leu Arg Ile Glu Thr Thr
 65                  70                  75                  80

Ile Val Ser Thr Gly Asn Val Pro Val Ser Val Arg Ile Ile Arg Pro
```

| | | | | 85 | | | | | 90 | | | | | 95 | | |
|---|---|---|---|---|---|---|---|---|---|---|---|---|---|---|---|---|

Lys Gly Lys Pro Lys Gly Val Val Phe Asp Ile His Gly Gly Trp
          100                    105                  110

Val Ile Gly Asn Ala Gln Met Asn Asp Asp Leu Asn Ile Gly Ile Val
     115                   120                   125

Asn Ala Cys Asn Val Ala Val Val Ser Val Asp Tyr Arg Leu Ala Leu
130                   135                   140

Ser Thr Pro Val Glu Gly Leu Met Asp Asp Cys Phe Ser Ala Ala Cys
145                   150                 155               160

Trp Leu Leu Gly Ser Asp Cys Lys Glu Phe Ala Gly Leu Pro Val Ile
                 165                   170               175

Val Val Gly Glu Ser Ala Gly Gly His Leu Ala Ala Thr Leu Leu
            180                   185               190

Lys Leu Lys Ala Arg Pro Asp Leu Leu Lys Arg Val Val Gly Thr Val
     195                   200                   205

Leu Tyr Tyr Gly Val Tyr Asp Leu Thr Gly Thr Lys Ser Val Arg Thr
210                   215                   220

Ala Gly Pro Glu Thr Leu Val Leu Asp Gly Pro Gly Met Val Gly Ala
225                   230                   235               240

Met Arg Leu Leu Ala Pro Asp Arg Thr Asp Glu Lys Arg Arg Glu Pro
                 245                   250               255

Pro Leu Ser Pro Leu Tyr Gly Asp Leu Thr Asp Leu Pro Pro Ala Leu
            260                   265               270

Met Phe Val Gly Glu Leu Asp Pro Leu Leu Asp Asp Thr Leu Glu Met
     275                   280                   285

Ala Glu Arg Trp Lys Asn Ser Ala Asp Val Glu Met His Leu Leu Pro
290                   295                   300

Glu Ser Pro His Gly Phe Ile His Phe Pro Thr Ala Leu Ala Arg Lys
305                   310                   315               320

Val Leu Ala Arg Ser His Glu Trp Ile Asn Ala Arg Met Glu Gly Arg
                 325                   330               335

Pro

<210> SEQ ID NO 17
<211> LENGTH: 483
<212> TYPE: DNA
<213> ORGANISM: Pseudomonas syringae pv. tomato DC3000

<400> SEQUENCE: 17

| | | |
|---|---|---|
| atgcaaacct atataccta tccaaaaaac cctcccaccg ttggtacagt tctgctgact | 60 |
| tcctatggct cattcgccca tgaaaacgag atacctaaat cttgtgctgc cgacgcttta | 120 |
| agagtaggca aagagctcgc tgatggtttc gatggcgagg ttcatcatct aggcgctctg | 180 |
| atgctgatga tttccgactt ccagcagag ccgctgctga agcatctgc tgctaagaaa | 240 |
| ggttctttgc taggaattac ttcgcttggc tacctattat cctatggatc tactggtgaa | 300 |
| aaagcgaagc gaatcatcga agcaggttgt ggtatttttc tcgtcagagt gagtggtgat | 360 |
| attgaaaacc ctaaagcaaa aattgaagtt tatagctctt ggtctgaata ccagaagttc | 420 |
| cttgaaccca ttttgaagac aggtgacttt tatccagtga aacgtcgtc gttttccgaa | 480 |
| taa | 483 |

<210> SEQ ID NO 18
<211> LENGTH: 160
<212> TYPE: PRT
<213> ORGANISM: Pseudomonas syringae pv. tomato DC3000

<400> SEQUENCE: 18

```
Met Gln Thr Tyr Ile Pro Tyr Pro Lys Asn Pro Pro Thr Val Gly Thr
 1               5                  10                  15
Val Leu Leu Thr Ser Tyr Gly Ser Phe Ala His Glu Asn Glu Ile Pro
            20                  25                  30
Lys Ser Cys Ala Ala Asp Ala Leu Arg Val Gly Lys Glu Leu Ala Asp
        35                  40                  45
Gly Phe Asp Gly Glu Val His His Leu Gly Ala Leu Met Leu Met Ile
    50                  55                  60
Ser Asp Phe Pro Ala Glu Pro Leu Leu Lys Ala Ser Ala Ala Lys Lys
65                  70                  75                  80
Gly Ser Leu Leu Gly Ile Thr Ser Leu Gly Tyr Leu Leu Ser Tyr Gly
                85                  90                  95
Ser Thr Gly Glu Lys Ala Lys Arg Ile Ile Glu Ala Gly Cys Gly Ile
            100                 105                 110
Phe Leu Val Arg Val Ser Gly Asp Ile Glu Asn Pro Lys Ala Lys Ile
        115                 120                 125
Glu Val Tyr Ser Ser Trp Ser Glu Tyr Gln Lys Phe Leu Glu Pro Ile
    130                 135                 140
Leu Lys Thr Gly Asp Phe Tyr Pro Val Lys Thr Ser Ser Phe Ser Glu
145                 150                 155                 160
```

<210> SEQ ID NO 19
<211> LENGTH: 1467
<212> TYPE: DNA
<213> ORGANISM: Pseudomonas syringae pv. tomato DC3000

<400> SEQUENCE: 19

```
atgatcaacc tcacccacat tgcgtcttca ttggcgcggg cagcgctcag cgattcgaca      60
aagccgaaga tggagcgcgc gataaacgtc gcgagccaca tcgctggcaa agtcgcgttg     120
caggtcacca gctcattact ggagcagaaa ggtctgctta cgagcgtca gcagaaaggg      180
ctctcgatga ttctgaaggc cttgagcggc aaggagccgg tgaacaatgt cgagacgcac     240
gaaggggag ccgattcaa tctggcgcga ccgccttcg acgtggccag cgttgtctgg       300
gagcgcgaca gtcgatgca taacgtgatg agctttctgg cgtcagcga cagcaagggc      360
aagatgttgt tctctctggg caagaagctg gcggatgcaa tggccaagcc tgagcctggc     420
aaggacaaca gtgaggccac aaatgcgcgc catgcctatt tctccagcaa cttgaaactg     480
aacaagttga tgaacgacct cactgaccag gttttcaaca agattcgcca gtcgaacggt     540
gatcgcgtgc gacgacccat gccagaacca ttctggagac cttacggcgc caacagcaa      600
gcgcgcccgc aaacgcctcc cggcactcgc ccacaagcca cagcgcccc gccaccgccg       660
ccgaaagcag agccacgacc tgcgtcgggc cggcctgacg gcgcccaaca gcaggcgcgc     720
ccggaaacgc cgcctcgtac tcgaccgcag gccaatagca ctccgccacc gccgccgaaa     780
gcagagccac gacctgcgtc gggccggcct gacggcgccc agcagcaagc acgcccggaa     840
acgccgccgc gcactcgccc gcaggcgaac agcacgccgc caccgccgcc caaggcagag     900
ccacgacctg cgtccggccg gcctgacggc gccaacagc aagcacgccc ggaaacgcca      960
cctcgcactc gccccaagc gaacagcgcg ccgcctccgc gcccaaagc agagccacga      1020
cctgcgtccg gccggcctga cggcacccaa cagcaagcac gcccggaaac gccacctcgc    1080
actcgccccc aagcgaacag cgcgccgcct ccgccgccca agcagaacc cagcgcaggc    1140
ggcgaacggc cttcaacggc gcggcccaat aacacatcgg ctgctgacgc atctgccagg    1200
```

```
gtgggcgatt ccgcacctgc caagccgccc gtcaagccgt tgtacgagca cttgggcctc   1260
actgacatgt cggtagactt atccgccgtt aaaaaggctt acagagatgc cgcgatgaag   1320
aaccaccctg ataaaaaccg cggcaacgag gccgaggcgg ccgagcgctt caaagtcatt   1380
tcaaatgcgt acaagatttt gtccgacccg gagttgcgca agcatacga caacggccgt   1440 atcaatgagg ctggtaatag ggcatga                                       1467
```

<210> SEQ ID NO 20
<211> LENGTH: 488
<212> TYPE: PRT
<213> ORGANISM: Pseudomonas syringae pv. tomato DC3000

<400> SEQUENCE: 20

```
Met Ile Asn Leu Thr His Ile Ala Ser Ser Leu Ala Arg Ala Ala Leu
 1               5                  10                  15

Ser Asp Ser Thr Lys Pro Lys Met Glu Arg Ala Ile Asn Val Ala Ser
            20                  25                  30

His Ile Ala Gly Lys Val Ala Leu Gln Val Thr Ser Ser Leu Leu Glu
        35                  40                  45

Gln Lys Gly Leu Leu Asn Glu Arg Gln Gln Lys Gly Leu Ser Met Ile
    50                  55                  60

Leu Lys Ala Leu Ser Gly Lys Glu Pro Val Asn Asn Val Glu Thr His
65                  70                  75                  80

Glu Gly Gly Gly Arg Phe Asn Leu Ala Arg Ala Ala Phe Asp Val Ala
                85                  90                  95

Ser Val Val Trp Glu Arg Asp Lys Ser Met His Asn Val Met Ser Phe
            100                 105                 110

Leu Gly Val Ser Asp Ser Lys Gly Lys Met Leu Phe Ser Leu Gly Lys
        115                 120                 125

Lys Leu Ala Asp Ala Met Ala Lys Pro Glu Pro Gly Lys Asp Asn Ser
    130                 135                 140

Glu Ala Thr Asn Ala Arg His Ala Tyr Phe Ser Ser Asn Leu Lys Leu
145                 150                 155                 160

Asn Lys Leu Met Asn Asp Leu Thr Asp Gln Val Phe Asn Lys Ile Arg
                165                 170                 175

Gln Ser Asn Gly Asp Arg Val Arg Arg Pro Met Pro Glu Pro Phe Trp
            180                 185                 190

Arg Pro Tyr Gly Ala Gln Gln Ala Arg Pro Gln Thr Pro Pro Gly
        195                 200                 205

Thr Arg Pro Gln Ala Asn Ser Ala Pro Pro Pro Pro Lys Ala Glu
    210                 215                 220

Pro Arg Pro Ala Ser Gly Arg Pro Asp Gly Ala Gln Gln Gln Ala Arg
225                 230                 235                 240

Pro Glu Thr Pro Pro Arg Thr Arg Pro Gln Ala Asn Ser Thr Pro Pro
                245                 250                 255

Pro Pro Pro Lys Ala Glu Pro Arg Pro Ala Ser Gly Arg Pro Asp Gly
            260                 265                 270

Ala Gln Gln Gln Ala Arg Pro Glu Thr Pro Pro Arg Thr Arg Pro Gln
        275                 280                 285

Ala Asn Ser Thr Pro Pro Pro Pro Lys Ala Glu Pro Arg Pro Ala
    290                 295                 300

Ser Gly Arg Pro Asp Gly Ala Gln Gln Gln Ala Arg Pro Glu Thr Pro
305                 310                 315                 320

Pro Arg Thr Arg Pro Gln Ala Asn Ser Ala Pro Pro Pro Pro Pro Lys
```

```
                    325                 330                 335
Ala Glu Pro Arg Pro Ala Ser Gly Arg Pro Asp Gly Thr Gln Gln Gln
                340                 345                 350

Ala Arg Pro Glu Thr Pro Pro Arg Thr Arg Pro Gln Ala Asn Ser Ala
            355                 360                 365

Pro Pro Pro Pro Lys Ala Glu Pro Ser Ala Gly Gly Glu Arg Pro
        370                 375                 380

Ser Thr Ala Arg Pro Asn Asn Thr Ser Ala Ala Asp Ala Ser Ala Arg
385                 390                 395                 400

Val Gly Asp Ser Ala Pro Ala Lys Pro Pro Val Lys Pro Leu Tyr Glu
                405                 410                 415

His Leu Gly Leu Thr Asp Met Ser Val Asp Leu Ser Ala Val Lys Lys
            420                 425                 430

Ala Tyr Arg Asp Ala Ala Met Lys Asn His Pro Asp Lys Asn Arg Gly
        435                 440                 445

Asn Glu Ala Glu Ala Ala Glu Arg Phe Lys Val Ile Ser Asn Ala Tyr
    450                 455                 460

Lys Ile Leu Ser Asp Pro Glu Leu Arg Lys Ala Tyr Asp Asn Gly Arg
465                 470                 475                 480

Ile Asn Glu Ala Gly Asn Arg Ala
                485

<210> SEQ ID NO 21
<211> LENGTH: 864
<212> TYPE: DNA
<213> ORGANISM: Pseudomonas syringae pv. tomato DC3000

<400> SEQUENCE: 21
atgaacatta cgccgctcac gtcagccgcg ggcaagggct cgtccgcaca aggcacagac      60
aaaatttcca ttcccaactc cacgcgcatg atcaatgccg cttcaatcaa gtggttgaat     120
aaggtgcgta gcgccatcag tgaccacatc cgcaccagca tcgagaaagg gaaactgttc     180
gagctcgcct ccttgggcag caacatgttc ggtgtcccgg ctctttcagc gcgcccctcg     240
acgctccaac ctgtgttggc gtttgaggct gaccccaatc acgacctgaa ccttgtcagg     300
gtctatatgc aggacagcgc cggcaagctc actccctggg acccgacgcc aacgcggtc     360 acgacgacgt cgaatccatc agagcctgat gcgcagagcg atacggcttc gtcatcatta     420
cctcggcggc ctcccgcagg ctcggtgctg agtttgctgg gcattgcgct ggatcacgcg     480
caacgccaca gtcctcgcgc ggacaggtct gccaagggac gacctggccg agaggagagg     540
aacggggcaa ggttcaatgc caagcaaaca aagccgacag aggctgaagc ctacggtgat     600
catcagacac ccaatcctga tttgcacagg caaaaagaga cagctcaacg cgttgctgaa     660
agcatcaaca gcatgcgaga gcagcaaaat ggaatgcaac gcgccgaagg gcttctcaga     720
gccaaagaag cgttgcaagc tcgggaagcc gcgcgcaagc agcttctgga cgtgctcgag     780
gccatccagg ctggccgtga agactccacc gacaagaaga tcagcgccac tgaaaagaac     840
gccacgggca tcaactacca gtga                                             864

<210> SEQ ID NO 22
<211> LENGTH: 287
<212> TYPE: PRT
<213> ORGANISM: Pseudomonas syringae pv. tomato DC3000

<400> SEQUENCE: 22

Met Asn Ile Thr Pro Leu Thr Ser Ala Ala Gly Lys Gly Ser Ser Ala
1               5                   10                  15
```

Gln Gly Thr Asp Lys Ile Ser Ile Pro Asn Ser Thr Arg Met Ile Asn
            20                  25                  30

Ala Ala Ser Ile Lys Trp Leu Asn Lys Val Arg Ser Ala Ile Ser Asp
        35                  40                  45

His Ile Arg Thr Ser Ile Glu Lys Gly Lys Leu Phe Glu Leu Ala Ser
    50                  55                  60

Leu Gly Ser Asn Met Phe Gly Val Pro Ala Leu Ser Ala Arg Pro Ser
65                  70                  75                  80

Thr Leu Gln Pro Val Leu Ala Phe Glu Ala Asp Pro Asn His Asp Leu
                85                  90                  95

Asn Leu Val Arg Val Tyr Met Gln Asp Ser Ala Gly Lys Leu Thr Pro
            100                 105                 110

Trp Asp Pro Thr Pro Asn Ala Val Thr Thr Ser Asn Pro Ser Glu
        115                 120                 125

Pro Asp Ala Gln Ser Asp Thr Ala Ser Ser Leu Pro Arg Arg Pro
    130                 135                 140

Pro Ala Gly Ser Val Leu Ser Leu Leu Gly Ile Ala Leu Asp His Ala
145                 150                 155                 160

Gln Arg His Ser Pro Arg Ala Asp Arg Ser Ala Lys Gly Arg Pro Gly
                165                 170                 175

Arg Glu Glu Arg Asn Gly Ala Arg Phe Asn Ala Lys Gln Thr Lys Pro
            180                 185                 190

Thr Glu Ala Glu Ala Tyr Gly Asp His Gln Thr Pro Asn Pro Asp Leu
        195                 200                 205

His Arg Gln Lys Glu Thr Ala Gln Arg Val Ala Glu Ser Ile Asn Ser
    210                 215                 220

Met Arg Glu Gln Gln Asn Gly Met Gln Arg Ala Glu Gly Leu Leu Arg
225                 230                 235                 240

Ala Lys Glu Ala Leu Gln Ala Arg Glu Ala Arg Lys Gln Leu Leu
                245                 250                 255

Asp Val Leu Glu Ala Ile Gln Ala Gly Arg Glu Asp Ser Thr Asp Lys
            260                 265                 270

Lys Ile Ser Ala Thr Glu Lys Asn Ala Thr Gly Ile Asn Tyr Gln
        275                 280                 285

<210> SEQ ID NO 23
<211> LENGTH: 429
<212> TYPE: DNA
<213> ORGANISM: Pseudomonas syringae pv. tomato DC3000

<400> SEQUENCE: 23
atgcgcacat ccgttaatgg tctgcttgag cacagcctga agaccctggg ctttgatact        60
tcggcattgc aggccttgcg cgacgacggt tatttactgt ggcaaggcaa ggataagcaa       120
gccagtcttc tggttccctc tactgacggc gacgcgcttt cgctatctg taccttgagc        180 cgtgtcgatc ccgagcacga cggacgtctg ctggcgcttg cattgcacct gaacctgtct       240
cctgtccaca cgatgagcgc atgtatagca cttgatgtcg agcaaaacac gttgtgtctt       300
cgctacaccc atgaccttgg cgggaacggg gcagataccc tgttgcttgc gctcgaaaac       360
gcccaagcgc ttgctgaaca gatcaagcag gtaatcgaaa actttaggca cgatcaggga       420
cgccgatag                                                              429

<210> SEQ ID NO 24
<211> LENGTH: 142
<212> TYPE: PRT

<213> ORGANISM: Pseudomonas syringae pv. tomato DC3000

<400> SEQUENCE: 24

```
Met Arg Thr Ser Val Asn Gly Leu Leu Glu His Ser Leu Lys Thr Leu
1               5                   10                  15
Gly Phe Asp Thr Ser Ala Leu Gln Ala Leu Arg Asp Asp Gly Tyr Leu
                20                  25                  30
Leu Trp Gln Gly Lys Asp Lys Gln Ala Ser Leu Leu Val Pro Ser Thr
            35                  40                  45
Asp Gly Asp Ala Leu Phe Ala Ile Cys Thr Leu Ser Arg Val Asp Pro
        50                  55                  60
Glu His Asp Gly Arg Leu Leu Ala Leu Ala Leu His Leu Asn Leu Ser
65                  70                  75                  80
Pro Val His Thr Met Ser Ala Cys Ile Ala Leu Asp Val Glu Gln Asn
                85                  90                  95
Thr Leu Cys Leu Arg Tyr Thr His Asp Leu Gly Gly Asn Gly Ala Asp
                100                 105                 110
Thr Leu Leu Leu Ala Leu Glu Asn Ala Gln Ala Leu Ala Glu Gln Ile
            115                 120                 125
Lys Gln Val Ile Glu Asn Phe Arg His Asp Gln Gly Arg Arg
        130                 135                 140
```

<210> SEQ ID NO 25
<211> LENGTH: 474
<212> TYPE: DNA
<213> ORGANISM: Pseudomonas syringae pv. tomato DC3000

<400> SEQUENCE: 25

```
atgatcgcgt tcgcaaccgg actgctagaa cacagcctga acggcttgg atacgacgcc      60
gcagatttgc aatcccttcg ggatgaaggg tatttgctgt ggcacgggaa aaacggtcac    120
accagcctgt tggtgcccgc tgctggcggg gatgcgcttt ttgtcatcag caccctgagc    180
tacatcgatc ctgaacagga cgggcggctg ctggcgcttg cgctgcattt gaacttgtcg    240
ccagcccaca ctctgggcgc cagtatcgcg ctggatatcg agcaaaatac cttgtgcctg    300
cgttacacgc acgacctcac tgggcacggc acagacaatt tgtcccgcgc gcttgaaagc    360
actcaggcac ttgccgagca gatcaagcag gtcatcgaaa ccttccgcag tgaattcgga    420
cgcccgccaa tgcccgccca cacagcccga cggccagatg ccgtggcgct ttag          474
```

<210> SEQ ID NO 26
<211> LENGTH: 157
<212> TYPE: PRT
<213> ORGANISM: Pseudomonas syringae pv. tomato DC3000

<400> SEQUENCE: 26

```
Met Ile Ala Phe Ala Thr Gly Leu Leu Glu His Ser Leu Lys Arg Leu
1               5                   10                  15
Gly Tyr Asp Ala Ala Asp Leu Gln Ser Leu Arg Asp Glu Gly Tyr Leu
                20                  25                  30
Leu Trp His Gly Lys Asn Gly His Thr Ser Leu Leu Val Pro Ala Ala
            35                  40                  45
Gly Gly Asp Ala Leu Phe Val Ile Ser Thr Leu Ser Tyr Ile Asp Pro
        50                  55                  60
Glu Gln Asp Gly Arg Leu Leu Ala Leu Ala Leu His Leu Asn Leu Ser
65                  70                  75                  80
Pro Ala His Thr Leu Gly Ala Ser Ile Ala Leu Asp Ile Glu Gln Asn
                85                  90                  95
```

```
Thr Leu Cys Leu Arg Tyr Thr His Asp Leu Thr Gly His Gly Thr Asp
            100                 105                 110

Asn Leu Ser Arg Ala Leu Glu Ser Thr Gln Ala Leu Ala Glu Gln Ile
        115                 120                 125

Lys Gln Val Ile Glu Thr Phe Arg Ser Glu Phe Gly Arg Pro Pro Met
130                 135                 140

Pro Ala His Thr Ala Arg Arg Pro Asp Ala Val Ala Leu
145                 150                 155

<210> SEQ ID NO 27
<211> LENGTH: 534
<212> TYPE: DNA
<213> ORGANISM: Pseudomonas syringae pv. tomato DC3000

<400> SEQUENCE: 27
gtgaaaaagt ctggcgctgg aactcaagcc tatgcgttgt tcgcctctgc gacgggaagc    60
tcgtcgaagg gcgttctaag taccattgcc aggcacctga cgggatgttt tgcacccaac   120
aagactgcgc ttcattcagc aacagccgtt tcgtatgagc tattgccggg caattattct   180
gtcgccgcca gtgtgcatgg cttgtcggtt gataccgcc agccggcgct gacacgactg    240
agtaacgtgc tgttcaatca ggcactggcg ctggacctgg agcgttttga cgagggcgcg   300
ccagccgaca aaatgttcag gccttcactg aaacgcgaag tgcccatcc ccgattggcc    360 gactcactgg gtggcgagca actggctgtg caaaccatgg agaagggcct taacggctg    420 gcagaggatc ctgcgcagtc ctttgcgcga tgccattcat tttttttaccc gatcagtagt  480 gataccactt cacctcaagc atcacttcat tctgtggcga gctcatctgg ctga         534

<210> SEQ ID NO 28
<211> LENGTH: 177
<212> TYPE: PRT
<213> ORGANISM: Pseudomonas syringae pv. tomato DC3000

<400> SEQUENCE: 28

Val Lys Lys Ser Gly Ala Gly Thr Gln Ala Tyr Ala Leu Phe Ala Ser
1               5                   10                  15

Ala Thr Gly Ser Ser Lys Gly Val Leu Ser Thr Ile Ala Arg His
            20                  25                  30

Leu Thr Gly Cys Phe Ala Pro Asn Lys Thr Ala Leu His Ser Ala Thr
        35                  40                  45

Ala Val Ser Tyr Glu Leu Leu Pro Gly Asn Tyr Ser Val Ala Ala Ser
    50                  55                  60

Val His Gly Leu Ser Val Asp His Arg Gln Pro Ala Leu Thr Arg Leu
65                  70                  75                  80

Ser Asn Val Leu Phe Asn Gln Ala Leu Ala Leu Asp Leu Glu Arg Phe
                85                  90                  95

Asp Glu Gly Ala Pro Ala Asp Glu Met Phe Arg Pro Ser Leu Lys Arg
            100                 105                 110

Glu Gly Ala His Pro Arg Leu Ala Asp Ser Leu Gly Gly Glu Gln Leu
        115                 120                 125

Ala Val Gln Thr Met Glu Lys Gly Leu Lys Arg Leu Ala Glu Asp Pro
130                 135                 140

Ala Gln Ser Phe Ala Arg Cys His Ser Phe Phe Tyr Pro Ile Ser Ser
145                 150                 155                 160

Asp Thr Thr Ser Pro Gln Ala Ser Leu His Ser Val Ala Ser Ser Ser
                165                 170                 175
```

Gly

<210> SEQ ID NO 29
<211> LENGTH: 1137
<212> TYPE: DNA
<213> ORGANISM: Pseudomonas syringae pv. tomato DC3000

<400> SEQUENCE: 29

```
atgaaaacag tcagcaatca ctcgatoccc agtacaaatc tcgtcgtgga tgcgggaacg      60
gaaacttcgg cgcagaaatc ccagccggtt tgcagcgaaa tccagcgtaa cagcaagatc     120
gaaaagcag tcatcgaaca cattgccgac cacccggcag cgaaaatgac aataagcgcg     180
ctggttgaca cgttgacaga cgttttttgtc agggctcatg gggaggttaa ggggtgggcc     240
gaaatcgtcc aggcagtctc tcgccctcat gacagtaatc gacacggcag tggagtgctc     300
agcccgcgct ttgatgtaat ggggagtgtt ggttggaatg cggcagctat ccgggccacc     360
agtcgcgtcg ggacgcttcg agagaaaggt acactgttca ctaaccttat gctcagtaac     420
aactttaaac atttgcttaa acgagtggtt aacgatccag ccttgcagca aaagctcgac     480
ggtgggttag acctcaacta tctgaaggct tgtgaaggcg atctttatgt catgtcaggg     540
tgggctgcac gggctagcga aagtcgtgaa caaattggca aagcccggta tgaaacggca     600
tcaaatctta gccagacgct gatcagtgca cgtgagttgg cttttcatcg tcacaatccg     660
gttaatcatc cgtctgccca aacgaaagtg ggcttcgata agggtttgcc tgaggaatct     720
gatctgcagg ttctgagagg ccatggcagc agtgtatgga gtgtaaaacc gggcagcgat     780
ttcgcaaagc gtgctgaagt ttctggaaag cctattatcg ccggcccgtc cggtaccgct     840
tcgcgcatgg tcgctgttgc gcgttttctg gcaccggctt gtttgaaaag cctgggtatt     900
gagagtgagc agaacctgaa agagcttgtg cggtatgcct gctatgccta tttcggtcag     960
gacagccacc attcgatgct tgaagtgaat cttggtgtcg cttcccatgg aatgccggaa    1020
caatgggacg acacgcttta taacgagcct ttcagtaatt caattaaagg tcgcgggttt    1080
ggtatagaca atctcgcgca taggcaagtc gtcaggcagg cggctcaaaa gtcatga       1137
```

<210> SEQ ID NO 30
<211> LENGTH: 378
<212> TYPE: PRT
<213> ORGANISM: Pseudomonas syringae pv. tomato DC3000

<400> SEQUENCE: 30

Met Lys Thr Val Ser Asn His Ser Ile Pro Ser Thr Asn Leu Val Val
1               5                   10                  15

Asp Ala Gly Thr Glu Thr Ser Ala Gln Lys Ser Gln Pro Val Cys Ser
            20                  25                  30

Glu Ile Gln Arg Asn Ser Lys Ile Glu Lys Ala Val Ile Glu His Ile
        35                  40                  45

Ala Asp His Pro Ala Ala Lys Met Thr Ile Ser Ala Leu Val Asp Thr
    50                  55                  60

Leu Thr Asp Val Phe Val Arg Ala His Gly Glu Val Lys Gly Trp Ala
65                  70                  75                  80

Glu Ile Val Gln Ala Val Ser Arg Pro His Asp Ser Asn Arg His Gly
            85                  90                  95

Ser Gly Val Leu Ser Pro Arg Phe Asp Val Met Gly Ser Val Gly Trp
        100                 105                 110

Asn Ala Ala Ala Ile Arg Ala Thr Ser Arg Val Gly Thr Leu Arg Glu
    115                 120                 125

```
Lys Gly Thr Leu Phe Thr Asn Leu Met Leu Ser Asn Asn Phe Lys His
            130                 135                 140

Leu Leu Lys Arg Val Val Asn Asp Pro Ala Leu Gln Gln Lys Leu Asp
145                 150                 155                 160

Gly Gly Leu Asp Leu Asn Tyr Leu Lys Ala Cys Glu Gly Asp Leu Tyr
                165                 170                 175

Val Met Ser Gly Trp Ala Ala Arg Ala Ser Glu Ser Arg Glu Gln Ile
            180                 185                 190

Gly Lys Ala Arg Tyr Glu Thr Ala Ser Asn Leu Ser Gln Thr Leu Ile
        195                 200                 205

Ser Ala Arg Glu Leu Ala Phe His Arg His Asn Pro Val Asn His Pro
    210                 215                 220

Ser Ala Gln Thr Lys Val Gly Phe Asp Lys Gly Leu Pro Glu Glu Ser
225                 230                 235                 240

Asp Leu Gln Val Leu Arg Gly His Gly Ser Ser Val Trp Ser Val Lys
                245                 250                 255

Pro Gly Ser Asp Phe Ala Lys Arg Ala Glu Val Ser Gly Lys Pro Ile
            260                 265                 270

Ile Ala Gly Pro Ser Gly Thr Ala Ser Arg Met Val Ala Val Ala Arg
        275                 280                 285

Phe Leu Ala Pro Ala Cys Leu Lys Ser Leu Gly Ile Glu Ser Glu Gln
    290                 295                 300

Asn Leu Lys Glu Leu Val Arg Tyr Ala Cys Tyr Ala Tyr Phe Gly Gln
305                 310                 315                 320

Asp Ser His His Ser Met Leu Glu Val Asn Leu Gly Val Ala Ser His
                325                 330                 335

Gly Met Pro Glu Gln Trp Asp Asp Thr Leu Tyr Asn Glu Pro Phe Ser
            340                 345                 350

Asn Ser Ile Lys Gly Arg Gly Phe Gly Ile Asp Asn Leu Ala His Arg
        355                 360                 365

Gln Val Val Arg Gln Ala Ala Gln Lys Ser
    370                 375

<210> SEQ ID NO 31
<211> LENGTH: 1173
<212> TYPE: DNA
<213> ORGANISM: Pseudomonas syringae pv. tomato DC3000

<400> SEQUENCE: 31
atgcggtttg atgctgcccg aggccagaag cccaaagccc ctatggatgc accgtcatca      60
ttacgtttgc gagcgatagc aggtggcatg cccagtgaag aagcaggaac gactgcacct     120
gctgacgtga atcagcctcc acctgctgat gttcgtccag aaatgggtgt aggtcctgtg     180
agactcttcg ttaaactgat ggtaggaact ctggcgctgt cgacaggagt ccgttttgca     240
agatacccag gtgatttcgc gaaggatccg ggaggcagtg tatgggcagc aatcaatctg     300
cagcatcgct cgagcgtcac acatcttgaa caaggcaata agacggttct tgagcgtttc     360
ggtgcacata ttccaaaaga cagtgcgtgt ttcaaagctc cgctgacgt cacacacgat      420
gttccctcag gcgtggcagg gcagtggaac cacaaaaccc aacgggtaaa actgaaccct     480
aacattcatt tcgagagcca tccggcacag gtcgccggac atgagttcat acactgttac     540
acgcatcctg agtttgtcga acgccatata aacatccgc actggaaagc cctgaacgaa      600
gggttgacga ctcgttttgac agagaaactg ccagaccccta agcgtctctt gcccattccc     660
ttggcaaagg atccctatca tggtttcaag ctgtccaccg ggactcctg gccggatgcg      720
```

```
gccaggcgaa tcgaagacga agttggcgaa gatgtgttgt tgaaagcgtt ctttggcggc      780
gatgaccagg ctattagtga agtagctaaa gccgctgctc agatctaccc caagattgcc      840
tcacgtatta ccgagaggga gttgtatcaa gcgggcagca tgcgtggagg acaacagctg      900
gccgagtgtt acgtaggtgc tttgctcaaa aacggtcaga aactgcctga cagttttacg      960
aattatctgc tacctgtatt tagctattca gatataagcc ctggtcacgc gaaaaaaata     1020
caggcgcaag cggaaaaaag tcaaaagcgg atgggaattg tgttcgatac agcgtttttt     1080
tcacctgacc tgaagaccca gagactggca cttggcatgc tacgggagga cctgctgatg     1140
cactggaaaa aagttattcc ggatagaaag taa                                  1173
```

<210> SEQ ID NO 32
<211> LENGTH: 390
<212> TYPE: PRT
<213> ORGANISM: Pseudomonas syringae pv. tomato DC3000

<400> SEQUENCE: 32

```
Met Arg Phe Asp Ala Ala Arg Gly Gln Lys Pro Lys Ala Pro Met Asp
 1               5                  10                  15

Ala Pro Ser Ser Leu Arg Leu Arg Ala Ile Ala Gly Gly Met Pro Ser
            20                  25                  30

Glu Glu Ala Gly Thr Thr Ala Pro Ala Asp Val Asn Gln Pro Pro Pro
        35                  40                  45

Ala Asp Val Arg Pro Glu Met Gly Val Gly Pro Val Arg Leu Phe Val
    50                  55                  60

Lys Leu Met Val Gly Thr Leu Ala Leu Ser Thr Gly Val Arg Phe Ala
65                  70                  75                  80

Arg Tyr Pro Gly Asp Phe Ala Lys Asp Pro Gly Gly Ser Val Trp Ala
                85                  90                  95

Ala Ile Asn Leu Gln His Arg Ser Ser Val Thr His Leu Glu Gln Gly
           100                 105                 110

Asn Lys Thr Val Leu Glu Arg Phe Gly Ala His Ile Pro Lys Asp Ser
       115                 120                 125

Ala Cys Phe Lys Ala Arg Ala Asp Val Thr His Asp Val Pro Ser Gly
   130                 135                 140

Val Ala Gly Gln Trp Asn His Lys Thr Gln Arg Val Lys Leu Asn Pro
145                 150                 155                 160

Asn Ile His Phe Glu Ser His Pro Ala Gln Val Ala Gly His Glu Phe
                165                 170                 175

Ile His Cys Tyr Thr His Pro Glu Phe Val Glu Arg His Ile Lys His
            180                 185                 190

Pro His Trp Lys Ala Leu Asn Glu Gly Leu Thr Thr Arg Leu Thr Glu
        195                 200                 205

Lys Leu Pro Asp Pro Lys Arg Leu Leu Pro Ile Pro Leu Ala Lys Asp
    210                 215                 220

Pro Tyr His Gly Phe Lys Leu Ser Thr Gly Asp Ser Trp Pro Asp Ala
225                 230                 235                 240

Ala Arg Arg Ile Glu Asp Glu Val Gly Glu Asp Val Leu Leu Lys Ala
                245                 250                 255

Phe Phe Gly Gly Asp Asp Gln Ala Ile Ser Glu Val Ala Lys Ala Ala
            260                 265                 270

Ala Gln Ile Tyr Pro Lys Ile Ala Ser Arg Ile Thr Glu Arg Glu Leu
        275                 280                 285

Tyr Gln Ala Gly Ser Met Arg Gly Gly Gln Gln Leu Ala Glu Cys Tyr
    290                 295                 300
```

```
Val Gly Ala Leu Leu Lys Asn Gly Gln Lys Leu Pro Asp Ser Phe Thr
305                 310                 315                 320

Asn Tyr Leu Leu Pro Val Phe Ser Tyr Ser Asp Ile Ser Pro Gly His
                325                 330                 335

Ala Lys Lys Ile Gln Ala Gln Ala Glu Lys Ser Gln Lys Arg Met Gly
            340                 345                 350

Ile Val Phe Asp Thr Ala Phe Phe Ser Pro Asp Leu Lys Thr Gln Arg
        355                 360                 365

Leu Ala Leu Gly Met Leu Arg Glu Asp Leu Leu Met His Trp Lys Lys
    370                 375                 380

Val Ile Pro Asp Arg Lys
385                 390

<210> SEQ ID NO 33
<211> LENGTH: 474
<212> TYPE: DNA
<213> ORGANISM: Pseudomonas syringae pv. tomato DC3000

<400> SEQUENCE: 33
atgaacaggc ttcacaagac cagtctgctg gcggctatat tgaccgcatc cccctgcatt       60
atggcagcta acgctcatgc tatgagttgt cctgtcccgc aaagcgtgaa gtacgttaat     120
ggtatctata tcgcgccgga aacgtttgct ggttgggagg ggaactgggt ttctcaacca     180
cacaagaaac actccattaa agagttttcc actgctttat atctttcagt ggataaaagt     240
cagaagggag gaacattgac taactgtagt tattcactaa gcggagataa tggcgtaata     300
gatcttgagt atcgaaaatc aggaaatgag aatagactaa agacacttat cgtttccatt     360
gaaggtcagc acaattggat taagagcgt ggcgcggttg gaattcaagg atatgaatgt     420
acaaagtcag catctgagtg tcagttcgtt ccgctgcggc taaacgagga ctga           474

<210> SEQ ID NO 34
<211> LENGTH: 157
<212> TYPE: PRT
<213> ORGANISM: Pseudomonas syringae pv. tomato DC3000

<400> SEQUENCE: 34

Met Asn Arg Leu His Lys Thr Ser Leu Leu Ala Ala Ile Leu Thr Ala
1               5                   10                  15

Ser Pro Cys Ile Met Ala Ala Asn Ala His Ala Met Ser Cys Pro Val
            20                  25                  30

Pro Gln Ser Val Lys Tyr Val Asn Gly Ile Tyr Ile Ala Pro Glu Thr
        35                  40                  45

Phe Ala Gly Trp Glu Gly Asn Trp Val Ser Gln Pro His Lys Lys His
    50                  55                  60

Ser Ile Lys Glu Phe Ser Thr Ala Leu Tyr Leu Ser Val Asp Lys Ser
65                  70                  75                  80

Gln Lys Gly Gly Thr Leu Thr Asn Cys Ser Tyr Ser Leu Ser Gly Asp
                85                  90                  95

Asn Gly Val Ile Asp Leu Glu Tyr Arg Lys Ser Gly Asn Glu Asn Arg
            100                 105                 110

Leu Lys Thr Leu Ile Val Ser Ile Glu Gly Gln His Asn Trp Ile Lys
        115                 120                 125

Glu Arg Gly Ala Val Gly Ile Gln Gly Tyr Glu Cys Thr Lys Ser Ala
    130                 135                 140

Ser Glu Cys Gln Phe Val Pro Leu Arg Leu Asn Glu Asp
145                 150                 155
```

<210> SEQ ID NO 35
<211> LENGTH: 1344
<212> TYPE: DNA
<213> ORGANISM: Pseudomonas syringae pv. tomato DC3000

<400> SEQUENCE: 35

```
atgcatcgtc ctataccgc aggccatacc acctcacgtc tcatcctaga tcagtcaaaa      60
caaatatcac gtaccccatc ggaaagtagc gcgcaatcag cgcttttctca gcaagcaagc     120
atgagcagcc cagttttgga gcggtcgaaa agtgcgccag ctttattgac tgcggcacag     180
cgcacgatgc ttgcacaagt gggagcctgt aacgctcatc tgacctcaga tgaaaacatg     240
gccatcaacg aactgagatc acacaagccc cttttaccta aggatacgtg gttttttcact     300
gatcctaaca aggacccaga tgatgtcgtg acctacacct gggcaagca attgcaggct      360
gagggctttg tgcacatcac ggatgtagtg gcgacactgg gtgatgctga agttcgctct     420
caacgtgccg agatggccaa aggcgtgttc aacaagcttg agttgcatga cgtgcatgtg     480
tcgcgtggtc gggattacgc aatgaattcg cttcagtcga aggaacatgc caaattttta     540
ctggaaggtc atgctttaag ggctggacct ggtgaaatac accgcgacag cttgcaggac     600
atgagcaggc gcctggcccg tgcgccacat ggagtcggta ttgtcgtaat tgcaggcatg     660
agtgatatca atgcgctcat cactacctgc ccggatatgg tgcgcgaacg ggttgatgac     720
atcaccatca tgggcggcgt cgagccttta aaggacgcag atggttttgt acagcctgat     780
gcacgcgctt acaacaatgc gaccgacatg gacgctgcgc gcagtctttta tcggaaagcg     840
caggagcttg gcattccact tcgtatagtg acaaaggagg cggcctataa acggcggtt      900
tcgccttcat tttacgaagg gatagcgggg agcggacatc cagtaggcca ctacctgaga     960
gacgttcaga gagtgcgtt gaaaggcctc tgggaaggta ttcaagctgg attgcttccc     1020
gggttggatg actcatggtt ctttcggacg ttcatgccga atgcacagat gaagcagca     1080
caactggata aaaataaaga gagttcgttt gaagatatct ggcctaaggt gacgaagcta     1140
aacctgtatg atcctctgac attactggcc tcagtgccag gggcggcaaa actgctatt     1200
aaaccaaaag ctatacacac agaaggattt ggtgttgtag agcaagtagg tccagatgat     1260
gtgacgcatc cagagaaagc aaagttattg atgtccgctt tagccaaatc tgcgcttgtc     1320
cagtcgacgg tagccccaga ttga                                           1344
```

<210> SEQ ID NO 36
<211> LENGTH: 447
<212> TYPE: PRT
<213> ORGANISM: Pseudomonas syringae pv. tomato DC3000

<400> SEQUENCE: 36

```
Met His Arg Pro Ile Thr Ala Gly His Thr Thr Ser Arg Leu Ile Leu
 1               5                  10                  15

Asp Gln Ser Lys Gln Ile Ser Arg Thr Pro Ser Glu Ser Ser Ala Gln
            20                  25                  30

Ser Ala Leu Ser Gln Gln Ala Ser Met Ser Ser Pro Val Leu Glu Arg
        35                  40                  45

Ser Lys Ser Ala Pro Ala Leu Leu Thr Ala Ala Gln Arg Thr Met Leu
    50                  55                  60

Ala Gln Val Gly Ala Cys Asn Ala His Leu Thr Ser Asp Glu Asn Met
65                  70                  75                  80

Ala Ile Asn Glu Leu Arg Ser His Lys Pro Leu Leu Pro Lys Asp Thr
                85                  90                  95
```

Trp Phe Phe Thr Asp Pro Asn Lys Asp Pro Asp Asp Val Val Thr Tyr
                100                 105                 110

Thr Leu Gly Lys Gln Leu Gln Ala Glu Gly Phe Val His Ile Thr Asp
            115                 120                 125

Val Val Ala Thr Leu Gly Asp Ala Glu Val Arg Ser Gln Arg Ala Glu
130                 135                 140

Met Ala Lys Gly Val Phe Asn Lys Leu Glu Leu His Asp Val His Val
145                 150                 155                 160

Ser Arg Gly Arg Asp Tyr Ala Met Asn Ser Leu Gln Ser Lys Glu His
                165                 170                 175

Ala Lys Phe Leu Leu Glu Gly His Ala Leu Arg Ala Gly Pro Gly Glu
            180                 185                 190

Ile His Arg Asp Ser Leu Gln Asp Met Ser Arg Arg Leu Ala Arg Ala
        195                 200                 205

Pro His Gly Val Gly Ile Val Val Ile Ala Gly Met Ser Asp Ile Asn
    210                 215                 220

Ala Leu Ile Thr Thr Cys Pro Asp Met Val Arg Glu Arg Val Asp Asp
225                 230                 235                 240

Ile Thr Ile Met Gly Gly Val Glu Pro Leu Lys Asp Ala Asp Gly Phe
                245                 250                 255

Val Gln Pro Asp Ala Arg Ala Tyr Asn Asn Ala Thr Asp Met Asp Ala
            260                 265                 270

Ala Arg Ser Leu Tyr Arg Lys Ala Gln Glu Leu Gly Ile Pro Leu Arg
        275                 280                 285

Ile Val Thr Lys Glu Ala Ala Tyr Lys Thr Ala Val Ser Pro Ser Phe
    290                 295                 300

Tyr Glu Gly Ile Ala Gly Ser Gly His Pro Val Gly His Tyr Leu Arg
305                 310                 315                 320

Asp Val Gln Lys Ser Ala Leu Lys Gly Leu Trp Glu Gly Ile Gln Ala
                325                 330                 335

Gly Leu Leu Pro Gly Leu Asp Asp Ser Trp Phe Phe Arg Thr Phe Met
            340                 345                 350

Pro Asn Ala Gln Ile Glu Ala Ala Gln Leu Asp Lys Asn Lys Glu Ser
        355                 360                 365

Ser Phe Glu Asp Ile Trp Pro Lys Val Thr Lys Leu Asn Leu Tyr Asp
    370                 375                 380

Pro Leu Thr Leu Leu Ala Ser Val Pro Gly Ala Ala Lys Leu Leu Phe
385                 390                 395                 400

Lys Pro Lys Ala Ile His Thr Glu Gly Phe Gly Val Val Glu Gln Val
                405                 410                 415

Gly Pro Asp Asp Val Thr His Pro Glu Lys Ala Lys Leu Leu Met Ser
            420                 425                 430

Ala Leu Ala Lys Ser Ala Leu Val Gln Ser Thr Val Ala Pro Asp
        435                 440                 445

<210> SEQ ID NO 37
<211> LENGTH: 366
<212> TYPE: DNA
<213> ORGANISM: Pseudomonas syringae pv. tomato DC3000

<400> SEQUENCE: 37
gtgaaaatca atctccccgc gctcagaaca acgtcttcac gcgtgcagat ctgcttgacc      60
gcagtcctgc tgtgcacacc gctgctgttt tccgcgcatg cccaggcagc cggcacgget     120 tctgaacaag ccaatgtgga agtgatgatt cgtcagctca acgcgctcga ggccgtcgcc     180

| | |
|---|---|
| cagcgcagtg tcgatcttcc acaagacccg gcccaacgct atcacctgga ctatccccgg | 240 |
| ttggtcagcg acatcgcgcg catccgccag ggcttgcaag actacctgtc gccgtcccgc | 300 |
| gcacagcccc gcgaccccgt ggagctatca ggccattaca acgtcagcgg tgatcacacg | 360 |
| ccatga | 366 |

<210> SEQ ID NO 38
<211> LENGTH: 121
<212> TYPE: PRT
<213> ORGANISM: Pseudomonas syringae pv. tomato DC3000

<400> SEQUENCE: 38

Val Lys Ile Asn Leu Pro Ala Leu Arg Thr Thr Ser Ser Arg Val Gln
 1               5                  10                  15

Ile Cys Leu Thr Ala Val Leu Leu Cys Thr Pro Leu Leu Phe Ser Ala
            20                  25                  30

His Ala Gln Ala Ala Gly Thr Ala Ser Glu Gln Ala Asn Val Glu Val
        35                  40                  45

Met Ile Arg Gln Leu Asn Ala Leu Glu Ala Val Ala Gln Arg Ser Val
    50                  55                  60

Asp Leu Pro Gln Asp Pro Ala Gln Arg Tyr His Leu Asp Tyr Pro Arg
65                  70                  75                  80

Leu Val Ser Asp Ile Ala Arg Ile Arg Gln Gly Leu Gln Asp Tyr Leu
                85                  90                  95

Ser Pro Ser Arg Ala Gln Pro Arg Asp Pro Val Glu Leu Ser Gly His
            100                 105                 110

Tyr Asn Val Ser Gly Asp His Thr Pro
        115                 120

<210> SEQ ID NO 39
<211> LENGTH: 1242
<212> TYPE: DNA
<213> ORGANISM: Pseudomonas syringae pv. tomato DC3000

<400> SEQUENCE: 39

| | |
|---|---|
| atgcgttcca gggttataac tacatcgctg gtagtcatta tgctctcatg tgcatcagcc | 60 |
| gctccagctt gcttctccgc agacatgact cccagcgtgt cgaacgagag cacgtcggag | 120 |
| gcggattttc agcaatggct ggctactttc cgcagcaatg caactactaa gggcatcgac | 180 |
| acagccacac tcgatcttgc tttccaaaac atcacgcttg acccgactgt gcaccagttg | 240 |
| gatatggcgc aaccagagtt cacgacggcc atctgggatt atttgtctga acgtctgact | 300 |
| ccgaagaata tccagcaagg gcaggagctt ctgcaaaaag agccagttct gaacgaggta | 360 |
| gagcgtcact acggtgtgga tgcgaagatt atcgcggcca tctggtgtat tgaaagcggc | 420 |
| tacggtaagg atattggtag tcgcgatgtg attcgttcct tggccacgct tgcttacaag | 480 |
| ggccggcgga tggattacgg ggctacacag ttgatggccg cccttcatat cgtgcaaaac | 540 |
| aaagacatcg cccgtgcgca attgattggc tcgtgggctg gcgcgatggg cagacgcaa | 600 |
| ttcatcccga cgacctatct cgactatgca gttgatttta accacgacaa tcggcgcgac | 660 |
| gtttggagtt cccgggccga tgcgctggcc tccactgcct cttatttaca acgcagcgct | 720 |
| tggaactcgc gcgtctcttg gggacaggag gtgcagttgc ccgagaattt cgattacgct | 780 |
| caggctgaca tgtcgatcaa gaagcccgtt gccgaatggc aacggctcgg ggtgatggga | 840 |
| acgaagcaag cgattccggg cgagctcgca caggagcaag catcggtcct gctgcccgca | 900 |
| ggttatcgcg ggccagcatt tatggtccta agtaatttcc gtagcatcct gcgctataac | 960 |

```
aactccactg cctatgcgct aacgatcggg ctactagccg acagttatgc tggcgggacc    1020
ggcgtgtctc acccgtggcc aactgataat cctcccttgg gcagcattgc gcaggtaacc    1080
gatttgcaga aactgctgac tgctaagggc tactccctgg gtgctgctga cggtgttata    1140
ggggcgatga cccgggcggc catccgggct taccagaagg atcagcattt gccacccgac    1200
ggttacgcca gcactgtact actggagagc ctgcgccgat ag                      1242
```

<210> SEQ ID NO 40
<211> LENGTH: 413
<212> TYPE: PRT
<213> ORGANISM: Pseudomonas syringae pv. tomato DC3000

<400> SEQUENCE: 40

```
Met Arg Ser Arg Val Ile Thr Thr Ser Leu Val Val Ile Met Leu Ser
 1               5                  10                  15

Cys Ala Ser Ala Ala Pro Ala Cys Phe Ser Ala Asp Met Thr Pro Ser
             20                  25                  30

Val Ser Asn Glu Ser Thr Ser Glu Ala Asp Phe Gln Gln Trp Leu Ala
         35                  40                  45

Thr Phe Arg Ser Asn Ala Thr Thr Lys Gly Ile Thr Ala Thr Leu
     50                  55                  60

Asp Leu Ala Phe Gln Asn Ile Thr Leu Asp Pro Thr Val His Gln Leu
 65                  70                  75                  80

Asp Met Ala Gln Pro Glu Phe Thr Thr Ala Ile Trp Asp Tyr Leu Ser
                 85                  90                  95

Glu Arg Leu Thr Pro Lys Asn Ile Gln Gln Gly Gln Glu Leu Leu Gln
            100                 105                 110

Lys Glu Pro Val Leu Asn Glu Val Glu Arg His Tyr Gly Val Asp Ala
        115                 120                 125

Lys Ile Ile Ala Ala Ile Trp Cys Ile Glu Ser Gly Tyr Gly Lys Asp
    130                 135                 140

Ile Gly Ser Arg Asp Val Ile Arg Ser Leu Ala Thr Leu Ala Tyr Lys
145                 150                 155                 160

Gly Arg Arg Met Asp Tyr Gly Ala Thr Gln Leu Met Ala Ala Leu His
                165                 170                 175

Ile Val Gln Asn Lys Asp Ile Ala Arg Ala Gln Leu Ile Gly Ser Trp
            180                 185                 190

Ala Gly Ala Met Gly Gln Thr Gln Phe Ile Pro Thr Thr Tyr Leu Asp
        195                 200                 205

Tyr Ala Val Asp Phe Asn His Asp Asn Arg Arg Asp Val Trp Ser Ser
    210                 215                 220

Arg Ala Asp Ala Leu Ala Ser Thr Ala Ser Tyr Leu Gln Arg Ser Ala
225                 230                 235                 240

Trp Asn Ser Arg Val Ser Trp Gly Gln Glu Val Gln Leu Pro Glu Asn
                245                 250                 255

Phe Asp Tyr Ala Gln Ala Asp Met Ser Ile Lys Lys Pro Val Ala Glu
            260                 265                 270

Trp Gln Arg Leu Gly Val Met Gly Thr Lys Gln Ala Ile Pro Gly Glu
        275                 280                 285

Leu Ala Gln Glu Gln Ala Ser Val Leu Leu Pro Ala Gly Tyr Arg Gly
    290                 295                 300

Pro Ala Phe Met Val Leu Ser Asn Phe Arg Ser Ile Leu Arg Tyr Asn
305                 310                 315                 320

Asn Ser Thr Ala Tyr Ala Leu Thr Ile Gly Leu Leu Ala Asp Ser Tyr
```

```
            325                 330                 335
Ala Gly Gly Thr Gly Val Ser His Pro Trp Pro Thr Asp Asn Pro Pro
            340                 345                 350

Leu Gly Ser Ile Ala Gln Val Thr Asp Leu Gln Lys Leu Leu Thr Ala
            355                 360                 365

Lys Gly Tyr Ser Leu Gly Ala Ala Asp Gly Val Ile Gly Ala Met Thr
            370                 375                 380

Arg Ala Ala Ile Arg Ala Tyr Gln Lys Asp Gln His Leu Pro Pro Asp
385                 390                 395                 400

Gly Tyr Ala Ser Thr Val Leu Leu Glu Ser Leu Arg Arg
            405                 410

<210> SEQ ID NO 41
<211> LENGTH: 960
<212> TYPE: DNA
<213> ORGANISM: Pseudomonas syringae pv. tomato DC3000

<400> SEQUENCE: 41
atgcttgctc ctgacggcgt agaaatcgat atcgtgctat caggtatatg cggaactgat    60
ctggcggtat tgtcgggccg tgaaggtgga gaggtgggca ttatacgcgg cacgaagca   120 gttggcatta ttatcgatgt aggtaaggat gtagtacacc tacaaaaagg gatgcgggtg   180
gtggttgatc ccaacgaata ctgtggcgtt tgcgaacctt gccgtcttgc taaaacgcac   240
ctatgcaatg gggggtgaa cgctgggttg gatatcgcag gtgtcaacaa acatggaact    300
tttgccgagc gcttcgttac tcgtgagcgt tttgtgtatc aattgccaga cgatatgagc   360
tgggcagctg gtgtgttggt tgagcctgtt gcctgcattc tgaataatat agaccaggcg   420
ttcattcgag cgggagagcg tgtgttgatc ctagggtctg gccctatgag tctgattgcg   480
cagatcgttc tgcgctcaat gggagttgac acgctcgcca ctgatcgaaa cacacatcgc   540
atacagttcg gccgctcaca aagtcttgat gttatacatg ccgatgatct tgagttgcag   600
atgcagcacc aagaaaagtt tgatgttgtt atcgatactg tcggtaatca gatcgataca   660
gcttcacgct acatcggtcg cggtgggaga attgtacttt ttggatttga tagtgactat   720
cactacatgc tgcctgtaaa gtacttcctg gttaacgcta tcagtattat ttctgctgga   780
gaatacaatc agcactttcc tagagcaatt cgtcttgtgc aaaaacttcc tgagctaggg   840
cggctggtaa cgcatcgcta cgtactagaa aatcactcgg aggttttcga tgcacttctg   900
aacgatgctt ccgcccccaa tataaaaagc gtattcacac caaatctcgc ttatctttaa   960

<210> SEQ ID NO 42
<211> LENGTH: 319
<212> TYPE: PRT
<213> ORGANISM: Pseudomonas syringae pv. tomato DC3000

<400> SEQUENCE: 42

Met Leu Ala Pro Asp Gly Val Glu Ile Asp Ile Val Leu Ser Gly Ile
1               5                   10                  15

Cys Gly Thr Asp Leu Ala Val Leu Ser Gly Arg Glu Gly Gly Glu Val
            20                  25                  30

Gly Ile Ile Arg Gly His Glu Ala Val Gly Ile Ile Asp Val Gly
            35                  40                  45

Lys Asp Val Val His Leu Gln Lys Gly Met Arg Val Val Asp Pro
        50                  55                  60

Asn Glu Tyr Cys Gly Val Cys Glu Pro Cys Arg Leu Ala Lys Thr His
65                  70                  75                  80
```

```
Leu Cys Asn Gly Gly Val Asn Ala Gly Leu Asp Ile Ala Gly Val Asn
                85                  90                  95

Lys His Gly Thr Phe Ala Glu Arg Phe Val Thr Arg Glu Arg Phe Val
            100                 105                 110

Tyr Gln Leu Pro Asp Asp Met Ser Trp Ala Ala Gly Val Leu Val Glu
            115                 120                 125

Pro Val Ala Cys Ile Leu Asn Asn Ile Asp Gln Ala Phe Ile Arg Ala
130                 135                 140

Gly Glu Arg Val Leu Ile Leu Gly Ser Gly Pro Met Ser Leu Ile Ala
145                 150                 155                 160

Gln Ile Val Leu Arg Ser Met Gly Val Asp Thr Leu Ala Thr Asp Arg
                165                 170                 175

Asn Thr His Arg Ile Gln Phe Gly Arg Ser Gln Ser Leu Asp Val Ile
            180                 185                 190

His Ala Asp Asp Leu Glu Leu Gln Met Gln His Gln Glu Lys Phe Asp
            195                 200                 205

Val Val Ile Asp Thr Val Gly Asn Gln Ile Asp Thr Ala Ser Arg Tyr
        210                 215                 220

Ile Gly Arg Gly Arg Ile Val Leu Phe Gly Phe Asp Ser Asp Tyr
225                 230                 235                 240

His Tyr Met Leu Pro Val Lys Tyr Phe Leu Val Asn Ala Ile Ser Ile
                245                 250                 255

Ile Ser Ala Gly Glu Tyr Asn Gln His Phe Pro Arg Ala Ile Arg Leu
            260                 265                 270

Val Gln Lys Leu Pro Glu Leu Gly Arg Leu Val Thr His Arg Tyr Val
            275                 280                 285

Leu Glu Asn His Ser Glu Val Phe Asp Ala Leu Leu Asn Asp Ala Ser
290                 295                 300

Ala Pro Asn Ile Lys Ser Val Phe Thr Pro Asn Leu Ala Tyr Leu
305                 310                 315

<210> SEQ ID NO 43
<211> LENGTH: 675
<212> TYPE: DNA
<213> ORGANISM: Pseudomonas syringae pv. tomato DC3000

<400> SEQUENCE: 43
atgaaagtta ctgtattcag tcagatatca attgatggca agttgacgat gggcaaaggc      60
gcatccagca agccgttgtt tcagaacttt gatgatgatg acatgcgttt tattcataag     120
ttccgcggcg aagtcgacgc aatcatggta gggcgcaata caattgttac tgacgatcca     180
caattgacca atcgctatga gtcgggtcgt aacccaatac gtatcattcc caccacctcc     240
ttagatctgc ctacttccgc cagtattttc aaatcaccag agaaaactat tatcgcaact     300
agcgaacagg ctcgtgatca tgaaatggtc aaacatatcc gtgcttgtgg aaaggaggtg     360
ctctttgccg gtgcaaagca tgtcgacttt acacgacttt tccctatgct ggaggcgcgc     420 ggaataaaacc acatcatggt tgagggcggt ggccacctga actggcaggt attcaatctc     480
gatctggtag atgaaattat actcatgcag gtgcctatca tcataggtgg tcggcaact      540 gcaacgcttg ctgacggggt ggggtatcgg gatatcaaca tggccaattc gtttacgctg     600
catgctttag aagcacgccc ccattacaat ctcatgcact tcaagcgcga atcgaacaat     660
cggagcccgt actga                                                      675

<210> SEQ ID NO 44
<211> LENGTH: 224
```

<212> TYPE: PRT
<213> ORGANISM: Pseudomonas syringae pv. tomato DC3000

<400> SEQUENCE: 44

Met Lys Val Thr Val Phe Ser Gln Ile Ser Ile Asp Gly Lys Leu Thr
1               5                   10                  15

Met Gly Lys Gly Ala Ser Ser Lys Pro Leu Phe Gln Asn Phe Asp Asp
            20                  25                  30

Asp Asp Met Arg Phe Ile His Lys Phe Arg Gly Glu Val Asp Ala Ile
        35                  40                  45

Met Val Gly Arg Asn Thr Ile Val Thr Asp Asp Pro Gln Leu Thr Asn
    50                  55                  60

Arg Tyr Glu Ser Gly Arg Asn Pro Ile Arg Ile Pro Thr Thr Ser
65                  70                  75                  80

Leu Asp Leu Pro Thr Ser Ala Ser Ile Phe Lys Ser Pro Glu Lys Thr
                85                  90                  95

Ile Ile Ala Thr Ser Glu Gln Ala Arg Asp His Glu Met Val Lys His
            100                 105                 110

Ile Arg Ala Cys Gly Lys Glu Val Leu Phe Ala Gly Ala Lys His Val
        115                 120                 125

Asp Phe Thr Arg Leu Phe Pro Met Leu Glu Ala Arg Gly Ile Asn His
    130                 135                 140

Ile Met Val Glu Gly Gly His Leu Asn Trp Gln Val Phe Asn Leu
145                 150                 155                 160

Asp Leu Val Asp Glu Ile Ile Leu Met Gln Val Pro Ile Ile Gly
                165                 170                 175

Gly Ala Ala Thr Ala Thr Leu Ala Asp Gly Val Gly Tyr Arg Asp Ile
            180                 185                 190

Asn Met Ala Asn Ser Phe Thr Leu His Ala Leu Glu Ala Arg Pro His
        195                 200                 205

Tyr Asn Leu Met His Phe Lys Arg Glu Ser Asn Arg Ser Pro Tyr
    210                 215                 220

<210> SEQ ID NO 45
<211> LENGTH: 588
<212> TYPE: DNA
<213> ORGANISM: Pseudomonas syringae pv. tomato DC3000

<400> SEQUENCE: 45
atggagcagg aaaagagttc ctgtttgcgc tacggcgtga cccttaatga aaaagatctg      60
tcacgttttt tgggaactac acagcactac atgtggagca cgattaaaaa tgagtacgcg     120
ctcactgaat ccatcgacca cttgatggca cagcatcaac agcaattaat gcgctcaatc     180
agttttgaat tgtttcaatc catgcctggc gtggaggcgc ttctcaattt actggagcat     240
accggagtgc cctgtgccgt agcctcttcg tctccacgta atttggtcga gcttatattg     300
aagaaaacga aattgcgtcg attttttcaaa gaggttattt gtggtactga tgttaaagag     360
agtaaaccga atccggagat ttttcttacg gcggccaagg gacttggagt gtcacctcgt     420
gcatgtctgg ttattgaaga ctcccatcac ggtgttaccg ctgcgaaggc cgcccatatg     480
tttttgtatag gtttgcgtca ttccagctca tttcagcagg atctgagcgc tgctgatctg     540
atcgccaata atcattatga catcaagcaa tggtttgcag aaaaatag                   588

<210> SEQ ID NO 46
<211> LENGTH: 195
<212> TYPE: PRT
<213> ORGANISM: Pseudomonas syringae pv. tomato DC3000

<400> SEQUENCE: 46

Met Glu Gln Glu Lys Ser Ser Cys Leu Arg Tyr Gly Val Thr Leu Asn
1               5                   10                  15

Glu Lys Asp Leu Ser Arg Phe Leu Gly Thr Thr Gln His Tyr Met Trp
            20                  25                  30

Ser Thr Ile Lys Asn Glu Tyr Ala Leu Thr Glu Ser Ile Asp His Leu
        35                  40                  45

Met Ala Gln His Gln Gln Leu Met Arg Ser Ile Ser Phe Glu Leu
    50                  55                  60

Phe Gln Ser Met Pro Gly Val Glu Ala Leu Leu Asn Leu Leu Glu His
65                  70                  75                  80

Thr Gly Val Pro Cys Ala Val Ala Ser Ser Ser Pro Arg Asn Leu Val
                85                  90                  95

Glu Leu Ile Leu Lys Lys Thr Lys Leu Arg Arg Phe Phe Lys Glu Val
            100                 105                 110

Ile Cys Gly Thr Asp Val Lys Glu Ser Lys Pro Asn Pro Glu Ile Phe
        115                 120                 125

Leu Thr Ala Ala Lys Gly Leu Gly Val Ser Pro Arg Ala Cys Leu Val
130                 135                 140

Ile Glu Asp Ser His His Gly Val Thr Ala Ala Lys Ala Ala His Met
145                 150                 155                 160

Phe Cys Ile Gly Leu Arg His Ser Ser Ser Phe Gln Gln Asp Leu Ser
                165                 170                 175

Ala Ala Asp Leu Ile Ala Asn Asn His Tyr Asp Ile Lys Gln Trp Phe
            180                 185                 190

Ala Glu Lys
        195

<210> SEQ ID NO 47
<211> LENGTH: 474
<212> TYPE: DNA
<213> ORGANISM: Pseudomonas syringae pv. tomato DC3000

<400> SEQUENCE: 47
atgaatgcgt tcgcaaccgg tcagcttgaa tacagcctga aaaagctggg atacgatgcc       60
gccgctttgc aggccctgcg cgaagaaggg tacttgctgt ggaaagggaa aaacgaccag      120
accagcttgc tggtgcccct cggccgatctg gatgcacttt tcgttatcaa cacgttgagc      180
tacatcgacc ccgagcatga cggacgtctg ctggcgcttg cattgcacct taacctgtcc      240
cctgtccata cgatgagcgc ctgcatagcc ctcgatgtcg agcaaaacac gttatgcctg      300
cgctacaccc atgaccttgg cgggagcggg gctgataccc tgttgcttgc gctcgaaaac      360
gcccaggcgc tggccgaaca ggtcaggcag gtgatcgaaa ccttcaggcg tgaccaaggg      420
cgtccgtccg ggcaaacgtc tttgtcccgg caatccagtg ctctgatgcg ataa           474

<210> SEQ ID NO 48
<211> LENGTH: 157
<212> TYPE: PRT
<213> ORGANISM: Pseudomonas syringae pv. tomato DC3000

<400> SEQUENCE: 48

Met Asn Ala Phe Ala Thr Gly Gln Leu Glu Tyr Ser Leu Lys Lys Leu
1               5                   10                  15

Gly Tyr Asp Ala Ala Ala Leu Gln Ala Leu Arg Glu Glu Gly Tyr Leu
            20                  25                  30

```
Leu Trp Lys Gly Lys Asn Asp Gln Thr Ser Leu Leu Val Pro Ser Ala
         35                  40                  45

Asp Leu Asp Ala Leu Phe Val Ile Asn Thr Leu Ser Tyr Ile Asp Pro
     50                  55                  60

Glu His Asp Gly Arg Leu Leu Ala Leu Ala Leu His Leu Asn Leu Ser
 65                  70                  75                  80

Pro Val His Thr Met Ser Ala Cys Ile Ala Leu Asp Val Glu Gln Asn
                 85                  90                  95

Thr Leu Cys Leu Arg Tyr Thr His Asp Leu Gly Gly Ser Gly Ala Asp
            100                 105                 110

Thr Leu Leu Leu Ala Leu Glu Asn Ala Gln Ala Leu Ala Glu Gln Val
        115                 120                 125

Arg Gln Val Ile Glu Thr Phe Arg Arg Asp Gln Gly Arg Pro Ser Gly
    130                 135                 140

Gln Thr Ser Leu Ser Arg Gln Ser Ser Ala Leu Met Arg
145                 150                 155
```

<210> SEQ ID NO 49
<211> LENGTH: 357
<212> TYPE: DNA
<213> ORGANISM: Pseudomonas syringae pv. tomato DC3000

<400> SEQUENCE: 49

```
atgaaaatat ccggctccac atcgcctgca cacacttcaa cgaattccgc gcagaagtcc    60
tcttcaaaag gctgctgag tggtttggcc aagcatttca aggggatgct cgtttctggc    120
aacacttctg gtcattcggc gctcgggcat tacgcgtcat ccagcagcgg ctccaaaggc   180
aaggcaccgg tacgggacga ttacagcaac ggaccgcaaa cacgccttaa caacacacct   240
ctgaaacgag cactggcccg agagcttgat cgctttggct acggttcatc ggcgaccgag   300
tcttttgacc gctcattgca gcgtaaggat aaaaatccag agcttgggaa ggtctga      357
```

<210> SEQ ID NO 50
<211> LENGTH: 118
<212> TYPE: PRT
<213> ORGANISM: Pseudomonas syringae pv. tomato DC3000

<400> SEQUENCE: 50

```
Met Lys Ile Ser Gly Ser Thr Ser Pro Ala His Thr Thr Asn Ser
  1               5                  10                  15

Ala Gln Lys Ser Ser Ser Lys Gly Leu Leu Ser Gly Leu Ala Lys His
             20                  25                  30

Phe Lys Gly Met Leu Val Ser Gly Asn Thr Ser Gly His Ser Ala Leu
         35                  40                  45

Gly His Tyr Ala Ser Ser Ser Gly Ser Lys Gly Lys Ala Pro Val
     50                  55                  60

Arg Asp Asp Tyr Ser Asn Gly Pro Gln Thr Arg Leu Asn Asn Thr Pro
 65                  70                  75                  80

Leu Lys Arg Ala Leu Ala Arg Glu Leu Asp Arg Phe Gly Tyr Gly Ser
                 85                  90                  95

Ser Ala Thr Glu Ser Phe Asp Arg Ser Leu Gln Arg Lys Asp Lys Asn
            100                 105                 110

Pro Glu Leu Gly Lys Val
        115
```

<210> SEQ ID NO 51
<211> LENGTH: 1299
<212> TYPE: DNA

<213> ORGANISM: Pseudomonas syringae pv. tomato DC3000

<400> SEQUENCE: 51

```
atgaaaaaat gtattgctct gctccttact ctggtcgtct gcgaaggtgc attggcagga      60
acggcacgtg atgaacagaa catcacgtct tacatcgaca gtcacggcac cgaacagatc     120
gcgttgcttg agaagctggt caacatcaac agcgggacag acaacgttga gggtgtcgtc     180
aaggtcggta acctgatcaa gccggagctg gaggcgttgg gtttcgagac cgcctggcac     240
gacctgccct cggcaatgaa ccatgccggc agccttgtcg ctgtgcatga cggcagcaag     300
tctgcaaaac gtattctgct gataggccat ctggatacgg tctttcctca acaagccgc      360
tttcagacgt tcgcttacct ggacggcggc aaaaaagcca agggccccgg cgtcattgat     420
gacaaaggcg gcgtggtcac gatgctttat gcattgcagg cgctcaagca cagcggcgcg     480
ctggaaaaga tgaacatctc ggtagtcttg ataggcgatg aagagctggc ggccaaaccg     540
accgagattt ccagagagtg gctgatcgcc gaagccaaaa gaagcgacat tgcgctgggc     600
ttcgaattcg ccttgtcgcc caatcaactg atcaccgagc gaagagggct gagcgaatgg     660
tttttgacca gcaccggcat cgacaaacat tcagcgacga tctttcagcc tgagaccggt     720
tttggtgcga tgtacgagtc ggcccgagtg cttgacgaga ttcgtcagaa actgtcgaac     780
gagcagggcc tgaccatcaa tccgggactc attctgggcg gctcaacggc tgtgaaagat     840
agcgccagtg ggcaaggcac ggcttctgga agaaagacaa cagttgcccg gatcacgtcg     900
gtgcatggtg atttgcgctt cagcagtgaa gaccagaggg cctctgcgga aacccgaatg     960
aaggacatag ccagtcaccc gctgccgcag accaacagcg acctgaaaat aaaagccatc    1020
atgccggtca tggcggatcg cgaaagcaat cgccaactac tggcagccta cagtcaggtc    1080
agccaggatc tcgacggacc tgctttggag tcggcgcctt cagcagaacg aggcggcgca    1140
gatatttcct atgtgaacaa gtatgtgact gcgagcctgg acggtcttgg tgcgtggggg    1200
gcaggtgcgc acagtgaaaa tgaaaccatc gagttgggct ccttgcccgt ggtgacgaaa    1260
cgggcggcta ttttcctgag ccgctatggt aaccagtga                           1299
```

<210> SEQ ID NO 52
<211> LENGTH: 432
<212> TYPE: PRT
<213> ORGANISM: Pseudomonas syringae pv. tomato DC3000

<400> SEQUENCE: 52

```
Met Lys Lys Cys Ile Ala Leu Leu Leu Thr Leu Val Val Cys Glu Gly
  1               5                  10                  15

Ala Leu Ala Gly Thr Ala Arg Asp Glu Gln Asn Ile Thr Ser Tyr Ile
             20                  25                  30

Asp Ser His Gly Thr Glu Gln Ile Ala Leu Leu Glu Lys Leu Val Asn
         35                  40                  45

Ile Asn Ser Gly Thr Asp Asn Val Glu Gly Val Val Lys Val Gly Asn
     50                  55                  60

Leu Ile Lys Pro Glu Leu Glu Ala Leu Gly Phe Glu Thr Ala Trp His
 65                  70                  75                  80

Asp Leu Pro Ser Ala Met Asn His Ala Gly Ser Leu Val Ala Val His
                 85                  90                  95

Asp Gly Ser Lys Ser Ala Lys Arg Ile Leu Leu Ile Gly His Leu Asp
            100                 105                 110

Thr Val Phe Pro Gln Thr Ser Arg Phe Gln Thr Phe Ala Tyr Leu Asp
        115                 120                 125
```

```
Gly Gly Lys Lys Ala Lys Gly Pro Gly Val Ile Asp Asp Lys Gly Gly
            130                 135                 140

Val Val Thr Met Leu Tyr Ala Leu Gln Ala Leu Lys His Ser Gly Ala
145                 150                 155                 160

Leu Glu Lys Met Asn Ile Ser Val Val Leu Ile Gly Asp Glu Leu
                165                 170                 175

Ala Ala Lys Pro Thr Glu Ile Ser Arg Glu Trp Leu Ile Ala Glu Ala
                180                 185                 190

Lys Arg Ser Asp Ile Ala Leu Gly Phe Glu Phe Ala Leu Ser Pro Asn
                195                 200                 205

Gln Leu Ile Thr Glu Arg Arg Gly Leu Ser Glu Trp Phe Leu Thr Ser
    210                 215                 220

Thr Gly Ile Asp Lys His Ser Ala Thr Ile Phe Gln Pro Glu Thr Gly
225                 230                 235                 240

Phe Gly Ala Met Tyr Glu Ser Ala Arg Val Leu Asp Glu Ile Arg Gln
                245                 250                 255

Lys Leu Ser Asn Glu Gln Gly Leu Thr Ile Asn Pro Gly Leu Ile Leu
                260                 265                 270

Gly Gly Ser Thr Ala Val Glu Asp Ser Ala Ser Gly Gln Gly Thr Ala
                275                 280                 285

Ser Gly Arg Lys Thr Thr Val Ala Arg Ile Thr Ser Val His Gly Asp
    290                 295                 300

Leu Arg Phe Ser Ser Glu Asp Gln Arg Ala Ser Ala Glu Thr Arg Met
305                 310                 315                 320

Lys Asp Ile Ala Ser His Pro Leu Pro Gln Thr Asn Ser Asp Leu Lys
                325                 330                 335

Ile Lys Ala Ile Met Pro Val Met Ala Asp Arg Glu Ser Asn Arg Gln
                340                 345                 350

Leu Leu Ala Ala Tyr Ser Gln Val Ser Gln Asp Leu Asp Gly Pro Ala
                355                 360                 365

Leu Glu Ser Ala Pro Ser Ala Glu Arg Gly Gly Ala Asp Ile Ser Tyr
                370                 375                 380

Val Asn Lys Tyr Val Thr Ala Ser Leu Asp Gly Leu Gly Ala Trp Gly
385                 390                 395                 400

Ala Gly Ala His Ser Glu Asn Glu Thr Ile Glu Leu Gly Ser Leu Pro
                405                 410                 415

Val Val Thr Lys Arg Ala Ala Ile Phe Leu Ser Arg Tyr Gly Asn Gln
                420                 425                 430

<210> SEQ ID NO 53
<211> LENGTH: 459
<212> TYPE: DNA
<213> ORGANISM: Pseudomonas syringae pv. tomato DC3000

<400> SEQUENCE: 53
atgaacccta taacacacag ctttagtcat cttgggtttt caaacgctca aagtacgtca      60
gcgctggcgc cggcggtaa taaagtgccg aactttgttt cgcgagggcg aggcaaagga     120
gtcccgcttg agcatttcaa caccgctgat gagtatcgtt tggcacgcca gcagggcggc     180
gtgctgaaat caatagacgg cagagagttc atgctactgc tgcagaagta cacggccgcc     240
gaaacaagcg acgaagaatt tgcggatttg agggccgcca taccgcgcta ttccattgac     300
ctggccgagc cgggtcaaac taaagtgctt tatcggggga tatcgctgcc ggagaagact     360
gcggcgcgat tactgaatat ctcttggggt tacgaaagtc gcgaaatagc ccatggtctt     420
atccatggct tgcgggtagt taaggaaggt ctgaagtag                            459
```

<210> SEQ ID NO 54
<211> LENGTH: 152
<212> TYPE: PRT
<213> ORGANISM: Pseudomonas syringae pv. tomato DC3000

<400> SEQUENCE: 54

```
Met Asn Pro Ile Thr His Ser Phe Ser His Leu Gly Phe Ser Asn Ala
  1               5                  10                  15

Gln Ser Thr Ser Ala Leu Ala Pro Gly Gly Asn Lys Val Pro Asn Phe
             20                  25                  30

Val Ser Arg Gly Arg Gly Lys Gly Val Pro Leu Glu His Phe Asn Thr
         35                  40                  45

Ala Asp Glu Tyr Arg Leu Ala Arg Gln Gln Gly Gly Val Leu Lys Ser
     50                  55                  60

Ile Asp Gly Arg Glu Phe Met Leu Leu Leu Gln Lys Tyr Thr Ala Ala
 65                  70                  75                  80

Glu Thr Ser Asp Glu Glu Phe Ala Asp Leu Arg Ala Ala Ile Pro Arg
                 85                  90                  95

Tyr Ser Ile Asp Leu Ala Glu Pro Gly Gln Thr Lys Val Leu Tyr Arg
            100                 105                 110

Gly Ile Ser Leu Pro Glu Lys Thr Ala Ala Arg Leu Leu Asn Ile Ser
        115                 120                 125

Trp Gly Tyr Glu Ser Arg Glu Ile Ala His Gly Leu Ile His Gly Leu
    130                 135                 140

Arg Val Val Lys Glu Gly Leu Lys
145                 150
```

<210> SEQ ID NO 55
<211> LENGTH: 2700
<212> TYPE: DNA
<213> ORGANISM: Pseudomonas syringae pv. tomato DC3000

<400> SEQUENCE: 55

| | | | | | |
|---|---|---|---|---|---|
| atgactactc | tgaccaccag | acagatacaa | ctcgcccacg | cttggacatc | cgttcataca | 60 |
| ggcgctggcc | tggccctgga | ctgggtcgcc | gatgtggccg | aaaaggtcga | ggaaatcgcc | 120 |
| accaaggccg | acgccctcag | ccgtgacttg | caccgcgcgc | gcaacctgtc | ccgcagcctt | 180 |
| gggcgggtct | cgacgacacc | catgggtatc | ggtttcttcg | gcttgtctca | ggcaggcaag | 240 |
| agctacctga | tttccgctct | ggcggcggac | gagaaaggcc | agttgctgac | ccggctgggt | 300 |
| actcagcaac | tggacttcat | caagcacgtg | aacccggtgg | gcggcggtaa | ggaggccacc | 360 |
| ggtctggtca | gcggttcac | ccgcaccgcc | gcgccaagtc | tggacccgca | ctttccggtg | 420 |
| gagctgcgtc | tgtttcgcga | ggtcgagatc | gccatcattt | tggccaacgc | ctggtttgag | 480 |
| gatttcgatc | atcagcgctt | gaacagccaa | gtcaccgatg | cgcagatcga | tgccctttg | 540 |
| cagcgtttcg | aggggcaatt | ggcagccgct | ccgacacctg | gcgtcagcag | tgacgacgtg | 600 |
| gtgctgctat | gggattacct | ggagcaccat | tacgctaacg | ccatgcgccc | gctgaacgcc | 660 |
| cgttattggc | cttgcgtggt | caaactggcg | ccgcgcttgt | cggcacgcga | gcgcgctcaa | 720 |
| ttgttcgagc | cgctgtgggg | cggcatcggc | aaaatgaccg | aaacctatga | gcaactggcc | 780 |
| tcggccctgc | accgctgggg | gctggcagag | acagttttg | cgcccatcag | cgcgctggtc | 840 |
| accgagcgcg | atgggcaact | ggtacaaagc | aaaagcatca | tcaacgtcga | cattctcagc | 900 |
| cgtcttggcg | gcagcgcgga | ctcggccatc | gaggtacgtc | cggccagtga | aggcactttg | 960 |
| cgccctgccg | tgtcggtgaa | tcgggccgaa | ctggcggcgc | tcaccaacga | gttgattttt | 1020 |

```
cgcctggata  cgaaccggc   caacgccatc  gtcaatagcg  tcgatctgct  cgacttccg    1080 ggctaccgca  gccggcagaa  gctgatgagc  atcaacgagg  ccagcgaagt  cgacagcaat   1140
ggcaccgcca  acaatccggt  cgccaggctg  ttgctgcgcg  gcaaggtcgc  ttacttgttt   1200
gagcgttaca  ccaacgagca  ggaaatgaac  gcgctggtga  tgtgcaccag  caccttcaag   1260
cagagcgaag  tggtgagcgt  cggtccggta  ctcaagagct  ggatcgacaa  gacccaaggc   1320
accagccccc  agcagcgcga  tggtcgggcc  agcggtctga  tctgggcgtt  gaccatgtgt   1380
gacggcttta  tcggcggcgc  gctcaacggc  gaggttgtgc  agtttcccga  aggttgcgac   1440
aacatgctca  aactgaccat  gatcgagcga  ttcggcaacg  aagactggat  gaaacaatgg   1500
ggcagcacgc  ctttcaaaaa  cacctatctg  gtgcgcaagc  cgcgcttcaa  gaccagcttc   1560
atcgagttgg  cggcggacgg  tgaagaacgc  gcttacaacg  actcatcgca  ctctgcgtta   1620
caggcattgc  aacaagcgtt  cagcaacagt  gaactggtca  agcgccatgt  ggcagaaccg   1680
caggacgcct  ggcaggcaat  gctgacactg  aacgacggcg  gcatgactcg  tttcagctcg   1740
gcgttcagcc  cgattgccaa  catcgacttc  aagttacagc  gtattgccga  gcaactggac   1800
gagttgatgg  tgcaattact  gccgcgcctg  gagcagtact  acgaagccgg  tggcgaagac   1860
gaacgggcca  ggaagaaggt  tatcgccaac  ctgattgccc  gcccgttcgc  gaccacgccg   1920
cacggcaaac  acgtgcttgg  cgaactgctc  ggttacatgt  cgttgccgga  acagcagttg   1980
cgcgaccttt  acctgaacgg  tgatttcgcc  agccctgcca  gcgacgccac  tgcaccggtg   2040
caggccgtcg  gcaagcctga  agtggaatac  gacatattcg  gcgaggccat  cgcagccact   2100
gccacggtgg  aaatacccgc  ggcaccggcc  gtagcgccgc  aataccagag  ccacgaacac   2160
cgtttcgccc  gagcggcctt  cgacctgtgg  gcaacgcacc  tgcgcaacct  cagccgtcgc   2220
cagcacctgc  tggacctgtt  ggagctgcct  gccgaggcca  tcgccctgct  ggtcaaggaa   2280
ctggtggtct  cgcgccagcg  cctggacttg  ccattgcagc  tcagcaacgc  gctgctcaag   2340
cgcgcccaga  gcggtgtgcg  caaagaaaac  ctggtgcagc  gccaagtgct  gaccgcgcaa   2400
ctgctgctca  cgacttcgc   cgcctggttc  gggcacaccg  cccagccggc  gggtcagcgg   2460
ccaacgggcc  tgctgggtgc  caaacaaccg  ctgtttgctt  tttatcaaaa  ggaaatgcca   2520
gggcgcttcc  cgcacctcgc  agcgcaagcc  gacgaccaga  gcgtgatttt  cgccgatgac   2580
tggatttctg  gcattgccat  tcatacccag  aaaaacgtcg  gccaccgcaa  gggcaaagaa   2640
atcactcctg  agcagaacga  ggccatgggc  cgcgtcatcc  aggcgttcaa  agcgagataa   2700
```

<210> SEQ ID NO 56
<211> LENGTH: 899
<212> TYPE: PRT
<213> ORGANISM: Pseudomonas syringae pv. tomato DC3000

<400> SEQUENCE: 56

```
Met Thr Thr Leu Thr Thr Arg Gln Ile Gln Leu Ala His Ala Trp Thr
 1               5                  10                  15

Ser Val His Thr Gly Ala Gly Leu Ala Leu Asp Trp Val Ala Asp Val
             20                  25                  30

Ala Glu Lys Val Glu Glu Ile Ala Thr Lys Ala Asp Ala Leu Ser Arg
         35                  40                  45

Asp Leu His Arg Ala Arg Asn Leu Ser Arg Ser Leu Gly Arg Val Ser
     50                  55                  60

Thr Thr Pro Met Gly Ile Gly Phe Phe Gly Leu Ser Gln Ala Gly Lys
 65                  70                  75                  80
```

```
Ser Tyr Leu Ile Ser Ala Leu Ala Ala Asp Glu Lys Gly Gln Leu Leu
                85                  90                  95

Thr Arg Leu Gly Thr Gln Gln Leu Asp Phe Ile Lys His Val Asn Pro
            100                 105                 110

Val Gly Gly Gly Lys Glu Ala Thr Gly Leu Val Thr Arg Phe Thr Arg
            115                 120                 125

Thr Ala Ala Pro Ser Leu Asp Pro His Phe Pro Val Glu Leu Arg Leu
            130                 135                 140

Phe Arg Glu Val Glu Ile Ala Ile Ile Leu Ala Asn Ala Trp Phe Glu
145                 150                 155                 160

Asp Phe Asp His Gln Arg Leu Asn Ser Gln Val Thr Asp Ala Gln Ile
                165                 170                 175

Asp Ala Leu Leu Gln Arg Phe Glu Gly Gln Leu Ala Ala Pro Thr
            180                 185                 190

Pro Gly Val Ser Ser Asp Asp Val Val Leu Leu Trp Asp Tyr Leu Glu
            195                 200                 205

His His Tyr Ala Asn Ala Met Arg Pro Leu Asn Ala Arg Tyr Trp Pro
    210                 215                 220

Cys Val Val Lys Leu Ala Pro Arg Leu Ser Ala Arg Glu Arg Ala Gln
225                 230                 235                 240

Leu Phe Glu Pro Leu Trp Gly Ile Gly Lys Met Thr Glu Thr Tyr
                245                 250                 255

Glu Gln Leu Ala Ser Ala Leu His Arg Leu Gly Leu Ala Glu Thr Val
            260                 265                 270

Phe Ala Pro Ile Ser Ala Leu Val Thr Glu Arg Asp Gly Gln Leu Val
            275                 280                 285

Gln Ser Lys Ser Ile Ile Asn Val Asp Ile Leu Ser Arg Leu Gly Gly
290                 295                 300

Ser Ala Asp Ser Ala Ile Glu Val Arg Pro Ala Ser Glu Gly Thr Leu
305                 310                 315                 320

Arg Pro Ala Val Ser Val Asn Arg Ala Glu Leu Ala Ala Leu Thr Asn
                325                 330                 335

Glu Leu Ile Phe Arg Leu Asp Asn Glu Pro Ala Asn Ala Ile Val Asn
                340                 345                 350

Ser Val Asp Leu Leu Asp Phe Pro Gly Tyr Arg Ser Arg Gln Lys Leu
            355                 360                 365

Met Ser Ile Asn Glu Ala Ser Glu Val Asp Ser Asn Gly Thr Ala Asn
            370                 375                 380

Asn Pro Val Ala Arg Leu Leu Arg Gly Lys Val Ala Tyr Leu Phe
385                 390                 395                 400

Glu Arg Tyr Thr Asn Glu Gln Glu Met Asn Ala Leu Val Met Cys Thr
                405                 410                 415

Ser Thr Phe Lys Gln Ser Glu Val Val Ser Val Gly Pro Val Leu Lys
            420                 425                 430

Ser Trp Ile Asp Lys Thr Gln Gly Thr Ser Pro Gln Arg Asp Gly
            435                 440                 445

Arg Ala Ser Gly Leu Ile Trp Ala Leu Thr Met Cys Asp Gly Phe Ile
    450                 455                 460

Gly Gly Ala Leu Asn Gly Glu Val Val Gln Phe Pro Glu Gly Cys Asp
465                 470                 475                 480

Asn Met Leu Lys Leu Thr Met Ile Glu Arg Phe Gly Asn Glu Asp Trp
                485                 490                 495

Met Lys Gln Trp Gly Ser Thr Pro Phe Lys Asn Thr Tyr Leu Val Arg
            500                 505                 510
```

Lys Pro Arg Phe Lys Thr Ser Phe Ile Glu Leu Ala Ala Asp Gly Glu
                515                 520                 525

Glu Arg Ala Tyr Asn Asp Ser His Ser Ala Leu Gln Ala Leu Gln
            530                 535                 540

Gln Ala Phe Ser Asn Ser Glu Leu Val Lys Arg His Val Ala Glu Pro
545                 550                 555                 560

Gln Asp Ala Trp Gln Ala Met Leu Thr Leu Asn Asp Gly Gly Met Thr
                565                 570                 575

Arg Phe Ser Ser Ala Phe Ser Pro Ile Ala Asn Ile Asp Phe Lys Leu
                580                 585                 590

Gln Arg Ile Ala Glu Gln Leu Asp Glu Leu Met Val Gln Leu Leu Pro
            595                 600                 605

Arg Leu Glu Gln Tyr Tyr Glu Ala Gly Gly Asp Glu Arg Ala Arg
            610                 615                 620

Lys Lys Val Ile Ala Asn Leu Ile Ala Arg Pro Phe Ala Thr Thr Pro
625                 630                 635                 640

His Gly Lys His Val Leu Gly Glu Leu Leu Gly Tyr Met Ser Leu Pro
                645                 650                 655

Glu Gln Gln Leu Arg Asp Leu Tyr Leu Asn Gly Asp Phe Ala Ser Pro
            660                 665                 670

Ala Ser Asp Ala Thr Ala Pro Val Gln Ala Val Gly Lys Pro Glu Val
            675                 680                 685

Glu Tyr Asp Ile Phe Gly Glu Ala Ile Ala Ala Thr Ala Thr Val Glu
            690                 695                 700

Ile Pro Ala Ala Pro Ala Val Ala Pro Gln Tyr Gln Ser His Glu His
705                 710                 715                 720

Arg Phe Ala Arg Ala Ala Phe Asp Leu Trp Ala Thr His Leu Arg Asn
                725                 730                 735

Leu Ser Arg Arg Gln His Leu Leu Asp Leu Leu Glu Leu Pro Ala Glu
            740                 745                 750

Ala Ile Ala Leu Leu Val Lys Glu Leu Val Val Cys Ala Glu Arg Leu
            755                 760                 765

Asp Leu Pro Leu Gln Leu Ser Asn Ala Leu Leu Lys Arg Ala Gln Ser
770                 775                 780

Gly Val Arg Lys Glu Asn Leu Val Gln Arg Gln Val Leu Thr Ala Gln
785                 790                 795                 800

Leu Leu Leu Asn Asp Phe Ala Ala Trp Phe Gly His Thr Ala Gln Pro
                805                 810                 815

Ala Gly Gln Arg Pro Thr Gly Leu Leu Gly Ala Lys Gln Pro Leu Phe
            820                 825                 830

Ala Phe Tyr Gln Lys Glu Met Pro Gly Arg Phe Pro His Leu Ala Ala
            835                 840                 845

Gln Ala Asp Asp Gln Ser Val Ile Phe Ala Asp Trp Ile Ser Gly
850                 855                 860

Ile Ala Ile His Thr Gln Lys Asn Val Gly His Arg Lys Gly Lys Glu
865                 870                 875                 880

Ile Thr Pro Glu Gln Asn Glu Ala Met Gly Arg Val Ile Gln Ala Phe
                885                 890                 895

Lys Ala Arg

<210> SEQ ID NO 57
<211> LENGTH: 795
<212> TYPE: DNA
<213> ORGANISM: Pseudomonas syringae pv. tomato DC3000

<400> SEQUENCE: 57

```
atgaatataa atcgacaact gcctgtatca ggctcggagc gattgttgac tcccgacgtg    60
ggcgtatctc gccaggcttg ttccgaaagg cattattcta ctggacagga tcggcatgat   120
ttttaccgtt ttgctgccag gctacatgtg gatgcgcagt gttttggtct gtcaatagac   180
gatttgatgg ataagttttc tgacaagcac ttcagggctg agcatcctga atacagggat   240
gtctatccgg aggaatgttc tgccatttat atgcataccg ctcaagacta ttctagtcac   300
ctcgtaaggg gggaaatagg aacgccgctg taccgagagg tcaataatta tcttcgactt   360
caacatgaga attctgggcg agaagctgaa attgataatc acgacgaaaa gctatcgcct   420
cacataaaaa tgctttcatc tgcgcttaat cgtttaatgg atgtcgccgc ttttagagga   480
acggtttata gaggcattcg cggtgattta gataccattg ctcggctcta ccatctattc   540
gatacgggcg gccggtacgt agagcccgct tcatgagta caactcgaat aaaggacagt    600
gcccaggtgt tgagccagg cacgccaaac aacatagctt tccagataag cctaaaaaga    660
ggcgccgaca tttcgggatc ttcccaagcg ccctcagagg aagaaatcat gctacccatg   720
atgagtgagt tcgtcattga acatgcatcc gctctttccg aaggaaagca tttatttgta   780
ttaagtcaga tttga                                                    795
```

<210> SEQ ID NO 58
<211> LENGTH: 264
<212> TYPE: PRT
<213> ORGANISM: Pseudomonas syringae pv. tomato DC3000

<400> SEQUENCE: 58

```
Met Asn Ile Asn Arg Gln Leu Pro Val Ser Gly Ser Glu Arg Leu Leu
  1               5                  10                  15

Thr Pro Asp Val Gly Val Ser Arg Gln Ala Cys Ser Glu Arg His Tyr
             20                  25                  30

Ser Thr Gly Gln Asp Arg His Asp Phe Tyr Arg Phe Ala Ala Arg Leu
         35                  40                  45

His Val Asp Ala Gln Cys Phe Gly Leu Ser Ile Asp Asp Leu Met Asp
     50                  55                  60

Lys Phe Ser Asp Lys His Phe Arg Ala Glu His Pro Glu Tyr Arg Asp
 65                  70                  75                  80

Val Tyr Pro Glu Glu Cys Ser Ala Ile Tyr Met His Thr Ala Gln Asp
                 85                  90                  95

Tyr Ser Ser His Leu Val Arg Gly Glu Ile Gly Thr Pro Leu Tyr Arg
            100                 105                 110

Glu Val Asn Asn Tyr Leu Arg Leu Gln His Glu Asn Ser Gly Arg Glu
        115                 120                 125

Ala Glu Ile Asp Asn His Asp Glu Lys Leu Ser Pro His Ile Lys Met
    130                 135                 140

Leu Ser Ser Ala Leu Asn Arg Leu Met Asp Val Ala Ala Phe Arg Gly
145                 150                 155                 160

Thr Val Tyr Arg Gly Ile Arg Gly Asp Leu Asp Thr Ile Ala Arg Leu
                165                 170                 175

Tyr His Leu Phe Asp Thr Gly Gly Arg Tyr Val Glu Pro Ala Phe Met
            180                 185                 190

Ser Thr Thr Arg Ile Lys Asp Ser Ala Gln Val Phe Glu Pro Gly Thr
        195                 200                 205

Pro Asn Asn Ile Ala Phe Gln Ile Ser Leu Lys Arg Gly Ala Asp Ile
    210                 215                 220
```

```
Ser Gly Ser Ser Gln Ala Pro Ser Glu Glu Ile Met Leu Pro Met
225                 230                 235                 240

Met Ser Glu Phe Val Ile Glu His Ala Ser Ala Leu Ser Glu Gly Lys
            245                 250                 255

His Leu Phe Val Leu Ser Gln Ile
            260

<210> SEQ ID NO 59
<211> LENGTH: 897
<212> TYPE: DNA
<213> ORGANISM: Pseudomonas syringae pv. tomato DC3000

<400> SEQUENCE: 59
atgaatatca gtcctgtatc gggtgcccac ggtagcagct acccttcagc tcaatccaca      60
gcatcgacgg catcgaaagg tccctctgga tcctttctca acagctcgg cggctgtttt     120
tcaccctgcc tgggtagcag ctctactggg gccatacttt ctcccgctca tgagcaggta     180
ttgagccaca cctattccag caatattaaa ggaaagttgc gcacgacgcc cccaaaagga     240
ccgtcgccca ggttgtctga cacacctatg aagcaggcgc tttcttcaat gatcgtacag     300
gagcgaaaac ggcttaaaag tcaacccaag tcattggcct cggatataga acgtccagac     360
agtatgatca aaaaagcgct tgatgaaaaa gacggccacc cgtttggcga gcgcttttca     420
gacgacgaat tcttgcgat tcatctctat acgagctgtc tttataggcc gatcaatcat     480
catctgcggt atgccccgaa caatgatgtt gcaccggttg tcgaggcact gaaaagtggt     540
ttggcaaagc ttgctcaaga ccctgattat caagtgtcta gccagcttca tagaggcatc     600
aagcaaaaga tgagtgatgg cgaggtcatg agtcgtttca aacgggtaa gacctatcgt     660
gatgaagcgt tcatgagcac atcaactcat atgcaggttt cagaagagtt tacctccgac     720
gttacgttgc acctgcggtc ctcatcagct gtcaatatag gccccttttc gaaaaatcca     780
tacgaggacg aagcgcttat ctcgcccctg acgcctttca aagtaaccgg tctgcgcaag     840
caggacgata agtggcacgt cgatttgaac gagatagcag ataattcaga cgagtga        897

<210> SEQ ID NO 60
<211> LENGTH: 298
<212> TYPE: PRT
<213> ORGANISM: Pseudomonas syringae pv. tomato DC3000

<400> SEQUENCE: 60

Met Asn Ile Ser Pro Val Ser Gly Ala His Gly Ser Ser Tyr Pro Ser
1               5                   10                  15

Ala Gln Ser Thr Ala Ser Thr Ala Ser Lys Gly Pro Ser Gly Ser Phe
            20                  25                  30

Leu Lys Gln Leu Gly Gly Cys Phe Ser Pro Cys Leu Gly Ser Ser Ser
        35                  40                  45

Thr Gly Ala Ile Leu Ser Pro Ala His Glu Gln Val Leu Ser His Thr
    50                  55                  60

Tyr Ser Ser Asn Ile Lys Gly Lys Leu Arg Thr Thr Pro Pro Lys Gly
65                  70                  75                  80

Pro Ser Pro Arg Leu Ser Asp Thr Pro Met Lys Gln Ala Leu Ser Ser
                85                  90                  95

Met Ile Val Gln Glu Arg Lys Arg Leu Lys Ser Gln Pro Lys Ser Leu
            100                 105                 110

Ala Ser Asp Ile Glu Arg Pro Asp Ser Met Ile Lys Lys Ala Leu Asp
        115                 120                 125
```

```
Glu Lys Asp Gly His Pro Phe Gly Glu Arg Phe Ser Asp Asp Glu Phe
    130                 135                 140

Leu Ala Ile His Leu Tyr Thr Ser Cys Leu Tyr Arg Pro Ile Asn His
145                 150                 155                 160

His Leu Arg Tyr Ala Pro Asn Asn Asp Val Ala Pro Val Val Glu Ala
                165                 170                 175

Leu Lys Ser Gly Leu Ala Lys Leu Ala Gln Asp Pro Asp Tyr Gln Val
            180                 185                 190

Ser Ser Gln Leu His Arg Gly Ile Lys Gln Lys Met Ser Asp Gly Glu
        195                 200                 205

Val Met Ser Arg Phe Lys Pro Gly Lys Thr Tyr Arg Asp Glu Ala Phe
    210                 215                 220

Met Ser Thr Ser Thr His Met Gln Val Ser Glu Glu Phe Thr Ser Asp
225                 230                 235                 240

Val Thr Leu His Leu Arg Ser Ser Ser Ala Val Asn Ile Gly Pro Phe
                245                 250                 255

Ser Lys Asn Pro Tyr Glu Asp Glu Ala Leu Ile Ser Pro Leu Thr Pro
            260                 265                 270

Phe Lys Val Thr Gly Leu Arg Lys Gln Asp Asp Lys Trp His Val Asp
        275                 280                 285

Leu Asn Glu Ile Ala Asp Asn Ser Asp Glu
    290                 295

<210> SEQ ID NO 61
<211> LENGTH: 507
<212> TYPE: DNA
<213> ORGANISM: Pseudomonas syringae pv. tomato DC3000

<400> SEQUENCE: 61
atgaatatta acccttccct gggcgctcat ggcagcgcct actcgtcgcc tcaaagtgat    60
acttcgaagg ccactggaaa agcacctgcg ccttcttttt tcaaacagtt gggcggctgt   120
ttttcgccgt gccttggttc ccatgcgtca agcagccaac aactgtccgc cagtcatgcg   180
cagacgctca gtcagaatta ctccagcaac attcaggga cgagccgcac acgccagccg    240
agagcaccct cgccacgcct gtcagatacg cccatgaagc aggcgctttc ctcaatgatc   300
gaacgcgagc gtttgcggct tcaaggtctt tcgggaggaa tgttctcggg cattgactcc   360
gccgatgcca tgattggtcg agcgctcacg aagaaggatt caaacccaaa ggctgcgcgt   420
tttagtgatg atgagtttct cgccgttcac ctctacacaa cttgcctcta cagacctatc   480
aatcatcatc ttcggtatca acactag                                      507

<210> SEQ ID NO 62
<211> LENGTH: 168
<212> TYPE: PRT
<213> ORGANISM: Pseudomonas syringae pv. tomato DC3000

<400> SEQUENCE: 62

Met Asn Ile Asn Pro Ser Leu Gly Ala His Gly Ser Ala Tyr Ser Ser
1               5                   10                  15

Pro Gln Ser Asp Thr Ser Lys Ala Thr Gly Lys Ala Pro Ala Pro Ser
            20                  25                  30

Phe Phe Lys Gln Leu Gly Gly Cys Phe Ser Pro Cys Leu Gly Ser His
        35                  40                  45

Ala Ser Ser Ser Gln Gln Leu Ser Ala Ser His Ala Gln Thr Leu Ser
    50                  55                  60

Gln Asn Tyr Ser Ser Asn Ile Gln Gly Thr Ser Arg Thr Arg Gln Pro
```

```
                 65                  70                  75                  80
            Arg Ala Pro Ser Pro Arg Leu Ser Asp Thr Pro Met Lys Gln Ala Leu
                             85                  90                  95

Ser Ser Met Ile Glu Arg Glu Arg Leu Arg Leu Gln Gly Leu Ser Gly
                        100                 105                 110

Gly Met Phe Ser Gly Ile Asp Ser Ala Asp Ala Met Ile Gly Arg Ala
                        115                 120                 125

Leu Thr Lys Lys Asp Ser Asn Pro Lys Ala Ala Arg Phe Ser Asp Asp
                    130                 135                 140

Glu Phe Leu Ala Val His Leu Tyr Thr Thr Cys Leu Tyr Arg Pro Ile
            145                 150                 155                 160

Asn His His Leu Arg Tyr Gln His
                        165

<210> SEQ ID NO 63
<211> LENGTH: 2823
<212> TYPE: DNA
<213> ORGANISM: Pseudomonas syringae pv. tomato DC3000

<400> SEQUENCE: 63
atgagctcga tcacgcacac caacacgccg caattggcgg tcagcgattc acggggtctg      60
ccggtacgca gtgtgcagtt ctatcgtggc gctgatggtc agcctgttga cgcgagggtg     120
acgcagcact atttcgacaa ggccgggcga ctgatcgcca gtcgcgatcc acgttttcc      180 agtcgtttga aatacggtgt ctgtgcgcct gtgaacctga tgcaaatcgt cagcttgtcc     240
ggggctttgc tgttatcgaa aagtgtcgat tcaggttggc gggtgagcct gaacggcgaa     300
gcggggcagt tagtcgacag ctgtgacgga cgtgacaacc cgcgccagat cgaatacgac     360
gggctgttgc gcccttttggc gatcaacgaa tcaggccgaa tgaccgagcg cttcacttat     420
ggcgggcctg ccactgctga gcataaccag tgcaatcaac tgattcgcca tgacgatacg     480
gcaggctcgc gcttgctgcg ggactatgga ctgtcgggta gggcgttgag cgaaaaaagg     540
tacttcctgc agtcgcccga cagcccggac tggccacttg ccgagcctga tcgtgatgca     600
ctgctcgagc cggtcggcct gcagacgcgc tgggctttca acgcgcaggg cgaggacctg     660
gcgcagactg acgcaaacgg taatgtccag cgtttcagtc acggtgtggc tgggcaactg     720
cacgctgttg aactgaccct ggccaatacg gcacagcggc aaacgctggt cagtgcaatt     780
cactacgacg cgttcaatca ggccgagcag gagacggcag gaaatggtgt ggtcagtcgc     840
tatgtgtatg atcaacagga cggtcggctg actgagctca gtgcgctatc tgccgacggc     900
tcagtgttgc aaaaactgaa ctacagctat gacccggcag gtaacgttct actcatcaac     960
gatgcctcgc aaccagaccg gtattgcggc aatcagcgta tcgagccgat aaaccgttac    1020
tgttacgaca cgttgtatca gttgatcgaa gccacggggc gggaggtcag aaacggggcc    1080
agccatggtc cggcgctacc cggtctgcaa cctctgccga cgtcgatcc ttgccaggtc     1140 agcaactaca cacagcgtta cagctacgac gctgcgggta acctgctgca aatgcgccac    1200
gaaggcgcgc acaacttcac cgcaacatg acgttgatc ccgacagcaa tcgcagcctg      1260
cccgacaatg acaggtatgt ggatttcgcc acgagttttg atgccaacgg caatctgctg    1320
caactcgtgc gtgggcagac catgagctgg gatgtgcgta atcagttgcg gcaaatcact    1380
accgtgcaac gtgaagacgc accgaatgat gaagagcgct atgtatacga cggccagggc    1440
cagcgctgcc gcaagatcag caccgcgcag gcatcaggtc gcacactgac caatgaagtt    1500
cgctacctgc cgggactgga agttcggacc acggccgatg agaaactct tcacgtcgtt      1560
```

-continued

```
acggctcagg cgggtcgcaa cagcgtgcgg gtgttgcact gggaagccgg aaaaccaggc    1620
gctattgcga acgatcaggt gcgttacagc ctgggtgatc atctgggctc gagcacgctg    1680
gagcttgatc agcaaggcgg cctgatcagc caggaaagtt attacccctt tggcggcacg    1740
gcctggtggg cggcgcgtag tgcagtggag gccaagtaca aaacagtgcg ttattcgggt    1800
aaagagcgcg atgccagcgg gctttattat tacgggttca ggtattacgc gccgtggttg    1860
cagcggtgga tcaatcctga cccggcgggg gatgtggatg ggttgaatct gtacaggatg    1920
gtcagaaata atccgcttgt ttacgttgat gcgaagggcc agcaacctga acctgttcca    1980
aaaactattc accagatctg gataggtgaa acaagaatgc cttgagagct caggttagc    2040 aatatcaaca gaaccgttga atggcttggg ggtataaag tgaagttgca tctggaaacg    2100
aggacgccgg aagcttattc ggaaatcgaa aaggatctga gatccgaagt ggttctgctt    2160
cctgattccc aggttttca aaacttcaag gagaagccgc tttatgcggc ctatgaagat    2220
ttccgaagaa acaatcagaa ttcgcttttc gcggtagacg ttttacgtat gcataccgtt    2280
catgagttgg gcgggattta ttcagatgtc gatgacgttt atgcaggtgc ggagactggc    2340
ggaatgacgc agttggggga taatccgctg tttgcagaac ctgatgaggt tttgacgctg    2400
gatcctgttc atgtcccttg ggagccccag aattctgttg aaagttttat ggtcaataac    2460
agctcatttg ccgctcattc aggtgcaggc gtcttacttg acatgatggg ggaaggagcg    2520
aaacgatatg atgaagccgt tgagggcgga agttatccgg atccgacggg catgaacggt    2580
ataggtctaa gtctgctctg gaatcctaac ccggcagtaa gagttcgaac gttatcgaat    2640
gtagtaggcc ccggcttgtt tacagacaca ctgcacgctt cggacacagc atacggtgag    2700
ctttttagta atctgaaagg cgtcgtcttt caaaaacagc cgttcacgtt tgccgaccaa    2760
atggccagga agatgccgct gcatcggcat ataaaaagcg cgcggcgca aacctggcgc    2820 tga                                                                  2823
```

<210> SEQ ID NO 64
<211> LENGTH: 940
<212> TYPE: PRT
<213> ORGANISM: Pseudomonas syringae pv. tomato DC3000

<400> SEQUENCE: 64

```
Met Ser Ser Ile Thr His Thr Asn Thr Pro Gln Leu Ala Val Ser Asp
  1               5                  10                  15

Ser Arg Gly Leu Pro Val Arg Ser Val Gln Phe Tyr Arg Gly Ala Asp
             20                  25                  30

Gly Gln Pro Val Asp Ala Arg Val Thr Gln His Tyr Phe Asp Lys Ala
         35                  40                  45

Gly Arg Leu Ile Ala Ser Arg Asp Pro Arg Phe Ser Ser Arg Leu Lys
     50                  55                  60

Tyr Gly Val Cys Ala Pro Val Asn Leu Met Gln Ile Val Ser Leu Ser
 65                  70                  75                  80

Gly Ala Leu Leu Leu Ser Lys Ser Val Asp Ser Gly Trp Arg Val Ser
                 85                  90                  95

Leu Asn Gly Glu Ala Gly Gln Leu Val Asp Ser Cys Asp Gly Arg Asp
            100                 105                 110

Asn Pro Arg Gln Ile Glu Tyr Asp Gly Leu Leu Arg Pro Leu Ala Ile
        115                 120                 125

Asn Glu Ser Gly Arg Met Thr Glu Arg Phe Thr Tyr Gly Gly Pro Ala
    130                 135                 140

Thr Ala Glu His Asn Gln Cys Asn Gln Leu Ile Arg His Asp Asp Thr
```

```
              145                 150                 155                 160
         Ala Gly Ser Arg Leu Leu Arg Asp Tyr Gly Leu Ser Gly Arg Ala Leu
                         165                 170                 175

Ser Glu Lys Arg Tyr Phe Leu Gln Ser Pro Asp Ser Pro Asp Trp Pro
                         180                 185                 190

Leu Ala Glu Pro Asp Arg Asp Ala Leu Leu Glu Pro Val Gly Leu Gln
                         195                 200                 205

Thr Arg Trp Ala Phe Asn Ala Gln Gly Glu Asp Leu Ala Gln Thr Asp
                         210                 215                 220

Ala Asn Gly Asn Val Gln Arg Phe Ser His Gly Val Ala Gly Gln Leu
         225                 230                 235                 240

His Ala Val Glu Leu Thr Leu Ala Asn Thr Ala Gln Arg Gln Thr Leu
                         245                 250                 255

Val Ser Ala Ile His Tyr Asp Ala Phe Asn Gln Ala Glu Gln Glu Thr
                         260                 265                 270

Ala Gly Asn Gly Val Val Ser Arg Tyr Val Tyr Asp Gln Gln Asp Gly
                         275                 280                 285

Arg Leu Thr Glu Leu Ser Ala Leu Ser Ala Asp Gly Ser Val Leu Gln
                         290                 295                 300

Lys Leu Asn Tyr Ser Tyr Asp Pro Ala Gly Asn Val Leu Leu Ile Asn
         305                 310                 315                 320

Asp Ala Ser Gln Pro Asp Arg Tyr Cys Gly Asn Gln Arg Ile Glu Pro
                         325                 330                 335

Ile Asn Arg Tyr Cys Tyr Asp Thr Leu Tyr Gln Leu Ile Glu Ala Thr
                         340                 345                 350

Gly Arg Glu Val Arg Asn Gly Ala Ser His Gly Pro Ala Leu Pro Gly
                         355                 360                 365

Leu Gln Pro Leu Pro Thr Leu Asp Pro Cys Gln Val Ser Asn Tyr Thr
                         370                 375                 380

Gln Arg Tyr Ser Tyr Asp Ala Ala Gly Asn Leu Leu Gln Met Arg His
         385                 390                 395                 400

Glu Gly Ala His Asn Phe Thr Arg Asn Met His Val Asp Pro Asp Ser
                         405                 410                 415

Asn Arg Ser Leu Pro Asp Asn Asp Arg Tyr Val Asp Phe Ala Thr Ser
                         420                 425                 430

Phe Asp Ala Asn Gly Asn Leu Leu Gln Leu Val Arg Gly Gln Thr Met
                         435                 440                 445

Ser Trp Asp Val Arg Asn Gln Leu Arg Gln Ile Thr Thr Val Gln Arg
         450                 455                 460

Glu Asp Ala Pro Asn Asp Glu Glu Arg Tyr Val Tyr Asp Gly Gln Gly
         465                 470                 475                 480

Gln Arg Cys Arg Lys Ile Ser Thr Ala Gln Ala Ser Gly Arg Thr Leu
                         485                 490                 495

Thr Asn Glu Val Arg Tyr Leu Pro Gly Leu Glu Val Arg Thr Thr Ala
                         500                 505                 510

Asp Gly Glu Thr Leu His Val Val Thr Ala Gln Ala Gly Arg Asn Ser
                         515                 520                 525

Val Arg Val Leu His Trp Glu Ala Gly Lys Pro Gly Ala Ile Ala Asn
                         530                 535                 540

Asp Gln Val Arg Tyr Ser Leu Gly Asp His Leu Gly Ser Ser Thr Leu
         545                 550                 555                 560

Glu Leu Asp Gln Gln Gly Gly Leu Ile Ser Gln Glu Ser Tyr Tyr Pro
                         565                 570                 575
```

Phe Gly Gly Thr Ala Trp Trp Ala Ala Arg Ser Ala Val Glu Ala Lys
            580                 585                 590

Tyr Lys Thr Val Arg Tyr Ser Gly Lys Glu Arg Asp Ala Ser Gly Leu
        595                 600                 605

Tyr Tyr Tyr Gly Phe Arg Tyr Tyr Ala Pro Trp Leu Gln Arg Trp Ile
610                 615                 620

Asn Pro Asp Pro Ala Gly Asp Val Asp Gly Leu Asn Leu Tyr Arg Met
625                 630                 635                 640

Val Arg Asn Asn Pro Leu Val Tyr Val Asp Ala Lys Gly Gln Gln Pro
                645                 650                 655

Glu Pro Val Pro Lys Thr Ile His Gln Ile Trp Ile Gly Glu Asn Lys
            660                 665                 670

Asn Ala Leu Arg Ala Gln Val Ser Asn Ile Asn Arg Thr Val Glu Met
        675                 680                 685

Ala Trp Gly Tyr Lys Val Lys Leu His Leu Glu Thr Arg Thr Pro Glu
690                 695                 700

Ala Tyr Ser Glu Ile Glu Lys Asp Leu Arg Ser Glu Val Val Leu Leu
705                 710                 715                 720

Pro Asp Ser Gln Val Phe Gln Asn Phe Lys Glu Lys Pro Leu Tyr Ala
                725                 730                 735

Ala Tyr Glu Asp Phe Arg Arg Asn Asn Gln Asn Tyr Ala Phe Ala Val
            740                 745                 750

Asp Val Leu Arg Met His Thr Val His Glu Leu Gly Gly Ile Tyr Ser
        755                 760                 765

Asp Val Asp Val Tyr Ala Gly Ala Glu Thr Gly Gly Met Thr Gln
770                 775                 780

Leu Gly Asp Asn Pro Leu Phe Ala Glu Pro Asp Glu Val Leu Thr Leu
785                 790                 795                 800

Asp Pro Val His Val Pro Trp Glu Pro Gln Asn Ser Val Glu Ser Phe
                805                 810                 815

Met Val Asn Asn Ser Ser Phe Ala Ala His Ser Gly Ala Gly Val Leu
            820                 825                 830

Leu Asp Met Met Gly Glu Gly Ala Lys Arg Tyr Asp Glu Ala Val Glu
        835                 840                 845

Gly Gly Ser Tyr Pro Asp Pro Thr Gly Met Asn Gly Ile Gly Leu Ser
850                 855                 860

Leu Leu Trp Asn Pro Asn Pro Ala Val Arg Val Arg Thr Leu Ser Asn
865                 870                 875                 880

Val Val Gly Pro Gly Leu Phe Thr Asp Thr Leu His Ala Ser Asp Thr
                885                 890                 895

Ala Tyr Gly Glu Leu Phe Ser Asn Leu Lys Gly Val Val Phe Gln Lys
            900                 905                 910

Gln Pro Phe Thr Phe Ala Asp Gln Met Ala Arg Lys Met Pro Leu His
        915                 920                 925

Arg His Ile Lys Ser Gly Ala Ala Gln Thr Trp Arg
930                 935                 940

<210> SEQ ID NO 65
<211> LENGTH: 534
<212> TYPE: DNA
<213> ORGANISM: Pseudomonas syringae pv. tomato DC3000

<400> SEQUENCE: 65
atgccgatca ccgcgcagca gttgctgcag atactcccga gcgctggcca gaaagccggc      60
gtttttgcac ccgtcctgaa cacagcgatg agcaagcacc agatcttgac gccgctgcgc     120

```
atcgcggctt tcatcgccca ggtcggtcat gagtccggcc aactgcgcta cgtccgcgag        180 atttggggc cgactccgca gcagctgggt tatgaaggcc gcaaggacct cggcaatacc         240
gtggcgggtg atggttcgaa gtaccgcggg cgcggcctga tccagatcac cggccgggcc        300
aactatgccg aatgcggcga ggcgctgggc ctagacctga tccatcaccc ggaactgctc        360
gagcagccgg agcacgccac aatgtcggca cgtggtact ggagcagccg tggcctgaac         420
tcgctggccg acaaagggga ctttcttcaa attacccgaa gaatcaacgg aggcaccaat       480
ggactggcgg atcggcaggc gctgtacgac cgggcgctga aggtgctggc gtga              534
```

<210> SEQ ID NO 66
<211> LENGTH: 177
<212> TYPE: PRT
<213> ORGANISM: Pseudomonas syringae pv. tomato DC3000

<400> SEQUENCE: 66

```
Met Pro Ile Thr Ala Gln Gln Leu Leu Gln Ile Leu Pro Ser Ala Gly
  1               5                  10                  15

Gln Lys Ala Gly Val Phe Ala Pro Val Leu Asn Thr Ala Met Ser Lys
                 20                  25                  30

His Gln Ile Leu Thr Pro Leu Arg Ile Ala Ala Phe Ile Ala Gln Val
             35                  40                  45

Gly His Glu Ser Gly Gln Leu Arg Tyr Val Arg Glu Ile Trp Gly Pro
         50                  55                  60

Thr Pro Gln Gln Leu Gly Tyr Glu Gly Arg Lys Asp Leu Gly Asn Thr
 65                  70                  75                  80

Val Ala Gly Asp Gly Ser Lys Tyr Arg Gly Arg Gly Leu Ile Gln Ile
                 85                  90                  95

Thr Gly Arg Ala Asn Tyr Ala Glu Cys Gly Glu Ala Leu Gly Leu Asp
            100                 105                 110

Leu Ile His His Pro Glu Leu Leu Glu Gln Pro Glu His Ala Thr Met
        115                 120                 125

Ser Ala Ala Trp Tyr Trp Ser Ser Arg Gly Leu Asn Ser Leu Ala Asp
    130                 135                 140

Lys Gly Asp Phe Leu Gln Ile Thr Arg Arg Ile Asn Gly Gly Thr Asn
145                 150                 155                 160

Gly Leu Ala Asp Arg Gln Ala Leu Tyr Asp Arg Ala Leu Lys Val Leu
                165                 170                 175

Ala
```

<210> SEQ ID NO 67
<211> LENGTH: 1137
<212> TYPE: DNA
<213> ORGANISM: Pseudomonas syringae pv. tomato DC3000

<400> SEQUENCE: 67

```
atgaatctaa cagctttagg ttcaaagctg tctcggtatc gcaagcagct tgcgatgagc        60
gaggaagaag tgtgtgcggt cacccacatc cccttgagc gcctgcagtc agttgaagcc        120
ggctctcagg cgcctacggg tgatgaagtg cttatcctgg ccgatctcta ccactgcaac       180
ttcaaattct tcatctcgaa cgagccgctc gcccccttg agcagaccga atcctgtat        240 cgcaggcacg gagctgagtt catcaaggag gatcgtagag ccgtccaaga attcctgtac      300
ctctgcgaaa cagaggactt cctgatgagt gagttgaagg ctatgaagct cgaatttccg       360
ctgccgcagg cttctgggaa ttttaagaat gatggaatcc gagcggctga agcctttcgc      420
```

```
ctttcaatc agcaccccac aaacgccgtg cctcgggatg tgtatcagga gattcgccaa    480
accggagtgc atgtgttccg tagaaagctt ggtaactcta acatttcggg gcttttcctg    540
gctcacccca cggctgggaa gtgcattctg gtcaactaca gcgaagacgt ataccggcag    600
cggtttagcg ctgcgcatga atttgctcac gctcttttcg atgcgcaggg tggcccagt     660 attacctact cccgtacgac taaggctgac ctagtcgaag tgagagcaaa caccttgcc    720 tcccggtatc tgatgccttc agaaatcctc cgacagctgc caacccctga gcaatggaca    780
caggaaaata cccagtattg ggctcatgag ttgcgagtca gctgcgttgc cttgggcata    840
ggtctgaagt ccgagggctt aattagcgag caagcattcc agaggataaa gtcgtaccgc    900
gttcctcgtg aactgaagat tgacccagaa ttgccggccc aattgacgac gcaacagcgt    960
gagcgaaagg ctaagttact ggaaaagggg ttatctgaca gctacgtcgc actgtgccta   1020
gacgctcaga gccgtggcat catcactcaa ggtcgattgg ctgaagcctt gcttagtgac   1080
ttgggaggcc ttcaagagct gctcagcctt tatggaagat cgcgcaatgg ccattga      1137

<210> SEQ ID NO 68
<211> LENGTH: 378
<212> TYPE: PRT
<213> ORGANISM: Pseudomonas syringae pv. tomato DC3000

<400> SEQUENCE: 68

Met Asn Leu Thr Ala Leu Gly Ser Lys Leu Ser Arg Tyr Arg Lys Gln
  1               5                  10                  15

Leu Ala Met Ser Glu Glu Val Cys Ala Val Thr His Ile Pro Leu
             20                  25                  30

Glu Arg Leu Gln Ser Val Glu Ala Gly Ser Gln Ala Pro Thr Gly Asp
         35                  40                  45

Glu Val Leu Ile Leu Ala Asp Leu Tyr His Cys Asn Phe Lys Phe Phe
     50                  55                  60

Ile Ser Asn Glu Pro Leu Ala Pro Phe Glu Gln Thr Glu Ile Leu Tyr
 65                  70                  75                  80

Arg Arg His Gly Ala Glu Phe Ile Lys Glu Asp Arg Arg Ala Val Gln
                 85                  90                  95

Glu Phe Leu Tyr Leu Cys Glu Thr Glu Asp Phe Leu Met Ser Glu Leu
            100                 105                 110

Lys Ala Met Lys Leu Glu Phe Pro Leu Pro Gln Ala Ser Gly Asn Phe
        115                 120                 125

Lys Asn Asp Gly Ile Arg Ala Ala Glu Ala Phe Arg Leu Phe Asn Gln
    130                 135                 140

His Pro Thr Asn Ala Val Pro Arg Asp Val Tyr Gln Glu Ile Arg Gln
145                 150                 155                 160

Thr Gly Val His Val Phe Arg Arg Lys Leu Gly Asn Ser Asn Ile Ser
                165                 170                 175

Gly Leu Phe Leu Ala His Pro Thr Ala Gly Lys Cys Ile Leu Val Asn
            180                 185                 190

Tyr Ser Glu Asp Val Tyr Arg Gln Arg Phe Ser Ala Ala His Glu Phe
        195                 200                 205

Ala His Ala Leu Phe Asp Ala Gln Gly Gly Pro Ser Ile Thr Tyr Ser
    210                 215                 220

Arg Thr Thr Lys Ala Asp Leu Val Glu Val Arg Ala Asn Thr Phe Ala
225                 230                 235                 240

Ser Arg Tyr Leu Met Pro Ser Glu Ile Leu Arg Gln Leu Pro Asn Pro
                245                 250                 255
```

Glu Gln Trp Thr Gln Glu Asn Thr Gln Tyr Trp Ala His Glu Leu Arg
            260                 265                 270

Val Ser Cys Val Ala Leu Gly Ile Gly Leu Lys Ser Glu Gly Leu Ile
        275                 280                 285

Ser Glu Gln Ala Phe Gln Arg Ile Lys Ser Tyr Arg Val Pro Arg Glu
    290                 295                 300

Leu Lys Ile Asp Pro Glu Leu Pro Ala Gln Leu Thr Thr Gln Gln Arg
305                 310                 315                 320

Glu Arg Lys Ala Lys Leu Leu Glu Lys Gly Leu Ser Asp Ser Tyr Val
                325                 330                 335

Ala Leu Cys Leu Asp Ala Gln Ser Arg Gly Ile Ile Thr Gln Gly Arg
            340                 345                 350

Leu Ala Glu Ala Leu Leu Ser Asp Leu Gly Gly Leu Gln Glu Leu Leu
        355                 360                 365

Ser Leu Tyr Gly Arg Ser Arg Asn Gly His
    370                 375

<210> SEQ ID NO 69
<211> LENGTH: 714
<212> TYPE: DNA
<213> ORGANISM: Pseudomonas syringae pv. tomato DC3000

<400> SEQUENCE: 69
atgaatatca accccttggc ttcttcatta cagaatcaac agcgcactct cttaggcccg     60 cccccctca attcatctgc tgctctgccg atcaagatcc ctgtggcgca tgataaagcg    120 cgtgaccta acgctgaatt ctataccacc gaggaaacgc cctggtttgc cggctacaaa    180
aagtcggagg caggacgcgc tattttagag aaaatgtctg agaaggaagc aaaagatatc    240
cgaggcgagt atctgggaaa ctacatgaaa gcctttgacg aaaccatatg tcgtatgtac    300
gacaattttc acgatttcaa acagcagctt ttttacctta atacggagct gtcaaaaaag    360
catttcggct tcacgctggg ctttaatcag gacattcagg tgaccgaccc ggacgaggta    420
ctcaccccgg cagagttcac gtacctgacc gagaagctga cgaacgcca acaactgaaa    480 gaggatctgc gtgcgcacgc aaaaattgtg atgacgctgc tcgaccatta caccgaaaaa    540
ttcgataacc ggcacaccct caatctggag agttacagca aggtcatcga ctacggacag    600
atcttcagcc gcaatcatat tggcaatttc atggacacga ttatctacca gatcgagcgc    660
aatgcgccga agcgtgagga agaaccaaaa cctctggttg atgtgcacgc ttga           714

<210> SEQ ID NO 70
<211> LENGTH: 237
<212> TYPE: PRT
<213> ORGANISM: Pseudomonas syringae pv. tomato DC3000

<400> SEQUENCE: 70

Met Asn Ile Asn Pro Leu Ala Ser Ser Leu Gln Asn Gln Gln Arg Thr
 1               5                  10                  15

Leu Leu Gly Pro Pro Pro Leu Asn Ser Ser Ala Ala Leu Pro Ile Lys
            20                  25                  30

Ile Pro Val Ala His Asp Lys Ala Arg Asp Pro Asn Ala Glu Phe Tyr
        35                  40                  45

Thr Thr Glu Glu Thr Pro Trp Phe Ala Gly Tyr Lys Lys Ser Glu Ala
    50                  55                  60

Gly Arg Ala Ile Leu Glu Lys Met Ser Glu Lys Glu Ala Lys Asp Ile
65                  70                  75                  80

Arg Gly Glu Tyr Leu Gly Asn Tyr Met Lys Ala Phe Asp Glu Thr Ile

-continued

```
                        85                  90                  95
Cys Arg Met Tyr Asp Asn Phe His Asp Phe Lys Gln Gln Leu Phe Tyr
                100                 105                 110

Leu Asn Thr Glu Leu Ser Lys Lys His Phe Gly Phe Thr Leu Gly Phe
            115                 120                 125

Asn Gln Asp Ile Gln Val Thr Asp Pro Asp Glu Val Leu Thr Pro Ala
        130                 135                 140

Glu Phe Thr Tyr Leu Thr Glu Lys Leu Asn Glu Arg Gln Gln Leu Lys
145                 150                 155                 160

Glu Asp Leu Arg Ala His Ala Lys Ile Val Met Thr Leu Leu Asp His
                165                 170                 175

Tyr Thr Glu Lys Phe Asp Asn Arg His Thr Leu Asn Leu Glu Ser Tyr
            180                 185                 190

Ser Lys Val Ile Asp Tyr Gly Gln Ile Phe Ser Arg Asn His Ile Gly
        195                 200                 205

Asn Phe Met Asp Thr Ile Ile Tyr Gln Ile Glu Arg Asn Ala Pro Lys
    210                 215                 220

Arg Glu Glu Glu Pro Lys Pro Leu Val Asp Val His Ala
225                 230                 235

<210> SEQ ID NO 71
<211> LENGTH: 3693
<212> TYPE: DNA
<213> ORGANISM: Pseudomonas syringae pv. tomato DC3000

<400> SEQUENCE: 71
atgggcctga tcggcgtcaa acagaacaaa ccgcaacagg cgcagaccta cctgacgcgc    60
ctgcaagcgc tgtcgccagc gccctggcag gcggtgcagc tggagcagga cattgccctc   120
ggccagccgc aaaatcaggc gctgctggat gatgcccgac gcctggccga cgccggtgag   180
cgtgacaagg cgaccggggt gtttcgccag ttgttcaacg gcgtttgcc tcaaggcact   240
gtcggccgcg agtactacac caacctgggc ttcaacaatg cggactggcc cgaggcgcgc   300
aagggttttg aacgcctgat gcggcagaac cctgacgact cgattctggc gctgttcttt   360
gccaagcacc tggcccgccg cgaagacagc cgcgccgaag gcatcgccgc tctggcgcgc   420
ctgagcactc atccggacat cgccggcgat gccgatcaga gctggcgcat ggcgctggtc   480
tggatcggcc cgcctgcggc tgcgcaagtg ccactgttcg acgcgtttct caaggttcat   540
cccgacgatc aggaaatccg cgaccagttg aacaagggtc gccagcagca tgccagcggc   600
gctgcctcag gctggcagca agacccgctg gtggcgcgcg gcttgaaggc gctggaaaaa   660
aatgatcatg tggcggccga agaagccttt gccgcccgcc tgaaaatcaa ggcggacgat   720
gccaacgtgc ttggcggcct gggcgtggtg cgtcagcagc agaaccggtt gcctgaagcc   780
gaacaattgc tgacccgcgc cacgcgccag cagggcggtg cgcgctggaa aaacgcgctg   840
gaaaacgtac agctctggac ctcgctgcaa gaggcccgtg acctgcaggc caagggcag    900
accggcaagg ctcaagcgtt gctggctcag gcgcagcggc aaaaccctga caatatcgac   960
gtgcgttga ccctggccga cgtgcaggtg caggccgggc aactgacgc cgcgcaagcg    1020
ggctatcgtc aggtactggc gacccagcgc ggtaatccgc aggcaatccg cgggctgatc   1080
aacgtgctgg cccagcgtgg tcaggctgat gaagcgttgc gcctgctcga cacattgtcg   1140
ccaggcgaac aggccaaact gggcgacagc ggtcgcttca aggcgctgcg ctccacccag   1200
gtggcgcggc tggccgagca gcgtggcgat gttcgcgctg cccaggtggc cttgaaagac   1260
gcggtgaaga acgacccgga caatgtctgg acgcgttttg atctggcgcg cctgtacctc   1320
```

```
aagaccgacg aagcgcccaa ggcccgcgcg ctgatcgacg agctgctcaa ggctcagccc      1380
aacaatatcg atgcgctcta caccagcgcg ctgctgtcag tggaaatggg ccagtggcag      1440
gacgcgcaga ccacgtttac gcgcatcccg gttgatcagc gcacgccgga catgaaagcg      1500
cttgctgacg aagtcaccat gaccgtgcag atcaatctgg ccatcggcat cgcccggcgc      1560
ggtcagcgcc aggaagcgtt ggcgctgctc gatcgcttgc aaccggtcgc cagcggcagc      1620
ccggagcgtc aactcacgct ggccagcgct tacatcgatg cgggcgagcc cgcgcgcggt      1680
cgggaaatgg cccgtgcggc catcgctcag gcccctttgc cgtcggccga cctgatgctg      1740
caatacgccg gtctgctgct cgcagcgggc gatgacgtgc aggtcaatgc gatcctgcgc      1800
aacgtgcagg gtcagccgat gagcgtgcag acccgcaaac gttttgatga ccttttgtac      1860
cgctaccgca ttcgtcaggc cgatctgctg cgtgaaggcg gtgatctggc gggcgcgtac      1920
gacacgctgg cacctgcttt ggcgcagcgc ccggacgaca ttcaggcggt gtcggccttc      1980
gcccgcatgt acaccgccaa tggcgacagc gcccgagcgt tcgagctgta caagcctttg      2040
ttgcagcgcc agcccaatga cccgcaagtg ttgctgggcg cagccgatgc ggcggtcaaa      2100
gcgcatgatt atggctttgc cgaaaaagcc ctgagccagt tccgcaaact ggagcgtaac      2160
gacccgcaga ccctgacgga ggccgcacgt atctaccaaa gcatggggca gaccggcgcg      2220
gccaccgagt tgctgcgcaa ggccgtggcc atcgaacaga gtgaaaaaca gcgcgcgatg      2280
gctgtgcagg ctgtgtcgac cagcaccacg tcgtccaacc cgtttgcgac gggcggctca      2340
cgtagcctgg cggcggcttc ggctattccg gctccggctc aggtgtcgct cagcggtggg      2400
agagcgcttg aaacaaacag tgcgcctgaa atatctgccc cgcgtgacac cgcttatccc      2460
ggccagatcg ccgcaccaca accgctgtct gccgcacgta cgcaaagtgt gcgcggcaat      2520
ccgttcatgg cagccaccga ccgcgatcag gccagcagcg cacagcaggc gctcaatcgc      2580
attcttgagc agcgcagtgg cttcgtcagt cagggcctgg ccgtgcgcag caataacagc      2640
gagtcgggtc tgagcaaact gaccgtggtc gagaccccgc tagaggtcaa tttgcctgcc      2700
ggtgataacc gggtggccgt gcgcgtcacg ccggtgtcgc tgaatgctgg cagcttgaag      2760
tcagatgcag gtgcccgttt tggcggtggc accagcggtg ctgccggttc gcagagcgac      2820
aagggtgtcg gtctggcggt ggcgttcgag cgccccgaag aaggcctcaa ggccgatatc      2880
ggcaccacgc cgatgggttt caaatacacc acggttgccg gcggcgcgag tgtcgaccgg      2940
ccgttgggta acaacccgga cctgcgctac ggcctcaacg tgtcacggcg tccggtgacg      3000
gacagcgtga cttcgtttgc cggttccaca gacgagcgca gcggcctgtc ctggggcggc      3060
gtcacggcca acggcgggcg cggtcagctc agctatgacg accagaccat cggcggttat      3120
ggctacggct cgtggcacaa actggttggc aacaacgtga atccaacac ccgaggcgaa       3180
gtgggtggcg gcgtttactg gtacctgcgc aatgccgagg acagcaaact gaccgcaggc      3240
ctgagcctga tgggcatgag ctatgacaat gaccagagct acttcacgta cggccacggt      3300
ggctatttca gcccgcagag cttctatgcc atcggcgtgc cggtgatgtg gcacagcgc       3360
accgagcgtt tcagctatca ggtcaagagc tcggtcgggg tccagcactt caagcaggac      3420
ggcgccgaat tcttccccga cgacagcacg ctacaggccg cttccgccca gcgctacaca      3480
gggcaaagca aaaccggaat tggctacaac ctgagcgcgg caggcgagta caagctcgat      3540
tccagcctgt tcatgggggc cagtctgggc ctggacaatg cccgggacta tcgccagttc      3600
agcggcgcgc tttacctgcg ttacatgttc gaggacataa ccggcccgat ggcactgccg      3660
gtcagccctt accgttcacc ttattccaac tga                                   3693
```

<210> SEQ ID NO 72
<211> LENGTH: 1230
<212> TYPE: PRT
<213> ORGANISM: Pseudomonas syringae pv. tomato DC3000

<400> SEQUENCE: 72

```
Met Gly Leu Ile Gly Val Lys Gln Asn Lys Pro Gln Gln Ala Gln Thr
1               5                   10                  15

Tyr Leu Thr Arg Leu Gln Ala Leu Ser Pro Ala Pro Trp Gln Ala Val
            20                  25                  30

Gln Leu Glu Gln Asp Ile Ala Leu Gly Gln Pro Gln Asn Gln Ala Leu
        35                  40                  45

Leu Asp Asp Ala Arg Arg Leu Ala Asp Ala Gly Glu Arg Asp Lys Ala
    50                  55                  60

Thr Gly Val Phe Arg Gln Leu Phe Asn Gly Arg Leu Pro Gln Gly Thr
65                  70                  75                  80

Val Gly Arg Glu Tyr Tyr Thr Asn Leu Gly Phe Asn Ala Asp Trp
                85                  90                  95

Pro Glu Ala Arg Lys Gly Phe Glu Arg Leu Met Arg Gln Asn Pro Asp
            100                 105                 110

Asp Ser Ile Leu Ala Leu Phe Phe Ala Lys His Leu Ala Arg Arg Glu
        115                 120                 125

Asp Ser Arg Ala Glu Gly Ile Ala Leu Ala Arg Leu Ser Thr His
    130                 135                 140

Pro Asp Ile Ala Gly Asp Ala Asp Gln Ser Trp Arg Met Ala Leu Val
145                 150                 155                 160

Trp Ile Gly Pro Pro Ala Ala Ala Gln Val Pro Leu Phe Asp Ala Phe
                165                 170                 175

Leu Lys Val His Pro Asp Asp Gln Glu Ile Arg Asp Gln Leu Asn Lys
            180                 185                 190

Gly Arg Gln Gln His Ala Ser Gly Ala Ala Ser Gly Trp Gln Gln Asp
        195                 200                 205

Pro Leu Val Ala Arg Gly Leu Lys Ala Leu Glu Lys Asn Asp His Val
    210                 215                 220

Ala Ala Glu Glu Ala Phe Ala Ala Arg Leu Lys Ile Lys Ala Asp Asp
225                 230                 235                 240

Ala Asn Val Leu Gly Gly Leu Gly Val Val Arg Gln Gln Asn Arg
                245                 250                 255

Leu Pro Glu Ala Glu Gln Leu Leu Thr Arg Ala Thr Arg Gln Gln Gly
            260                 265                 270

Gly Ala Arg Trp Lys Asn Ala Leu Glu Asn Val Gln Leu Trp Thr Ser
        275                 280                 285

Leu Gln Glu Ala Arg Asp Leu Gln Ala Lys Gly Gln Thr Gly Lys Ala
    290                 295                 300

Gln Ala Leu Leu Ala Gln Ala Arg Gln Asn Pro Asp Asn Ile Asp
305                 310                 315                 320

Val Arg Leu Thr Leu Ala Asp Val Gln Val Ala Gly Gln Leu Asp
                325                 330                 335

Ala Ala Gln Ala Gly Tyr Arg Gln Val Leu Ala Thr Gly Arg Gly Asn
            340                 345                 350

Pro Gln Ala Ile Arg Gly Leu Ile Asn Val Leu Ala Gln Arg Gly Gln
        355                 360                 365

Ala Asp Glu Ala Leu Arg Leu Leu Asp Thr Leu Ser Pro Gly Glu Gln
    370                 375                 380
```

```
Ala Lys Leu Gly Asp Ser Gly Arg Phe Lys Ala Leu Arg Ser Thr Gln
385                 390                 395                 400

Val Ala Arg Leu Ala Glu Gln Arg Gly Asp Val Arg Ala Ala Gln Val
                405                 410                 415

Ala Leu Lys Asp Ala Val Lys Asn Asp Pro Asp Asn Val Trp Thr Arg
            420                 425                 430

Phe Asp Leu Ala Arg Leu Tyr Leu Lys Thr Asp Glu Ala Pro Lys Ala
        435                 440                 445

Arg Ala Leu Ile Asp Glu Leu Leu Lys Ala Gln Pro Asn Asn Ile Asp
    450                 455                 460

Ala Leu Tyr Thr Ser Ala Leu Leu Ser Val Glu Met Gly Gln Trp Gln
465                 470                 475                 480

Asp Ala Gln Thr Thr Phe Thr Arg Ile Pro Val Asp Gln Arg Thr Pro
                485                 490                 495

Asp Met Lys Ala Leu Ala Asp Glu Val Thr Met Thr Val Gln Ile Asn
            500                 505                 510

Leu Ala Ile Gly Ile Ala Arg Arg Gly Gln Arg Gln Glu Ala Leu Ala
        515                 520                 525

Leu Leu Asp Arg Leu Gln Pro Val Ala Ser Gly Ser Pro Glu Arg Gln
    530                 535                 540

Leu Thr Leu Ala Ser Ala Tyr Ile Asp Ala Gly Glu Pro Ala Arg Gly
545                 550                 555                 560

Arg Glu Met Ala Arg Ala Ala Ile Ala Gln Ala Pro Leu Pro Ser Ala
                565                 570                 575

Asp Leu Met Leu Gln Tyr Ala Gly Leu Leu Ala Ala Gly Asp Asp
            580                 585                 590

Val Gln Val Asn Ala Ile Leu Arg Asn Val Gln Gly Pro Met Ser
        595                 600                 605

Val Gln Thr Arg Lys Arg Phe Asp Asp Leu Leu Tyr Arg Tyr Arg Ile
    610                 615                 620

Arg Gln Ala Asp Leu Leu Arg Glu Gly Gly Asp Leu Ala Gly Ala Tyr
625                 630                 635                 640

Asp Thr Leu Ala Pro Ala Leu Ala Gln Arg Pro Asp Asp Ile Gln Ala
                645                 650                 655

Val Ser Ala Phe Ala Arg Met Tyr Thr Ala Asn Gly Asp Ser Ala Arg
            660                 665                 670

Ala Phe Glu Leu Tyr Lys Pro Leu Leu Gln Arg Gln Pro Asn Asp Pro
        675                 680                 685

Gln Val Leu Leu Gly Ala Ala Asp Ala Ala Val Lys Ala His Asp Tyr
    690                 695                 700

Gly Phe Ala Glu Lys Ala Leu Ser Gln Phe Arg Lys Leu Glu Arg Asn
705                 710                 715                 720

Asp Pro Gln Thr Leu Thr Glu Ala Ala Arg Ile Tyr Gln Ser Met Gly
                725                 730                 735

Gln Thr Gly Ala Ala Thr Glu Leu Leu Arg Lys Ala Val Ala Ile Glu
            740                 745                 750

Gln Ser Glu Lys Gln Arg Ala Met Ala Val Gln Ala Val Ser Thr Ser
        755                 760                 765

Thr Thr Ser Ser Asn Pro Phe Ala Thr Gly Gly Ser Arg Ser Leu Ala
    770                 775                 780

Ala Ala Ser Ala Ile Pro Ala Pro Ala Gln Val Ser Leu Ser Gly Gly
785                 790                 795                 800

Arg Ala Leu Glu Thr Asn Ser Ala Pro Glu Ile Ser Ala Pro Arg Asp
```

-continued

```
                805                 810                 815
Thr Ala Tyr Pro Gly Gln Ile Ala Ala Pro Gln Pro Leu Ser Ala Ala
            820                 825                 830

Arg Thr Gln Ser Val Arg Gly Asn Pro Phe Met Ala Ala Thr Asp Arg
            835                 840                 845

Asp Gln Ala Ser Ser Ala Gln Gln Ala Leu Asn Arg Ile Leu Glu Gln
            850                 855                 860

Arg Ser Gly Phe Val Ser Gln Gly Leu Ala Val Arg Ser Asn Asn Ser
865                 870                 875                 880

Glu Ser Gly Leu Ser Lys Leu Thr Val Val Glu Thr Pro Leu Glu Val
                885                 890                 895

Asn Leu Pro Ala Gly Asp Asn Arg Val Ala Val Arg Val Thr Pro Val
            900                 905                 910

Ser Leu Asn Ala Gly Ser Leu Lys Ser Asp Ala Gly Ala Arg Phe Gly
            915                 920                 925

Gly Gly Thr Ser Gly Ala Ala Gly Ser Gln Ser Asp Lys Gly Val Gly
            930                 935                 940

Leu Ala Val Ala Phe Glu Arg Pro Glu Glu Gly Leu Lys Ala Asp Ile
945                 950                 955                 960

Gly Thr Thr Pro Met Gly Phe Lys Tyr Thr Thr Val Ala Gly Ala
                965                 970                 975

Ser Val Asp Arg Pro Leu Gly Asn Asn Pro Asp Leu Arg Tyr Gly Leu
            980                 985                 990

Asn Val Ser Arg Arg Pro Val Thr Asp Ser Val Thr Ser Phe Ala Gly
            995                 1000                1005

Ser Thr Asp Glu Arg Ser Gly Leu Ser Trp Gly Gly Val Thr Ala Asn
    1010                1015                1020

Gly Gly Arg Gly Gln Leu Ser Tyr Asp Asp Gln Thr Ile Gly Gly Tyr
1025                1030                1035                1040

Gly Tyr Gly Ser Trp His Lys Leu Val Gly Asn Asn Val Lys Ser Asn
                1045                1050                1055

Thr Arg Gly Glu Val Gly Gly Gly Val Tyr Trp Tyr Leu Arg Asn Ala
            1060                1065                1070

Glu Asp Ser Lys Leu Thr Ala Gly Leu Ser Leu Met Gly Met Ser Tyr
        1075                1080                1085

Asp Asn Asp Gln Ser Tyr Phe Thr Tyr Gly His Gly Gly Tyr Phe Ser
        1090                1095                1100

Pro Gln Ser Phe Tyr Ala Ile Gly Val Pro Val Met Trp Ala Gln Arg
1105                1110                1115                1120

Thr Glu Arg Phe Ser Tyr Gln Val Lys Ser Ser Val Gly Val Gln His
            1125                1130                1135

Phe Lys Gln Asp Gly Ala Glu Phe Phe Pro Asp Asp Ser Thr Leu Gln
            1140                1145                1150

Ala Ala Ser Ala Gln Arg Tyr Thr Gly Gln Ser Lys Thr Gly Ile Gly
            1155                1160                1165

Tyr Asn Leu Ser Ala Ala Gly Glu Tyr Lys Leu Asp Ser Ser Leu Phe
    1170                1175                1180

Met Gly Ala Ser Leu Gly Leu Asp Asn Ala Arg Asp Tyr Arg Gln Phe
1185                1190                1195                1200

Ser Gly Ala Leu Tyr Leu Arg Tyr Met Phe Glu Asp Ile Thr Gly Pro
            1205                1210                1215

Met Ala Leu Pro Val Ser Pro Tyr Arg Ser Pro Tyr Ser Asn
        1220                1225                1230
```

<210> SEQ ID NO 73
<211> LENGTH: 540
<212> TYPE: DNA
<213> ORGANISM: Pseudomonas syringae pv. tomato DC3000

<400> SEQUENCE: 73

```
atgaaactga tacgacagat ccgctcgcag ggtcgtcagt cgcccttgtt cgaggacctt    60
gcccagctcg aggggcgcaa gcgtcaatgg ctggccgagc gcgccgtgca gttcgcactg   120
ggcttgcacg gccgccggcc agaggtcgat aacccttca aaggcaaact gcgtgaagac    180
ctgtgctgca tcatgttcga tgacctgtcg ctgcacaccc tggtcgagcg ttacgcggcc   240
agtgaagccc tgcgacgaca cgacagcgag tacttcagca aactgatcgc cacgacacga   300
aataccgtgg aacggcgcat cgtctttcac gggctgctgg aacacttcga caggctgttg   360
cctatcgaaa agagcatcta ccaactcaac taccgcagcg ttcaatacgc gcacctggag   420
caggaagaag ccctgtacgg caaactgata tggaacaac ccattagtgc actgctggaa    480
gtgcacacgc tgagtggct tcttgagaat ctgtcttcgt ttgagttttc gattgattga   540
```

<210> SEQ ID NO 74
<211> LENGTH: 179
<212> TYPE: PRT
<213> ORGANISM: Pseudomonas syringae pv. tomato DC3000

<400> SEQUENCE: 74

Met Lys Leu Ile Arg Gln Ile Arg Ser Gln Gly Arg Gln Ser Pro Leu
1               5                   10                  15

Phe Glu Asp Leu Ala Gln Leu Glu Gly Arg Lys Arg Gln Trp Leu Ala
            20                  25                  30

Glu Arg Ala Val Gln Phe Ala Leu Gly Leu His Gly Arg Arg Pro Glu
        35                  40                  45

Val Asp Asn Pro Phe Lys Gly Lys Leu Arg Glu Asp Leu Cys Cys Ile
    50                  55                  60

Met Phe Asp Asp Leu Ser Leu His Thr Leu Val Glu Arg Tyr Ala Ala
65                  70                  75                  80

Ser Glu Ala Leu Arg Arg His Asp Ser Glu Tyr Phe Ser Lys Leu Ile
                85                  90                  95

Ala Thr Thr Arg Asn Thr Val Glu Arg Arg Ile Val Phe His Gly Leu
            100                 105                 110

Leu Glu His Phe Asp Arg Leu Leu Pro Ile Glu Lys Ser Ile Tyr Gln
        115                 120                 125

Leu Asn Tyr Arg Ser Val Gln Tyr Ala His Leu Glu Gln Glu Glu Ala
    130                 135                 140

Leu Tyr Gly Lys Leu Ile Met Glu Gln Pro Ile Ser Ala Leu Leu Glu
145                 150                 155                 160

Val His Thr Pro Glu Trp Leu Leu Glu Asn Leu Ser Ser Phe Glu Phe
                165                 170                 175

Ser Ile Asp

<210> SEQ ID NO 75
<211> LENGTH: 492
<212> TYPE: DNA
<213> ORGANISM: Pseudomonas syringae pv. tomato DC3000

<400> SEQUENCE: 75

```
atgcgactga ctactaaagg ccgatacgct gtgacagcca tgcttgacct ggcgttacat    60
gcgcagaacg ggccagtgtc tctggccgac atctccgagc ggcagggcat ttccctgtct   120
```

-continued

| | |
|---|---:|
| tatctcgaac agttgttcgc caaactgcgt cgcggcaatc tggtttccag tgttcgtggt | 180 |
| ccgggcggcg gttatcagct gtctcgtgac atgaaaggca tccaggtcgc ccaagtcgtc | 240 |
| gacgcggtca atgaatcggt cgatgccacg cgttgtcagg gctgggtga ttgccacgct | 300 |
| ggcgatacct gcctgaccca ccacttgtgg tgcgatctga gccagcagat tcacgaattt | 360 |
| ctaagcggta tcagcttggc ggatcttgtc actcgccgtg aggtacaaga agtcgctcag | 420 |
| cgccaggata tgcgccgtgg tcataaccac acgtcgcaac tgggtaagat cgaaacgtcc | 480 |
| gccgtcgaat ga | 492 |

<210> SEQ ID NO 76
<211> LENGTH: 163
<212> TYPE: PRT
<213> ORGANISM: Pseudomonas syringae pv. tomato DC3000

<400> SEQUENCE: 76

Met Arg Leu Thr Thr Lys Gly Arg Tyr Ala Val Thr Ala Met Leu Asp
1               5                   10                  15
Leu Ala Leu His Ala Gln Asn Gly Pro Val Ser Leu Ala Asp Ile Ser
            20                  25                  30
Glu Arg Gln Gly Ile Ser Leu Ser Tyr Leu Glu Gln Leu Phe Ala Lys
        35                  40                  45
Leu Arg Arg Gly Asn Leu Val Ser Ser Val Arg Gly Pro Gly Gly Gly
    50                  55                  60
Tyr Gln Leu Ser Arg Asp Met Lys Gly Ile Gln Val Ala Gln Val Val
65                  70                  75                  80
Asp Ala Val Asn Glu Ser Val Asp Ala Thr Arg Cys Gln Gly Leu Gly
                85                  90                  95
Asp Cys His Ala Gly Asp Thr Cys Leu Thr His His Leu Trp Cys Asp
            100                 105                 110
Leu Ser Gln Gln Ile His Glu Phe Leu Ser Gly Ile Ser Leu Ala Asp
        115                 120                 125
Leu Val Thr Arg Arg Glu Val Gln Glu Val Ala Gln Arg Gln Asp Met
    130                 135                 140
Arg Arg Gly His Asn His Thr Ser Gln Leu Gly Lys Ile Glu Thr Ser
145                 150                 155                 160
Ala Val Glu

<210> SEQ ID NO 77
<211> LENGTH: 3441
<212> TYPE: DNA
<213> ORGANISM: Pseudomonas syringae pv. tomato DC3000

<400> SEQUENCE: 77

| | |
|---|---:|
| atgaataccg tcagaaaacc cataacacca cggatgctca gcatgaccga taaaaacggc | 60 |
| acccatcgac aacgacgtgc tgcactgttc cccaaaaccc cggcgaccgc caccagcctg | 120 |
| tgcccttca gagggcctaa tatcgccatc gtcccggtgc gctatgcgct ggatcgctcg | 180 |
| cgctatgacg ctgaccccgc gcaactgaag ccactgccca agacggcca atgggcccac | 240 |
| ctgccgacgc tgaaaactcg cagttacacc ttacgccaac tgtacgacgg ctacgtttac | 300 |
| gtgttcgacg aaaacggccg gacgttgac gaatacgcag cctcagccag cgacggccat | 360 |
| ctgagccgca tcgtctggac cgatgcacac atcggtaacg accagcgaag cggtgccggt | 420 |
| gaagggcaac cctttgtgct ttaccgcgt gaccaccgcc tgcacatcgc cttttctccc | 480 |
| ctgcaatgga catggcgaat gtgcgagcac atgcgctccc acgccccaag ccgcgcgttg | 540 |

```
tggatgaagg cgctggacct ggccagctac tgcctcacca tggccgaacc ggacaccctg    600
ccgctggatc gcatcgccga ggccgtggcg gatatcgaca aagactgtgt tgtggaagat    660
ggccgttttg cagattcggc gattcccagt gttcgcccgc catcagaagg tgcagaaccc    720
tatccgttat gggcaccgct gggcgccgat gtcttctggc agggcagcgt ctacgatcag    780
gacagctctc tggtcattgc cctcaatgac ccgctcgccg ttttcaacga cttgggcatg    840
cagctggcgg ccgatcaggc ggcttttcgg gaatggcaaa gcgcccacga acacaagatc    900
cagattgccc agaccgtcgc cacgctgtgc ggtgcagaga gcgaagcaga gaagctgcca    960
gcatcggtgc gcggtgatgc gctgcgcacg catcagtacc tgagcgaggt cgaagcctac   1020
tttgaacaat gcattcttga agaagcacag atcagcagta gcaacgttcc tggagatttt   1080
ctgctgctgc cggacatgtt caagagcctg acatgcgcaa atcgatcga aacacgttat    1140
ggcagcgcgc cgaccgatga gggcgcgcag gcctggaaag atcgccacaa atggcggcgc   1200
gaggtcgatc tgagcagtgc gcgtcagtac cttttgcagc acctgccgac cggagacaaa   1260
cgcctgcaac aggtgcgtga cacgcaaagc gatttccagc actgggcggc acatataggc   1320
accgaaccgc tcaagctgtt catcgacacc acacacccga aaaccctgct gtatttgcag   1380
acgatcatgc tcaatctgca gatcatctat gcgcaggaca gcgccgcaaa tgcctggctc   1440
gccgagcagg aagccaacac cagcagcctg tttggcaccc tgcgttatgg ttttgcca    1500
gcgctcaagc acgccctgca tcaggaagcc gacgcactgc tgaacggcct cggcgacgtc   1560
actaatctgg ccacgcgcat cggtgaactc aatggcgtgc tcaaccatca gggttttgcc   1620
gacaagccgt ggatgaaggc gctgaaacag cctgttcaag acaccttcaa agccctcggc   1680
gaactggcca gcgtgccgg caaagccagg tttgaaagtg tattactggc atgggtgccc    1740
atcgacagcc gcatggccct tggcaagcag cagaacatcg ttgcgttgct tcgcaccctg   1800
ctgatcggcc agatattgct cgactcgaca gcacgcgtcg cgatcaatga gcagacagtg   1860
accaagctca acagtgggt aagtgagtgg caagtcctca acaagcaaat cagcgagctg   1920
gtgcgcagtt ggcaataccc gaacgcctac aacacgcgcc aaagcaccgc tcgcaaattg   1980
caggcccata acacaaaact gcgcgttcac gaactgagca tccctgccct gctcgacttt   2040
cagaacaacg aatacgccaa gctattgcag gacgagattc gtcagtactt ccagtctggc   2100
aaaaccctcg ccacggactg gctcgcccgc gccaaaggct ggaccgaccg actgggcggc   2160
gttgctggca cgatcacctg gggcgtggtc atgcttaacc tgatcaatac cgccttcctc   2220
tatcgggacc ttacccggga cggggatttc agtaccaagg acattggcaa ggtgacgtat   2280
ggattggggt acagcttcaa tctgttgatg gcggtgtttg tggacgcgcc gtggagcatc   2340
ataagggacg caacgccagc gctgatcgat ggcaagaatg tggccattct ggacaggtcc   2400
agtgcgtact ggaaagccaa gggaaatgca gcgtggggtg atgcgatacg tgggttcagg   2460
gtttcgatgg tggcgatggg tgggtttggg cttgcgcgcg ttacgcttga attatttgat   2520
gttacagatg attttcacgc agctaaaaca tcagaagaaa catatggaat tggcatcaag   2580
gggttttccg tagtggtgat gggattgggt gctgcgccc agctaatggc aggcatttct   2640
cccgctggcg ttttacgat tatcgcaatg agtccgtggt tcagcgtagc gctactggca   2700
gcaggcttga tttatcttt tgctacgatg gcccttaatt acttcaagca agacagtgtc   2760
ggctggtggc tacgcaagtg ctgttggtcc ataacccaag actatcgcta tgctgagact   2820
gcggaaggta agcatgacga agtgcgcgcg ctgatggaaa taaaattatc tccgcaggtc   2880
catgtaaaaa gcaccgtgaa ttatgaaaac cgttatcttg gcaaaaacga tcactacagc   2940
```

```
gtagcggtac aaaatggcgc gggggtacaa gtgcgcttgc cgaatcttct acgcgggctg    3000
tccgtgcatt tcaatatcgt tagtagcaag agaccatggg gcgtgctgcc cgtagaaaaa    3060
atagatcagc cgatacatga agcttttctg gaccacgggc aattcaggaa agtcgaacag    3120
ttcgggatgt ttaccaacaa gcctgctggc aaggcgagtg aagactatac ctaccccgc    3180 atgccacctg aaaacgaaga cctcatctgg gaaacctggg tgccgctcga caaggacgca    3240
acgtatcttg agttgcaaat ctggtacccg gccaatcttt taaatcctgg cggagacgat    3300
agaagctatc tgtttcagat ggagcttggc acaaaaggcg ataccgctat tgacggcctg    3360
gctgcagtgg aactcgaggt aaaggcatca agcaggattg gcgctctgac cctagaagtc    3420
gcagagggca cacctgtatg a                                              3441
```

<210> SEQ ID NO 78
<211> LENGTH: 1146
<212> TYPE: PRT
<213> ORGANISM: Pseudomonas syringae pv. tomato DC3000

<400> SEQUENCE: 78

```
Met Asn Thr Val Arg Lys Pro Ile Thr Pro Arg Met Leu Ser Met Thr
 1               5                  10                  15

Asp Lys Asn Gly Thr His Arg Gln Arg Arg Ala Ala Leu Phe Pro Lys
            20                  25                  30

Thr Pro Ala Thr Ala Thr Ser Leu Cys Pro Phe Arg Gly Pro Asn Ile
        35                  40                  45

Ala Ile Val Pro Val Arg Tyr Ala Leu Asp Arg Ser Arg Tyr Asp Ala
    50                  55                  60

Asp Pro Ala Gln Leu Lys Pro Leu Pro Lys Asp Gly Gln Trp Ala His
65                  70                  75                  80

Leu Pro Thr Leu Lys Thr Arg Ser Tyr Thr Leu Arg Gln Leu Tyr Asp
                85                  90                  95

Gly Tyr Val Tyr Val Phe Asp Glu Thr Ala Gly Thr Leu His Glu Tyr
            100                 105                 110

Ala Ala Ser Ala Ser Asp Gly His Leu Ser Arg Ile Val Trp Thr Asp
        115                 120                 125

Ala His Ile Gly Asn Asp Gln Arg Ser Gly Ala Gly Glu Gly Gln Pro
    130                 135                 140

Phe Val Leu Tyr Pro Arg Asp His Arg Leu His Ile Ala Phe Ser Pro
145                 150                 155                 160

Leu Gln Trp Thr Trp Arg Met Cys Glu His Met Arg Ser His Ala Pro
                165                 170                 175

Ser Arg Ala Leu Trp Met Lys Ala Leu Asp Leu Ala Ser Tyr Cys Leu
            180                 185                 190

Thr Met Ala Glu Pro Asp Thr Leu Pro Leu Asp Arg Ile Ala Glu Ala
        195                 200                 205

Val Ala Asp Ile Asp Lys Asp Cys Val Val Glu Asp Gly Arg Phe Ala
    210                 215                 220

Asp Ser Ala Ile Pro Ser Val Arg Pro Ser Glu Gly Ala Glu Pro
225                 230                 235                 240

Tyr Pro Leu Trp Ala Pro Leu Gly Ala Asp Val Phe Trp Gln Gly Ser
                245                 250                 255

Val Tyr Asp Gln Asp Ser Ser Leu Val Ile Ala Leu Asn Asp Pro Leu
            260                 265                 270

Ala Val Phe Asn Asp Leu Gly Met Gln Leu Ala Ala Asp Gln Ala Ala
        275                 280                 285
```

-continued

```
Phe Arg Glu Trp Gln Ser Ala His Glu His Lys Ile Gln Ile Ala Gln
    290                 295                 300
Thr Val Ala Thr Leu Cys Gly Ala Glu Ser Ala Glu Lys Leu Pro
305                 310                 315                 320
Ala Ser Val Arg Gly Asp Ala Leu Arg Thr His Gln Tyr Leu Ser Glu
                325                 330                 335
Val Glu Ala Tyr Phe Glu Gln Cys Ile Leu Glu Glu Ala Gln Ile Ser
            340                 345                 350
Ser Ser Asn Val Pro Gly Asp Phe Leu Leu Leu Pro Asp Met Phe Lys
        355                 360                 365
Ser Leu Asp Met Arg Lys Ser Ile Glu Thr Arg Tyr Gly Ser Ala Pro
    370                 375                 380
Thr Asp Glu Gly Ala Gln Ala Trp Lys Asp Arg His Lys Trp Arg Arg
385                 390                 395                 400
Glu Val Asp Leu Ser Ser Ala Arg Gln Tyr Leu Leu Gln His Leu Pro
                405                 410                 415
Thr Gly Asp Lys Arg Leu Gln Gln Val Arg Asp Thr Gln Ser Asp Phe
            420                 425                 430
Gln His Trp Ala Ala His Ile Gly Thr Glu Pro Leu Lys Leu Phe Ile
        435                 440                 445
Asp Thr Thr His Pro Lys Thr Leu Leu Tyr Leu Gln Thr Ile Met Leu
    450                 455                 460
Asn Leu Gln Ile Ile Tyr Ala Gln Asp Ser Ala Ala Asn Ala Trp Leu
465                 470                 475                 480
Ala Glu Gln Glu Ala Asn Thr Ser Ser Leu Phe Gly Thr Leu Arg Tyr
                485                 490                 495
Gly Phe Ser Pro Ala Leu Lys His Ala Leu His Gln Glu Ala Asp Ala
            500                 505                 510
Leu Leu Asn Gly Leu Gly Asp Val Thr Asn Leu Ala Thr Arg Ile Gly
        515                 520                 525
Glu Leu Asn Gly Val Leu Asn His Gln Gly Phe Ala Asp Lys Pro Trp
    530                 535                 540
Met Lys Ala Leu Lys Gln Pro Val Gln Asp Thr Phe Lys Ala Leu Gly
545                 550                 555                 560
Glu Leu Ala Ser Gly Ala Gly Lys Ala Arg Phe Glu Ser Val Leu Leu
                565                 570                 575
Ala Trp Val Pro Ile Asp Ser Arg Met Ala Leu Gly Lys Gln Gln Asn
            580                 585                 590
Ile Val Ala Leu Leu Arg Thr Leu Leu Ile Gly Gln Ile Leu Leu Asp
        595                 600                 605
Ser Thr Ala Arg Val Ala Ile Asn Glu Gln Thr Val Thr Lys Leu Lys
    610                 615                 620
Gln Trp Val Ser Glu Trp Gln Val Leu Asn Lys Gln Ile Ser Glu Leu
625                 630                 635                 640
Val Arg Ser Trp Gln Tyr Pro Asn Ala Tyr Asn Thr Arg Gln Ser Thr
                645                 650                 655
Ala Arg Lys Leu Gln Ala His Lys His Lys Leu Arg Val His Glu Leu
            660                 665                 670
Ser Ile Pro Ala Leu Leu Asp Phe Gln Asn Asn Glu Tyr Ala Lys Leu
        675                 680                 685
Leu Gln Asp Glu Ile Arg Gln Tyr Phe Gln Ser Gly Lys Thr Leu Ala
    690                 695                 700
Thr Asp Trp Leu Ala Arg Ala Lys Gly Trp Thr Asp Arg Leu Gly Gly
```

```
            705                 710                 715                 720
Val Ala Gly Thr Ile Thr Trp Gly Val Val Met Leu Asn Leu Ile Asn
                    725                 730                 735

Thr Ala Phe Leu Tyr Arg Asp Leu Thr Arg Asp Gly Asp Phe Ser Thr
                740                 745                 750

Lys Asp Ile Gly Lys Val Thr Tyr Gly Leu Gly Tyr Ser Phe Asn Leu
            755                 760                 765

Leu Met Ala Val Phe Val Asp Ala Pro Trp Ser Ile Ile Arg Asp Ala
        770                 775                 780

Thr Pro Ala Leu Ile Asp Gly Lys Asn Val Ala Ile Leu Asp Arg Ser
785                 790                 795                 800

Ser Ala Tyr Trp Lys Ala Lys Gly Asn Ala Ala Trp Gly Asp Ala Ile
                805                 810                 815

Arg Gly Phe Arg Val Ser Met Val Ala Met Gly Gly Phe Gly Leu Ala
                820                 825                 830

Ala Val Thr Leu Glu Leu Phe Asp Val Thr Asp Phe His Ala Ala
            835                 840                 845

Lys Thr Ser Glu Glu Thr Tyr Gly Ile Gly Ile Lys Gly Phe Ser Val
        850                 855                 860

Val Val Met Gly Leu Gly Ala Ala Gln Leu Met Ala Gly Ile Ser
865                 870                 875                 880

Pro Ala Gly Val Phe Thr Ile Ile Ala Met Ser Pro Trp Phe Ser Val
                885                 890                 895

Ala Leu Leu Ala Ala Gly Leu Ile Tyr Leu Phe Ala Thr Met Ala Leu
                900                 905                 910

Asn Tyr Phe Lys Gln Asp Ser Val Gly Trp Trp Leu Arg Lys Cys Cys
            915                 920                 925

Trp Ser Ile Thr Gln Asp Tyr Arg Tyr Ala Glu Thr Ala Glu Gly Lys
        930                 935                 940

His Asp Glu Val Arg Ala Leu Met Glu Ile Lys Leu Ser Pro Gln Val
945                 950                 955                 960

His Val Lys Ser Thr Val Asn Tyr Glu Asn Arg Tyr Leu Gly Lys Asn
                965                 970                 975

Asp His Tyr Ser Val Ala Val Gln Asn Gly Ala Gly Val Gln Val Arg
            980                 985                 990

Leu Pro Asn Leu Leu Arg Gly Leu Ser Val His Phe Asn Ile Val Ser
        995                 1000                1005

Ser Lys Arg Pro Trp Gly Val Leu Pro Val Lys Ile Asp Gln Pro
    1010                1015                1020

Ile His Glu Ala Phe Leu Asp His Gly Gln Phe Arg Lys Val Glu Gln
1025                1030                1035                1040

Phe Gly Met Phe Thr Asn Lys Pro Ala Gly Lys Ala Ser Glu Asp Tyr
                1045                1050                1055

Thr Tyr Pro Arg Met Pro Pro Glu Asn Glu Asp Leu Ile Trp Glu Thr
            1060                1065                1070

Trp Val Pro Leu Asp Lys Asp Ala Thr Tyr Leu Glu Leu Gln Ile Trp
        1075                1080                1085

Tyr Pro Ala Asn Leu Leu Asn Pro Gly Gly Asp Asp Arg Ser Tyr Leu
    1090                1095                1100

Phe Gln Met Glu Leu Gly Thr Lys Gly Asp Thr Ala Ile Asp Gly Leu
1105                1110                1115                1120

Ala Ala Val Glu Leu Glu Val Lys Ala Ser Ser Arg Ile Gly Ala Leu
                1125                1130                1135
```

Thr Leu Glu Val Ala Glu Gly Thr Pro Val
        1140                1145

<210> SEQ ID NO 79
<211> LENGTH: 630
<212> TYPE: DNA
<213> ORGANISM: Pseudomonas syringae pv. tomato DC3000

<400> SEQUENCE: 79
atgtgcctgg tggcgagcct gtcggtgctg gcaggcatga ccgatgccat cggcttcatg      60
gccaccggcg atttcgtctc gttcatgagc ggcaacacca cgcgccttgc ggtggcgatc     120
agtgatggcg atttgagcgt cacactccgt ctggccctgg ccatctttgc gtttattgcc     180
ggcaatgcac tgggcgttgt cgttgcgcgc ctgggcaacc ggcgcgccct gcccttactg     240
ctggctatcg ccacgctgtt gtgtgccgct gcggcgtggc cgttggcgaa caatatgctt     300
gccctgatct gggcgattct ggcgatgggc atgctcaacg ccgctgtcga gcaggtcaac     360
gggctgccgg tgggcctgac ctacgtgacc ggcgcgctgt cgcgactggg cgcggtctg      420 ggccgctgga tgctcggcga acgccgggat ggctggcgca ttcaactggt cccgtgggcc     480
gggatgttca ttggcgcagt gatcggcgcg ttgcttgaac atcgtctggg gctcaatgcc     540
ttgctggtca gcgccagcct gtcagcgtta atggcgctgg tgtcgctgaa aatcccgcat     600
cgctggcaac gtcagtacat gccgcgctga                                      630

<210> SEQ ID NO 80
<211> LENGTH: 209
<212> TYPE: PRT
<213> ORGANISM: Pseudomonas syringae pv. tomato DC3000

<400> SEQUENCE: 80

Met Cys Leu Val Ala Ser Leu Ser Val Leu Ala Gly Met Thr Asp Ala
 1               5                  10                  15

Ile Gly Phe Met Ala Thr Gly Asp Phe Val Ser Phe Met Ser Gly Asn
            20                  25                  30

Thr Thr Arg Leu Ala Val Ala Ile Ser Asp Gly Asp Leu Ser Val Thr
        35                  40                  45

Leu Arg Leu Ala Leu Ala Ile Phe Ala Phe Ile Ala Gly Asn Ala Leu
    50                  55                  60

Gly Val Val Val Ala Arg Leu Gly Asn Arg Arg Ala Leu Pro Leu Leu
65                  70                  75                  80

Leu Ala Ile Ala Thr Leu Leu Cys Ala Ala Ala Trp Pro Leu Ala
                85                  90                  95

Asn Asn Met Leu Ala Leu Ile Trp Ala Ile Leu Ala Met Gly Met Leu
            100                 105                 110

Asn Ala Ala Val Glu Gln Val Asn Gly Leu Pro Val Gly Leu Thr Tyr
        115                 120                 125

Val Thr Gly Ala Leu Ser Arg Leu Gly Arg Gly Leu Gly Arg Trp Met
    130                 135                 140

Leu Gly Glu Arg Arg Asp Gly Trp Arg Ile Gln Leu Val Pro Trp Ala
145                 150                 155                 160

Gly Met Phe Ile Gly Ala Val Ile Gly Ala Leu Leu Glu His Arg Leu
                165                 170                 175

Gly Leu Asn Ala Leu Leu Val Ser Ala Ser Leu Ser Ala Leu Met Ala
            180                 185                 190

Leu Val Ser Leu Lys Ile Pro His Arg Trp Gln Arg Gln Tyr Met Pro
        195                 200                 205

Arg

<210> SEQ ID NO 81
<211> LENGTH: 882
<212> TYPE: DNA
<213> ORGANISM: Pseudomonas syringae pv. tomato DC3000

<400> SEQUENCE: 81

```
atgagagggc ttggtgttct gagcatgaac caccagtttc agggcaatac cctgttcaaa      60
gaaataagcg gtaccagctt ttccgcgccc tacatcaccc atcttgcggg ccgtctcctt     120
aacgagcacc cagaggcatc ggcgaacctc ttgcgcgcta tgctggtgaa tcatgcgtca     180
tgtctagcg aggtcgagac gactttctcc gacgacatga ggaagggcta caaagctaat     240
aaggcgaccc acaaccgtga atatcgcgc gatgtgagtg gttacggcca agtgaatgag     300
gcagacctgt ttcggtcttc cgaccattgc gttgtgctga tgtgtgaaga gtccattgag     360
aaggactcgt gccagttcta cgaactgcct ttgcccactt cgtttcttcg cagggctaga     420
ggggcaaggc acctgagcgt cacgctggct tattctcctg ccgtcaggac aactcggttg     480
gactatctgg caactcagat cagttatcgc ctagtgaaag gttcgtcgct tgaggaagtc     540
caggcctcgt ttaactacga caagcaggac gaaacgaaga cccgtggaga tgacgctgag     600
cagaatcgag acatcactgc tcagttgaga agccgcggga ccgtccagtc ctcgcggtgg     660
acgttcaaga agcgaaatcc agaagaaaaa tggtttgtag ttgtgatccg ccaggatcgg     720
gaatggaatc atcccgacgt gctggatcga gaatcttacg ccctggtggt aacagttgct     780
gatcgtgaca acgaacacgc gcagttgtat gccgaaattc aagccaagct gacgcttcaa     840
aatcaggtgc gtgaagaggc aaggcagcgg gctgttctgt aa                        882
```

<210> SEQ ID NO 82
<211> LENGTH: 293
<212> TYPE: PRT
<213> ORGANISM: Pseudomonas syringae pv. tomato DC3000

<400> SEQUENCE: 82

```
Met Arg Gly Leu Gly Val Leu Ser Met Asn His Gln Phe Gln Gly Asn
  1               5                  10                  15

Thr Leu Phe Lys Glu Ile Ser Gly Thr Ser Phe Ser Ala Pro Tyr Ile
             20                  25                  30

Thr His Leu Ala Gly Arg Leu Leu Asn Glu His Pro Glu Ala Ser Ala
         35                  40                  45

Asn Leu Leu Arg Ala Met Leu Val Asn His Ala Ser Leu Ser Ser Glu
     50                  55                  60

Val Glu Thr Thr Phe Ser Asp Asp Met Arg Lys Gly Tyr Lys Ala Asn
 65                  70                  75                  80

Lys Ala Thr His Asn Arg Glu Ile Ser Arg Asp Val Ser Gly Tyr Gly
                 85                  90                  95

Gln Val Asn Glu Ala Asp Leu Phe Arg Ser Ser Asp His Cys Val Val
            100                 105                 110

Leu Met Cys Glu Glu Ser Ile Glu Lys Asp Ser Cys Gln Phe Tyr Glu
        115                 120                 125

Leu Pro Leu Pro Thr Ser Phe Leu Arg Arg Ala Arg Gly Ala Arg His
    130                 135                 140

Leu Ser Val Thr Leu Ala Tyr Ser Pro Ala Val Arg Thr Thr Arg Leu
145                 150                 155                 160

Asp Tyr Leu Ala Thr Gln Ile Ser Tyr Arg Leu Val Lys Gly Ser Ser
                165                 170                 175
```

Leu Glu Glu Val Gln Ala Ser Phe Asn Tyr Asp Lys Gln Asp Glu Thr
                180                 185                 190

Lys Thr Arg Gly Asp Asp Ala Glu Gln Asn Arg Asp Ile Thr Ala Gln
            195                 200                 205

Leu Arg Ser Arg Gly Thr Val Gln Ser Ser Arg Trp Thr Phe Lys Lys
        210                 215                 220

Arg Asn Pro Glu Glu Lys Trp Phe Val Val Ile Arg Gln Asp Arg
225                 230                 235                 240

Glu Trp Asn His Pro Asp Val Leu Asp Arg Glu Ser Tyr Ala Leu Val
                245                 250                 255

Val Thr Val Ala Asp Arg Asp Asn Glu His Ala Gln Leu Tyr Ala Glu
            260                 265                 270

Ile Gln Ala Lys Leu Thr Leu Gln Asn Gln Val Arg Glu Glu Ala Arg
        275                 280                 285

Gln Arg Ala Val Leu
    290

<210> SEQ ID NO 83
<211> LENGTH: 846
<212> TYPE: DNA
<213> ORGANISM: Pseudomonas syringae pv. tomato DC3000

<400> SEQUENCE: 83
atgggcattg gcggtttgct taaacctttg gtcgattttt taccgaagtt gccgacctta      60
cgcaccaaga tttcctcgcc ttccatcagc tacgcgcgtt tgcaaagcga tgcgtcccag     120
gtacgcagta aattgggatt gggtgagcgc agcgtgctgg ttatgaagc gctgatcgcc      180 gagttcaagg cgtgcggggc ggttctggtg cccgttcttt ggggacaaaa gcagcaacac     240
aagaatgcgt tgcacattct attgccggcg tcagatgtca cctttgtctt cgtcaacctg     300
gataccaagc tggaagactt caagttttgg atggcccacg agttagcgca tgtctacact     360
cctgagcttg cgggtagtga cgaggggag gattttgcgg atgcctttgc cggtgccctg      420
ctgtttcctg aggcttgcgt gcagctagcg tatgccgagg cggcgcaagc gcctagcgca     480
gctggggagg tgagtgtcct tcagcagcat gcccggcatc accaaatttc actgaacacg     540
gtgttccagc aggcgcaggg atatgcggcg gaaacaatc tgccatcctt acgggtaccg      600
gaaaggacaa ttcacgcggt gcgcaacagc tccacgccgc agttggtcag tacgatcctg     660
tttgatccga ctccacccaa accggcgcaa tacattgccg cagcgtcgaa tgtgtttcag     720
tctgagttct tcctggcgct gaaacgcatg attcgcgagc acgggacggg cccgtcgtat     780
gttcagcaaa tcatggatgt atcactcagt gatgcctccg cgctttacgg cgagctcgcg     840
cgttga                                                                846

<210> SEQ ID NO 84
<211> LENGTH: 281
<212> TYPE: PRT
<213> ORGANISM: Pseudomonas syringae pv. tomato DC3000

<400> SEQUENCE: 84

Met Gly Ile Gly Gly Leu Leu Lys Pro Leu Val Asp Phe Leu Pro Lys
1               5                   10                  15

Leu Pro Thr Leu Arg Thr Lys Ile Ser Ser Pro Ile Ser Tyr Ala
            20                  25                  30

Arg Leu Gln Ser Asp Ala Ser Gln Val Arg Ser Lys Leu Gly Leu Gly
        35                  40                  45

```
Glu Arg Ser Val Leu Gly Tyr Glu Ala Leu Ile Ala Glu Phe Lys Ala
 50                  55                  60

Cys Gly Ala Val Leu Val Pro Val Leu Trp Gly Gln Lys Gln Gln His
 65                  70                  75                  80

Lys Asn Ala Leu His Ile Leu Pro Ala Ser Asp Val Thr Phe Val
                 85                  90                  95

Phe Val Asn Leu Asp Thr Lys Leu Glu Asp Phe Lys Phe Trp Met Ala
                100                 105                 110

His Glu Leu Ala His Val Tyr Thr Pro Glu Leu Ala Gly Ser Asp Glu
            115                 120                 125

Gly Glu Asp Phe Ala Asp Ala Phe Ala Gly Ala Leu Leu Phe Pro Glu
130                 135                 140

Ala Cys Val Gln Leu Ala Tyr Ala Glu Ala Ala Gln Ala Pro Ser Ala
145                 150                 155                 160

Ala Gly Glu Val Ser Val Leu Gln Gln His Ala Arg His Gln Ile
                165                 170                 175

Ser Leu Asn Thr Val Phe Gln Gln Ala Gln Gly Tyr Ala Ala Glu Asn
            180                 185                 190

Asn Leu Pro Ser Leu Arg Val Pro Glu Arg Thr Ile His Ala Val Arg
            195                 200                 205

Asn Ser Ser Thr Pro Gln Leu Val Ser Thr Ile Leu Phe Asp Pro Thr
210                 215                 220

Pro Pro Lys Pro Ala Gln Tyr Ile Ala Ala Ser Asn Val Phe Gln
225                 230                 235                 240

Ser Glu Phe Phe Leu Ala Leu Lys Arg Met Ile Arg Glu His Gly Thr
                245                 250                 255

Gly Pro Ser Tyr Val Gln Gln Ile Met Asp Val Ser Leu Ser Asp Ala
            260                 265                 270

Ser Ala Leu Tyr Gly Glu Leu Ala Arg
            275                 280

<210> SEQ ID NO 85
<211> LENGTH: 525
<212> TYPE: DNA
<213> ORGANISM: Pseudomonas syringae pv. tomato DC3000

<400> SEQUENCE: 85
atgaagcagc tcgcggcagg cagcaatgtg catgttcttg aaaatgagtc tttccagata      60
gataaggtgc gcttttttgg ggccacagct tggacagatt tcgcaacagg tgaaagcgtg     120
taccaagcgt cccaggaggc aaggcgaggc atgaatgact ttcgcttgat ccgtgcaggc     180
gagggttacc gcgcattgag catcagtgat gtgatcagtc gaaatcatcg aacttacgag     240
tggctcaagg aagagctcgc catggagttc gatggtcaga ccattgtcat cactcatcat     300
tgcccgttgg tcaattactg tggcccagag cagggctcac cgctaatgcc tgcttattca     360
aatgattggc cagaactcgt tcgtcaggct gatgtgtggg tctttgggca cacgcacagt     420
catgtcgatg tcatggtgga aggatgccga ctcattagta accctagagg ttatccaggt     480
gagagttgcg gctttgccaa tgactttgtg gtcgatatta actag                    525

<210> SEQ ID NO 86
<211> LENGTH: 174
<212> TYPE: PRT
<213> ORGANISM: Pseudomonas syringae pv. tomato DC3000

<400> SEQUENCE: 86

Met Lys Gln Leu Ala Ala Gly Ser Asn Val His Val Leu Glu Asn Glu
```

```
                1               5                  10                 15
            Ser Phe Gln Ile Asp Lys Val Arg Phe Leu Gly Ala Thr Ala Trp Thr
                            20                  25                  30

Asp Phe Ala Thr Gly Glu Ser Val Tyr Gln Ala Ser Gln Glu Ala Arg
                        35                  40                  45

Arg Gly Met Asn Asp Phe Arg Leu Ile Arg Ala Gly Glu Gly Tyr Arg
                    50                  55                  60

Ala Leu Ser Ile Ser Asp Val Ile Ser Arg Asn His Arg Thr Tyr Glu
             65                  70                  75                  80

Trp Leu Lys Glu Glu Leu Ala Met Glu Phe Asp Gly Gln Thr Ile Val
                            85                  90                  95

Ile Thr His His Cys Pro Leu Val Asn Tyr Cys Gly Pro Glu Gln Gly
                        100                 105                 110

Ser Pro Leu Met Pro Ala Tyr Ser Asn Asp Trp Pro Glu Leu Val Arg
                    115                 120                 125

Gln Ala Asp Val Trp Val Phe Gly His Thr His Ser His Val Asp Val
                130                 135                 140

Met Val Glu Gly Cys Arg Leu Ile Ser Asn Pro Arg Gly Tyr Pro Gly
            145                 150                 155                 160

Glu Ser Cys Gly Phe Ala Asn Asp Phe Val Val Asp Ile Asn
                            165                 170
```

<210> SEQ ID NO 87
<211> LENGTH: 2307
<212> TYPE: DNA
<213> ORGANISM: Pseudomonas syringae pv. tomato DC3000

<400> SEQUENCE: 87

| | |
|---|---|
| atgacgctga cgcagcgtca ggcatggcat cgcgaggcac agcggtttgg cgagcaggtg | 60 |
| gtgaacatgc gcaaagccag caaggagcac ttcggccagg cggaaaatga cagccgcacc | 120 |
| tatccggcgc gctttatcga ccagcaactg gctcaactgc tgaaccggct atccatcgct | 180 |
| gcaacggcgc aacagatcaa tatttcactg acctacagga cgggcaccga agtgctcgaa | 240 |
| attcccggcg cgcctgtatt gccagaaacc gagaccgaga cgtttcact caggcaactg | 300 |
| gtgcataccc aggccctgcg caccaaggcc aaggatgccg tgcttctacg cgctgtcgac | 360 |
| gccgaaggcg tcccccttgc gcacttggac aagcaggcc taaccgagct gattgccacg | 420 |
| ctggaagatc accgatacct cagtgattac cttgacctgc acctgaaaac ctcggcgtat | 480 |
| gcacagcagc tcaagcggtc agaaaaagcc atgttgcaag ctcagatgaa gatgcgcctg | 540 |
| ctggagatcg agcaacaggc ttttgcacca gccggtcgcg agtggatcaa ggctgtgctg | 600 |
| gattcgccag ccccccaagg acgtcgaacc atggcagggg aaagcattga agtccgtttt | 660 |
| ttcagcgtca ccaattcaa gatgaccaat gtcatgctga ttgctccagc cggtaaattc | 720 |
| gagaaggggc gctggtgct tgcacgctg atgcttccg acggtgtggt tttccgctgg | 780 |
| tttaacagca tgtatcacct gaccaccagc tttctggaag aggcacccctt ccagcagtat | 840 |
| ctgattcagc aaataccggt ttccaggcgt cttgagacgc tgcatgccat gcagtacgaa | 900 |
| aaggaagcca agcattggcg tccgccagaa gtattcaccc aactgacgct gctaccgatc | 960 |
| ccgtcaaggc tgctgcgccc agtcgtgttt gtcagccaga gcaaagacat ttacgaggaa | 1020 |
| aatcacgaga ccaagatcaa ccatctgatc aacgaagcca acggcagat gagcctgtcc | 1080 |
| accggtacag gcaatcgggg tcggggcttc gatctgatcg cgagcattgc gattctgttt | 1140 |
| ctgcctggcg cgatcatgat gcctgtctcg ctgggcgctg gcctttacaa aacctggagc | 1200 |

```
gcttttttcga aaatcgatga aaacgacctg gaaggtgccg ccgaggagtt tctgagcgcc   1260
ctcagctatc ttgccattac cttggtcggc catttggcgc tggccttgaa accggcagga   1320
agcgccgcaa aaacggtgag acgtccgcac ctggtacgca gagtcggtcg tgatgggcag   1380
gcacagatcg gctacctcct gtcgcattca aaagcgccgc gtttcccaga ctcgaaattg   1440
atcgctgcaa tggaccccaa acgcttcgtc gccattgagg tagaaggcca gacctgctta   1500
ataagccggc gggccaacct gttcggccac tcacgccttt atcgggtaaa cccgatggat   1560
gcaacgcaac tggtgcacga gcaggagttt gccttgcgca gcaccaacgg cacctggaaa   1620
atcgtgggca aacagatcct gcgcatgagt cagtccgcaa tccgcaatgc ccaggctcaa   1680
ctgaccagcc tgacaaatct ctggccggcg tctctggagg aagcaagtag cgccgaacgc   1740
ttgagcttcg agaccgacta cctggcgctg gcccagacat ccaacgcaga aaactattcc   1800
gaaatagtcg cctacgtgga aagcggttca acagacatca acccgctgct gcgaagcggc   1860
gtgcgcaacg ccaccacgcg cagattttta cgtcagttcc ataaactcaa tgcgtgggaa   1920
ggcactgcct ttcgcgccac ctatgtgtcc agcgacgggg tggcatgcct tgagcgcgaa   1980
gtgggttcgg tgttcaccga caacggcgtg cagtctgcat cggtgtcgcg agccaatgcc   2040
tccagatgga gccaggacgg gttcgtgagc agcaacgcca atgccgcaaa ccacccggtg   2100
ttcttcatct ttgcaccggg agtgcccaag aagaacatgt tcaccggctt tcttggcgat   2160
cacgtggcaa tcccgccagg cacgtgcgtg caactgggtg cgaccaagcg gataaacgga   2220
cagctgtttg cctggttcga tgcgcccgaa caaatggtcg atcagaccta cgatctctat   2280
acaggagaac aggaactctg ggtctga                                        2307
```

<210> SEQ ID NO 88
<211> LENGTH: 768
<212> TYPE: PRT
<213> ORGANISM: Pseudomonas syringae pv. tomato DC3000

<400> SEQUENCE: 88

```
Met Thr Leu Thr Gln Arg Gln Ala Trp His Arg Glu Ala Gln Arg Phe
 1               5                  10                  15

Gly Glu Gln Val Val Asn Met Arg Lys Ala Ser Lys Glu His Phe Gly
                20                  25                  30

Gln Ala Glu Asn Asp Ser Arg Thr Tyr Pro Ala Arg Phe Ile Asp Gln
            35                  40                  45

Gln Leu Ala Gln Leu Leu Asn Arg Leu Ser Ile Ala Ala Thr Ala Gln
        50                  55                  60

Gln Ile Asn Ile Ser Leu Thr Tyr Arg Thr Gly Thr Glu Val Leu Glu
 65                  70                  75                  80

Ile Pro Gly Ala Pro Val Leu Pro Glu Thr Glu Thr Glu Asn Val Ser
                85                  90                  95

Leu Arg Gln Leu Val His Thr Gln Ala Leu Arg Thr Lys Ala Lys Asp
            100                 105                 110

Ala Val Leu Leu Arg Ala Val Asp Ala Glu Gly Val Pro Leu Ala His
        115                 120                 125

Leu Asp Lys Gln Ala Val Thr Glu Leu Ile Ala Thr Leu Glu Asp His
    130                 135                 140

Arg Tyr Leu Ser Asp Tyr Leu Asp Leu His Leu Lys Thr Ser Ala Tyr
145                 150                 155                 160

Ala Gln Gln Leu Lys Arg Ser Glu Lys Ala Met Leu Gln Ala Gln Met
                165                 170                 175

Lys Met Ala Leu Leu Glu Ile Glu Gln Gln Ala Phe Ala Pro Ala Gly
```

```
                180                 185                 190
Arg Glu Trp Ile Lys Ala Val Leu Asp Ser Pro Ala Pro Gln Gly Arg
            195                 200                 205

Arg Thr Met Ala Gly Glu Ser Ile Glu Val Arg Phe Phe Ser Val Asn
210                 215                 220

Gln Phe Lys Met Thr Asn Val Met Leu Ile Ala Pro Ala Gly Lys Phe
225                 230                 235                 240

Glu Lys Gly Pro Leu Val Leu Cys Thr Leu Asp Ala Ser Asp Gly Val
            245                 250                 255

Val Phe Arg Trp Phe Asn Ser Met Tyr His Leu Thr Thr Ser Phe Leu
                260                 265                 270

Glu Glu Ala Pro Phe Gln Gln Tyr Leu Ile Gln Ile Pro Val Ser
            275                 280                 285

Arg Arg Leu Glu Thr Leu His Ala Met Gln Tyr Glu Lys Glu Ala Lys
290                 295                 300

His Trp Arg Pro Pro Glu Val Phe Thr Gln Leu Thr Leu Leu Pro Ile
305                 310                 315                 320

Pro Ser Arg Leu Leu Arg Pro Val Val Phe Val Ser Gln Ser Lys Asp
                325                 330                 335

Ile Tyr Glu Glu Asn His Glu Thr Lys Ile Asn His Leu Ile Asn Glu
            340                 345                 350

Ala Lys Arg Gln Met Ser Leu Ser Thr Gly Thr Gly Gln Ser Gly Arg
            355                 360                 365

Gly Phe Asp Leu Ile Ala Ser Ile Ala Ile Leu Phe Leu Pro Gly Ala
370                 375                 380

Ile Met Met Pro Val Ser Leu Gly Ala Gly Leu Tyr Lys Thr Trp Ser
385                 390                 395                 400

Ala Phe Ser Lys Ile Asp Glu Asn Asp Leu Glu Gly Ala Ala Glu Glu
                405                 410                 415

Phe Leu Ser Ala Leu Ser Tyr Leu Ala Ile Thr Leu Val Gly His Leu
            420                 425                 430

Ala Leu Ala Leu Lys Pro Ala Gly Ser Ala Ala Lys Thr Val Arg Arg
            435                 440                 445

Pro His Leu Val Arg Arg Val Gly Arg Asp Gly Gln Ala Gln Ile Gly
450                 455                 460

Tyr Leu Leu Ser His Ser Lys Ala Pro Arg Phe Pro Asp Ser Lys Leu
465                 470                 475                 480

Ile Ala Ala Met Asp Pro Lys Arg Phe Val Ala Ile Glu Val Glu Gly
                485                 490                 495

Gln Thr Cys Leu Ile Ser Arg Arg Ala Asn Leu Phe Gly His Ser Arg
            500                 505                 510

Leu Tyr Arg Val Asn Pro Met Asp Ala Thr Gln Leu Val His Glu Gln
            515                 520                 525

Glu Phe Ala Leu Arg Ser Thr Asn Gly Thr Trp Lys Ile Val Gly Lys
530                 535                 540

Gln Ile Leu Arg Met Ser Gln Ser Ala Ile Arg Asn Ala Gln Ala Gln
545                 550                 555                 560

Leu Thr Ser Leu Thr Asn Leu Trp Pro Ala Ser Leu Glu Glu Ala Ser
                565                 570                 575

Ser Ala Glu Arg Leu Ser Phe Glu Thr Asp Tyr Leu Ala Leu Ala Gln
            580                 585                 590

Thr Ser Asn Ala Glu Asn Tyr Ser Glu Ile Val Ala Tyr Val Glu Ser
            595                 600                 605
```

```
Gly Ser Thr Asp Ile Asn Pro Leu Leu Arg Ser Gly Val Arg Asn Ala
            610                 615                 620

Thr Thr Arg Arg Phe Leu Arg Gln Phe His Lys Leu Asn Ala Trp Glu
625                 630                 635                 640

Gly Thr Ala Phe Arg Ala Thr Tyr Val Ser Ser Asp Gly Val Ala Cys
                645                 650                 655

Leu Glu Arg Glu Val Gly Ser Val Phe Thr Asp Asn Gly Val Gln Ser
            660                 665                 670

Ala Ser Val Ser Arg Ala Asn Ala Ser Arg Trp Ser Gln Asp Gly Phe
            675                 680                 685

Val Ser Ser Asn Ala Asn Ala Ala Asn His Pro Val Phe Phe Ile Phe
            690                 695                 700

Ala Pro Gly Val Pro Lys Lys Asn Met Phe Thr Gly Phe Leu Gly Asp
705                 710                 715                 720

His Val Ala Ile Pro Pro Gly Thr Cys Val Gln Leu Gly Ala Thr Lys
                725                 730                 735

Arg Ile Asn Gly Gln Leu Phe Ala Trp Phe Asp Ala Pro Glu Gln Met
            740                 745                 750

Val Asp Gln Thr Tyr Asp Leu Tyr Thr Gly Glu Gln Glu Leu Trp Val
            755                 760                 765

<210> SEQ ID NO 89
<211> LENGTH: 2745
<212> TYPE: DNA
<213> ORGANISM: Pseudomonas syringae pv. tomato DC3000

<400> SEQUENCE: 89
atgactcagc taaaccctgc gggacaaccg cccgcagaac cgacccgaat cgtcaaagct     60
cacattgacc tcatggatcc tgccgaaagc gctgactacg aggcgacccg aatggcattg    120
ctcgcagcga tgcaaagcgg caatgccgcg atcaacctcg aacagattcg gctcaagccc    180
gacccagcgt ccgggttcgg cgaatactgc gctgagaaag ctgcgctacc tcacccggtc    240
caggccgaaa accaggaact cccgtttcag atagacagcg atggcagcgt cagtctggca    300
ttgatgctgc gctataacta cggggttgtcg ctgccgcaat cgcctgacga acagcgatc    360 aaaaccctgc tcaatacgct ggcagaactt cgcaccagtc aagaactggg gcttattgat    420
cagttcgaca tcaaggccat gctgaccatg caaaatctgc aggatctgaa gcgagcctgc    480
attgagtacc ttggcaccga cggtggcacg ctgctaggca agctgggtgc tgaaataatt    540
gcctcctgcc cactggcaga tgtgcagaac tccccggtga cggttattgc ccggattctc    600
agatcggaac cggcaagggc attggggcaa cgctgctgg cacagcttgg tcggcctgaa    660
gaagaaacgg acgcgtccct gacaacactc gtggaccgga ttttatggta tgccatcagt    720
agcgatcttc atgatccaga aaaccggaag ccaggagaaa ttgccggcta ccattcacc    780 caggccgaaa accagggacg ccgccacgct gacatcctga cgatattca aaccacctg    840 atcaccacgg gcaaggctga gtctgtcaac gaagcaataa ttgcctgctt catacttgca    900
ctcgatgact gcccggaatg gctggtcagc agtgttcccg atgatctgcc atacggctgt    960
acagaggtgt gggtcaactt tcaacatggg gtcacacttg cggaagtcat cgagtttggc   1020
tcgtcacgct ggatgaactt tgaagacctg atcgagctgc cggtgatttt caacaaaaag   1080
atggacaccg aagagcagca agtcgcctat gtcgcaacgc gcatgcccat tcttctgact   1140
tgggcccagg ccaacggtta cattcgtacc cagagcgacc tgccttactc cgaacaagag   1200
atagaacagg ccgccagcgc gtttgaacac tccgagaaac aatcccttga agctgcgaac   1260
```

```
gccttgatcc ggaaagcgcc agaacgcaaa gccatggcta tcagtgccat gaagaagcg     1320
cggaggacgc ctgaaataga aaaatactt gagcaggaag attactggtt ccgcccatc      1380
gatctcggca tcaggctggc ggtgctacgc aaaaatcaca cgcctgtcta tcgcgatcac    1440
caaggcacgc tctcaccgtc aaatctgcca tacgacccct acggcataaa acacaaggcg    1500
tcgtcgttgc tggagatcta catggcaggt gaaaacattg atgactggag actgccgggg    1560
cgcaacagca acgagggcct gcttccatc aaccgtgaaa tgcagttgtt gtacaaggcg     1620
ctgccagaca tcaatcaaag gttcgagagt gaatttcagg cttatctggc agatgcccgt    1680
aaggcgtatg cgacgattat cagaaagttg ctgactcacc tgccgctcaa gcaccgcatg    1740
gcgatcgaaa atggtgaggt gtcgctacac tcactcagat tgccgaccaa ggacgtgctg    1800
gcggcgacag agagcgaaaa acatcggag ccgttgcgag ggcgcacggg ctttgtcatc     1860
aaagctgtct acgagggcaa aaccacgttt tacgaggtgt ttccgttatc gatgattgta    1920
cgctatcgcc ctgatctgga ggcccttctc aagaacggtg tggtcggtat agattttggg   1980
gacattctgc ctcccacccg tataccggta gcggtttata acggaatcac aatgccatttt  2040
gatcagggag cctatttgaa cggtcagcta cctgagcctg gggcaagcgc tgtgatgatt   2100
gcagaaacca ttggtgaacg atttgattct tcaagtgcag aggtcgggca acaccagcct   2160
ccgacctcgt tttcaaaacg ctctactggc attgccgaga ccatcacaac atcgcttttc   2220
tacgtcaacg aagatgcact cttttgcacac tgcaaaagcc tcacgcaggt agaaatagat  2280
aacggtgccc caggtgcgct cgaagaggtg tccagctttc tgatacacct gacgccctgg   2340
ccggaaatcg aaaacattct gtccggagag aaagcgctta tgaggggagg agcaatcggt   2400
ctggcgcttt acatgattcc ctatgtggga cccgcgggca agttgctcgc aggcacggca   2460
aaagtcgtta cccgcctggg caaaagcctc ataaccagcg tagcaaagt ccaggtctcg    2520
aaattgctca tcacggccgg caccaccctg aaagacgccc cgctgatcat gatcagacag    2580
gccccctgaca tgaccagtaa agcaatgact ggcgtttcgc aattcgtcgt gaaacacgtc   2640
acctggaaat ttctggcgat acgtataggt attggtttaa gccgcaggct tgtagccatc    2700
atgagcaggc agcaggccca ggccgcaaag caagaggcca cgtaa                   2745
```

<210> SEQ ID NO 90
<211> LENGTH: 914
<212> TYPE: PRT
<213> ORGANISM: Pseudomonas syringae pv. tomato DC3000

<400> SEQUENCE: 90

Met Thr Gln Leu Asn Pro Ala Gly Gln Pro Ala Glu Pro Thr Arg
  1               5                  10                  15

Ile Val Lys Ala His Ile Asp Leu Met Asp Pro Ala Glu Ser Ala Asp
                 20                  25                  30

Tyr Glu Ala Thr Arg Met Ala Leu Leu Ala Ala Met Gln Ser Gly Asn
         35                  40                  45

Ala Ala Ile Asn Leu Glu Gln Ile Arg Leu Lys Pro Asp Pro Ala Ser
     50                  55                  60

Gly Phe Gly Glu Tyr Cys Ala Glu Lys Ala Ala Leu Pro His Pro Val
 65                  70                  75                  80

Gln Ala Glu Asn Gln Glu Leu Pro Phe Gln Ile Asp Ser Asp Gly Ser
                 85                  90                  95

Val Ser Leu Ala Leu Met Leu Arg Tyr Asn Tyr Gly Leu Ser Leu Pro
            100                 105                 110

Gln Ser Pro Asp Glu Thr Ala Ile Lys Thr Leu Leu Asn Thr Leu Ala

```
            115                 120                 125
Glu Leu Arg Thr Ser Gln Glu Leu Gly Leu Ile Asp Gln Phe Asp Ile
130                 135                 140

Lys Ala Met Leu Thr Met Gln Asn Leu Gln Asp Leu Lys Arg Ala Cys
145                 150                 155                 160

Ile Glu Tyr Leu Gly Thr Asp Gly Gly Thr Leu Leu Gly Lys Leu Gly
                    165                 170                 175

Ala Glu Ile Ile Ala Ser Cys Pro Leu Ala Asp Val Gln Asn Ser Pro
                180                 185                 190

Val Thr Val Ile Ala Arg Ile Leu Arg Ser Glu Pro Ala Arg Ala Leu
                195                 200                 205

Gly Gln Thr Leu Leu Ala Gln Leu Gly Arg Pro Glu Glu Thr Asp
210                 215                 220

Ala Ser Leu Thr Thr Leu Val Asp Arg Ile Leu Trp Tyr Ala Ile Ser
225                 230                 235                 240

Ser Asp Leu His Asp Pro Glu Asn Arg Lys Pro Gly Glu Ile Ala Gly
                    245                 250                 255

Tyr Pro Phe Thr Gln Ala Glu Asn Gln Gly Arg Arg His Ala Asp Ile
                260                 265                 270

Leu Asn Asp Ile His Asn His Leu Ile Thr Thr Gly Lys Ala Glu Ser
                275                 280                 285

Val Asn Glu Ala Ile Ile Ala Cys Phe Ile Leu Ala Leu Asp Asp Cys
290                 295                 300

Pro Glu Trp Leu Val Ser Ser Val Pro Asp Asp Leu Pro Tyr Gly Cys
305                 310                 315                 320

Thr Glu Val Trp Val Asn Phe Gln His Gly Val Thr Leu Ala Glu Val
                    325                 330                 335

Ile Glu Phe Gly Ser Ser Arg Trp Met Asn Phe Glu Asp Leu Ile Glu
                340                 345                 350

Leu Pro Val Ile Phe Asn Lys Lys Met Asp Thr Glu Glu Gln Gln Val
                355                 360                 365

Ala Tyr Val Ala Thr Arg Met Pro Ile Leu Leu Thr Trp Ala Gln Ala
370                 375                 380

Asn Gly Tyr Ile Arg Thr Gln Ser Asp Leu Pro Tyr Ser Glu Gln Glu
385                 390                 395                 400

Ile Glu Gln Ala Ala Ser Ala Phe Glu His Ser Glu Lys Gln Ser Leu
                    405                 410                 415

Glu Ala Ala Asn Ala Leu Ile Arg Lys Ala Pro Glu Arg Lys Ala Met
                420                 425                 430

Ala Ile Ser Ala Met Lys Glu Ala Arg Arg Thr Pro Glu Ile Glu Lys
                435                 440                 445

Ile Leu Glu Gln Glu Asp Tyr Trp Phe Pro Pro Ile Asp Leu Gly Ile
450                 455                 460

Arg Leu Ala Val Leu Arg Lys Asn His Thr Pro Val Tyr Arg Asp His
465                 470                 475                 480

Gln Gly Thr Leu Ser Pro Ser Asn Leu Pro Tyr Asp Pro Tyr Gly Ile
                    485                 490                 495

Lys His Lys Ala Ser Ser Leu Leu Glu Ile Tyr Met Ala Gly Glu Asn
                500                 505                 510

Ile Asp Asp Trp Arg Leu Pro Gly Arg Asn Ser Asn Glu Gly Leu Leu
                515                 520                 525

Pro Ile Asn Arg Glu Met Gln Leu Leu Tyr Lys Ala Leu Pro Asp Ile
    530                 535                 540
```

```
Asn Gln Arg Phe Glu Ser Glu Phe Gln Ala Tyr Leu Ala Asp Ala Arg
545                 550                 555                 560

Lys Ala Tyr Ala Thr Ile Ile Arg Lys Leu Thr His Leu Pro Leu
                565                 570                 575

Lys His Arg Met Ala Ile Glu Asn Gly Glu Val Ser Leu His Ser Leu
                580                 585                 590

Arg Leu Pro Thr Lys Asp Val Leu Ala Ala Thr Glu Ser Glu Lys His
                595                 600                 605

Arg Glu Pro Leu Arg Gly Arg Thr Gly Phe Val Ile Lys Ala Val Tyr
                610                 615                 620

Glu Gly Lys Thr Thr Phe Tyr Glu Val Phe Pro Leu Ser Met Ile Val
625                 630                 635                 640

Arg Tyr Arg Pro Asp Leu Glu Ala Leu Leu Lys Asn Gly Val Val Gly
                645                 650                 655

Ile Asp Phe Trp Asp Ile Leu Pro Pro Thr Arg Ile Pro Val Ala Val
                660                 665                 670

Tyr Asn Gly Ile Thr Met Pro Phe Asp Gln Gly Ala Tyr Leu Asn Gly
                675                 680                 685

Gln Leu Pro Glu Pro Gly Ala Ser Ala Val Met Ile Ala Glu Thr Ile
690                 695                 700

Gly Glu Arg Phe Asp Ser Ser Ser Ala Glu Val Gly Gln His Gln Pro
705                 710                 715                 720

Pro Thr Ser Phe Ser Lys Arg Ser Thr Gly Ile Ala Glu Thr Ile Thr
                725                 730                 735

Thr Ser Leu Phe Tyr Val Asn Glu Asp Ala Leu Phe Ala His Cys Lys
                740                 745                 750

Ser Leu Thr Gln Val Glu Ile Asp Asn Gly Ala Pro Gly Ala Leu Glu
                755                 760                 765

Glu Val Ser Ser Phe Leu Ile His Leu Thr Pro Trp Pro Glu Ile Glu
770                 775                 780

Asn Ile Leu Ser Gly Glu Lys Ala Leu Met Arg Gly Gly Ala Ile Gly
785                 790                 795                 800

Leu Ala Leu Tyr Met Ile Pro Tyr Val Gly Pro Ala Gly Lys Leu Leu
                805                 810                 815

Ala Gly Thr Ala Lys Val Val Thr Arg Leu Gly Lys Ser Leu Ile Thr
                820                 825                 830

Ser Gly Ser Lys Val Gln Val Ser Lys Leu Leu Ile Thr Ala Gly Thr
                835                 840                 845

Thr Leu Lys Asp Ala Pro Leu Ile Met Ile Arg Gln Ala Pro Asp Met
850                 855                 860

Thr Ser Lys Ala Met Thr Gly Val Ser Gln Phe Val Lys His Val
865                 870                 875                 880

Thr Trp Lys Phe Leu Ala Ile Arg Ile Gly Ile Gly Leu Ser Arg Arg
                885                 890                 895

Leu Val Ala Ile Met Ser Arg Gln Gln Ala Gln Ala Ala Lys Gln Glu
                900                 905                 910

Ala Thr

<210> SEQ ID NO 91
<211> LENGTH: 882
<212> TYPE: DNA
<213> ORGANISM: Pseudomonas syringae pv. tomato DC3000

<400> SEQUENCE: 91
atgtctgtta cttcatctgt cctgcgactg tcgcgcctga gcgtgtcgtt atcactttttg    60
```

-continued

```
ggcatgctgt cgtctgcact gtttgccggc gcggcattcg ccagcgacga dacgcaactg    120
atcgaatccc tcaacgccta ccgtggccag gcgcagcgct gtggcgagca ggtgtccatg    180
gaactgccgc cgctgagcac cgacccgcgt ctggtgctgc cgccagtgg caacctgaac    240 ctgcaacagt cgctgacccg cgcgtcttat ccgatggtca ccgtgcaggc gatcagtctg    300
tccggaccgc gagatgcggc gtcggcgttg aaggcggtgc aggagagttt ctgccgcgtg    360
gtgctggacc cgcagttcgt cgatatcggg gtcagccggg acgggcgcga ctggcgcatc    420
gtgctggcgc gctcgctggt ggcatcacgt ctgggtgact ggcaagcaga aggtcagaaa    480
attctggaga tgatcaacac cgcccgtacc caggcgcgtc agtgcggttc gcaatccttc    540
gcggccacta caccgttgag ctggaatcag gtattgggga cggccgcaca aggacactcg    600
caggcaatgg ccaatcagaa cttctttgac acaaggggc gcgacggccg cacgccgggt    660
gacagggccg agcttgccgg ctatctgggg cagcagatcg gtgagaatat tgccgcaggc    720
caggacactg cccgcaaggt ggtggacggc tggctggtca gcccgggcca ctgcgcaaac    780
ctgatgaccc ccggttttcg cgagctggga ccgcctacg cgatggaccc caaaagtgac    840
gcggggattt actggacagc catgttcggc acgcagcaat ag                       882
```

<210> SEQ ID NO 92
<211> LENGTH: 293
<212> TYPE: PRT
<213> ORGANISM: Pseudomonas syringae pv. tomato DC3000

<400> SEQUENCE: 92

```
Met Ser Val Thr Ser Val Leu Arg Leu Ser Arg Leu Ser Val Ser
 1               5                  10                  15

Leu Ser Leu Leu Gly Met Leu Ser Ser Ala Leu Phe Ala Gly Ala Ala
                20                  25                  30

Phe Ala Ser Asp Glu Thr Gln Leu Ile Glu Ser Leu Asn Ala Tyr Arg
            35                  40                  45

Gly Gln Ala Gln Arg Cys Gly Glu Gln Val Ser Met Glu Leu Pro Pro
        50                  55                  60

Leu Ser Thr Asp Pro Arg Leu Val Leu Pro Ala Ser Gly Asn Leu Asn
    65                  70                  75                  80

Leu Gln Gln Ser Leu Thr Arg Ala Ser Tyr Pro Met Val Thr Val Gln
                85                  90                  95

Ala Ile Ser Leu Ser Gly Pro Arg Asp Ala Ala Ser Ala Leu Lys Ala
            100                 105                 110

Val Gln Glu Ser Phe Cys Arg Val Val Leu Asp Pro Gln Phe Val Asp
        115                 120                 125

Ile Gly Val Ser Arg Asp Gly Arg Asp Trp Arg Ile Val Leu Ala Arg
    130                 135                 140

Ser Leu Val Ala Ser Arg Leu Gly Asp Trp Gln Ala Glu Gly Gln Lys
145                 150                 155                 160

Ile Leu Glu Met Ile Asn Thr Ala Arg Thr Gln Ala Arg Gln Cys Gly
                165                 170                 175

Ser Gln Ser Phe Ala Ala Thr Thr Pro Leu Ser Trp Asn Gln Val Leu
            180                 185                 190

Gly Thr Ala Ala Gln Gly His Ser Gln Ala Met Ala Asn Gln Asn Phe
        195                 200                 205

Phe Asp His Lys Gly Arg Asp Gly Arg Thr Pro Gly Asp Arg Ala Glu
    210                 215                 220

Leu Ala Gly Tyr Leu Gly Gln Gln Ile Gly Glu Asn Ile Ala Ala Gly
```

Gln Asp Thr Ala Arg Lys Val Val Asp Gly Trp Leu Val Ser Pro Gly
225                 230                 235                 240

His Cys Ala Asn Leu Met Thr Pro Gly Phe Arg Glu Leu Gly Ala Ala
            245                 250                 255

Tyr Ala Met Asp Pro Lys Ser Asp Ala Gly Ile Tyr Trp Thr Ala Met
        260                 265                 270

Phe Gly Thr Gln Gln
        275                 280                 285

Phe Gly Thr Gln Gln
    290

<210> SEQ ID NO 93
<211> LENGTH: 1533
<212> TYPE: DNA
<213> ORGANISM: Pseudomonas syringae pv. tomato DC3000

<400> SEQUENCE: 93

```
atgccgttat taaactggtc cagacacatg gttcatttaa cagccatcgg ccttatcagc      60
attccggctg cctatgcagc ggacaccctg acccgcgaca atggcgcagc ggtcggcgac     120
aaccagaact ctcagactgc aggcgcccaa gggcctgtcc tgctgcaaga cgtacagctg     180
ctgcagaagc tgcagcgttt tgatcgcgag cgtatcccgg agcgtgtggt ccacgcacgc     240
ggcactggcg tgaaaggcga attcacagcg tccgccgaca tcagcgacct gagcaaggcg     300
accgtcttca aatcgggtga agaccccg gtattcgtac gttttcttc cgtggtccac        360
ggcaaccact cgccagaaac cctgcgcgac ccgcatggct cgccaccaa gttctacacc      420
gctgatggca actgggacct ggtaggcaac aacttcccga cgttcttcat ccgcgacgcc     480
atcaagttcc cggacatggt gcacgccttc aagcctgacc cgcgtaccaa cctgacaaac     540
gactcgcgcc gcttcgactt cttctcgcat gtaccggaag ccacgcgcac gctgaccctg     600
ctgtactcca cgaaggcac accgaccggc tatcgcttca tggacggcaa cggcgttcac      660
gcctacaaac tggtcaacgc caaaggcgaa gtgcactacg tcaagttcca ctggaagacg     720
ctgcaaggca tcaagaacct cgaccctaaa gaagtcgctc aggttcagtc caaggactac     780
agccacctga ccaacgacct ggtcggcgcc atcaagaagg gtgacttccc gaaatgggac     840
ctgtacatcc aggtgctgaa acctgaagac ctggccaagt cgacttcga cccgctggac      900
gccaccaaaa tctggcctga tgtgccagag aagaaaatcg ccagatggt cctgaacaag     960
aacgtcgaca cttcttcca ggaaaccgag caggtcgcca tggcacccgc caacctggtc     1020
cctggtatcg agccttccga agaccgtctg ctgcaaggtc gagtgttctc ctatgccgac    1080
acgcaaatgt atcgcctggg tgccaacggc ctgagcctgc cggtcaacca gccaaaggtt    1140
gcagtgaaca acggcaatca ggatggcgcg atgaacagcg gcaaaaccac cagcggcgtg    1200
aactacgagc ctagccgtct ggaaccccgt cctgccgatg agaaagcacg ttacagcgag    1260
ctgccaatca gcggcactac ccagcaggcg aagatcacgc gtgagcagaa cttcaagcag    1320
gcgggtgatc tgtatcgctc ttacaacgcg aaagagcaga ccgacctggt gcagagcttc    1380
ggtgaatcgc tggccgacac tgacaccgaa agcaagaaca tcatgctgtc gttcctctac    1440
aaggcagacc ccacctatgg cactcgggta accgaagcgg ccaaaggcga tctggccaag    1500
gtcaagtcac tggctgccag cctgaaagac tga                                  1533
```

<210> SEQ ID NO 94
<211> LENGTH: 510
<212> TYPE: PRT
<213> ORGANISM: Pseudomonas syringae pv. tomato DC3000

<400> SEQUENCE: 94

```
Met Pro Leu Leu Asn Trp Ser Arg His Met Val His Leu Thr Ala Ile
 1               5                  10                  15

Gly Leu Ile Ser Ile Pro Ala Ala Tyr Ala Ala Asp Thr Leu Thr Arg
             20                  25                  30

Asp Asn Gly Ala Ala Val Gly Asp Asn Gln Asn Ser Gln Thr Ala Gly
         35                  40                  45

Ala Gln Gly Pro Val Leu Leu Gln Asp Val Gln Leu Leu Gln Lys Leu
     50                  55                  60

Gln Arg Phe Asp Arg Glu Arg Ile Pro Glu Arg Val His Ala Arg
 65                  70                  75                  80

Gly Thr Gly Val Lys Gly Glu Phe Thr Ala Ser Ala Asp Ile Ser Asp
                 85                  90                  95

Leu Ser Lys Ala Thr Val Phe Lys Ser Gly Glu Lys Thr Pro Val Phe
            100                 105                 110

Val Arg Phe Ser Val Val His Gly Asn His Ser Pro Glu Thr Leu
            115                 120                 125

Arg Asp Pro His Gly Phe Ala Thr Lys Phe Tyr Thr Ala Asp Gly Asn
130                 135                 140

Trp Asp Leu Val Gly Asn Asn Phe Pro Thr Phe Phe Ile Arg Asp Ala
145                 150                 155                 160

Ile Lys Phe Pro Asp Met Val His Ala Phe Lys Pro Asp Pro Arg Thr
                165                 170                 175

Asn Leu Asp Asn Asp Ser Arg Arg Phe Asp Phe Phe Ser His Val Pro
            180                 185                 190

Glu Ala Thr Arg Thr Leu Thr Leu Leu Tyr Ser Asn Glu Gly Thr Pro
        195                 200                 205

Thr Gly Tyr Arg Phe Met Asp Gly Asn Gly Val His Ala Tyr Lys Leu
    210                 215                 220

Val Asn Ala Lys Gly Glu Val His Tyr Val Lys Phe His Trp Lys Thr
225                 230                 235                 240

Leu Gln Gly Ile Lys Asn Leu Asp Pro Lys Glu Val Ala Gln Val Gln
                245                 250                 255

Ser Lys Asp Tyr Ser His Leu Thr Asn Asp Leu Val Gly Ala Ile Lys
            260                 265                 270

Lys Gly Asp Phe Pro Lys Trp Asp Leu Tyr Ile Gln Val Leu Lys Pro
        275                 280                 285

Glu Asp Leu Ala Lys Phe Asp Phe Asp Pro Leu Asp Ala Thr Lys Ile
    290                 295                 300

Trp Pro Asp Val Pro Glu Lys Lys Ile Gly Gln Met Val Leu Asn Lys
305                 310                 315                 320

Asn Val Asp Asn Phe Phe Gln Glu Thr Glu Gln Val Ala Met Ala Pro
                325                 330                 335

Ala Asn Leu Val Pro Gly Ile Glu Pro Ser Glu Asp Arg Leu Leu Gln
            340                 345                 350

Gly Arg Val Phe Ser Tyr Ala Asp Thr Gln Met Tyr Arg Leu Gly Ala
        355                 360                 365

Asn Gly Leu Ser Leu Pro Val Asn Gln Pro Lys Val Ala Val Asn Asn
    370                 375                 380

Gly Asn Gln Asp Gly Ala Met Asn Ser Gly Lys Thr Thr Ser Gly Val
385                 390                 395                 400

Asn Tyr Glu Pro Ser Arg Leu Glu Pro Arg Pro Ala Asp Glu Lys Ala
                405                 410                 415
```

```
Arg Tyr Ser Glu Leu Pro Ile Ser Gly Thr Thr Gln Gln Ala Lys Ile
            420                 425                 430

Thr Arg Glu Gln Asn Phe Lys Gln Ala Gly Asp Leu Tyr Arg Ser Tyr
435                 440                 445

Asn Ala Lys Glu Gln Thr Asp Leu Val Gln Ser Phe Gly Glu Ser Leu
    450                 455                 460

Ala Asp Thr Asp Thr Glu Ser Lys Asn Ile Met Leu Ser Phe Leu Tyr
465                 470                 475                 480

Lys Ala Asp Pro Thr Tyr Gly Thr Arg Val Thr Glu Ala Ala Lys Gly
                485                 490                 495

Asp Leu Ala Lys Val Lys Ser Leu Ala Ala Ser Leu Lys Asp
            500                 505                 510

<210> SEQ ID NO 95
<211> LENGTH: 489
<212> TYPE: DNA
<213> ORGANISM: Pseudomonas syringae pv. tomato DC3000

<400> SEQUENCE: 95 atggggggttt cgagctgcgg caaaagtgcc gtcggtgcag aaatcgcccg taacagcggc      60
ggtcgcctga tcgaaggcga tgcgttccat ccccaggcca acatcgacaa gatgagcgcc     120
ggcacccccc tcaccgacga agaccgtgcc ggctggctga cccgtctggg tgaagaactg     180
gccgcagccc ttgccaaggg cgaacatccg gtgctgacct gttcggcact caagctcatt     240
tatcgtgaac gcctgcgtgc ggcggtgccg ggcctgggtt ttgtcttttct cgaactgagc     300 aaagagctgg ccaccgagcg ttgcgccaac cggaccgggc atttcatgcc tgcgagtctg     360
gtcgatagcc agttcgcgac cctggaacca ccgatcggcg agccactgac cctggtggtc     420
gatgccagca agcctatcga tgtaattggt gaacaagccg cggcatggtg gaaaggctct     480
cacgcctga                                                              489

<210> SEQ ID NO 96
<211> LENGTH: 162
<212> TYPE: PRT
<213> ORGANISM: Pseudomonas syringae pv. tomato DC3000

<400> SEQUENCE: 96

Met Gly Val Ser Ser Cys Gly Lys Ser Ala Val Gly Ala Glu Ile Ala
 1                5                  10                  15

Arg Asn Ser Gly Gly Arg Leu Ile Glu Gly Asp Ala Phe His Pro Gln
            20                  25                  30

Ala Asn Ile Asp Lys Met Ser Ala Gly Thr Pro Leu Thr Asp Glu Asp
        35                  40                  45

Arg Ala Gly Trp Leu Thr Arg Leu Gly Glu Glu Leu Ala Ala Ala Leu
    50                  55                  60

Ala Lys Gly Glu His Pro Val Leu Thr Cys Ser Ala Leu Lys Leu Ile
65                  70                  75                  80

Tyr Arg Glu Arg Leu Arg Ala Ala Val Pro Gly Leu Gly Phe Val Phe
                85                  90                  95

Leu Glu Leu Ser Lys Glu Leu Ala Thr Glu Arg Cys Ala Asn Arg Thr
            100                 105                 110

Gly His Phe Met Pro Ala Ser Leu Val Asp Ser Gln Phe Ala Thr Leu
        115                 120                 125

Glu Pro Pro Ile Gly Glu Pro Leu Thr Leu Val Val Asp Ala Ser Lys
    130                 135                 140

Pro Ile Asp Val Ile Gly Glu Gln Ala Ala Ala Trp Trp Lys Gly Ser
```

```
                145                 150                 155                 160

His Ala

<210> SEQ ID NO 97
<211> LENGTH: 3405
<212> TYPE: DNA
<213> ORGANISM: Pseudomonas syringae pv. tomato DC3000

<400> SEQUENCE: 97
atgcgaccgg tgtctatgtt ttccctgcgt tccatttgtg ctgccgcact gtttgcgctt      60
tgcctgtcta tcttcccggc gctggccgcc gagccgccca cccgcgatgc cgtgcagcaa     120
agcctcgaca agattgccga ccgcaagctg ccggatgccg atcagaaggc cttgcagcag     180
gtgcttgagc agacgctggc gtttctcaac agcaaagacg cagcgagca aaagctgacc      240 gcgctcaagc agcagctggc tcaagcgcca aaacagacct cggacaacca gcgcgagctg     300
gcccggttga agaaagcaa agtcgttgcc gttgcacagc gctacggtgg cctcgatgtg      360
ccgcaactgg agcaactgct cagccagcgc agcacccagc aaagtgatct gcaaagcgag     420
cttaacgacg ccaacagcct ggccatcacc gcgcaaaccc ggccggagcg ggcgcagact     480
gaaatcagcg ccaatcagac acgcatccag cagatcaatg ccatcctcaa gaatggcaaa     540
gacaacggca agaccctgag tgccgatcag cgcaatctgc tcaatgcgga actggcctcg     600
atcaacgcgc tgaacctgct gcgccgtcag gaactggccg gcaacagcca gttacaggac     660
ctgggcaaca gccagcacga cttgctgacc gaaaaagtcg cccgccagga gcaggaaatt     720
caggacctgc aaaccctgat caacgacaag cgccgagccc agtcgcagaa accgtggcg      780 gacctgtctc tggaagcgca gaaatccggt ggcagcagcc tcctggcgac cgagagcgcc     840
gccaacctca gctgtccga ttacctgctg cgcggcaccg accgtctcaa cgagctgacc      900
cagcaaaacc tcaagaccaa gcagcaactg gacaacctga cgcagaccga tcaagccctc     960
agcgagcaga tcaacgtgct gagcggcagc ctgctgctgt ccaagattct ctacaagcaa    1020
aaacagtcgt tgccgcacct ggaactggac aaaggcctgg ctgacgaaat cgccaacatc    1080
cgcctttatc agttcgacat caatcagcaa cgcgagcaga tgagcacacc gaccgcttac    1140
gtcgaacgac tgctcgccac ccagcccccg gaaaatatca ccccgcaact gcgcaggacg    1200
ctgcttgatc tggccatcac ccgcagcgac ctgctcgaac gcctgaaccg cgagctgagc    1260
gcgttgctca acgagtccat cacgctgcaa ttgaaccaga agcagttgac cagtaccgcc    1320
gtcggcctgc gctccacgct ggacgagcag atgttctgga tccccagcaa caagccgctg    1380
gatctggagt ggttccagaa catctggccg cgcctgcaaa acaggtcgc gaccctgccc     1440 tggacgtcca gcctcagcga gctgtcggac ggcttgacac aacgcccgct gctgtttctg    1500
ccattgttac tgctgatcgg tgtactgacc tggaggcgca aggcgcttta ccagaagctc    1560
aaccggctgc acgccgacat cggccacttc aaacgcgaca gtcagtggaa accccgttg     1620 gcgctgctga tcaacgtgct gctggccatg ccggtcgcat ggggctggc gctgtgcggc     1680 tacgccttgc aaatcgatgc gcgcgggcaa acgccaacc ttggcgaggc cttgctgcag     1740
atcgcgctgg cctggctagt gttctacacc gcctaccgcg tgctggcccc gtccggcgtt    1800
gcgcaactgc actttcgctg gaaccggcg caggtcgcgt tcttgcgcgg ctgggttcgt      1860
cgcctggggt tggtggtgct ggcgctggtc ccgtggtgg cggtcgccga gcatcaaccg     1920
gccgcgctgg ccgacgacgt gctgggtatc ggcgtggtgc tgacctgtta cgcgctgatg    1980
acctggctgc tgggccgatt gctgctctcc agccctacgc accacaacgc gtcgctgttc    2040
```

```
cgcaagacgc tgggtgtggc gttcacggca ttgccggtcg cgctgtttct ggcggtgtgc    2100
ttcggctact actacaccgc actcaagctc agcgaccgtc tgatcgacac gctgtacctg    2160
atgatgatct ggctgatggt cgaggccacc ttcgttcgtg gtctgggcgt tgccgcgcgg    2220
cgactggcct accagcgtgc gctggccaaa cgtcaggctg cgcgagaaaa cggtgacagc    2280
gacatccccg tcgaagaacc gaaactggac atcgaacagg tcaaccagca gtcgctgcgc    2340
ctgattcgtc tggccttgct ggctggtttc gtcggcgcgt tgtacctggt ctgggccgag    2400
ctgatcacgg tgttcgccta cctggacaac atcatcctct acgaataccc aagcggcaca    2460
ggcgccaaca tgagcatggt gccgatcagc ctgagcgact tcctcggtgc cggggtcatc    2520
atcgtcatta cctttgtgct ggcgggcaac ctgcccggct tgctcgaggt gctggttctg    2580
tcacgcatga acctggcgca aggcagcgcc tatgcgacca ccacgctgct ctcctacacc    2640
atcgccggca tcggctttgt gaccacgctg tccacattag gcgtgagctg ggacaagctg    2700
cagtggctgg tcgcagcgct gtcggtgggc ctggggttcg gcatgcagga gatcttcgcc    2760
aacttcattt ccggcatcat gatcctcttc gagcgcccgg tacggatcgg cgacaccatc    2820
accatcggcg ccctgtcggg tacggtcagc aagatccgca tccgcgccac gaccatcacc    2880
gacttcgacc gcaaggacat tatcgtcccg aacaagacct tcatcaccgg ccagctcatc    2940
aactggtcac tgactgacac cgtcacccgc gtaacgctca agctgggtgt ggattacggc    3000
tcggacctgg acctcgtgcg ctccctgctg ctgcaagccg cacgggaaaa ccctcgggtg    3060
ctcaaggagc agagcccat tgtctacttc ctgaacttcg gcgaaagcac cctcgaccac    3120
gaactgcgca tgcacgttcg cgacctgggc gaccgcaacc cggtactcga cgagatcaac    3180
cgcttcatca ccgcgagtt caagaaacag cacatcaaca tctcgttccg ccagatggag    3240
atctacctca aaaacaccca gggcctggaa tacaaactgg tgcccgccga accaggcgaa    3300
aagcacggcg caccggctgg gcaaaccacg ctgcaaccgg taaacaccaa agtagccccg    3360
gcaaccaaag atgcgccaga gccgccggag ttgaggctgg actga                   3405
```

<210> SEQ ID NO 98
<211> LENGTH: 1134
<212> TYPE: PRT
<213> ORGANISM: Pseudomonas syringae pv. tomato DC3000

<400> SEQUENCE: 98

```
Met Arg Pro Val Ser Met Phe Ser Leu Arg Ser Ile Cys Ala Ala Ala
  1               5                  10                  15

Leu Phe Ala Leu Cys Leu Ser Ile Phe Pro Ala Leu Ala Ala Glu Pro
             20                  25                  30

Pro Thr Arg Asp Ala Val Gln Gln Ser Leu Asp Lys Ile Ala Asp Arg
         35                  40                  45

Lys Leu Pro Asp Ala Asp Gln Lys Ala Leu Gln Gln Val Leu Glu Gln
     50                  55                  60

Thr Leu Ala Phe Leu Asn Ser Lys Asp Asp Ser Glu Gln Lys Leu Thr
 65                  70                  75                  80

Ala Leu Lys Gln Gln Leu Ala Gln Ala Pro Lys Gln Thr Ser Asp Asn
                 85                  90                  95

Gln Arg Glu Leu Ala Arg Leu Lys Glu Ser Lys Val Val Ala Val Ala
            100                 105                 110

Gln Arg Tyr Gly Gly Leu Asp Val Pro Gln Leu Glu Gln Leu Leu Ser
        115                 120                 125

Gln Arg Ser Thr Gln Gln Ser Asp Leu Gln Ser Glu Leu Asn Asp Ala
    130                 135                 140
```

-continued

```
Asn Ser Leu Ala Ile Thr Ala Gln Thr Arg Pro Glu Arg Ala Gln Thr
145                 150                 155                 160
Glu Ile Ser Ala Asn Gln Thr Arg Ile Gln Gln Ile Asn Ala Ile Leu
                165                 170                 175
Lys Asn Gly Lys Asp Asn Gly Lys Thr Leu Ser Ala Asp Gln Arg Asn
            180                 185                 190
Leu Leu Asn Ala Glu Leu Ala Ser Ile Asn Ala Leu Asn Leu Leu Arg
        195                 200                 205
Arg Gln Glu Leu Ala Gly Asn Ser Gln Leu Gln Asp Leu Gly Asn Ser
    210                 215                 220
Gln His Asp Leu Leu Thr Glu Lys Val Ala Arg Gln Glu Gln Glu Ile
225                 230                 235                 240
Gln Asp Leu Gln Thr Leu Ile Asn Asp Lys Arg Ala Gln Ser Gln
                245                 250                 255
Lys Thr Val Ala Asp Leu Ser Leu Glu Ala Gln Lys Ser Gly Gly Ser
            260                 265                 270
Ser Leu Leu Ala Thr Glu Ser Ala Ala Asn Leu Lys Leu Ser Asp Tyr
        275                 280                 285
Leu Leu Arg Gly Thr Asp Arg Leu Asn Glu Leu Thr Gln Gln Asn Leu
        290                 295                 300
Lys Thr Lys Gln Gln Leu Asp Asn Leu Thr Gln Thr Asp Gln Ala Leu
305                 310                 315                 320
Ser Glu Gln Ile Asn Val Leu Ser Gly Ser Leu Leu Leu Ser Lys Ile
                325                 330                 335
Leu Tyr Lys Gln Lys Gln Ser Leu Pro His Leu Glu Leu Asp Lys Gly
            340                 345                 350
Leu Ala Asp Glu Ile Ala Asn Ile Arg Leu Tyr Gln Phe Asp Ile Asn
        355                 360                 365
Gln Gln Arg Glu Gln Met Ser Thr Pro Thr Ala Tyr Val Glu Arg Leu
    370                 375                 380
Leu Ala Thr Gln Pro Pro Glu Asn Ile Thr Pro Gln Leu Arg Arg Thr
385                 390                 395                 400
Leu Leu Asp Leu Ala Ile Thr Arg Ser Asp Leu Leu Glu Arg Leu Asn
                405                 410                 415
Arg Glu Leu Ser Ala Leu Leu Asn Glu Ser Ile Thr Leu Gln Leu Asn
            420                 425                 430
Gln Lys Gln Leu Thr Ser Thr Ala Val Gly Leu Arg Ser Thr Leu Asp
        435                 440                 445
Glu Gln Met Phe Trp Ile Pro Ser Asn Lys Pro Leu Asp Leu Glu Trp
    450                 455                 460
Phe Gln Asn Ile Trp Pro Arg Leu Gln Lys Gln Val Ala Thr Leu Pro
465                 470                 475                 480
Trp Thr Ser Ser Leu Ser Glu Leu Ser Asp Gly Leu Thr Gln Arg Pro
                485                 490                 495
Leu Leu Phe Leu Pro Leu Leu Leu Ile Gly Val Leu Thr Trp Arg
            500                 505                 510
Arg Lys Ala Leu Tyr Gln Lys Leu Asn Arg Leu His Ala Asp Ile Gly
        515                 520                 525
His Phe Lys Arg Asp Ser Gln Trp Lys Thr Pro Leu Ala Leu Leu Ile
    530                 535                 540
Asn Val Leu Leu Ala Met Pro Val Ala Leu Gly Leu Ala Leu Cys Gly
545                 550                 555                 560
Tyr Ala Leu Gln Ile Asp Ala Arg Gly Gln Asn Ala Asn Leu Gly Glu
```

```
                565                 570                 575
Ala Leu Leu Gln Ile Ala Leu Ala Trp Leu Val Phe Tyr Thr Ala Tyr
                580                 585                 590

Arg Val Leu Ala Pro Ser Gly Val Ala Gln Leu His Phe Arg Trp Glu
                595                 600                 605

Pro Ala Gln Val Ala Phe Leu Arg Gly Trp Val Arg Arg Leu Gly Leu
                610                 615                 620

Val Val Leu Ala Leu Val Ala Val Val Ala Val Ala Glu His Gln Pro
625                 630                 635                 640

Ala Ala Leu Ala Asp Asp Val Leu Gly Ile Gly Val Val Leu Thr Cys
                645                 650                 655

Tyr Ala Leu Met Thr Trp Leu Leu Gly Arg Leu Leu Leu Ser Ser Pro
                660                 665                 670

Thr His His Asn Ala Ser Leu Phe Arg Lys Thr Leu Gly Val Ala Phe
                675                 680                 685

Thr Ala Leu Pro Val Ala Leu Phe Leu Ala Val Cys Phe Gly Tyr Tyr
                690                 695                 700

Tyr Thr Ala Leu Lys Leu Ser Asp Arg Leu Ile Asp Thr Leu Tyr Leu
705                 710                 715                 720

Met Met Ile Trp Leu Met Val Glu Ala Thr Phe Val Arg Gly Leu Gly
                725                 730                 735

Val Ala Ala Arg Arg Leu Ala Tyr Gln Arg Ala Leu Ala Lys Arg Gln
                740                 745                 750

Ala Ala Arg Glu Asn Gly Asp Ser Asp Ile Pro Val Glu Glu Pro Lys
                755                 760                 765

Leu Asp Ile Glu Gln Val Asn Gln Gln Ser Leu Arg Leu Ile Arg Leu
                770                 775                 780

Ala Leu Leu Ala Gly Phe Val Gly Ala Leu Tyr Leu Val Trp Ala Glu
785                 790                 795                 800

Leu Ile Thr Val Phe Ala Tyr Leu Asp Asn Ile Leu Tyr Glu Tyr
                805                 810                 815

Thr Ser Gly Thr Gly Ala Asn Met Ser Met Val Pro Ile Ser Leu Ser
                820                 825                 830

Asp Phe Leu Gly Ala Gly Val Ile Ile Val Ile Thr Phe Val Leu Ala
                835                 840                 845

Gly Asn Leu Pro Gly Leu Leu Glu Val Leu Val Leu Ser Arg Met Asn
                850                 855                 860

Leu Ala Gln Gly Ser Ala Tyr Ala Thr Thr Thr Leu Leu Ser Tyr Thr
865                 870                 875                 880

Ile Ala Gly Ile Gly Phe Val Thr Thr Leu Ser Thr Leu Gly Val Ser
                885                 890                 895

Trp Asp Lys Leu Gln Trp Leu Val Ala Ala Leu Ser Val Gly Leu Gly
                900                 905                 910

Phe Gly Met Gln Glu Ile Phe Ala Asn Phe Ile Ser Gly Ile Met Ile
                915                 920                 925

Leu Phe Glu Arg Pro Val Arg Ile Gly Asp Thr Ile Thr Ile Gly Ala
                930                 935                 940

Leu Ser Gly Thr Val Ser Lys Ile Arg Ile Arg Ala Thr Thr Ile Thr
945                 950                 955                 960

Asp Phe Asp Arg Lys Asp Ile Ile Val Pro Asn Lys Thr Phe Ile Thr
                965                 970                 975

Gly Gln Leu Ile Asn Trp Ser Leu Thr Asp Thr Val Arg Val Thr
                980                 985                 990
```

```
Leu Lys Leu Gly Val Asp Tyr Gly Ser Asp Leu Asp Leu Val Arg Ser
        995                1000                1005

Leu Leu Leu Gln Ala Ala Arg Glu Asn Pro Arg Val Leu Lys Glu Pro
    1010                1015                1020

Glu Pro Ile Val Tyr Phe Leu Asn Phe Gly Glu Ser Thr Leu Asp His
1025                1030                1035                1040

Glu Leu Arg Met His Val Arg Asp Leu Gly Asp Arg Asn Pro Val Leu
        1045                1050                1055

Asp Glu Ile Asn Arg Phe Ile Asn Arg Glu Phe Lys Lys Gln His Ile
            1060                1065                1070

Asn Ile Ser Phe Arg Gln Met Glu Ile Tyr Leu Lys Asn Thr Gln Gly
        1075                1080                1085

Leu Glu Tyr Lys Leu Val Pro Ala Glu Pro Gly Glu Lys His Gly Ala
    1090                1095                1100

Pro Ala Gly Gln Thr Thr Leu Gln Pro Val Asn Thr Lys Val Ala Pro
1105                1110                1115                1120

Ala Thr Lys Asp Ala Pro Glu Pro Pro Glu Leu Arg Leu Asp
        1125                1130
```

<210> SEQ ID NO 99
<211> LENGTH: 1113
<212> TYPE: DNA
<213> ORGANISM: Pseudomonas syringae pv. tomato DC3000

<400> SEQUENCE: 99

```
atgtcaacgt tgaatcatac gtctgctgta aattgccgcg tcagttttga tggtgaccgt      60
tgctatgtag acaccccccat ccagatcatg ccgggtgagc gatgggctgt aaatatcgta    120
cctaacgatt tagtcacaat ccactacgag gccgccagca atcacgacta cccctttgctg   180
ctggccagca taaaaaatct gtttaccgat gagcgttgtg tcgtgctaaa gcccggcctt     240
acacagcaag ctttgaacat gtattttttca gaggttaaca gccttaaacc taacgcgact     300
catgttcgct tgttgcatcg agcgcagcgt attttttctag aaaacatgat ccgtagcgta    360
cagataaccct cgcaaggtat cagcgtcact ttcgcaaccg ccgaattcaa aaattataac    420
taccagctaa aggtggataa atatactttt gcaaggcttg acaaggggta ccctctctat     480
tcggagctgg ttgaaaacac ctggataacg aaattatccg tagcccataa tattctgtat     540
tccatctctg tgagcctgga ccactcaagc acaccttata cactttttttc aggaaccctc    600
gcggaagaca atatagtcca gccgatacgg gcgcttttca ccgacaacac catgactcaa    660
ctcacctcct tggccgatca gaaaaccgtg gatgccttgt atacgacggt caatggcaac    720
ccggttatca gcatcaaaaa acgcgcagat tatcggtctt atctgaacat cgcacagaag    780
ttactgcttc caagaaccta caccaaagta gtacggacag tgagcagcct gtctgtgcat    840
tttacggggg aggcgtacaa acaattcaac tacaagatgc ttgtcaacaa tgcttatgca    900
tccgagatca cccgagggaa ggcttattac tccagcgtga gcaatggggt gtggaccact    960
tccggtacgc atgacagcga cgacaactgc aaagtcactt gtgattacaa gggcgcaacc   1020
tacgtcctgt acgagagtaa tgcggcagat agacgcactg aaacctgggc acaagacccg   1080
tacgttactc attgcgaccc gagagacctg taa                                1113
```

<210> SEQ ID NO 100
<211> LENGTH: 370
<212> TYPE: PRT
<213> ORGANISM: Pseudomonas syringae pv. tomato DC3000

<400> SEQUENCE: 100

Met Ser Thr Leu Asn His Thr Ser Ala Val Asn Cys Arg Val Ser Phe
1               5                   10                  15

Asp Gly Asp Arg Cys Tyr Val Asp Thr Pro Ile Gln Ile Met Pro Gly
            20                  25                  30

Glu Arg Trp Ala Val Asn Ile Val Pro Asn Asp Leu Val Thr Ile His
        35                  40                  45

Tyr Glu Ala Ala Ser Asn His Asp Tyr Pro Leu Leu Leu Ala Ser Ile
    50                  55                  60

Lys Asn Leu Phe Thr Asp Glu Arg Cys Val Val Leu Lys Pro Gly Leu
65                  70                  75                  80

Thr Gln Gln Ala Leu Asn Met Tyr Phe Ser Glu Val Asn Ser Leu Lys
                85                  90                  95

Pro Asn Ala Thr His Val Arg Leu Leu His Arg Ala Gln Arg Ile Phe
            100                 105                 110

Leu Glu Asn Met Ile Arg Ser Val Gln Ile Thr Ser Gln Gly Ile Ser
        115                 120                 125

Val Thr Phe Ala Thr Ala Glu Phe Lys Asn Tyr Asn Tyr Gln Leu Lys
130                 135                 140

Val Asp Lys Tyr Thr Phe Ala Arg Leu Asp Lys Gly Tyr Pro Leu Tyr
145                 150                 155                 160

Ser Glu Leu Val Glu Asn Thr Trp Ile Thr Lys Leu Ser Val Ala His
                165                 170                 175

Asn Ile Leu Tyr Ser Ile Ser Val Ser Leu Asp His Ser Ser Thr Pro
            180                 185                 190

Tyr Thr Leu Phe Ser Gly Thr Leu Ala Glu Asp Asn Ile Val Gln Pro
        195                 200                 205

Ile Arg Ala Leu Phe Thr Asp Asn Thr Met Thr Gln Leu Thr Ser Leu
    210                 215                 220

Ala Asp Gln Lys Thr Val Asp Ala Leu Tyr Thr Thr Val Asn Gly Asn
225                 230                 235                 240

Pro Val Ile Ser Ile Lys Lys Arg Ala Asp Tyr Arg Ser Tyr Leu Asn
                245                 250                 255

Ile Ala Gln Lys Leu Leu Leu Pro Arg Thr Tyr Thr Lys Val Val Arg
            260                 265                 270

Thr Val Ser Ser Leu Ser Val His Phe Thr Gly Glu Ala Tyr Lys Gln
        275                 280                 285

Phe Asn Tyr Lys Met Leu Val Asn Asn Ala Tyr Ala Ser Glu Ile Thr
    290                 295                 300

Arg Gly Lys Ala Tyr Tyr Ser Ser Val Ser Asn Gly Val Trp Thr Thr
305                 310                 315                 320

Ser Gly Thr His Asp Ser Asp Asp Asn Cys Lys Val Thr Cys Asp Tyr
                325                 330                 335

Lys Gly Ala Thr Tyr Val Leu Tyr Glu Ser Asn Ala Ala Asp Arg Arg
            340                 345                 350

Thr Glu Thr Trp Ala Gln Asp Pro Tyr Val Thr His Cys Asp Pro Arg
        355                 360                 365

Asp Leu
    370

<210> SEQ ID NO 101
<211> LENGTH: 714
<212> TYPE: DNA
<213> ORGANISM: Pseudomonas syringae pv. tomato DC3000

<400> SEQUENCE: 101

```
atgcgcctga tcgcgcagat tctgcccggc ctgccggaaa acaccactta cagcgccgcc      60
gctgcgtcca cacccctggc gcgggccatg cccaacgcca ttcgcaatgc gctgggcacc     120
ctggggctgg tggctgcgcg cacccagcca agcatctttc cgttgccgtc gcgcaacgtc     180
agcggtggcg aaaagagga cgacctggag attctgctca aactcgcggc cgccgctgtt     240
tcgcgcctgc aaagccacca gttgggcggc ctggagcaga cccgtaccaa tgccgatggc     300
actcaggtga ctacatggca actggaagtg ccgatgcgca acgcccatga catcgtgccg     360
ttgcaggtca aggtgcagcg cgaagacaag cctgatcagg acgccaccga agaccgcgac     420
gatatcgaga tcaaggaaac ccgtgaaaaa ctctggaaag tcgatctggc tttcgacctg     480
gagccgcttg gccccatgca ggtgcatgcg caactgctgc gcggcacgct gtccagccag     540
ttatgggccg agcgcccgga tagcgcaaca ctgatcgaac atgaactggg gcatttgcgc     600
gagcgcctga ttgcctgcgg cctggccgtc ggggaactgg cgtgcagcca tggcgttccg     660
ccgcaagggc cgcgcaccgc cctcgaacaa cgctggatcg acgagaacgc ctga           714
```

<210> SEQ ID NO 102
<211> LENGTH: 237
<212> TYPE: PRT
<213> ORGANISM: Pseudomonas syringae pv. tomato DC3000

<400> SEQUENCE: 102

```
Met Arg Leu Ile Ala Gln Ile Leu Pro Gly Leu Pro Glu Asn Thr Thr
  1               5                  10                  15

Tyr Ser Ala Ala Ala Ser Asn Thr Leu Ala Arg Ala Met Pro Asn
             20                  25                  30

Ala Ile Arg Asn Ala Leu Gly Thr Leu Gly Leu Val Ala Ala Arg Thr
         35                  40                  45

Gln Pro Ser Ile Phe Pro Leu Pro Ser Arg Asn Val Ser Gly Gly Glu
     50                  55                  60

Lys Glu Asp Asp Leu Glu Ile Leu Leu Lys Leu Ala Ala Ala Val
 65                  70                  75                  80

Ser Arg Leu Gln Ser His Gln Leu Gly Gly Leu Glu Gln Thr Arg Thr
                 85                  90                  95

Asn Ala Asp Gly Thr Gln Val Thr Thr Trp Gln Leu Glu Val Pro Met
            100                 105                 110

Arg Asn Ala His Asp Ile Val Pro Leu Gln Val Lys Val Gln Arg Glu
        115                 120                 125

Asp Lys Pro Asp Gln Asp Ala Thr Glu Asp Arg Asp Ile Glu Ile
    130                 135                 140

Lys Glu Thr Arg Glu Lys Leu Trp Lys Val Asp Leu Ala Phe Asp Leu
145                 150                 155                 160

Glu Pro Leu Gly Pro Met Gln Val His Ala Gln Leu Leu Arg Gly Thr
                165                 170                 175

Leu Ser Ser Gln Leu Trp Ala Glu Arg Pro Asp Ser Ala Thr Leu Ile
            180                 185                 190

Glu His Glu Leu Gly His Leu Arg Glu Arg Leu Ile Ala Cys Gly Leu
        195                 200                 205

Ala Val Gly Glu Leu Ala Cys Ser His Gly Val Pro Pro Gln Gly Pro
    210                 215                 220

Arg Thr Ala Leu Glu Gln Arg Trp Ile Asp Glu Asn Ala
225                 230                 235
```

<210> SEQ ID NO 103

```
<211> LENGTH: 690
<212> TYPE: DNA
<213> ORGANISM: Pseudomonas syringae pv. tomato DC3000

<400> SEQUENCE: 103
atgagtagcg tcgcagcact gatcaccata tcgactggac agacgcagtt cgttaaagtc      60
gcgcggacgt cattttctgt gctacgaatc ccctcgccg gcagatgtcg tgtccgggat     120
cagttgacca ctacaataaa gacagagcag aaacccataa aaataggggg aagagacgtg     180
agcctaaatg atcacttgaa aaaagcattg aattctgatt ccagcgacga gcttgatgaa     240
atcaccgacc tttatgtgac gttgcctgca gaggtcttca gttgcttgac catttcactc     300
gaagggaatt ggaaggaaat tgatagcgtc tggtctgctc ggttagacgc agcagattca     360
aagaataata caaatgtca cgtccatatc gccaaaacca agcatcgatc ctcaaaaagc     420
aaacaggttt cttggaacag tgatggtagc cggcatgata aaaaaacatt cgatgtaacg     480
ctgggacaga gcagaaaggc ccaggcgata gctaggaaat ttttaggcct tggcgagtcc     540
ataagccttg aaagcaaaga ttccaagcag atggttgaaa gacctctact cagcactgct     600
acatcctttt cgaatgatgg aaaagaggtg aaggtcgagt tctacgtgga agaatccacc     660
gcccaccttc ccgcatggtt acgatggtag                                     690

<210> SEQ ID NO 104
<211> LENGTH: 229
<212> TYPE: PRT
<213> ORGANISM: Pseudomonas syringae pv. tomato DC3000

<400> SEQUENCE: 104

Met Ser Ser Val Ala Ala Leu Ile Thr Ile Ser Thr Gly Gln Thr Gln
  1               5                  10                  15

Phe Val Lys Val Ala Arg Thr Ser Phe Ser Val Leu Arg Ile Pro Leu
             20                  25                  30

Ala Gly Arg Cys Arg Val Arg Asp Gln Leu Thr Thr Thr Ile Lys Thr
         35                  40                  45

Glu Gln Lys Pro Ile Lys Ile Gly Gly Arg Asp Val Ser Leu Asn Asp
     50                  55                  60

His Leu Lys Lys Ala Leu Asn Ser Asp Ser Asp Glu Leu Asp Glu
 65                  70                  75                  80

Ile Thr Asp Leu Tyr Val Thr Leu Pro Ala Glu Val Phe Ser Cys Leu
                 85                  90                  95

Thr Ile Ser Leu Glu Gly Asn Trp Lys Glu Ile Asp Ser Val Trp Ser
            100                 105                 110

Ala Arg Leu Asp Ala Ala Asp Ser Lys Asn Asn Thr Lys Cys His Val
        115                 120                 125

His Ile Ala Lys Thr Lys His Arg Ser Ser Lys Ser Lys Gln Val Ser
    130                 135                 140

Trp Asn Ser Asp Gly Ser Arg His Asp Lys Lys Thr Phe Asp Val Thr
145                 150                 155                 160

Leu Gly Gln Ser Arg Lys Ala Gln Ala Ile Ala Arg Lys Phe Leu Gly
                165                 170                 175

Leu Gly Glu Ser Ile Ser Leu Glu Ser Lys Asp Ser Lys Gln Met Val
            180                 185                 190

Glu Arg Pro Leu Leu Ser Thr Ala Thr Ser Phe Ser Asn Asp Gly Lys
        195                 200                 205

Glu Val Lys Val Glu Phe Tyr Val Glu Glu Ser Thr Ala His Leu Pro
    210                 215                 220
```

Ala Trp Leu Arg Trp
225

<210> SEQ ID NO 105
<211> LENGTH: 2949
<212> TYPE: DNA
<213> ORGANISM: Pseudomonas syringae pv. tomato DC3000

<400> SEQUENCE: 105

| | | | | | |
|---|---|---|---|---|---|
| atgaagccaa | tccatactgc | ccgatacaac | gcctggaatc | agttggagca | ggagaccgcc | 60 |
| catgactggc | tgggggccaa | acccttggcc | agcagcaccc | ttggctaccg | ctacgatgac | 120 |
| tggaaccagc | gatgctgcac | cacgaccgat | gacaacgtac | agacttatga | gtattcagac | 180 |
| ccgatcggca | gcgacgtaca | taaaggccca | atccagaaaa | cctggaaaca | gagtggcgac | 240 |
| ccggagggcc | gcatcagtgg | ccgcagcgaa | acctggctga | atctgttcgg | caaaccggac | 300 |
| cggatccgga | cgctgaccgc | tggtaaaacg | ggtcgcagcc | gcacgcacag | catgagccgc | 360 |
| agccggaacc | tgaccacgac | tgagcaggaa | ctgagcaggc | agacctttct | gtacgacggg | 420 |
| ctgggacgct | gcaccgagca | gcgcgatgca | ctccagcaaa | gcaccctgtt | cagctacgac | 480 |
| aactggtcac | gcatggtctc | ctccacgctt | gcagacggca | gcgtcatcaa | ccggagttat | 540 |
| gcgccgcaaa | gcagcagtga | gctggcaacg | atgctcgagg | tcgtgcacca | gaacggcacc | 600 |
| accagaaccg | tggcaggtac | acagaaattt | gacgggcttg | agcgtgtgac | gcagaccaaa | 660 |
| acaggtgacc | gcgtcgaaca | gttcaactac | gacgccggtg | agatgcagcc | caggtcgcgc | 720 |
| acaacagccg | ggctggacaa | catcaacttt | acctacactc | gggcgctcac | tgatcagatt | 780 |
| ttttccagca | cggctccgga | tgaaacggcc | aaattcgatt | atgacaagac | cagtgcccgc | 840 |
| ctcatcgaag | cgacgaaccc | gcaaggcacg | cgcacttacc | gctatgacgt | gcacaatcaa | 900 |
| ctgacgggag | agacttggga | caatctgctg | ggtcaggctt | gggaaacccg | acaccaatca | 960 |
| tcgctgctgg | gtcggccgat | caagcgcacc | gatctcaaaa | aggcgaggc | ggcgggcgca | 1020 |
| gagacccgtt | acgactacga | cacgctcggc | agaatcaggt | ttatcaacca | gagcaacctg | 1080 |
| cgcaccacaa | tcgactatga | cgtgctgggc | cagctctgca | aggtggccac | cgaggacctg | 1140 |
| caggccggaa | ctggcgtgat | catcgacatg | gaatacgacg | accagggaca | ggaaattctc | 1200 |
| agaacccaga | ccgcaagcaa | ccaagcggcg | ttgaccttga | ctcaaacgtg | ggcagtggac | 1260 |
| gggcttttga | aaacccgcga | cctgcaacag | gcgggtagcc | cctgctgca | cgaaacgttt | 1320 |
| agctacgacc | ccagaggccg | cctgacactg | gtgaattacc | tgggtagcag | cttgccgaga | 1380 |
| gacgaactgc | aaagggagat | gaccagacaa | atattcagct | tcgacgagct | ggacaacatt | 1440 |
| acgctatgcc | agaccaggtt | taccgatggc | acctctgagc | gagcagcttt | caaatacggc | 1500 |
| agccccggcg | acgataagca | taaagaccgc | tgccagcttt | tgagtattgc | ctacacgccg | 1560 |
| cccagaaaaa | caccggaccc | gacattcagt | tacgacgcca | acggtaacca | gcttaaagac | 1620 |
| gagcatggca | acagtctgca | ttacgatagc | cagagccgcc | tgctgcaggt | cgcagaaacc | 1680 |
| ggcggtgccc | ctatcagcca | ataccgttat | gacggccaca | atcaactggt | cgccaccagg | 1740 |
| gatggcaatg | aaagcgagat | tttgcggttc | tatgagggtc | atcaactgag | cagcacggtg | 1800 |
| caggaagatc | aacgcactca | gtacctgcat | ctcggcgaac | agccgctggg | ccagcagatt | 1860 |
| gtggacgacg | ccgagcaaac | cctgttgcta | ctgactgacg | caaaccagag | cgttatgggt | 1920 |
| gaatttcaac | aaggccagct | gcgcaaggcg | gtctacagtg | cctacgggga | gcgccacagc | 1980 |
| gaggaggcgc | tgctgagcac | tgccgggttt | aacggtgaag | tacgcgaagc | cgccaacggc | 2040 |
| tggtatctgt | tgggcaatgg | ctaccgggcc | tacaaccctc | tcctgatgcg | cttccacagc | 2100 |

```
ccggattttc tcagcccctt cgccgaaggc ggcgtcaacc cctacaccta ctgcctgggc    2160
aaccccatcg ccctgcgcga cccgacagga catgatgcca gcggtcagac tggccggttg    2220
agacggcccg atgaggggc tttgccaatg caacaaggtg gcggagatat catgggttgg    2280
gtgggtgtag aataggcgt tgttttcacc gtattgggcg ttgccgctac catagccacg    2340
ttaggaacag ccacaccggt taccggcccg gtaactgtcc tgggcatttc catgaccgcc    2400
agcgctgccg cggccgtttc gacagtctcg accggtgcgt tgatcgtcgg tacggcattg    2460
acagcggctt caactacggc caatacagtt gccattgtaa ataacgatca gacgccgga    2520 gaagtcggcg gctggttggg tattgccgct gtgcccgttg gcttggtagg gtttggcgcg    2580
ggggctgtgg tggcgagggc agttgcggct gcggctaaag ttgcggctgc caacgctggt    2640
acgatcggtg tccgcagcgt cagcagaata ggcctcgctg ctgctggtgc ccgcagaacc    2700
atttccagcg ctgccagcag cgctcggcgc caaatcagca acatgttagg cagaatctta    2760
ccccgtgctc taaacaggac tgctgctact gcacgccgga ttccaagcgt tacaagtggc    2820
ggatcaggac cagggccatc attatttaca cagactacct ttaacgaatc gattgggatg    2880
acgcagacca ctattttttc aacgaatgcg agcggaatcc caccggccac gcaggtaact    2940
cgaatctag                                                             2949
```

<210> SEQ ID NO 106
<211> LENGTH: 982
<212> TYPE: PRT
<213> ORGANISM: Pseudomonas syringae pv. tomato DC3000

<400> SEQUENCE: 106

```
Met Lys Pro Ile His Thr Ala Arg Tyr Asn Ala Trp Asn Gln Leu Glu
  1               5                  10                  15

Gln Glu Thr Ala His Asp Trp Leu Gly Ala Lys Pro Leu Ala Ser Ser
             20                  25                  30

Thr Leu Gly Tyr Arg Tyr Asp Asp Trp Asn Gln Arg Cys Cys Thr Thr
         35                  40                  45

Thr Asp Asp Asn Val Gln Thr Tyr Glu Tyr Ser Asp Pro Ile Gly Ser
     50                  55                  60

Asp Val His Lys Gly Pro Ile Gln Lys Thr Trp Lys Gln Ser Gly Asp
 65                  70                  75                  80

Pro Glu Gly Arg Ile Ser Gly Arg Ser Glu Thr Trp Leu Asn Leu Phe
                 85                  90                  95

Gly Lys Pro Asp Arg Ile Arg Thr Leu Thr Ala Gly Lys Thr Gly Arg
            100                 105                 110

Ser Arg Thr His Ser Met Ser Arg Ser Arg Asn Leu Thr Thr Thr Glu
        115                 120                 125

Gln Glu Leu Ser Arg Gln Thr Phe Leu Tyr Asp Gly Leu Gly Arg Cys
    130                 135                 140

Thr Glu Gln Arg Asp Ala Leu Gln Gln Ser Thr Leu Phe Ser Tyr Asp
145                 150                 155                 160

Asn Trp Ser Arg Met Val Ser Ser Thr Leu Ala Asp Gly Ser Val Ile
                165                 170                 175

Asn Arg Ser Tyr Ala Pro Gln Ser Ser Ser Glu Leu Ala Thr Met Leu
            180                 185                 190

Glu Val Val His Gln Asn Gly Thr Thr Arg Thr Val Ala Gly Thr Gln
        195                 200                 205

Lys Phe Asp Gly Leu Glu Arg Val Thr Gln Thr Lys Thr Gly Asp Arg
    210                 215                 220
```

```
Val Glu Gln Phe Asn Tyr Asp Ala Gly Glu Met Gln Pro Arg Ser Arg
225                 230                 235                 240

Thr Thr Ala Gly Leu Asp Asn Ile Asn Phe Thr Tyr Thr Arg Ala Leu
            245                 250                 255

Thr Asp Gln Ile Phe Ser Ser Thr Ala Pro Asp Glu Thr Ala Lys Phe
            260                 265                 270

Asp Tyr Asp Lys Thr Ser Ala Arg Leu Ile Glu Ala Thr Asn Pro Gln
            275                 280                 285

Gly Thr Arg Thr Tyr Arg Tyr Asp Val His Asn Gln Leu Thr Gly Glu
290                 295                 300

Thr Trp Asp Asn Leu Leu Gly Gln Ala Trp Glu Thr Arg His Gln Ser
305                 310                 315                 320

Ser Leu Leu Gly Arg Pro Ile Lys Arg Thr Asp Leu Lys Lys Gly Glu
            325                 330                 335

Ala Ala Gly Ala Glu Thr Arg Tyr Asp Tyr Asp Thr Leu Gly Arg Ile
            340                 345                 350

Arg Phe Ile Asn Gln Ser Asn Leu Arg Thr Thr Ile Asp Tyr Asp Val
            355                 360                 365

Leu Gly Gln Leu Cys Lys Val Ala Thr Glu Asp Leu Gln Ala Gly Thr
370                 375                 380

Gly Val Ile Ile Asp Met Glu Tyr Asp Asp Gln Gly Gln Glu Ile Leu
385                 390                 395                 400

Arg Thr Gln Thr Ala Ser Asn Gln Ala Ala Leu Thr Leu Thr Gln Thr
            405                 410                 415

Trp Ala Val Asp Gly Leu Leu Lys Thr Arg Asp Leu Gln Gln Ala Gly
            420                 425                 430

Ser Pro Leu Leu His Glu Thr Phe Ser Tyr Asp Pro Arg Gly Arg Leu
            435                 440                 445

Thr Leu Val Asn Tyr Leu Gly Ser Ser Leu Pro Arg Asp Glu Leu Gln
450                 455                 460

Arg Glu Met Thr Arg Gln Ile Phe Ser Phe Asp Glu Leu Asp Asn Ile
465                 470                 475                 480

Thr Leu Cys Gln Thr Arg Phe Thr Asp Gly Thr Ser Glu Arg Ala Ala
            485                 490                 495

Phe Lys Tyr Gly Ser Pro Gly Asp Asp Lys His Lys Asp Arg Cys Gln
            500                 505                 510

Leu Leu Ser Ile Ala Tyr Thr Pro Pro Arg Lys Thr Pro Asp Pro Thr
            515                 520                 525

Phe Ser Tyr Asp Ala Asn Gly Asn Gln Leu Lys Asp Glu His Gly Asn
530                 535                 540

Ser Leu His Tyr Asp Ser Gln Ser Arg Leu Leu Gln Val Ala Glu Thr
545                 550                 555                 560

Gly Gly Ala Pro Ile Ser Gln Tyr Arg Tyr Asp Gly His Asn Gln Leu
            565                 570                 575

Val Ala Thr Arg Asp Gly Asn Glu Ser Glu Ile Leu Arg Phe Tyr Glu
            580                 585                 590

Gly His Gln Leu Ser Ser Thr Val Gln Glu Asp Gln Arg Thr Gln Tyr
            595                 600                 605

Leu His Leu Gly Glu Gln Pro Leu Gly Gln Gln Ile Val Asp Asp Ala
            610                 615                 620

Glu Gln Thr Leu Leu Leu Leu Thr Asp Ala Asn Gln Ser Val Met Gly
625                 630                 635                 640

Glu Phe Gln Gln Gly Gln Leu Arg Lys Ala Val Tyr Ser Ala Tyr Gly
```

|     |     |     |     | 645 |     |     |     | 650 |     |     |     | 655 |     |
|-----|-----|-----|-----|-----|-----|-----|-----|-----|-----|-----|-----|-----|-----|
Glu Arg His Ser Glu Glu Ala Leu Leu Ser Thr Ala Gly Phe Asn Gly
                660                 665                 670

Glu Val Arg Glu Ala Ala Asn Gly Trp Tyr Leu Leu Gly Asn Gly Tyr
        675                 680                 685

Arg Ala Tyr Asn Pro Leu Leu Met Arg Phe His Ser Pro Asp Phe Leu
690                 695                 700

Ser Pro Phe Ala Glu Gly Val Asn Pro Tyr Thr Tyr Cys Leu Gly
705                 710                 715                 720

Asn Pro Ile Ala Leu Arg Asp Pro Thr Gly His Asp Ala Ser Gly Gln
                725                 730                 735

Thr Gly Arg Leu Arg Arg Pro Asp Glu Gly Ala Leu Pro Met Gln Gln
                740                 745                 750

Gly Gly Gly Asp Ile Met Gly Trp Val Gly Val Gly Ile Gly Val Val
                755                 760                 765

Phe Thr Val Leu Gly Val Ala Ala Thr Ile Ala Thr Leu Gly Thr Ala
770                 775                 780

Thr Pro Val Thr Gly Pro Val Thr Val Leu Gly Ile Ser Met Thr Ala
785                 790                 795                 800

Ser Ala Ala Ala Val Ser Thr Val Ser Thr Gly Ala Leu Ile Val
            805                 810                 815

Gly Thr Ala Leu Thr Ala Ala Ser Thr Thr Ala Asn Thr Val Ala Ile
                820                 825                 830

Val Asn Asn Asp Gln Thr Ala Gly Glu Val Gly Gly Trp Leu Gly Ile
                835                 840                 845

Ala Ala Val Pro Val Gly Leu Val Gly Phe Gly Ala Gly Ala Val Val
850                 855                 860

Ala Arg Ala Val Ala Ala Ala Lys Val Ala Ala Asn Ala Gly
865                 870                 875                 880

Thr Ile Gly Val Arg Ser Val Ser Arg Ile Gly Leu Ala Ala Ala Gly
                885                 890                 895

Ala Arg Arg Thr Ile Ser Ser Ala Ala Ser Ser Ala Arg Arg Gln Ile
                900                 905                 910

Ser Asn Met Leu Gly Arg Ile Leu Pro Arg Ala Leu Asn Arg Thr Ala
                915                 920                 925

Ala Thr Ala Arg Arg Ile Pro Ser Val Thr Ser Gly Gly Ser Gly Pro
                930                 935                 940

Gly Pro Ser Leu Phe Thr Gln Thr Thr Phe Asn Glu Ser Ile Gly Met
945                 950                 955                 960

Thr Gln Thr Thr Ile Phe Ser Thr Asn Ala Ser Gly Ile Pro Pro Ala
                965                 970                 975

Thr Gln Val Thr Arg Ile
            980

<210> SEQ ID NO 107
<211> LENGTH: 495
<212> TYPE: DNA
<213> ORGANISM: Pseudomonas syringae pv. tomato DC3000

<400> SEQUENCE: 107
atgcggtgtg tgaggcgatc aagaaggttc tttaagctgc aagctgcaag ctgcaagaaa      60
aagcaggacc gctttagctt agctgacgct ccactgagta ctttccatcg aacgatccga     120
aaaaccctgc ctcgaaagct tgtcagaccc ttttctgaat cagctatcga ggtagtcatg     180
tccatcgaac cccaacgtca gaaagaacag ccacccggcc agcacacgcc agcggatcag     240

```
ggcccggatc gcaatgatcc ggccatcgag ccgcaggttt cggacgtaga gccggagact    300
gaaaaaggtg acggccagac gcaaggccag acccctgccc ccagccaaag ccagtcacaa    360
agtcagaatc agagccagca gtccaacggc agcgcttacg tgcctgacta tgagccgcag    420
gaaaaaaagg aagaccagcg caatcatcag cccactcaag cactgatgc tgatatcgac    480 accaatgcgg gctga                                                    495
```

<210> SEQ ID NO 108
<211> LENGTH: 164
<212> TYPE: PRT
<213> ORGANISM: Pseudomonas syringae pv. tomato DC3000

<400> SEQUENCE: 108

```
Met Arg Cys Val Arg Ser Arg Arg Phe Phe Lys Leu Gln Ala Ala
  1               5                  10                  15

Ser Cys Lys Lys Lys Gln Asp Arg Phe Ser Leu Ala Asp Ala Pro Leu
                 20                  25                  30

Ser Thr Phe His Arg Thr Ile Arg Lys Thr Leu Pro Arg Lys Leu Val
             35                  40                  45

Arg Pro Phe Ser Glu Ser Ala Ile Glu Val Val Met Ser Ile Glu Pro
         50                  55                  60

Gln Arg Gln Lys Glu Gln Pro Gly Gln His Thr Pro Ala Asp Gln
     65                  70                  75              80

Gly Pro Asp Arg Asn Asp Pro Ala Ile Glu Pro Gln Val Ser Asp Val
                 85                  90                  95

Glu Pro Glu Thr Glu Lys Gly Asp Gly Gln Thr Gln Gly Gln Thr Pro
            100                 105                 110

Ala Pro Ser Gln Ser Gln Ser Gln Ser Gln Asn Gln Ser Gln Gln Ser
        115                 120                 125

Asn Gly Ser Ala Tyr Val Pro Asp Tyr Glu Pro Gln Glu Lys Lys Glu
    130                 135                 140

Asp Gln Arg Asn His Gln Pro Thr Gln Gly Thr Asp Ala Asp Ile Asp
145                 150                 155                 160

Thr Asn Ala Gly
```

<210> SEQ ID NO 109
<211> LENGTH: 702
<212> TYPE: DNA
<213> ORGANISM: Pseudomonas syringae pv. tomato DC3000

<400> SEQUENCE: 109

```
atgcccgtca ctggtgcagg ctttatcaag cgtttgacgc aattgtccct ctgcgccggc     60
atggcgctgg tcccggtggc cgtacaggca gccgaaagcg atccttggga aggcatcaac    120
cgttccattt tcagcttcaa cgataccctt gacgcttata cgctcaagcc gctggcaaag    180
ggttatcagt acatcgctcc gcagtttgtc gaagacggta ttcataactt cttcagcaat    240
atcggcgatg tcggcaatct ggcgaacaac gtcttgcagg ccaaacctga gcggccggt     300 gtagataccg cacgccttat cgtcaacact acgttcggtc tgctgggctt cattgacgtc    360
ggcacccgca tgggcctgca acgcagtgat gaagacttcg ccagacact gggctactgg    420 ggtgtgccaa gcgccccgtt cgtggtgatt ccgctgctgg gccaagcac ggtgcgtgac    480 gccattgcca agtacccgga cacctacacc tccccgtacc gctatattga tcacgtaccc    540
acccgcaaca cggcgttggg cgtcaatctg gtcgacacgc gtgccagcct gctgtccgcc    600
gagcgcctgg tcagtggtga tcgctacacc ttcatccgca acgcttactt gcagaaccgc    660
```

```
gaattcaagg tcaaggacgg gcaggtcgaa gacgattttt aa                        702
```

<210> SEQ ID NO 110
<211> LENGTH: 233
<212> TYPE: PRT
<213> ORGANISM: Pseudomonas syringae pv. tomato DC3000

<400> SEQUENCE: 110

```
Met Pro Val Thr Gly Ala Gly Phe Ile Lys Arg Leu Thr Gln Leu Ser
 1               5                  10                  15

Leu Cys Ala Gly Met Ala Leu Val Pro Val Ala Val Gln Ala Ala Glu
            20                  25                  30

Ser Asp Pro Trp Glu Gly Ile Asn Arg Ser Ile Phe Ser Phe Asn Asp
        35                  40                  45

Thr Leu Asp Ala Tyr Thr Leu Lys Pro Leu Ala Lys Gly Tyr Gln Tyr
    50                  55                  60

Ile Ala Pro Gln Phe Val Glu Asp Gly Ile His Asn Phe Phe Ser Asn
 65                  70                  75                  80

Ile Gly Asp Val Gly Asn Leu Ala Asn Asn Val Leu Gln Ala Lys Pro
                85                  90                  95

Glu Ala Ala Gly Val Asp Thr Ala Arg Leu Ile Val Asn Thr Thr Phe
            100                 105                 110

Gly Leu Leu Gly Phe Ile Asp Val Gly Thr Arg Met Gly Leu Gln Arg
        115                 120                 125

Ser Asp Glu Asp Phe Gly Gln Thr Leu Gly Tyr Trp Gly Val Pro Ser
    130                 135                 140

Gly Pro Phe Val Val Ile Pro Leu Leu Gly Pro Ser Thr Val Arg Asp
145                 150                 155                 160

Ala Ile Ala Lys Tyr Pro Asp Thr Tyr Thr Ser Pro Tyr Arg Tyr Ile
                165                 170                 175

Asp His Val Pro Thr Arg Asn Thr Ala Leu Gly Val Asn Leu Val Asp
            180                 185                 190

Thr Arg Ala Ser Leu Leu Ser Ala Glu Arg Leu Val Ser Gly Asp Arg
        195                 200                 205

Tyr Thr Phe Ile Arg Asn Ala Tyr Leu Gln Asn Arg Glu Phe Lys Val
    210                 215                 220

Lys Asp Gly Gln Val Glu Asp Asp Phe
225                 230
```

<210> SEQ ID NO 111
<211> LENGTH: 1194
<212> TYPE: DNA
<213> ORGANISM: Pseudomonas syringae pv. tomato DC3000

<400> SEQUENCE: 111

```
atgacacttt caaccctgcg ccctaccccg cgccagcagt atgaatcgcc cgagtcagcc    60
gaggatttca cccagcggct ggccgacctg acccgcacgc tggccgaaac agccgagcag   120
tacgacatca gcgcgcagtt ccctcacgcc aacttccgct tgctgcacag ccacggactg   180
ctcggcctga ccgtgcctgc cgaactgggc ggcggcgctg ccgacctgtc gcgggcgcag   240
caggtcatca gcgcagtggc cagaggcgag ccttcgacag cgctgattct ggtcatgcag   300
tacctgcagc attccaggct gcaggacaac cgcaactggc cgagccacct gcgcgaacag   360
gtggccaaag acgccgtgca cgagggcgcg ctgatcaacg cgctgcgtgt cgaacccgac   420
ctgggcacac ctgcgcgtgg cggcttgccg ggcaccatcg cccggcgcag cgccgaaggc   480
```

```
tggcgcatca gcggcagcaa gatctactcc accggcagcc atggcctgac ctggttcgcc    540
gtgtgggcgc gcagcgatga cgaggacccg ctggtcggca gttggctggt gcacaaggac    600
acgcccggga tcagcatcgt cgaggactgg gaccatctgg gcatgcgcgc acctgcagc     660 cacgaggtca ggttcgacaa cgtgcgagtg ccgctcgaac acgcggtcag cgtcagtccg    720
tggagcgccc cgcaatccga gcttgatggt gccggcatgc tgtggatgtc ggtgctgctg    780
tcgtcggtct acgatggcat cgctcaatct gcccgcgact ggctggtgca ctggctggaa    840
cagcgcacgc cttccaacct gggcgccgcg ctgtcgaccc tgccgcgctt tcaggaaaca    900
gtcgggcaga tcgacacact gctgttcgcc aaccgcagcc tgctggagtc cgccgcccaa    960
gggcacacac ccgcacagca tgccgcgcag atcaaatacc tggtgaccgg caatgccatc   1020
cgcgcagtgg aactggccat tgaggcctcg ggcaatcccg ggctttcacg cactaacccg   1080
ctgcagcgtc attaccgcaa cgtgctatgc ggccgggtgc atacgccgca gaacgacgcc   1140
gtgttgatgg gcgtgggcaa agcggtattt gcggcacgca gcagagcca gtaa          1194
```

<210> SEQ ID NO 112
<211> LENGTH: 397
<212> TYPE: PRT
<213> ORGANISM: Pseudomonas syringae pv. tomato DC3000

<400> SEQUENCE: 112

```
Met Thr Leu Ser Thr Leu Arg Pro Thr Pro Arg Gln Gln Tyr Glu Ser
1               5                   10                  15

Pro Glu Ser Ala Glu Asp Phe Thr Gln Arg Leu Ala Asp Leu Thr Arg
            20                  25                  30

Thr Leu Ala Glu Thr Ala Glu Gln Tyr Asp Ile Ser Ala Gln Phe Pro
        35                  40                  45

His Ala Asn Phe Arg Leu Leu His Ser His Gly Leu Leu Gly Leu Thr
    50                  55                  60

Val Pro Ala Glu Leu Gly Gly Gly Ala Ala Asp Leu Ser Arg Ala Gln
65                  70                  75                  80

Gln Val Ile Ser Ala Val Ala Arg Gly Glu Pro Ser Thr Ala Leu Ile
                85                  90                  95

Leu Val Met Gln Tyr Leu Gln His Ser Arg Leu Gln Asp Asn Arg Asn
            100                 105                 110

Trp Pro Ser His Leu Arg Glu Gln Val Ala Lys Asp Ala Val His Glu
        115                 120                 125

Gly Ala Leu Ile Asn Ala Leu Arg Val Glu Pro Asp Leu Gly Thr Pro
    130                 135                 140

Ala Arg Gly Gly Leu Pro Gly Thr Ile Ala Arg Arg Ser Ala Glu Gly
145                 150                 155                 160

Trp Arg Ile Ser Gly Ser Lys Ile Tyr Ser Thr Gly Ser His Gly Leu
                165                 170                 175

Thr Trp Phe Ala Val Trp Ala Arg Ser Asp Asp Glu Asp Pro Leu Val
            180                 185                 190

Gly Ser Trp Leu Val His Lys Asp Thr Pro Gly Ile Ser Ile Val Glu
        195                 200                 205

Asp Trp Asp His Leu Gly Met Arg Ala Thr Cys Ser His Glu Val Arg
    210                 215                 220

Phe Asp Asn Val Arg Val Pro Leu Glu His Ala Val Ser Val Ser Pro
225                 230                 235                 240

Trp Ser Ala Pro Gln Ser Glu Leu Asp Gly Ala Gly Met Leu Trp Met
                245                 250                 255
```

```
Ser Val Leu Leu Ser Ser Val Tyr Asp Gly Ile Ala Gln Ser Ala Arg
                260                 265                 270

Asp Trp Leu Val His Trp Leu Glu Gln Arg Thr Pro Ser Asn Leu Gly
            275                 280                 285

Ala Ala Leu Ser Thr Leu Pro Arg Phe Gln Glu Thr Val Gly Gln Ile
290                 295                 300

Asp Thr Leu Leu Phe Ala Asn Arg Ser Leu Leu Glu Ser Ala Ala Gln
305                 310                 315                 320

Gly His Thr Pro Ala Gln His Ala Ala Gln Ile Lys Tyr Leu Val Thr
                325                 330                 335

Gly Asn Ala Ile Arg Ala Val Glu Leu Ala Ile Glu Ala Ser Gly Asn
            340                 345                 350

Pro Gly Leu Ser Arg Thr Asn Pro Leu Gln Arg His Tyr Arg Asn Val
        355                 360                 365

Leu Cys Gly Arg Val His Thr Pro Gln Asn Asp Ala Val Leu Met Gly
    370                 375                 380

Val Gly Lys Ala Val Phe Ala Ala Arg Lys Gln Ser Gln
385                 390                 395

<210> SEQ ID NO 113
<211> LENGTH: 882
<212> TYPE: DNA
<213> ORGANISM: Pseudomonas syringae pv. tomato DC3000

<400> SEQUENCE: 113
atgaatctca caacacttcc tcttgcgctc agcattgctt gcgctgcggc catcacacct      60
gccttcgcgg gcacaagcgt ctctgaggct tcacacaaag tgaatgtgca gcaagttcgt     120
aacgcgacgg taaagatctc ctacggcggc acgacctttc tgatcgaccc gatgctggcc     180
aaaaagggaa cctacccagg gtttgaaaat acctatcgaa gcaatctgcg caatccactg     240
gttgatctga ccgaatcgcc caccgaagtg atcgccggta tcgacgcagt atcgtcact      300 catacgcacc ttgaccattg gacgatgct gcacaaaaag tgctgcctaa agacatccct     360
ctgttcaccc agcatgaaaa agacgcgcag ctgattcgct ctcaaggttt caagaacgta     420
cgcgtattga ctgatgaagc cgaattcggc ggcgtcaaaa ttaccaagac cggtgggcag     480
catggcaccg acgaaatgta tgccgtgcca gccctcgcga agcctctggg tgaagcaatg     540
ggcgttgtat ttcaagcccc gggctacaag accctctacc tcgctggtga cactgtctgg     600
cgtaaagagg tcgatcaggc tatcgagaac tattgtcccg aagtcatcgt actcaatgcc     660
ggcaaagcaa aaatgacggg gtatgagggg gcgatcatca tgggggaaga ggatgtactg     720
cgcgcttcac aggtcgcgaa gaacgcgaaa atcgtcgctg tacacatgaa tgcaatcaac     780
catatgtccc tgacccgtga gcaattgcgc gcttacgtca gcagcaggg tatcgaaagt     840 cgtgtagaca taccggaaga tggcgcttca ctggagttct ga                        882

<210> SEQ ID NO 114
<211> LENGTH: 293
<212> TYPE: PRT
<213> ORGANISM: Pseudomonas syringae pv. tomato DC3000

<400> SEQUENCE: 114

Met Asn Leu Thr Thr Leu Pro Leu Ala Leu Ser Ile Ala Cys Ala Ala
1               5                   10                  15

Ala Ile Thr Pro Ala Phe Ala Gly Thr Ser Val Ser Glu Ala Ser His
            20                  25                  30

Lys Val Asn Val Gln Gln Val Arg Asn Ala Thr Val Lys Ile Ser Tyr
```

|                      |                      |                      |                      |                      |
|----------------------|----------------------|----------------------|----------------------|----------------------|
|                      | 35                   | 40                   | 45                   |                      |

Gly Gly Thr Thr Phe Leu Ile Asp Pro Met Leu Ala Lys Lys Gly Thr
 50                                  55                                  60

Tyr Pro Gly Phe Glu Asn Thr Tyr Arg Ser Asn Leu Arg Asn Pro Leu
 65                                  70                      75                                  80

Val Asp Leu Thr Glu Ser Pro Thr Glu Val Ile Ala Gly Ile Asp Ala
                     85                                  90                                  95

Val Ile Val Thr His Thr His Leu Asp His Trp Asp Asp Ala Ala Gln
                100                                 105                                 110

Lys Val Leu Pro Lys Asp Ile Pro Leu Phe Thr Gln His Glu Lys Asp
            115                                 120                                 125

Ala Gln Leu Ile Arg Ser Gln Gly Phe Lys Asn Val Arg Val Leu Thr
130                                 135                                 140

Asp Glu Ala Glu Phe Gly Gly Val Lys Ile Thr Lys Thr Gly Gly Gln
145                                 150                                 155                                 160

His Gly Thr Asp Glu Met Tyr Ala Val Pro Ala Leu Ala Lys Pro Leu
                165                                 170                                 175

Gly Glu Ala Met Gly Val Val Phe Gln Ala Pro Gly Tyr Lys Thr Leu
            180                                 185                                 190

Tyr Leu Ala Gly Asp Thr Val Trp Arg Lys Glu Val Asp Gln Ala Ile
            195                                 200                                 205

Glu Asn Tyr Cys Pro Glu Val Ile Val Leu Asn Ala Gly Lys Ala Lys
            210                                 215                                 220

Met Thr Gly Tyr Glu Gly Ala Ile Ile Met Gly Glu Glu Asp Val Leu
225                                 230                                 235                                 240

Arg Ala Ser Gln Val Ala Lys Asn Ala Lys Ile Val Ala Val His Met
                245                                 250                                 255

Asn Ala Ile Asn His Met Ser Leu Thr Arg Glu Gln Leu Arg Ala Tyr
                260                                 265                                 270

Val Lys Gln Gln Gly Ile Glu Ser Arg Val Asp Ile Pro Glu Asp Gly
            275                                 280                                 285

Ala Ser Leu Glu Phe
    290

<210> SEQ ID NO 115
<211> LENGTH: 2379
<212> TYPE: DNA
<213> ORGANISM: Pseudomonas syringae pv. tomato DC3000

<400> SEQUENCE: 115

| | | | | | |
|---|---|---|---|---|---|
| atgcatctgt | tgccgtttgc | gcgttacccc | ttatcacctg | cagaaacacc | taaacccaag | 60 |
| gtgaccatga | aggttggaga | tttcagggct | tacgacaccg | ctccagcacc | cggagtgacc | 120 |
| actgcgtcct | gcggacaact | ggcaatcggc | accaagttag | aaatcatcga | gaccgccgag | 180 |
| aatggcgaac | ttacttatgc | caagggtaag | attctatctg | gcagcgtgaa | gcaggggggca | 240 |
| accaaaaaac | gggtcgaggg | ggcggaggtc | tggttcgctt | atttgaaaaa | cggcgaaccc | 300 |
| tacaaaaact | cagtccctaa | gcgcatctgg | ctcgctgacg | atgtgcctga | gcagcaaga | 360 |
| cccaattact | ggcagggtaa | ggtcaaagcc | tcagtagtga | ataagttgcc | gctgtacgat | 420 |
| gatcctgcca | gccctacaaa | tggccagcct | gcaggcgccc | ggaagggggac | tctggagctg | 480 |
| gtcatgaaca | gcgtcatcga | gtttaactct | tcggaagtcg | tcaacctggc | gctggatggc | 540 |
| aagctgcatc | ggatggccaa | gtgcacgatg | ctgagtggcg | gcctgcgggg | tcatggtgcg | 600 |
| gttcccccca | gcttttgggc | atgtgttgaa | atgaccctg | ctaataaagt | attgaaatgg | 660 |

```
gactcggtaa cgccgaccag ttttgatacg gtcgttatga cgagcaccgg agtgaaggcg    720
ggcgatccaa ttggctatct tggacaaacc gaaaatctca ccggtgaaaa tggcggcgtc    780
agcagcaaat accaggttca cgtcgaaatt ttcacagccg atgctgaggt taaagacttc    840
ctcaagaaca ccgcgggttt gaagattggg aagcaatacc tgcaccttgc aagcggggct    900
gtactcaagc aaaaagcgcc cgcgaccggc accacagcac tcaagcaaga ccatgcggtt    960
gacttggcta agccacaat tgtcaaagaa ggcaccgatg actggtatga ggtcagcgtg   1020
atcgaggacg atcagcctgt agccggcctg ataaaaaag ccactgcgct agtcatcaca   1080
cagcacgatt gggaaaaatt gggctttcag atcgtagagg agaacaacgc agcagccgat   1140
ggtttcttgg acccggatgc aatgccacag ttcttcaaag acctattcgc gaagatcgac   1200
aagaaccacg atggtgaggt ggagcctgct gaactggctg aggctcttaa gaaaccggaa   1260
accagaaccc agtgggccag gcttgttgcc catcaccta cggagtggaa agataaggca   1320
ggctccccca gtggagcaa gttggataaa ctgctggaaa cgtcgccgaa gatgttgaaa   1380
catgaaaaag aacgcattga taaatatgta tttgggatg agttgtcagg gaaagctaag   1440
atgacctcaa gtttaatatg gcattttcat ccggtagaat tcatttcaac atttagcgca   1500
aaaaaagtct gcgcttgcaa cgccatagtt aaggctactc gctgggtttc ttccagtaag   1560
acgcactatg gcccattgca tacgggtgat aaagagcttg ggagtgcacc tcagtgggat   1620
gacctggtct cagaaggaaa aataacggaa gaggagaaaa aattattgt tgtaatgtct   1680
ggaaacgagg caaaaattaa cggagtacaa agttatgata gcgaaataat tactgccggc   1740
gcgatgcaga aaacaattaa cttgtccggt ggcggtgagc tgccactaca agttaagaag   1800
tttaaaaatc agcatcccga ggcgtacatc gaatactttg attctcaagg ctggaagttg   1860
gatgagacag gtgattcggc gaaaatgtat tatcaagggc cggctcgagc tagtggcgca   1920
aagctggaag gaaaggcgct gaaggataat ttaaaaattg gttgcagtga atcgacattt   1980
gggaaggtgg ttgactgtca acctgtttca gtgatggcct cgctatcgc aagtccgtta   2040
tatatccaga tacaaataat ggattttata gaaaggttac gtagttcttt aacgaagaag   2100
cccacaggct ataactttac tgctggggga ttttttcaaga cctctctcgg aaaagctgtg   2160
gttttggatc acgatataaa tcgacccggg tatgtgaagg atgacttggg atctgctctt   2220
gacactttt ttgctcaaaa tccaacagtc agccgggata ttgatacatg gggcgcagca   2280
tatagcgtta atgagcgaaa agttttagac ctgtatggcg ctcgaagaag aatgaccaat   2340
gcattgcttc gatacaatca cttgaaggcg gagttataa                         2379
```

<210> SEQ ID NO 116
<211> LENGTH: 792
<212> TYPE: PRT
<213> ORGANISM: Pseudomonas syringae pv. tomato DC3000

<400> SEQUENCE: 116

```
Met His Leu Leu Pro Phe Ala Arg Tyr Pro Leu Ser Pro Ala Glu Thr
 1               5                  10                  15

Pro Lys Pro Lys Val Thr Met Lys Val Gly Asp Phe Arg Ala Tyr Asp
            20                  25                  30

Thr Ala Pro Ala Pro Gly Val Thr Thr Ala Ser Cys Gly Gln Leu Ala
        35                  40                  45

Ile Gly Thr Lys Leu Glu Ile Ile Glu Thr Ala Glu Asn Gly Glu Leu
    50                  55                  60

Thr Tyr Ala Lys Gly Lys Ile Leu Ser Gly Ser Val Lys Gln Gly Ala
65                  70                  75                  80
```

```
Thr Lys Lys Arg Val Glu Gly Ala Glu Val Trp Phe Ala Tyr Leu Lys
                85                  90                  95

Asn Gly Glu Pro Tyr Lys Asn Ser Val Pro Lys Arg Ile Trp Leu Ala
            100                 105                 110

Asp Asp Val Pro Glu Arg Ala Arg Pro Asn Tyr Trp Gln Gly Lys Val
            115                 120                 125

Lys Ala Ser Val Val Asn Lys Leu Pro Leu Tyr Asp Asp Pro Ala Ser
130                 135                 140

Pro Thr Asn Gly Gln Pro Ala Gly Ala Arg Lys Gly Thr Leu Glu Leu
145                 150                 155                 160

Val Met Asn Ser Val Ile Glu Phe Asn Ser Ser Glu Val Val Asn Leu
                165                 170                 175

Ala Leu Asp Gly Lys Leu His Arg Met Ala Lys Cys Thr Met Leu Ser
            180                 185                 190

Gly Gly Leu Arg Gly His Gly Ala Val Pro Pro Ser Phe Trp Ala Cys
            195                 200                 205

Val Glu Asn Asp Pro Ala Asn Lys Val Leu Lys Trp Asp Ser Val Thr
210                 215                 220

Pro Thr Ser Phe Asp Thr Val Val Met Thr Ser Thr Gly Val Lys Ala
225                 230                 235                 240

Gly Asp Pro Ile Gly Tyr Leu Gly Gln Thr Glu Asn Leu Thr Gly Glu
            245                 250                 255

Asn Gly Gly Val Ser Ser Lys Tyr Gln Val His Val Glu Ile Phe Thr
            260                 265                 270

Ala Asp Ala Glu Val Lys Asp Phe Leu Lys Asn Thr Ala Gly Leu Lys
            275                 280                 285

Ile Gly Lys Gln Tyr Leu His Leu Ala Ser Gly Ala Val Leu Lys Gln
            290                 295                 300

Lys Ala Pro Ala Thr Gly Thr Thr Ala Leu Lys Gln Asp His Ala Val
305                 310                 315                 320

Asp Leu Ala Lys Ala Thr Ile Val Lys Glu Gly Thr Asp Asp Trp Tyr
                325                 330                 335

Glu Val Ser Val Ile Glu Asp Asp Gln Pro Val Ala Gly Leu Ile Lys
            340                 345                 350

Lys Ala Thr Ala Leu Val Ile Thr Gln His Asp Trp Glu Lys Leu Gly
            355                 360                 365

Phe Gln Ile Val Glu Glu Asn Asn Ala Ala Asp Gly Phe Leu Asp
370                 375                 380

Pro Asp Ala Met Pro Gln Phe Phe Lys Asp Leu Phe Ala Lys Ile Asp
385                 390                 395                 400

Lys Asn His Asp Gly Glu Val Glu Pro Ala Glu Leu Ala Glu Ala Leu
                405                 410                 415

Lys Lys Pro Glu Thr Arg Thr Gln Trp Ala Arg Leu Val Ala His His
            420                 425                 430

Pro Thr Glu Trp Lys Asp Lys Ala Gly Ser Pro Lys Trp Ser Lys Leu
            435                 440                 445

Asp Lys Leu Leu Glu Thr Ser Pro Lys Met Leu Lys His Glu Lys Glu
            450                 455                 460

Arg Ile Asp Lys Tyr Val Phe Trp Asp Glu Leu Ser Gly Lys Ala Lys
465                 470                 475                 480

Met Thr Ser Ser Leu Ile Trp His Phe His Pro Val Glu Phe Ile Ser
                485                 490                 495

Thr Phe Ser Ala Lys Lys Val Cys Ala Cys Asn Ala Ile Val Lys Ala
```

```
                 500              505              510
Thr Arg Trp Val Ser Ser Lys Thr His Tyr Gly Pro Leu His Thr
            515                  520                  525
Gly Asp Lys Glu Leu Gly Ser Ala Pro Gln Trp Asp Asp Leu Val Ser
            530                  535                  540
Glu Gly Lys Ile Thr Glu Glu Lys Lys Ile Ile Val Val Met Ser
545                 550                  555                  560
Gly Asn Glu Ala Lys Ile Asn Gly Val Gln Ser Tyr Asp Ser Glu Ile
                565                  570                  575
Ile Thr Ala Gly Ala Met Gln Lys Thr Ile Asn Leu Ser Gly Gly Gly
            580                  585                  590
Glu Leu Pro Leu Gln Val Lys Lys Phe Lys Asn Gln His Pro Glu Ala
            595                  600                  605
Tyr Ile Glu Tyr Phe Asp Ser Gln Gly Trp Lys Leu Asp Glu Thr Gly
            610                  615                  620
Asp Ser Ala Lys Met Tyr Tyr Gln Gly Pro Ala Arg Ala Ser Gly Ala
625                 630                  635                  640
Lys Leu Glu Gly Lys Ala Leu Lys Asp Asn Leu Lys Ile Gly Cys Ser
                645                  650                  655
Glu Ser Thr Phe Gly Lys Val Val Asp Cys Gln Pro Val Ser Val Met
            660                  665                  670
Ala Cys Ala Ile Ala Ser Pro Leu Tyr Ile Gln Ile Gln Ile Met Asp
            675                  680                  685
Phe Ile Glu Arg Leu Arg Ser Ser Leu Thr Lys Lys Pro Thr Gly Tyr
            690                  695                  700
Asn Phe Thr Ala Gly Gly Phe Phe Lys Thr Ser Leu Gly Lys Ala Val
705                 710                  715                  720
Val Leu Asp His Asp Ile Asn Arg Pro Gly Tyr Val Lys Asp Asp Leu
                725                  730                  735
Gly Ser Ala Leu Asp Thr Phe Phe Ala Gln Asn Pro Thr Val Ser Arg
            740                  745                  750
Asp Ile Asp Thr Trp Gly Ala Ala Tyr Ser Val Asn Glu Arg Lys Val
            755                  760                  765
Leu Asp Leu Tyr Gly Ala Arg Arg Arg Met Thr Asn Ala Leu Leu Arg
            770                  775                  780
Tyr Asn His Leu Lys Ala Glu Leu
785                 790

<210> SEQ ID NO 117
<211> LENGTH: 1554
<212> TYPE: DNA
<213> ORGANISM: Pseudomonas syringae pv. tomato DC3000

<400> SEQUENCE: 117
atgcggccgt tgcctgcgtt cagtattttg cagtttgatc cgttgaaacg ttcgggtcct      60
gcgctgacgg tcgaacgtga tacaccggtc gatagcaagc ctattaatga cgtgcgttgt     120
cgcttccgta cgtgctaccc gaccgaagtt caggcgctgg atctgaccgc gctgaattac     180
tcggtgaaag gcggtggttc gttgctcagc ctgcgcctgg agatgagcgc tgaaggtcac     240
ttgggtgagc ttgaactgag ccgcctgcgt ctgcactttg caggcgagcg ctatatcagc     300
cagatgctgt acctctgcct gctacgcaat ctcgagggta tcgagctgat ccctctggac     360
gctgccggca agcccatcga cggtgtcaat ggcgcgccaa tggcgttcaa gatgccgggc     420
gaccgtgtac agccggtagg gtttgccgaa gaagaggcgt tgatcccgta tccgctgaac     480
```

```
acgttccgcg gttatcgcta cctgcaggag tacttcgcgt ttcaggacaa gttcctgttc    540
gtcgacatca acgtctgga tctgctcaac gcactgccag aagagacact caaacaagtg    600
cgcggccttg agttgcgctt tgatattcgc aagagcggca ttcagcgtct tcgtcccacc    660
ctggataacg taaagctgta ttgcacgccg atcgtcaact tgttcaagca cgacgccttg    720
ccgattcgcc ttgatggcaa gcaggacgag tacctgctgc tgcccgccga tatggcctg     780
gaaacctgtg gtgtgttttc ggttgaaacc gtgaccggtt ggaagccggg aggtcttggc    840
tatcaggatt atgtgccgtt cgaatccttt gagcacgacc ccagtttcga cgtgcccaac    900
agccgtccgc attacagcat tcgccagcgt tcttctttgc tccatgaagg cctcgacact    960
tatctgagtt tcggcattcg ccatacagaa gcgcacgaaa ccctgtcgat cgagttgatg   1020
tgcaccaatc agaacctgcc acgcaaactc aaactgggcg aaatcaacgt ggcctgcgaa   1080
gatacgccgg agttttgag tttccgcaat atcacaccgg ctacctccag tttcgcgccc    1140
ccgctgaacc gtgacttcct gtggaagttg atcagcaata tgtcgctcaa ttacttgtct   1200
ctggctgacg tcaatgcgct gaaggtgatt ctggaaacct acgatttgcc ccgttactac   1260
gaccagcacg cggaaaaagt cagcaagcgc ctgttgggcg gtttgaaatc gatcaagcat   1320
caacacgtgg acagattgca ccgagggtta ccggtacgcg gattgcgcac tgagctgacc   1380
atcgacccgg aagggtatat cggcgaaggc gacatgtttg tattcgcttc ggttctcaac   1440
gagttttcg cgctttacgc cagtctcaat tcgtaccacg agctgcgggt aaaaagcaca   1500
cagggagagg tgtaccaatg gacaccacgt atgggcctcc agcccctgct ttaa          1554
```

<210> SEQ ID NO 118  
<211> LENGTH: 517  
<212> TYPE: PRT  
<213> ORGANISM: Pseudomonas syringae pv. tomato DC3000

<400> SEQUENCE: 118

```
Met Arg Pro Leu Pro Ala Phe Ser Ile Leu Gln Phe Asp Pro Leu Lys
  1               5                  10                  15

Arg Ser Gly Pro Ala Leu Thr Val Glu Arg Asp Thr Pro Val Asp Ser
             20                  25                  30

Lys Pro Ile Asn Asp Val Arg Cys Arg Phe Arg Thr Cys Tyr Pro Thr
         35                  40                  45

Glu Val Gln Ala Leu Asp Leu Thr Ala Leu Asn Tyr Ser Val Lys Gly
     50                  55                  60

Gly Gly Ser Leu Leu Ser Leu Arg Leu Glu Met Ser Ala Glu Gly His
 65                  70                  75                  80

Leu Gly Glu Leu Glu Leu Ser Arg Leu Arg Leu His Phe Ala Gly Glu
                 85                  90                  95

Arg Tyr Ile Ser Gln Met Leu Tyr Leu Cys Leu Leu Arg Asn Leu Glu
            100                 105                 110

Gly Ile Glu Leu Ile Pro Leu Asp Ala Ala Gly Lys Pro Ile Asp Gly
        115                 120                 125

Val Asn Gly Ala Pro Met Ala Phe Lys Met Pro Gly Asp Arg Val Gln
    130                 135                 140

Pro Val Gly Phe Ala Glu Glu Ala Leu Ile Pro Tyr Pro Leu Asn
145                 150                 155                 160

Thr Phe Arg Gly Tyr Arg Tyr Leu Gln Glu Tyr Phe Ala Phe Gln Asp
                165                 170                 175

Lys Phe Leu Phe Val Asp Ile Asn Gly Leu Asp Leu Leu Asn Ala Leu
            180                 185                 190
```

Pro Glu Glu Thr Leu Lys Gln Val Arg Gly Leu Glu Leu Arg Phe Asp
    195                 200                 205

Ile Arg Lys Ser Gly Ile Gln Arg Leu Arg Pro Thr Leu Asp Asn Val
    210                 215                 220

Lys Leu Tyr Cys Thr Pro Ile Val Asn Leu Phe Lys His Asp Ala Leu
225                 230                 235                 240

Pro Ile Arg Leu Asp Gly Lys Gln Asp Glu Tyr Leu Leu Pro Ala
                245                 250                 255

Glu Tyr Gly Leu Glu Thr Cys Gly Val Phe Ser Val Glu Thr Val Thr
                260                 265                 270

Gly Trp Lys Pro Gly Leu Gly Tyr Gln Asp Tyr Val Pro Phe Glu
            275                 280                 285

Ser Phe Glu His Asp Pro Ser Phe Asp Val Pro Asn Ser Arg Pro His
    290                 295                 300

Tyr Ser Ile Arg Gln Arg Ser Ser Leu Leu His Gly Leu Asp Thr
305                 310                 315                 320

Tyr Leu Ser Phe Gly Ile Arg His Thr Glu Ala His Glu Thr Leu Ser
                325                 330                 335

Ile Glu Leu Met Cys Thr Asn Gln Asn Leu Pro Arg Lys Leu Lys Leu
                340                 345                 350

Gly Glu Ile Asn Val Ala Cys Glu Asp Thr Pro Glu Phe Leu Ser Phe
                355                 360                 365

Arg Asn Ile Thr Pro Ala Thr Ser Ser Phe Ala Pro Pro Leu Asn Arg
    370                 375                 380

Asp Phe Leu Trp Lys Leu Ile Ser Asn Met Ser Leu Asn Tyr Leu Ser
385                 390                 395                 400

Leu Ala Asp Val Asn Ala Leu Lys Val Ile Leu Glu Thr Tyr Asp Leu
                405                 410                 415

Pro Arg Tyr Tyr Asp Gln His Ala Glu Lys Val Ser Lys Arg Leu Leu
                420                 425                 430

Gly Gly Leu Lys Ser Ile Lys His Gln His Val Asp Arg Leu His Arg
            435                 440                 445

Gly Leu Pro Val Arg Gly Leu Arg Thr Glu Leu Thr Ile Asp Pro Glu
    450                 455                 460

Gly Tyr Ile Gly Glu Gly Asp Met Phe Val Phe Ala Ser Val Leu Asn
465                 470                 475                 480

Glu Phe Phe Ala Leu Tyr Ala Ser Leu Asn Ser Tyr His Glu Leu Arg
                485                 490                 495

Val Lys Ser Thr Gln Gly Glu Val Tyr Gln Trp Thr Pro Arg Met Gly
            500                 505                 510

Leu Gln Pro Leu Leu
        515

<210> SEQ ID NO 119
<211> LENGTH: 5874
<212> TYPE: DNA
<213> ORGANISM: Pseudomonas syringae pv. tomato DC3000

<400> SEQUENCE: 119
atggtcaagg ttacctcttc cggatttact gccaaccctc tctctcatca tgcggacagt      60
gtttcccccg cgaacagtcc ccctcagtta ccggagcctg tgcatctggt tgatttaagc     120
gagtcgtccc gcaagggcgg catgcgaaat cggccgcatg ccagtttgaa cagtcaggtg     180
ctcgaactgc aagcggtgcc gtcgcaacgt ggaaagcatg ttcgtgtcag aagtcatgcc     240
gatggcgaga gtgtcattaa tgcctggctg gcaaagcgcc cctcggttca aagcgaaacc     300

```
agtcttgata acgatggcaa actggtgcgt tacaccccg tgaatcatga gccgctggcg    360
ccgcgcaatg aggcgttttt cacctcggtg ccggggatgt tgatggccgt tttgacggtc    420
caccccgaga tggaacatgg catcagcggg gacataactg ctgatgctgt ggctgcccgg    480
cttgccgaac cgccaatagg gttgctaacc ggaatctggc agtcttccca tgatcgagcc    540
tatctggagc gtggcggtgt ggtgcatacc gccaatatgg aagagcgctg ggcgccgttg    600
acgctgccag gcatcaatcc ccgagagccc ctgcgaatgg ccggtttgca ggccgatggt    660
ggagtctatc tgcataacgg cagccaactg tggcgcttga ccgaaactgc cgccgagtcc    720
gtgaccaccg aaaaccttcc tgaaggtgcg gcggtacgca ttggcgccgg tggcgaggtg    780
catgggctgc atgaaggcgc gcttcattcg aatggcattt cccgtccaat cgagctttgg    840
cggccaaaag ctggcgcgcc ggggcgcgag cagagtccgg cgcgcccgt tgatttgctg    900
ccgttaccgg gtggcaccgc tgcactgatc cttgatgaca agggacgtat ttatcacgct    960
gatctgaaag gcacaggcgc tgttgaagcc caccggctga aattacctgc tgactttgcg   1020
cagggtaaag gttgggccgt gaccgccatg ggattgtccc gagacgacac tgttcatctg   1080
atgctgcagg atcagaacgg gcgtcgcatg agcttgcagc gagcaccggg cgaggcgctg   1140
tttcgtcctg cgtacctgct ggatcgcccg ttgctgctgc tctataccga agggctgcat   1200
gttccgtcgg aggccgcggt gcagtcgcac gttcagcttg atggtcatgc tcaactgggg   1260
catatcgatg gcgtgctgca ttataaagcg gctcccgatc agtcatggga acggctaaag   1320
cagtcgggcg cgaaccgct gacggggtttg actgctcttt attccagccc gctgggattt   1380
atcgacagga aaccggtttt cgctttagtg ggggatgccc ggcaggtggt cgagttgaaa   1440
ctggagggggc gtacatcctg gttgccgagc gatgccgagc ttccgcgtca ccctgcgggc   1500
gggcctttgg cggtgatacc ggatacggta gcgttacgca ccagcccgat cgcgcagttt   1560
gacgagcctg tacaggcgct ggcggttcac ggtaatcgcc gggtcgtcgc gctgacggat   1620
tcggggcgat taatggctgc cgatgcggac accccagccc gccgacttcc cacgttgcag   1680
cgccccatcg ccatcgccgt agggctcaac gatcagttac tggtgctgca tcatccccat   1740
agccagcgcc cccagttgaa acggttgagt gcgaaagatg actgggagcc ggtgccgata   1800
attctgccgg gtattgttca cccttcaagt cttcgcgcta ctcgcacggg gcaaatacaa   1860
gtgcagctgg gagaaaactg gcatacgttg ctgccatcaa tgacgtcgca cgataatcag   1920
cgcttacctg cccgcgtaaa acctgaacca gaggggatg aggcgccgtc ggcgaatttc   1980
ctggcgggta gcaacgccct cgccaatcag cagcaagcca gtcgtatcag cacaccgcat   2040
catgacgcat cggtggttac gacgctggcg gggacaacag ccaacaaccc gttgacgatg   2100
gcgtcgagcc tacaggcagt ggttgatacg acccgcgctc aggtaggcgc gttggcgaga   2160
gatgtagtgg gcgcagcggc gaacagcacg atgcgggcaa tggcgcatac cttgggtgtt   2220
gtactgccgc caacgcctca ggagaagcgc ctggccagtt tccataatga ggcgaaacag   2280
gcttatacat caggaaaaat actgtttgag catctgccgt cactcgcgca agtgcgcgtc   2340
gcttcagccg tagggccgtc ggacggagaa agattcgggc tgtcacatca gcaaacgcaa   2400
cgcttgttga cgctgcgaga ggggaagctg gaagcgctgt tacgcgactt gcgcaagatc   2460
ggctttcatg aaggggtgat catgggcgat atggcgaca gcgacagtgc gcacggtctt   2520
gtttcgacga catcgacacc aacgttccgg ctggccgagc tatggcgacg gcagcattcg   2580
cgagtggata aggcgctgtc ttccgctgga ttatccagat cggaagatat ttttccggac   2640
ttgaacctaa gtatcaacgc gttggctggc ggcgcggcgc tgaatgcgga tcgtatgagc   2700
```

```
gaacgtgaag ctgagttgtt gagcgttttg tgcgaggtca gcgaaaaaat gatgcgcgct    2760
ggcgtacgct tgccggcaga tgatggaagc gttgacagcg cccacagcca ggcgccatac    2820
ggcttgagaa cagcaggatt gattgcaggt ctggtggact atgatgcgct gttgagcagt    2880
accgacgcgc aggcgctgga aatggcggag cgacttcagc aagatgccag gcttgctgca    2940
ttgtgcaaac tcggtctgtc ttcgtgsggt caattagcgg ccttcgatga tgtggtgacg    3000
acgtttcgcg aacagatatc gttaccgggc tcggcacgcc gcacccagtt gctcaaaaat    3060
cttggcttgc cacccgatgc cgcgccgac gaaatggcgg cgcgcatgtc cgacttactc    3120
ctggatctgt tcaaccggag caccttcttt tcgacgcagt cgcgtggtct ggaactgcgc    3180
ggttcgttgg gatcggctga ctggaaacat ctcaatgcgt tcagcgtcgg cgtgactggc    3240
gaggcgcttc aagtgctcgg cgtagagcgc atcggcgatg gcaaggacgg cgatgccggg    3300
ttggtcgcgt tttttgtgcg ccacgccaaa gcctctgtat ctgcgacgtc agggatcgga    3360
atcgatttca agccaggccc cggcactggc ggccgtgtta ttgattcgcg accgggtcgc    3420
tcgatgaact cgacgtgggg aggctctacc aacctgggta tttccggcgc gtaccagcat    3480
ggtcagggcg ccgccgtgat catcgcaccg tcgacgatct ccgatttcgt gcggctgtta    3540
ttcgatgtca accatcccga taccacccaa atcctgcgca ccggtgtgaa cggtggttcg    3600
attggtcttg atctgtttga aaccaatgtg aatgcctctg tggggcgaa cgtcagcgta    3660
tcgccattca gcctgagcca gaaatatggg ccacagaaac cgacggcaga tgcggccgtc    3720
tctggcccag acaatcggcg cagcaccgcg tcagggtcgt tgtcggtagg cgggacggct    3780
caggctggcg cgcactgggg gcaaatggag ttgcacctgg atcacgcctg gccgatatt    3840
atcggtctgg aatttcaggg ccgcacggat ttcaatcttg aattcaatag cggcctgaat    3900
ctgggaggcg cgctgtcttc cgcgctgggc gataaccccc aaaagttgat aaatgcgtcc    3960
actggaaacg gcaatctgca actcgccggc atccgcgtcg cgtcaagcga tgtgcagttg    4020
ccgaccgatg ctgtggttga cgacaagcgc cgtggcccct tcctgtcgac ggccagctat    4080
aaacgcacct tcgataccga agttgccaag cctgttacgg ccggggagtg gagccagatg    4140
cgccagcgcc ttgccaaagc cttttcctgac aatatcgcag agttgggcgc gctcgattac    4200
cccaccaggc ccggtgagcg tatcgcgacc atcaaacagg tgattgaccg catacaaggt    4260
gcgaaggcgc gtagcgtgga agccgtcggt gcaatggacg gaaaggcatt gcaccgtcag    4320
cgtttcgatg ccgcgagaga aatgtcgaac gccggcaaca gcgtatggcg ggcgagttcc    4380
gaaattgagc gcgcctcgat cgtggagatg ctgcatcagt tgcgtcagca ggaacaaagc    4440
gccgtccaga atcacgcccg agccattccc ggcgcgcgtg tggaattcaa cctgttcggt    4500
cgtgaatcgc tggaaacggt ggtctttcac gccatcggtc atctgggct tggcagcaag    4560
ctgaacgatc tggcggagct gcgtcgcaag gtgccgggtc tcgatcaggt catgctgagt    4620
ttccagtcgt tgcccaaggt caatcaggtg cgctacgttt ttgagatgcg ccctcaggcg    4680
aggttcgcca tcaatgacgc gctactggcg cgcgagcagc aggcatcggc acgtgcgctc    4740
ggtttgcagg gaccctcggg aagtgaattg aattggcgcg cgttctgga caagatcaaa    4800
accacgcctg acctttatcg gctggcggcg atcgccgtac ataacaccga tgaaaacccc    4860
gtgacctcaa gaatagggct gccgctgctg aatgtgtcgg ccacaggcgc gacatcgcat    4920
cagttgttcg aggcggaaat ccagttccga tacggtctgt atgacggtct gcaagggtt    4980
gagttgctga aggccggaaa cagggcattg cagtcgccgt tacgggcatt acagcaatcc    5040
ggtattcagg ccctggggca gagaacccag gccggggagg ttgcgtatgg cccccccttcg    5100
```

```
ccgcgcaaag agtcgccgtt gcgcaccgca gtggatgctg ctgcgctgac aacgagtgac      5160
atcgcgcgac aacttgaggt taaagtccag cgcatgaata ccgcgcatga gcgtgaggcg      5220
aatgctatca gttcgttcca gcaggcttat gggatcgcgt ccgcgcatct agacaggctg      5280
cttttgcgca ttcctgaatt gccattacct gaaattgatg accgcgacgt cgatggagga      5340
cgtgtgcgcg gtacatttgc gtcgctccag cgacatcatc aggcgctgga tgacgctata      5400
agtgccatgc atcaggccag cgaaaaggtg tacacgatac ctggcaagca ggccactcaa      5460
gagcaagacc cggcgctggc tcaactgctc tctgttgaaa acgtcggcg ttcgctcggg       5520 catgccttgg aaacactggc gggcagaggg gtggaagcgg gcacggccac agggcttgaa      5580
cttaacaggg tctcatcgca agtgaatgat ctggtcgctc gccggacgc gctgctaagg       5640 cagcgtgaaa gcggtgttca ggagggcggt ctggatagcg aagagctgga aatggaactt      5700
caattgacca cctcagtgct gcagcggttg cgcgccgatt tgctcggcga gcggcaggcg      5760
atggaggcta ccgccaaacg cctggatcag gcgagccgcg ctgccctcga aggtgagcgc      5820
agcttcagcg acgccgtgcg tgacagggcg tggggcgaac tcgataacgt gtag            5874
```

<210> SEQ ID NO 120
<211> LENGTH: 1957
<212> TYPE: PRT
<213> ORGANISM: Pseudomonas syringae pv. tomato DC3000

<400> SEQUENCE: 120

```
Met Val Lys Val Thr Ser Ser Gly Phe Thr Ala Asn Pro Leu Ser His
  1               5                  10                  15

His Ala Asp Ser Val Ser Pro Ala Asn Ser Pro Pro Gln Leu Pro Glu
             20                  25                  30

Pro Val His Leu Val Asp Leu Ser Glu Ser Ser Arg Lys Gly Gly Met
         35                  40                  45

Arg Asn Arg Pro His Ala Ser Leu Asn Ser Gln Val Leu Glu Leu Gln
     50                  55                  60

Ala Val Pro Ser Gln Arg Gly Lys His Val Arg Val Arg Ser His Ala
 65                  70                  75                  80

Asp Gly Glu Ser Val Ile Asn Ala Trp Leu Ala Lys Arg Pro Ser Val
                 85                  90                  95

Gln Ser Glu Thr Ser Leu Asp Asn Asp Gly Lys Leu Val Arg Tyr Thr
            100                 105                 110

Pro Val Asn His Glu Pro Leu Ala Pro Arg Asn Glu Ala Phe Phe Thr
        115                 120                 125

Ser Val Pro Gly Met Leu Met Ala Val Leu Thr Val His Pro Glu Met
    130                 135                 140

Glu His Gly Ile Ser Gly Asp Ile Thr Ala Asp Ala Val Ala Ala Arg
145                 150                 155                 160

Leu Ala Glu Pro Pro Ile Gly Leu Leu Thr Gly Ile Trp Gln Ser Ser
                165                 170                 175

His Asp Arg Ala Tyr Leu Glu Arg Gly Gly Val Val His Thr Ala Asn
            180                 185                 190

Met Glu Glu Arg Trp Ala Pro Leu Thr Leu Pro Gly Ile Asn Pro Arg
        195                 200                 205

Glu Pro Leu Arg Met Ala Gly Leu Gln Ala Asp Gly Val Tyr Leu
    210                 215                 220

His Asn Gly Ser Gln Leu Trp Arg Leu Thr Glu Thr Ala Ala Glu Ser
225                 230                 235                 240
```

-continued

```
Val Thr Thr Glu Asn Leu Pro Glu Gly Ala Ala Val Arg Ile Gly Ala
                245                 250                 255

Gly Gly Glu Val His Gly Leu His Glu Gly Ala Leu His Ser Asn Gly
            260                 265                 270

Ile Ser Arg Pro Ile Glu Leu Trp Arg Pro Lys Ala Gly Ala Pro Gly
        275                 280                 285

Arg Glu Gln Ser Pro Ala Arg Pro Val Asp Leu Leu Pro Leu Pro Gly
    290                 295                 300

Gly Thr Ala Ala Leu Ile Leu Asp Asp Lys Gly Arg Ile Tyr His Ala
305                 310                 315                 320

Asp Leu Lys Gly Thr Gly Ala Val Glu Ala His Arg Leu Lys Leu Pro
                325                 330                 335

Ala Asp Phe Ala Gln Gly Lys Gly Trp Ala Val Thr Ala Met Gly Leu
            340                 345                 350

Ser Arg Asp Asp Thr Val His Leu Met Leu Gln Asp Gln Asn Gly Arg
        355                 360                 365

Arg Met Ser Leu Gln Arg Ala Pro Gly Glu Ala Leu Phe Arg Pro Ala
    370                 375                 380

Tyr Leu Leu Asp Arg Pro Leu Leu Leu Leu Tyr Thr Glu Gly Leu His
385                 390                 395                 400

Val Pro Ser Glu Ala Ala Val Gln Ser His Val Gln Leu Asp Gly His
                405                 410                 415

Ala Gln Leu Gly His Ile Asp Gly Val Leu His Tyr Lys Ala Ala Pro
            420                 425                 430

Asp Gln Ser Trp Glu Arg Leu Lys Gln Ser Gly Gly Glu Pro Leu Thr
        435                 440                 445

Gly Leu Thr Ala Leu Tyr Ser Ser Pro Leu Gly Phe Ile Asp Arg Lys
    450                 455                 460

Pro Val Phe Ala Leu Val Gly Asp Ala Arg Gln Val Val Glu Leu Lys
465                 470                 475                 480

Leu Glu Gly Arg Thr Ser Trp Leu Pro Ser Asp Ala Glu Leu Pro Arg
                485                 490                 495

His Pro Ala Gly Gly Pro Leu Ala Val Ile Pro Asp Thr Val Ala Leu
            500                 505                 510

Arg Thr Ser Pro Ile Ala Gln Phe Asp Glu Pro Val Gln Ala Leu Ala
        515                 520                 525

Val His Gly Asn Arg Arg Val Val Ala Leu Thr Asp Ser Gly Arg Leu
    530                 535                 540

Met Ala Ala Asp Ala Asp Thr Pro Ala Arg Arg Leu Pro Thr Leu Gln
545                 550                 555                 560

Arg Pro Ile Ala Ile Ala Val Gly Leu Asn Asp Gln Leu Leu Val Leu
                565                 570                 575

His His Pro His Ser Gln Arg Pro Gln Leu Lys Arg Leu Ser Ala Lys
            580                 585                 590

Asp Asp Trp Glu Pro Val Pro Ile Ile Leu Pro Gly Ile Val His Pro
        595                 600                 605

Ser Ser Leu Arg Ala Thr Arg Thr Gly Gln Ile Gln Val Gln Leu Gly
    610                 615                 620

Glu Asn Trp His Thr Leu Leu Pro Ser Met Thr Ser His Asp Asn Gln
625                 630                 635                 640

Arg Leu Pro Ala Arg Val Lys Pro Glu Pro Glu Gly Asp Glu Ala Pro
                645                 650                 655

Ser Ala Asn Phe Leu Ala Gly Ser Asn Ala Leu Ala Asn Gln Gln Gln
            660                 665                 670
```

Ala Ser Arg Ile Ser Thr Pro His His Asp Ala Ser Val Val Thr Thr
            675                 680                 685

Leu Ala Gly Thr Thr Ala Asn Asn Pro Leu Thr Met Ala Ser Ser Leu
        690                 695                 700

Gln Ala Val Val Asp Thr Thr Arg Ala Gln Val Gly Ala Leu Ala Arg
705                 710                 715                 720

Asp Val Val Gly Ala Ala Asn Ser Thr Met Arg Ala Met Ala His
                725                 730                 735

Thr Leu Gly Val Val Leu Pro Pro Thr Pro Gln Glu Lys Arg Leu Ala
            740                 745                 750

Ser Phe His Asn Glu Ala Lys Gln Ala Tyr Thr Ser Gly Lys Ile Leu
        755                 760                 765

Phe Glu His Leu Pro Ser Leu Ala Gln Val Arg Val Ala Ser Ala Val
770                 775                 780

Gly Pro Ser Asp Gly Glu Arg Phe Gly Leu Ser His Gln Gln Thr Gln
785                 790                 795                 800

Arg Leu Leu Thr Leu Arg Glu Gly Lys Leu Glu Ala Leu Leu Arg Asp
            805                 810                 815

Leu Arg Lys Ile Gly Phe His Glu Val Ile Met Gly Asp Met Gly
        820                 825                 830

Asp Ser Asp Ser Ala His Gly Leu Val Ser Thr Thr Ser Thr Pro Thr
        835                 840                 845

Phe Arg Leu Ala Glu Leu Trp Arg Arg Gln His Ser Arg Val Asp Lys
    850                 855                 860

Ala Leu Ser Ser Ala Gly Leu Ser Arg Ser Glu Asp Ile Phe Pro Asp
865                 870                 875                 880

Leu Asn Leu Ser Ile Asn Ala Leu Ala Gly Ala Ala Leu Asn Ala
            885                 890                 895

Asp Arg Met Ser Glu Arg Glu Ala Glu Leu Leu Ser Val Leu Cys Glu
        900                 905                 910

Val Ser Glu Lys Met Met Arg Ala Gly Val Arg Leu Pro Ala Asp Asp
    915                 920                 925

Gly Ser Val Asp Ser Ala His Ser Gln Ala Pro Tyr Gly Leu Arg Thr
        930                 935                 940

Ala Gly Leu Ile Ala Gly Leu Val Asp Tyr Asp Ala Leu Leu Ser Ser
945                 950                 955                 960

Thr Asp Ala Gln Ala Leu Glu Met Ala Glu Arg Leu Gln Gln Asp Ala
            965                 970                 975

Arg Leu Ala Ala Leu Cys Lys Leu Gly Leu Ser Ser Trp Gly Gln Leu
        980                 985                 990

Ala Ala Phe Asp Asp Val Val Thr Phe Arg Glu Gln Ile Ser Leu
            995                 1000                1005

Pro Gly Ser Ala Arg Arg Thr Gln Leu Leu Lys Asn Leu Gly Leu Pro
    1010                1015                1020

Pro Asp Ala Ala Pro Asp Glu Met Ala Ala Arg Met Ser Asp Leu Leu
1025                1030                1035                1040

Leu Asp Leu Phe Asn Arg Ser Thr Phe Phe Ser Thr Gln Ser Arg Gly
            1045                1050                1055

Leu Glu Leu Arg Gly Ser Leu Gly Ser Ala Asp Trp Lys His Leu Asn
                1060                1065                1070

Ala Phe Ser Val Gly Val Thr Gly Glu Ala Leu Gln Val Leu Gly Val
        1075                1080                1085

Glu Arg Ile Gly Asp Gly Lys Asp Gly Asp Ala Gly Leu Val Ala Phe

-continued

```
               1090                1095                1100
Phe Val Arg His Ala Lys Ala Ser Val Ser Ala Thr Ser Gly Ile Gly
1105                1110                1115                1120

Ile Asp Phe Lys Pro Gly Pro Gly Thr Gly Gly Arg Val Ile Asp Ser
               1125                1130                1135

Arg Pro Gly Arg Ser Met Asn Ser Thr Trp Gly Gly Ser Thr Asn Leu
               1140                1145                1150

Gly Ile Ser Gly Ala Tyr Gln His Gly Gln Gly Ala Ala Val Ile Ile
               1155                1160                1165

Ala Pro Ser Thr Ile Ser Asp Phe Val Arg Leu Leu Phe Asp Val Asn
               1170                1175                1180

His Pro Asp Thr Thr Gln Ile Leu Arg Thr Gly Val Asn Gly Gly Ser
               1185                1190                1195                1200

Ile Gly Leu Asp Leu Phe Glu Thr Asn Val Asn Ala Ser Val Gly Ala
               1205                1210                1215

Asn Val Ser Val Ser Pro Phe Ser Leu Ser Gln Lys Tyr Gly Pro Gln
               1220                1225                1230

Lys Pro Thr Ala Asp Ala Ala Val Ser Gly Pro Asp Asn Arg Arg Ser
               1235                1240                1245

Thr Ala Ser Gly Ser Leu Ser Val Gly Gly Thr Ala Gln Ala Gly Ala
               1250                1255                1260

His Trp Gly Gln Met Glu Leu His Leu Asp His Ala Trp Ala Asp Ile
1265                1270                1275                1280

Ile Gly Leu Glu Phe Gln Gly Arg Thr Asp Phe Asn Leu Glu Phe Asn
               1285                1290                1295

Ser Gly Leu Asn Leu Gly Gly Ala Leu Ser Ser Ala Leu Gly Asp Asn
               1300                1305                1310

Pro Gln Lys Leu Ile Asn Ala Ser Thr Gly Asn Gly Asn Leu Gln Leu
               1315                1320                1325

Ala Gly Ile Arg Val Ala Ser Ser Asp Val Gln Leu Pro Thr Asp Ala
               1330                1335                1340

Val Val Asp Asp Lys Arg Arg Gly Pro Phe Leu Ser Thr Ala Ser Tyr
1345                1350                1355                1360

Lys Arg Thr Phe Asp Thr Glu Val Ala Lys Pro Val Thr Ala Gly Glu
               1365                1370                1375

Trp Ser Gln Met Arg Gln Arg Leu Ala Lys Ala Phe Pro Asp Asn Ile
               1380                1385                1390

Ala Glu Leu Gly Ala Leu Asp Tyr Pro Thr Arg Pro Gly Glu Arg Ile
               1395                1400                1405

Ala Thr Ile Lys Gln Val Ile Asp Arg Ile Gln Gly Ala Lys Ala Arg
               1410                1415                1420

Ser Val Glu Ala Val Gly Ala Met Asp Gly Lys Ala Leu His Arg Gln
1425                1430                1435                1440

Arg Phe Asp Ala Ala Arg Glu Met Ser Asn Ala Gly Asn Ser Val Trp
               1445                1450                1455

Arg Ala Ser Ser Glu Ile Glu Arg Ala Ser Ile Val Glu Met Leu His
               1460                1465                1470

Gln Leu Arg Gln Gln Glu Gln Ser Ala Val Gln Asn His Ala Arg Ala
               1475                1480                1485

Ile Pro Gly Ala Arg Val Glu Phe Asn Leu Phe Gly Arg Glu Ser Leu
               1490                1495                1500

Glu Thr Val Val Phe His Ala Ile Gly His Leu Gly Leu Gly Ser Lys
1505                1510                1515                1520
```

-continued

Leu Asn Asp Leu Ala Glu Leu Arg Arg Lys Val Pro Gly Leu Asp Gln
            1525                1530                1535

Val Met Leu Ser Phe Gln Ser Leu Pro Lys Val Asn Gln Val Arg Tyr
        1540                1545                1550

Val Phe Glu Met Arg Pro Gln Ala Arg Phe Ala Ile Asn Asp Ala Leu
    1555                1560                1565

Leu Ala Arg Glu Gln Gln Ala Ser Ala Arg Ala Leu Gly Leu Gln Gly
1570                1575                1580

Pro Ser Gly Ser Glu Leu Asn Trp Arg Gly Val Leu Asp Lys Ile Lys
1585                1590                1595                1600

Thr Thr Pro Asp Leu Tyr Arg Leu Ala Ala Ile Ala Val His Asn Thr
            1605                1610                1615

Asp Glu Asn Pro Val Thr Ser Arg Ile Gly Leu Pro Leu Leu Asn Val
        1620                1625                1630

Ser Ala Thr Gly Ala Thr Ser His Gln Leu Phe Glu Ala Glu Ile Gln
    1635                1640                1645

Phe Arg Tyr Gly Leu Tyr Asp Gly Leu Gln Gly Val Glu Leu Leu Glu
1650                1655                1660

Ala Gly Asn Arg Ala Leu Gln Ser Pro Leu Arg Ala Leu Gln Gln Ser
1665                1670                1675                1680

Gly Ile Gln Ala Leu Gly Gln Arg Thr Gln Ala Gly Glu Val Ala Tyr
            1685                1690                1695

Gly Pro Pro Ser Pro Arg Lys Glu Ser Pro Leu Arg Thr Ala Val Asp
        1700                1705                1710

Ala Ala Ala Leu Thr Thr Ser Asp Ile Ala Arg Gln Leu Glu Val Lys
    1715                1720                1725

Val Gln Arg Met Asn Thr Ala His Glu Arg Glu Ala Asn Ala Ile Ser
1730                1735                1740

Ser Phe Gln Gln Ala Tyr Gly Ile Ala Ser Ala His Leu Asp Arg Leu
1745                1750                1755                1760

Leu Leu Arg Ile Pro Glu Leu Pro Leu Pro Glu Ile Asp Asp Arg Asp
            1765                1770                1775

Val Asp Gly Gly Arg Val Arg Gly Thr Phe Ala Ser Leu Gln Arg His
        1780                1785                1790

His Gln Ala Leu Asp Asp Ala Ile Ser Ala Met His Gln Ala Ser Glu
    1795                1800                1805

Lys Val Tyr Thr Ile Pro Gly Lys Gln Ala Thr Gln Glu Gln Asp Pro
1810                1815                1820

Ala Leu Ala Gln Leu Leu Ser Val Glu Lys Arg Arg Arg Ser Leu Gly
1825                1830                1835                1840

His Ala Leu Glu Thr Leu Ala Gly Arg Gly Val Glu Ala Gly Thr Ala
            1845                1850                1855

Thr Gly Leu Glu Leu Asn Arg Val Ser Ser Gln Val Asn Asp Leu Val
        1860                1865                1870

Ala Arg Arg Asp Ala Leu Leu Arg Gln Arg Glu Ser Gly Val Gln Glu
    1875                1880                1885

Gly Gly Leu Asp Ser Glu Glu Leu Glu Met Glu Leu Gln Leu Thr Thr
1890                1895                1900

Ser Val Leu Gln Arg Leu Arg Ala Asp Leu Leu Gly Glu Arg Gln Ala
1905                1910                1915                1920

Met Glu Ala Thr Ala Lys Arg Leu Asp Gln Ala Ser Arg Ala Ala Leu
            1925                1930                1935

Glu Gly Glu Arg Ser Phe Ser Asp Ala Val Arg Asp Arg Ala Trp Gly
        1940                1945                1950

Glu Leu Asp Asn Val
        1955

<210> SEQ ID NO 121
<211> LENGTH: 864
<212> TYPE: DNA
<213> ORGANISM: Pseudomonas syringae pv. tomato DC3000

<400> SEQUENCE: 121

```
atgaacatta cgccgctcac gtcagccgcg ggcaagggct cgtccgcaca aggcacagac    60
aaaatttcca ttcccaactc cacgcgcatg atcaatgccg cttcaatcaa gtggttgaat   120
aaggtgcgta gcgccatcag tgaccacatc cgcaccagca tcgagaaagg gaaactgttc   180
gagctcgcct ccttgggcag caacatgttc ggtgtcccgg ctctttcagc cgcccctcg    240
acgctccaac ctgtgttggc gtttgaggct gaccccaatc acgacctgaa ccttgtcagg   300
gtctatatgc aggacagcgc cggcaagctc actccctggg accgacgcc caacgcggtc    360
acgacgacgt cgaatccatc agagcctgat gcgcagagcg atacggcttc gtcatcatta   420
cctcggcggc ctcccgcagg ctcggtgctg agtttgctgg cattgcgct ggatcacgcg    480
caacgccaca gtcctcgcgc ggacaggtct gccaagggac gacctggccg agaggagagg   540
aacgggcaa ggttcaatgc caagcaaaca aagccgacag aggctgaagc ctacggtgat   600
catcagacac ccaatcctga tttgcacagg caaaaagaga cagctcaacg cgttgctgaa   660
agcatcaaca gcatgcgaga gcagcaaaat ggaatgcaac gcgccgaagg gcttctcaga   720
gccaaagaag cgttgcaagc tcgggaagcc gcgcgcaagc agcttctgga cgtgctcgag   780
gccatccagg ctggccgtga agactccacc gacaagaaga tcagcgccac tgaaaagaac   840
gccacgggca tcaactacca gtga                                           864
```

<210> SEQ ID NO 122
<211> LENGTH: 287
<212> TYPE: PRT
<213> ORGANISM: Pseudomonas syringae pv. tomato DC3000

<400> SEQUENCE: 122

Met Asn Ile Thr Pro Leu Thr Ser Ala Ala Gly Lys Gly Ser Ser Ala
 1               5                  10                  15

Gln Gly Thr Asp Lys Ile Ser Ile Pro Asn Ser Thr Arg Met Ile Asn
            20                  25                  30

Ala Ala Ser Ile Lys Trp Leu Asn Lys Val Arg Ser Ala Ile Ser Asp
        35                  40                  45

His Ile Arg Thr Ser Ile Glu Lys Gly Lys Leu Phe Glu Leu Ala Ser
    50                  55                  60

Leu Gly Ser Asn Met Phe Gly Val Pro Ala Leu Ser Ala Arg Pro Ser
65                  70                  75                  80

Thr Leu Gln Pro Val Leu Ala Phe Glu Ala Asp Pro Asn His Asp Leu
                85                  90                  95

Asn Leu Val Arg Val Tyr Met Gln Asp Ser Ala Gly Lys Leu Thr Pro
            100                 105                 110

Trp Asp Pro Thr Pro Asn Ala Val Thr Thr Thr Ser Asn Pro Ser Glu
        115                 120                 125

Pro Asp Ala Gln Ser Asp Thr Ala Ser Ser Leu Pro Arg Arg Pro
    130                 135                 140

Pro Ala Gly Ser Val Leu Ser Leu Leu Gly Ile Ala Leu Asp His Ala
145                 150                 155                 160

```
Gln Arg His Ser Pro Arg Ala Asp Arg Ser Ala Lys Gly Arg Pro Gly
            165                 170                 175

Arg Glu Glu Arg Asn Gly Ala Arg Phe Asn Ala Lys Gln Thr Lys Pro
        180                 185                 190

Thr Glu Ala Glu Ala Tyr Gly Asp His Gln Thr Pro Asn Pro Asp Leu
        195                 200                 205

His Arg Gln Lys Glu Thr Ala Gln Arg Val Ala Glu Ser Ile Asn Ser
    210                 215                 220

Met Arg Glu Gln Gln Asn Gly Met Gln Arg Ala Glu Gly Leu Leu Arg
225                 230                 235                 240

Ala Lys Glu Ala Leu Gln Ala Arg Glu Ala Arg Lys Gln Leu Leu
            245                 250                 255

Asp Val Leu Glu Ala Ile Gln Ala Gly Arg Glu Asp Ser Thr Asp Lys
        260                 265                 270

Lys Ile Ser Ala Thr Glu Lys Asn Ala Thr Gly Ile Asn Tyr Gln
            275                 280                 285

<210> SEQ ID NO 123
<211> LENGTH: 837
<212> TYPE: DNA
<213> ORGANISM: Pseudomonas syringae pv. tomato DC3000

<400> SEQUENCE: 123
atgaccttaa gaatcaatac tcgttctgct accccggttg tacctctgga aacaggctct      60
acatcgcagc cgacaccacc gccggtcacg gcaagagcga ctgagcctcc ccccgtcgcc     120
aatcctgcgg cgcctaaatc agcgccaggt gttcagcaag cacacgggct gaagacgcgc     180
atcgctggca agctttccga acgtcagacc aatttcagtc tcgggattcc cggcactggt     240
cgtactctca accggcccct tgcgcagcgg gattccggag gaaggtgagca ggtatcgaac     300 gaggagagtc atgatccgtt gctcaaggaa gcgcatgaac tgcagcgtat ggtggagtcg     360
gcgctgaccc atctgaaggc ggcaccgacg tctctctggg agcgtcccgc cccttcaacg     420
gtaaggcgta ttaccaccaa gattttttccg tggctaaagc ctgccccgct gcgcgaagtc     480
gcaagcaatg gcagcaacgc caagaccaag atcaagatca actcacagca aagccctgaa     540
accatcgcag cggcggtgaa agagctgagc acccggctcg atcaccagag caaggtgctc     600
gccacagcca cccacgcact ggtcgctgcg cgtgagcatc ttgaatcgct cgaacaggcc     660
accccgccct cgtcgaccga accactggac catgccaggg ctcgcgttca acaagccgac     720
tccaccaccc gcctggccag tcagcaactt cgtgagctga ttcagggtac agacgtgttg     780
caactgggcg cgctgagtga agggcaggat caggttgaac agaaagccga gttttct       837

<210> SEQ ID NO 124
<211> LENGTH: 279
<212> TYPE: PRT
<213> ORGANISM: Pseudomonas syringae pv. tomato DC3000

<400> SEQUENCE: 124

Met Thr Leu Arg Ile Asn Thr Arg Ser Ala Thr Pro Val Val Pro Leu
1               5                   10                  15

Glu Thr Gly Ser Thr Ser Gln Pro Thr Pro Pro Val Thr Ala Arg
            20                  25                  30

Ala Thr Glu Pro Pro Val Ala Asn Pro Ala Ala Pro Lys Ser Ala
        35                  40                  45

Pro Gly Val Gln Gln Ala His Gly Leu Lys Thr Arg Ile Ala Gly Lys
    50                  55                  60
```

```
Leu Ser Glu Arg Gln Thr Asn Phe Ser Leu Gly Ile Pro Gly Thr Gly
 65                  70                  75                  80

Arg Thr Leu Asn Arg Pro Leu Arg Ser Gly Ile Pro Glu Glu Gly Glu
                 85                  90                  95

Gln Val Ser Asn Glu Glu Ser His Asp Pro Leu Leu Lys Glu Ala His
            100                 105                 110

Glu Leu Gln Arg Met Val Glu Ser Ala Leu Thr His Leu Lys Ala Ala
        115                 120                 125

Pro Thr Ser Leu Trp Glu Arg Pro Ala Pro Ser Thr Val Arg Arg Ile
130                 135                 140

Thr Thr Lys Ile Phe Pro Trp Leu Lys Pro Ala Pro Leu Arg Glu Val
145                 150                 155                 160

Ala Ser Asn Gly Ser Asn Ala Lys Thr Lys Ile Lys Ile Asn Ser Gln
                165                 170                 175

Gln Ser Pro Glu Thr Ile Ala Ala Val Lys Glu Leu Ser Thr Arg
            180                 185                 190

Leu Asp His Gln Ser Lys Val Leu Ala Thr Ala Thr His Ala Leu Val
        195                 200                 205

Ala Ala Arg Glu His Leu Glu Ser Leu Glu Gln Ala Thr Pro Pro Ser
210                 215                 220

Ser Thr Glu Pro Leu Asp His Ala Arg Ala Arg Val Gln Gln Ala Asp
225                 230                 235                 240

Ser Thr Thr Arg Leu Ala Ser Gln Gln Leu Arg Glu Leu Ile Gln Gly
                245                 250                 255

Thr Asp Val Leu Gln Leu Gly Ala Leu Ser Glu Gly Gln Asp Gln Val
            260                 265                 270

Glu Gln Lys Ala Glu Phe Ser
        275

<210> SEQ ID NO 125
<211> LENGTH: 615
<212> TYPE: DNA
<213> ORGANISM: Pseudomonas syringae pv. tomato DC3000

<400> SEQUENCE: 125
ataggtaata tttgcggcac ctcgggctca cgtcatgtgt atagcccatc ccatacacaa     60
cgaataactt cagctccctc tacatccact catgttggtg gagatacact gacatccatt    120
catcagcttt cgcatagtca gagagagcag tttctgaaca tgcatgatcc aatgagagta    180
atgggacttg accatgatac cgagcttttc agaacgacgg atagtcgcta tataaaaaac    240
gataaactcg cgggcaatcc acaatccatg gcgagtatcc ttatgcatga agaactgcgc    300
cccaatcgtt ttgccagcca tacaggtgcc caaccacacg aagcaagggc gtacgttccg    360
aaaagaataa aagccaccga tctaggagtt ccatcactga acgtaatgac tggctcgcta    420
gcgcgagacg gaattagagc ttatgatcac atgagtgata atcaggtctc tgtcaaaatg    480
cgactgggag attttctcga aagggggtggc aaggtctatg ccgacgcttc gtctgtagct    540
gacgatgggg aaacatcaca agctctgatt gtcacattgc ccaaaggaca gaaagtgccg    600
gtcgaaaggg tctga                                                     615

<210> SEQ ID NO 126
<211> LENGTH: 204
<212> TYPE: PRT
<213> ORGANISM: Pseudomonas syringae pv. tomato DC3000

<400> SEQUENCE: 126
```

-continued

```
Met Gly Asn Ile Cys Gly Thr Ser Gly Ser Arg His Val Tyr Ser Pro
1               5                   10                  15

Ser His Thr Gln Arg Ile Thr Ser Ala Pro Ser Thr Ser Thr His Val
            20                  25                  30

Gly Gly Asp Thr Leu Thr Ser Ile His Gln Leu Ser His Ser Gln Arg
        35                  40                  45

Glu Gln Phe Leu Asn Met His Asp Pro Met Arg Val Met Gly Leu Asp
    50                  55                  60

His Asp Thr Glu Leu Phe Arg Thr Thr Asp Ser Arg Tyr Ile Lys Asn
65                  70                  75                  80

Asp Lys Leu Ala Gly Asn Pro Gln Ser Met Ala Ser Ile Leu Met His
                85                  90                  95

Glu Glu Leu Arg Pro Asn Arg Phe Ala Ser His Thr Gly Ala Gln Pro
            100                 105                 110

His Glu Ala Arg Ala Tyr Val Pro Lys Arg Ile Lys Ala Thr Asp Leu
        115                 120                 125

Gly Val Pro Ser Leu Asn Val Met Thr Gly Ser Leu Ala Arg Asp Gly
    130                 135                 140

Ile Arg Ala Tyr Asp His Met Ser Asp Asn Gln Val Ser Val Lys Met
145                 150                 155                 160

Arg Leu Gly Asp Phe Leu Glu Arg Gly Gly Lys Val Tyr Ala Asp Ala
                165                 170                 175

Ser Ser Val Ala Asp Asp Gly Glu Thr Ser Gln Ala Leu Ile Val Thr
            180                 185                 190

Leu Pro Lys Gly Gln Lys Val Pro Val Glu Arg Val
        195                 200
```

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: HIV TAT domain

<400> SEQUENCE: 127

```
Tyr Gly Arg Lys Lys Arg Arg Gln Arg Arg Arg
1               5                   10
```

<210> SEQ ID NO 128
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 128
agtaggatcc atagaaaaat accataggggg tgca         34

<210> SEQ ID NO 129
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 129
agtatctaga tcacttgtca tcgtcgtcct tgtagtcgtc aatcacatgc gcttg     55

<210> SEQ ID NO 130
<211> LENGTH: 28

```
<212> TYPE: DNA
<213> ORGANISM: Artificial Sequence
<220> FEATURE:
<223> OTHER INFORMATION: Description of Artificial Sequence:  primer

<400> SEQUENCE: 130
atgcggatcc cgtatgacct tgtaaaat                                        28

<210> SEQ ID NO 131
<211> LENGTH: 58
<212> TYPE: DNA
<213> ORGANISM: Artificial Sequence
<220> FEATURE:
<223> OTHER INFORMATION: Description of Artificial Sequence:  primer

<400> SEQUENCE: 131
atgctctaga tcaagcgtaa tctggaacat cgtatgggta gccgttgtaa aactgctt      58

<210> SEQ ID NO 132
<211> LENGTH: 32
<212> TYPE: DNA
<213> ORGANISM: Artificial Sequence
<220> FEATURE:
<223> OTHER INFORMATION: Description of Artificial Sequence:  primer

<400> SEQUENCE: 132
agtcggatcc gataatcctg gatgatccat tg                                   32

<210> SEQ ID NO 133
<211> LENGTH: 55
<212> TYPE: DNA
<213> ORGANISM: Artificial Sequence
<220> FEATURE:
<223> OTHER INFORMATION: Description of Artificial Sequence:  primer

<400> SEQUENCE: 133
agtcctcgag tcacttgtca tcgtcgtcct tgtagtcttg atgtgccctg tactt         55

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 134
agtaaagctt acgggcaggt attgcaag                                        28

<210> SEQ ID NO 135
<211> LENGTH: 55
<212> TYPE: DNA
<213> ORGANISM: Artificial Sequence
<220> FEATURE:
<223> OTHER INFORMATION: Description of Artificial Sequence:  primer

<400> SEQUENCE: 135
agtatctaga tcacttgtca tcgtcgtcct tgtagtcttt tttgggcagc cagcg         55

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 136
agtaggatcc tgcctccaac tattggct                                        28
```

<210> SEQ ID NO 137
<211> LENGTH: 55
<212> TYPE: DNA
<213> ORGANISM: Artificial Sequence
<220> FEATURE:
<223> OTHER INFORMATION: Description of Artificial Sequence: primer

<400> SEQUENCE: 137
agtatctaga tcacttgtca tcgtcgtcct tgtagtctct cgctttgaac gcctg    55

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 138
ataggatccc gagaacggcg cggacgtg    28

<210> SEQ ID NO 139
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 139
atatctagat catttatcat catcatcttt ataatcctcg tcagagctct ctgc    54

<210> SEQ ID NO 140
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 140
gatggatcca cgcacataac aacggtg    27

<210> SEQ ID NO 141
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 141
atatctagat catttatcat catcatcttt ataatcaatc tgacttaata c    51

<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 142
attggtacct ctagaggatc caaccttcaa tctgaa    36

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: primer -continued

<400> SEQUENCE: 143
atgtcgactt agcggtagag cattgcg         27

<210> SEQ ID NO 144
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 144
gcgaattcgt tagttgattt tgtctagcg       29

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 145
gaggatccgc cgttgtaaaa ctgcttaga       29

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 146
gtaaaacgac ggccagt                    17

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 147
atgagaattc gcatctccat gcatctt         27

<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 148
cggactcgag ctcagggcgc gaaactga        28

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 149
gtatggtacc ccgacctggc aaccgcag        28

<210> SEQ ID NO 150
<211> LENGTH: 40

```
<212> TYPE: DNA
<213> ORGANISM: Artificial Sequence
<220> FEATURE:
<223> OTHER INFORMATION: Description of Artificial Sequence: primer

<400> SEQUENCE: 150
agtcctcgag actaaagagg gtatacgaat gggaaatata                          40

<210> SEQ ID NO 151
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 151
agtcgatatc tcattgccag ttacggtacg ggc                                 33

<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 152
gatggatcca agtaaccggt ctgcaca                                        27

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 153
atatctagat catttatcat catcatcttt atatgacttt tgagccgcct g             51

<210> SEQ ID NO 154
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 154
ggcctcgaga tggacgggtc cggggagcag ctt                                 33

<210> SEQ ID NO 155
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 155
ggcactagtt cagcccatct tcttccagat ggtg                                34

<210> SEQ ID NO 156
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 156 cacctatttta attcgttgag aaacaatgaa aata                               34
```

```
<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 157
gacatctcgt ctcgccaagc c                                          21

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 158
caccaagcaa cgtctggagg caacaatgca                                 30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 159
gtcgcctagg aaattattta gttcccatga                                 30

<210> SEQ ID NO 160
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 160
caccaagatc ggagaggatc agaatatggc g                               31

<210> SEQ ID NO 161
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 161
ggggactatt ctaaaagcat acttggc                                    27

<210> SEQ ID NO 162
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 162
caccttagcg taaggagcta acaatgaacc c                               31

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: primer
```

```
<400> SEQUENCE: 163
gtttcgcgcc ctgagcgc                                                  18

<210> SEQ ID NO 164
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 164
cacccatagg ggtgcaataa caatgaatag a                                   31

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 165
gtcaatcaca tgcgcttggc c                                              21

<210> SEQ ID NO 166
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 166
aaaaagcagg cttcgaagga gatagaacca tgtatagccc atcc                     44

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 167
agaaagctgg gtaacagacc ctttcgac                                       28

<210> SEQ ID NO 168
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 168
cacccacata ggatatgtaa acaatgcaaa taaagaac                            38

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 169
gccgttgtaa aactgcttag aggc                                           24

<210> SEQ ID NO 170
<211> LENGTH: 30
```

```
<212> TYPE: DNA
<213> ORGANISM: Artificial Sequence
<220> FEATURE:
<223> OTHER INFORMATION: Description of Artificial Sequence:  primer

<400> SEQUENCE: 170
caccacaaag aggttttcaa acaatgaatc                                       30

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 171
gcagtagagc gtgtcgcgac                                                  20

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 172
atacataacg ctggccta                                                    18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 173
cggatccatg acaatcgt                                                    18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 174
gcaaatcctt taagctct                                                    18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 175
tgtttcgcta agccactg                                                    18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 176
tcgcgccaaa ccagggag                                                    18
```

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 177
tcccacattc tgcaacgc                                              18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 178
aaccccattc agtcacgc                                              18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 179
tttgccatgc gtgattgc                                              18

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 180
cctctacgat ctattcaa                                              18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 181
ggcaatgctc gcggcctg                                              18

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 182
tccggtagct cgtcagcg                                              18

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: primer

```
<400> SEQUENCE: 183
gtggatgacc acatagttat g                                              21

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 184
agcccatccc atacacaa                                                  18

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 185
cactttctgt cctttggg                                                  18

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 186
tattcagctt caagaatg                                                  18

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence:  primer

<400> SEQUENCE: 187
acccgcatag acctgtctg                                                 19

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence:  primer

<400> SEQUENCE: 188
atcactccgt ctcgatatc                                                 19

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 189
tgccctgtac ttcatgcg                                                  18

<210> SEQ ID NO 190
<211> LENGTH: 18
```

```
<212> TYPE: DNA
<213> ORGANISM: Artificial Sequence
<220> FEATURE:
<223> OTHER INFORMATION: Description of Artificial Sequence:  primer

<400> SEQUENCE: 190
ctatgtattt caaaacac                                                   18

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence:  primer

<400> SEQUENCE: 191
atcaccctct gtaattccc                                                  19

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 192
cgcatttcaa ccagctca                                                   18

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 193
cagcaccgga agcccttc                                                   18

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 194
ggtaatattt gtggtacttc                                                 20

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 195
cagatgtaac gtgacatc                                                   18

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence:  primer

<400> SEQUENCE: 196
acagtcagca atcactcg                                                   18
```

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 197
tacactccat acactgctg                                                     19

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 198
ttgaattcat gaaaatacat aacgctgg                                           28

<210> SEQ ID NO 199
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 199
ttctcgagtc agacatctcg tctcgc                                             26

<210> SEQ ID NO 200
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 200
ttggatccgt atgcacgcaa atcctttaag ctc                                     33

<210> SEQ ID NO 201
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 201
ttctcgagtc agtcgcctag gaaattattt agttcc                                  36

<210> SEQ ID NO 202
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 202
ttgaattcat gaatagagtt tccggtagct c                                       31

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: primer

```
<400> SEQUENCE: 203
ttctcgagtc agtcaatcac atgcgcttgg                                    30

<210> SEQ ID NO 204
<211> LENGTH: 31
<212> TYPE: DNA
<213> ORGANISM: Artificial Sequence
<220> FEATURE:
<223> OTHER INFORMATION: Description of Artificial Sequence:  primer

<400> SEQUENCE: 204
ttgaattcat gggtaatatt tgcggcacct c                                  31

<210> SEQ ID NO 205
<211> LENGTH: 26
<212> TYPE: DNA
<213> ORGANISM: Artificial Sequence
<220> FEATURE:
<223> OTHER INFORMATION: Description of Artificial Sequence:  primer

<400> SEQUENCE: 205
ttctcgagtc agacccttc gaccgg                                         26

<210> SEQ ID NO 206
<211> LENGTH: 32
<212> TYPE: DNA
<213> ORGANISM: Artificial Sequence
<220> FEATURE:
<223> OTHER INFORMATION: Description of Artificial Sequence:  primer

<400> SEQUENCE: 206
ttgaattcat gcaaataaag aacagtcatc tc                                 32

<210> SEQ ID NO 207
<211> LENGTH: 33
<212> TYPE: DNA
<213> ORGANISM: Artificial Sequence
<220> FEATURE:
<223> OTHER INFORMATION: Description of Artificial Sequence:  primer

<400> SEQUENCE: 207
ttctcgagtc agccgttgta aaactgctta gag                                33

<210> SEQ ID NO 208
<211> LENGTH: 1185
<212> TYPE: DNA
<213> ORGANISM: Pseudomonas syringae pv. tomato DC3000

<400> SEQUENCE: 208
atgactgcct acgatgtaga aaaggaatgg agcagaattt ccaatactgc cgctaaaact    60
caccagaaca acgattttga aggtttcacc taccaggact tcagaaccca cgtaccgatc   120
atggacaagg aaggcttcgc ggcacaaacc gaacgctgcc ttgagcgcaa cgagcgcaac   180
tgcctgatcg gctttaccag tggcaccagc ggcaacctca acgctgtta ttactactac   240 gactgtgaag tcgatgaaga cagttcccgc tccaacgtct ccgcagcaa tggtttcatt   300 caacccggtg atcgctgcgc caacctgttc accatcaacc tgttttctgc cctgaacaac   360
atcaccacca tgatggccgg taactgcggt gcgcatgtgg tgtccgtagg cgatatcacc   420
ctgctgacca agagtcactt cgaggcgctc aactcgatca agctcaacgt actgctcggc   480
gtaccctcga ccatcctgca gttcatcgat gccatgcagc agcacggtgt gcacatcgat   540
atcgaaaagg tcgtcttcaa tggcgagggc ctgaaaacct tcagaagaa atcatcagg    600
```

-continued

```
gaagcctttg cgaacaggt ctccatcgtc ggcgtatatg gcagttccga gggcggcatt    660
ctgggtttca ccaacagccc ttgccacacc gaatacgagt ttctttccga caaatacttc    720
atcgagaaag aaggcgacag catcctcatc acctcgttga cccgcgagaa cttcacaccg    780
ctgctccggt atcgcctggg agacaccgca acgctttcgc tgaaaggcga caagctctat    840
ttgactgaca tccagcggga ggacatgagc ttcaacttca tgggcaacct cattggtctg    900
ggcatcattc aacaagcgat caaacagaca ctgggccgca cgctggaaat ccaggttcac    960
ctgtcagtga ctgatgcgcg caaagaactg gtgaccgttt cgttcaggc ctcggaagtc    1020 aacgaagatg aacgcgccag aatcgaaaca gccatcgccg atattccgga catcaacgag    1080
gcctatcaga aagaccaggg cagcgtgctg gttgtgcgca aggatgccag agactacgcc    1140
gtctcggagc gaggcaaaat gctctacatc attgaccgca ggaat                   1185
```

<210> SEQ ID NO 209
<211> LENGTH: 395
<212> TYPE: PRT
<213> ORGANISM: Pseudomonas syringae pv. tomato DC3000

<400> SEQUENCE: 209

```
Met Thr Ala Tyr Asp Val Glu Lys Glu Trp Ser Arg Ile Ser Asn Thr
 1               5                  10                  15

Ala Ala Lys Thr His Gln Asn Asn Asp Phe Glu Gly Phe Thr Tyr Gln
            20                  25                  30

Asp Phe Arg Thr His Val Pro Ile Met Asp Lys Glu Gly Phe Ala Ala
        35                  40                  45

Gln Thr Glu Arg Cys Leu Glu Arg Asn Glu Arg Asn Cys Leu Ile Gly
    50                  55                  60

Phe Thr Ser Gly Thr Ser Gly Asn Leu Lys Arg Cys Tyr Tyr Tyr Tyr
65                  70                  75                  80

Asp Cys Glu Val Asp Glu Asp Ser Ser Arg Ser Asn Val Phe Arg Ser
                85                  90                  95

Asn Gly Phe Ile Gln Pro Gly Asp Arg Cys Ala Asn Leu Phe Thr Ile
            100                 105                 110

Asn Leu Phe Ser Ala Leu Asn Asn Ile Thr Thr Met Met Ala Gly Asn
        115                 120                 125

Cys Gly Ala His Val Val Ser Val Gly Asp Ile Thr Leu Leu Thr Lys
    130                 135                 140

Ser His Phe Glu Ala Leu Asn Ser Ile Lys Leu Asn Val Leu Leu Gly
145                 150                 155                 160

Val Pro Ser Thr Ile Leu Gln Phe Ile Asp Ala Met Gln Gln His Gly
                165                 170                 175

Val His Ile Asp Ile Glu Lys Val Val Phe Asn Gly Glu Gly Leu Lys
            180                 185                 190

Thr Phe Gln Lys Lys Ile Ile Arg Glu Ala Phe Gly Glu Gln Val Ser
        195                 200                 205

Ile Val Gly Val Tyr Gly Ser Ser Glu Gly Gly Ile Leu Gly Phe Thr
    210                 215                 220

Asn Ser Pro Cys His Thr Glu Tyr Glu Phe Leu Ser Asp Lys Tyr Phe
225                 230                 235                 240

Ile Glu Lys Glu Gly Asp Ser Ile Leu Ile Thr Ser Leu Thr Arg Glu
                245                 250                 255

Asn Phe Thr Pro Leu Leu Arg Tyr Arg Leu Gly Asp Thr Ala Thr Leu
            260                 265                 270
```

```
                -continued

Ser Leu Lys Gly Asp Lys Leu Tyr Leu Thr Asp Ile Gln Arg Glu Asp
        275                 280                 285

Met Ser Phe Asn Phe Met Gly Asn Leu Ile Gly Leu Gly Ile Ile Gln
    290                 295                 300

Gln Ala Ile Lys Gln Thr Leu Gly Arg Thr Leu Glu Ile Gln Val His
305             310                 315                 320

Leu Ser Val Thr Asp Ala Arg Lys Glu Leu Val Thr Val Phe Val Gln
                325                 330                 335

Ala Ser Glu Val Asn Glu Asp Glu Arg Ala Arg Ile Glu Thr Ala Ile
                340                 345                 350

Ala Asp Ile Pro Asp Ile Asn Glu Ala Tyr Gln Lys Asp Gln Gly Ser
        355                 360                 365

Val Leu Val Val Arg Lys Asp Ala Arg Asp Tyr Ala Val Ser Glu Arg
        370                 375                 380

Gly Lys Met Leu Tyr Ile Ile Asp Arg Arg Asn
385             390                 395
```

US 8,716,460 B2

PSEUDOMONAS AVR AND HOP PROTEINS, THEIR ENCODING NUCLEIC ACIDS, AND USE THEREOF

This application is a division of U.S. patent application Ser. No. 10/365,742, filed Feb. 12, 2003, which claims benefit of U.S. Provisional Patent Application Ser. Nos. 60/356,408, filed Feb. 12, 2002, and 60/380,185, filed May 10, 2002, which are hereby incorporated by reference in their entirety.

This work was supported by National Science Foundation Grant Nos. MCB-9982646 and IBN-0096348, National Science Foundation Plant Genome Research Program Cooperative Agreement DBI-0077622, and National Research Initiative Competitive Grants Program, U.S. Department of Agriculture, Grant No. 01-35319-10019. The U.S. Government may have certain rights in this invention.

FIELD OF THE INVENTION

The present invention relates to isolated DNA molecules corresponding to the open reading frames of *Pseudomonas syringae* pv. *tomato* DC3000, the isolated avirulence effector proteins and hrp-dependent outer proteins encoded thereby, as well as their various uses.

BACKGROUND OF THE INVENTION

The plant pathogenic bacterium *Pseudomonas syringae* is noted for its diverse and host-specific interactions with plants. A specific strain may be assigned to one of at least 40 pathovars based on its host range among different plant species and then further assigned to a race based on differential interactions among cultivars of the host. In host plants the bacteria typically grow to high population levels in leaf intercellular spaces and then produce necrotic lesions. In nonhost plants or in host plants with race-specific resistance, the bacteria elicit the hypersensitive response (HR), a rapid, defense-associated programmed death of plant cells in contact with the pathogen (Alfano & Collmer, *J. Bacteriol.* 179:5655-5662 (1997)). The ability to produce either of these reactions in plants appears to be directed by hrp (HR and pathogenicity) and hrc (HR and conserved) genes that encode a type III protein secretion pathway and by avr (avirulence) and hop (Hrp-dependent outer protein) genes that encode effector proteins injected into plant cells by the pathway (Alfano & Collmer, *J. Bacteriol.* 179:5655-5662 (1997)). These effectors may also betray the parasite to the HR-triggering R-gene surveillance system of potential hosts (hence the avr designation), and plant breeding for resistance based on such gene-for-gene (avr-R) interactions may produce complex combinations of races and differential cultivars (Keen, *Annu. Rev. Genet.* 24:447-463 (1990)). hrp/hrc genes are probably universal among necrosis-causing gram-negative plant pathogens, and they have been sequenced in *P. syringae* pv. *syringae* (Psy) 61, *Erwinia amylovora* Ea321, *Xanthomonas campestris* pv. *vesicatoria* (Xcv) 85-10, and *Ralstonia solanacearum* GM11000 (Alfano & Collmer, *J. Bacteriol.* 179:5655-5662 (1997)). Based on their distinct gene arrangements and regulatory components, the hrp/hrc gene clusters of these four bacteria can be divided into two groups: I (*Pseudomonas* and *Erwinia*) and II (*Xanthomonas* and *Ralstonia*). The discrepancy between the distribution of these groups and the phylogeny of the bacteria provides some evidence that hrp/hrc gene clusters have been horizontally acquired and, therefore, may represent pathogenicity islands (Pais) (Alfano & Collmer, *J. Bacteriol.* 179:5655-5662 (1997)).

Virulence effector proteins delivered to or into host cells by type III secretion systems are key factors in the pathogenicity of many bacteria, including animal pathogens in the genera *Salmonella, Yersinia, Shigella,* and *Escherichia*, and plant pathogens in the genera *Pseudomonas, Erwinia, Xanthomonas, Ralstonia*, and *Pantoea* (Galan & Collmer, *Science* 284:1322-1328 (1999)). In plant pathogens, the type III secretion machinery is referred to as the hypersensitive response and pathogenicity (Hrp) system because secretion mutants typically lose their ability to elicit the defense-associated hypersensitive response in nonhost plants and to grow parasitically or be pathogenic in host plants (Alfano & Collmer, *J. Bacteriol.* 179:5655-5662 (1997)). These phenotypes demonstrate the importance of the Hrp system in bacterium-plant interactions, and global identification of effectors will be important for understanding the pathogenesis of bacteria that use type III secretion systems. Unfortunately, several factors have hindered searches for type III effector genes. These factors include: (i) effectors are often redundant with mutants having only subtle phenotypes; (ii) with few exceptions (see e.g., Miao & Miller, *Proc. Natl. Acad. Sci. USA* 97:7539-7544 (2000)) motifs that can identify proteins as substrates for type III secretion have not been recognized (Lloyd et al., *Mol. Microbiol.* 39:520-532) (2001); (iii) many effectors show no similarity to known proteins; and (iv) some pathogens have multiple type III secretion systems which deliver different sets of effectors (Cornelis & Van Gijsegem, *Annu. Rev. Microbiol.* 54:735-774 (2000)). Thus, a complete inventory of type III effector genes is lacking for any pathogen, although it seems that pathogens such as *Salmonella* may have many such genes (Worley et al., *Mol. Microbiol.* 36:749-761 (2000)).

Plant pathogen type III effector proteins are mostly designated Avr or Hop, depending on whether their primary phenotype involves plant reaction or secretion behavior. Many effectors were initially discovered through their ability to betray the pathogen to the host R (resistance) gene surveillance system, thereby rendering the pathogen avirulent on a test plant (Keen, *Annu. Rev. Genet.* 24:447-463 (1990)). Over 25 effector genes have been identified by Avr or Hop phenotypes in various *P. syringae* pathovars and races (Vivian & Arnold, *J. Plant Pathol.* 82:163-178 (2000); Alfano et al., *Proc. Natl. Acad. Sci. USA* 97:4856-4861 (2000)). The encoded effectors seem to determine both basic pathogenicity and host range, but the number of such proteins produced by any single strain has not been systematically investigated. *P. s. tomato* DC3000 is known to carry at least three avr genes, avrPto (Ronald et al., *J. Bacteriol.* 174:1604-1611 (1992)), avrPtoB (Kim et al., *Cell* 109:589-598 (2002)), and avrE (Lorang & Keen, *Mol. Plant-Microbe Interact.* 8:49-57 (1995)), with the latter being in the Hrp pathogenicity island along with five other candidate effector genes (Alfano et al., *Proc. Natl. Acad. Sci.* 97:4856-486 (2000); Lorang & Keen, *Mol. Plant-Microbe Interact.* 8:49-57 (1995)).

The present invention is a further advance in the effort to identify, clone, and sequence Avr and Hop proteins or polypeptides from plant pathogens.

SUMMARY OF THE INVENTION

One aspect of the present invention relates to an isolated nucleic acid molecule that includes a nucleotide sequence which (i) encodes a protein or polypeptide having the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, or SEQ ID NO: 209; or (ii) hybridizes, under stringency conditions comprising a hybridization medium which includes 0.9×SSC at a temperature of 42° C., to a DNA molecule complementary to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, OR SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, or SEQ ID NO: 208; or (iii) is complementary to the nucleic acid molecules of (i) and (ii). Expression vectors, host cells, and transgenic plants which include the DNA molecules of the present invention are also disclosed. Methods of making such host cells and transgenic plant are disclosed.

A further aspect of the present invention relates to isolated effector proteins or polypeptides encoded by the nucleic acid molecules of the present invention. Compositions which contain the proteins or polypeptides are also disclosed.

Yet another aspect of the present invention relates to methods of imparting disease resistance to a plant. According to one approach, this method is carried out by transforming a plant cell with a heterologous DNA molecule of the present invention and regenerating a transgenic plant from the transformed plant cell, wherein the transgenic plant expresses the heterologous DNA molecule under conditions effective to impart disease resistance. According to another approach, this method is carried out by treating a plant with a protein or polypeptide of the present invention under conditions effective to impart disease resistance to the treated plant.

A further aspect of the present invention relates to a method of causing eukaryotic cell death which includes: introducing into a eukaryotic cell a cytotoxic *Pseudomonas* protein of the present invention, said introducing being performed under conditions effective to cause cell death.

A still further aspect of the present invention relates to a method of treating a cancerous condition which includes introducing a cytotoxic *Pseudomonas* protein of the present invention into cancer cells of a patient under conditions effective to cause death of cancer cells, thereby treating the cancerous condition.

Yet another aspect of the present invention relates to a method of inhibiting programmed cell death which includes introducing into a eukaryotic cell susceptible to programmed cell death, a protein of the present invention that is a hypersensitive response suppressor, said introducing being performed under conditions effective to inhibit programmed cell death of the eukaryotic cell.

Yet another aspect of the present invention relates to a method of modifying a metabolic pathway in a cell which includes: introducing into a cell a protein or polypeptide of the present invention which interacts with a native cellular protein involved in a metabolic pathway, wherein the protein or polypeptide modifies the metabolic pathway through its interaction with the native cellular protein.

It is believed that bacteria have evolved effector proteins to make exquisite alterations in host metabolism. While plant disease resistance, suppression of programmed cell death, and cancer cell toxicity are important uses, as mentioned above, it is believed that these effector proteins can be used to modify or effect metabolic targets in eukaryotes, including both yeasts and higher order species, such as plants and animals. It is noteworthy that several of the effector proteins disclosed herein have homologs in other phytopathogenic bacteria. Thus, these proteins appear to represent a set of effectors that are conserved among *Pseudomonas, Erwinia, Xanthomonas,* and *Ralstonia* spp. By disrupting or augmenting the function of these effectors through, for example, transgenic expression thereof in a host plant, it is believed that use of these effectors may lead to widely applicable means for controlling diseases of plants.

BRIEF DESCRIPTION OF THE DRAWINGS

FIGS. 1A-C illustrate assays for Hrp system-dependent secretion in culture or translocation in planta of candidate effector proteins. *P. s. tomato* DC3000 and a Hrp secretion mutant derivative were used for tests of newly identified candidate effectors (1A-B). DC3000 or a DC3000 hrcC mutant (Yuan & He, *J. Bacteriol.* 178:6399-6402 (1996), which is hereby incorporated by reference in its entirety) carrying test ORFs (i.e., candidate effectors) fused to either the FLAG (F) or hemagglutinin (HA) epitopes were grown in Hrp-inducing media, and cultures were separated into cell (lanes 1-3) and supernatant (lanes 4 and 5) fractions and analyzed by SDS/PAGE and immunoblotting. Lanes 1 and 4, wild-type DC3000; lanes 2 and 5, wild-type DC3000 (pTestORF); lanes 3 and 6, DC3000 hrcC mutant (pTestORF). As an additional control against leakage, pCPP2318 was included in all strains, which encodes the mature form of β-lactamase (β-lac). The presence of an epitope-tagged protein in the supernatant fraction of the wild type (lane 5), but absence in the hrcC secretion mutant (lane 6), indicated that the test ORF encoded a secreted product. In FIG. 1C, an AvrRpt2 translocation assay was performed with DC3000 HopPtoG. Test strains were infiltrated into *A. thaliana* Col-0 (RPS2) and Col-0 rps2-201 (rps2) plants. Plant responses were scored 18 h after inoculation for hypersensitive response (HR) or no visible response (N).

FIGS. 2A-C illustrate pHIR11-dependent HR is suppressed by HopPtoE, and a *P. s. tomato* DC3000 hopPtoE mutant exhibits an enhanced HR. FIG. 2A is a schematic representation of the pHIR11-based suppression assay in *P. fluorescens* (Pf) 55. When DC3000 effectors are individually expressed in trans in Pf(pHIR11), they can potentially suppress the HopPsyA-dependent HR. FIG. 2B shows *N. tabacum* cv. *xanthi* leaves that were infiltrated with Pf(pHIR11) (left panel) or Pf(pHIR11, phopPtoE)(right panel). 'N' denotes no HR. FIG. 2C shows quantitative differences in the ability of DC3000 wild-type (WT), hopPtoE mutant UNL139, and complemented mutant UNL139 (phopPtoE) to elicit the HR in *N. tabacum* cv. *xanthi* leaves. Different dilutions of bacterial cells/ml (1, $10^8$ cells/ml; 2, $10^7$ cells/ml; 3, $10^6$ cells/ml; and 4, $10^5$ cells/ml) were infiltrated into leaves, then leaves were photographed after 24 hr.

FIG. 3A is an image of an immunoblot showing that AvrPto is type III-secreted from DC3000 (WT), but not from a secretiondefective DC3000 hrcC mutant (hrcC). β-Lactamase (β-Lac) was used as a lysis control. C, cell pellet fractions; S, supernatant fractions. FIG. 3B is an image showing that the HR elicited in *N. tabacum* cv. *xanthi* by DC3000 is inhibited when hopPtoE is expressed in trans. FIG. 3C shows the results of *P. fluorescens*(pHIR11) mixing experiments in *N. tabacum* cv. *xanthi*, demonstrating that HR suppression can occur when HopPtoE and HopPsyA are TTSS-delivered by different bacteria. pLN18 is a pHIR11 derivative that lacks hopPsyA, but encodes a functional TTSS. pCPP2089 (Huang et al., *Mol. Plant-Microbe Interact.* 4:469-476 (1991), which is hereby incorporated by reference in its entirety) is a pHIR11 derivative encoding a defective TTSS.

FIGS. 4A-C identify *P. s. tomato* DC3000 effectors that suppress the HR on tobacco and *Arabidopsis*. FIG. 4A lists DC3000 effectors that were tested in the pHIR11 assay. A 'y' indicates that the effector inhibited the HR, an 'n' indicates that it did not, and a 'y*' indicates that it partially suppressed the HR. Refer to the Materials and Methods for information regarding effector constructs. The nucleic acid and amino acid sequences of AvrPphE$_{Pto}$, AvrPpiB1$_{Pto}$, HopPtoB, HopPtoC, HopPtoD1, HopPtoD2, HopPtoF (previously designated AvrPphF$_{Pto}$ ORF2), HopPtoJ, and HopPtoK are disclosed in U.S. patent application Ser. No. 09/825,414 to Collmer et al., filed Apr. 2, 2002, which is hereby incorporated by reference in its entirety. The nucleic acid and amino acid sequence of AvrPto is reported at Genbank Accession L20425; Salmeron & Staskawicz, *Mol. Gen. Genet.* 239:6-16 (1993), each of which is hereby incorporated by reference in its entirety. The nucleic acid and amino acid sequence of AvrPtoB is reported at Genbank Accession AY074795 and Kim et al., *Cell* 109:589-598 (2002), each of which is hereby incorporated by reference in its entirety. AvrPtoB was independently shown to suppress the programmed cell death elicited by AvrPto or by heterologously-expressed BAX in *Nicotiana benthamiana* (Abramovitch et al., *EMBO J.* 22:60-69 (2003), which is hereby incorporated by reference in its entirety). FIG. 4B is an image of *N. tabacum* cv. *xanthi* leaves that were infiltrated with *P. fluorescens*(pHIR11) with different effector constructs (noted above each picture). Complete suppression of the HR is denoted with 'N'. FIG. 4C is an image of the same strains (as illustrated in FIG. 4B) infiltrated into *Arabidopsis* Ws-0, producing identical results.

In FIG. 5A, *N. tabacum* cv. *xanthi* leaves were co-infiltrated with *A. tumefaciens* C58C1 carrying phopPsyA and another strain carrying each candidate suppressor. All of the suppressive effectors identified in the pHIR11 screen also suppressed the HR elicited by HopPsyA in this test. In FIG. 5B, an immunoblot of plant tissues with different agroinfiltrations shows that each HA epitope-tagged effector was made in planta. The asterisks indicates a protein of the predicted size of the effector in that lane.

In FIG. 7A, *Agrobacterium* C58C1 strains carrying binary vectors that encode Bax or a specific effector were co-infiltrated into *N. benthamiana* leaves. Leaves were photographed after 7 days. N* indicates that the HR was nearly absent. Effector constructs were the same as in FIG. 4. In FIG. 7B, yeast strain EGY48 carrying plasmids that encoded for Bax (pJG4-5-Bax) and a specific effector were spotted on plates at 5-fold dilutions. Expression of Bax was induced by galactose, whereas effector expression was constitutive. Only AvrPpiB1 was unable to suppress Bax-induced killing. Bcl-xL (pGilda-Bcl-xL), an animal protein known to inhibit Bax-induced PCD, was used as a positive control.

DETAILED DESCRIPTION OF THE INVENTION

Figure 3A:
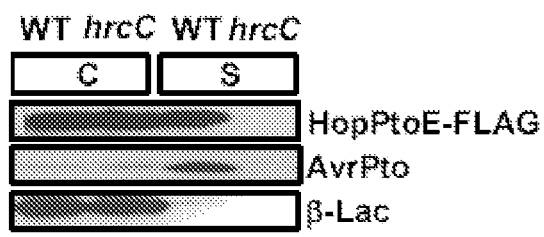
FIGS. 3A-C illustrate that HR suppression is not due to blocking TTSS, and the TTSS is functional.

One aspect of the present invention relates to *Pseudomonas syringae* pv. *syringae* DC 3000 nucleic acid molecules which encode Avr or Hop effector proteins.

A first nucleic acid molecule encodes HopPtoI (ORF1) and has a nucleotide sequence according to SEQ ID NO: 1 as follows:

```
atgcttatcgggcacagcttgcatcacatgcgacccactgctgtggattc
tagcctaccaacttccgcaactagccagactatcagcaataccaaaagtc
ggctggatccgcatcgtgtccgtgaacttacattcatcggagtgggtagt
agtgttgcctacctactcaatgagcttaatggtcgctttgccgatagcgg
ggtaacaacgccgttttttaggaaaagtcagtattgtaggcaaggacgact
cttgggccgagaatgttcgtgggaaaggttatattaaccaccagactgaa
attataagccaatgggaccaacaggttccaaaatatgatcctaactatgc
tgctcgtgccgaatttctgcgagtaaccgaagacagttgacgcgaacag
tggagttaggcgcagaacatttgaaagcacaggtaacaggcatttcgcga
ttggatgacggttgttttcgaataaatctggacaatggccagattttgca
aagccgacagattgtactggggactggtgccggacccctaccagtatct
ggaacagcgttacatcacacactcaagcagaaaaacgactggacaacatc
aaattgcatgagcagaaagccttgcgtggcaaggtgctggacctggatga
gtttatgcgagcgagtgatgcctctcccagacgtttgctggaaaaacgg
tggtgatacatggaccaaatgcaggcattgatgcagctgaacgtgccggg
gagcttggggcaaatgcggtttggtttacccgcagtacgaatccggtatt
gctggatggcaatcaactaaaattcgcgccagagctggccaaaagcgcta
tacataaagttgacaaattagatattcgcccaacaaaactagagaatggt
```

```
ttcgcattgcgactacattacagttcgctaggacaagactcacgggagcc aaagaaggtgctagatgcggactattatgtgtacgccatgggtcaagata ttcataagccgggtagcgcagcggccatactaggcagtcttcttgaccac ctagaacctatatatgactacgatcaagtctatagcgaccagcctttcaa gacagtaataggcttgcaaagtcgcggctccaatagcgataatggtttaa ttattgtcggggcggcagttgctcagctggccactaatgttcagcatagc tataaggaccacgcgttggatcgtatacttgaggaaatgaccaggctccc cgaaaagcaaacagaaaagctatcacaaatgctgttagaaggtgcgccat cagtacagatccagacatatctaaaaacctggcagttagatagcggtcaa ccgccagataaacaggtactgcagaatcaagtagaaaactatctggcggc ccgagactacttccagcggcaaaccaacgaacaaaagggcaacctggacg gggttgccgcagaggtaaaaaatcaaaccttaaccgaggttgcatcggtc atcgtgtcaccacagttaggcacgatcaaggcctccgctgcagcattgtc gggacttatgccagcatatgtggctaacggcgaaaataactttaccaccg ataatcgaactatgctccgtgccggcattgcagcaagatatccgaatata ggtaacgctgaagccagtgcatttatcgatgaagtagtaactttgcgtca ccttaatagtcagcgttttattgagaaggtagcaggcgaaatgatggaca aaggagctcaaccactggtgtcgttacgcccccggtcctaggtgtcccg gcgtcggtcaggactgcttatgaggcttacttgcacgcgctgaattctgg agcgcacgatggtacgccgttaagtcagcgctggctgcccaaaaaatag
```

The HopPtoI protein encoded by this nucleic acid molecule has an amino acid sequence according to SEQ ID NO: 2 as follows:

```
MLIGHSLHHMRPTAVDSSLPTSATSQTISNTKSRLDPHRVRELTFIGVGS

SVAYLLNELNGRFADSGVTTPFLGKVSIVGKDDSWAENVRGKGYINHQTE

IISQWDQQVPKYDPNYAARAEFSASNRRQLTRTVELGAEHLKAQVTGISR

LDDGCFRINLDNGQILQSRQIVLGTGAGPHTSIWNSVTSHTQAEKRLDNI

KLHEQKALRGKVLDLDEFMRASDASPQTFAGKTVVIHGPNAGIDAAERAG

ELGANAVWFTRSTNPVLLDGNQLKFAPELAKSAIHKVDKLDIRPTKLENG

FALRLHYSSLGQDSREPKKVLDADYYVYAMGQDIHKPGSAAAILGSLLDH

LEPIYDYDQVYSDQPFKTVIGLQSRGSNSDNGLIIVGAAVAQLATNVQHS

YKDHALDRILEEMTRLPEKQTEKLSQMLLEGAPSVQIQTYLKTWQLDSGQ

PPDKQVLQNQVENYLAARDYFQRQTNEQKGNLDGVAAEVKNQTLTEVASV

IVSPQLGTIKASAAALSGLMPAYVANGENNFTTDNRTMLRAGIAARYPNI

GNAFASAFIDEVVTLRHLNSQRFIEKVAGEMMDKGAQPLVSLRPPVLGVP

ASVRTAYEAYLHALNSGAHDGTPLSQRWLPKK
```

HopPtoI has been shown to be a protein that is secreted by DC3000.

A second nucleic acid molecule encodes HopPtoH (ORF2) and has a nucleotide sequence according to SEQ ID NO: 3 as follows:

```
atgatcactccgtctcgatatccaggcatctatatcgccccctcagtaa cgaaccgacagcagctcacacatttaaagaacaagcagaggaagcacttg accatatcagcgccgcaccctctggcgataagctattgcgaaaaatatcc actcttgccagtcaaaaagatagaaaagtcacgctaaaagagattgaaat aaataaccagtgttataccgaagctgttctgagcagraggcaactggaaa agtacgaaccagaaaactttaacgagaaccggcacattgcatcacagcta tcacgaaaggggacctttaccaaaggtgaaggaagcaacgcgattattgg ctggtcaccagacaaagcaagcatacgcttaaatcagaatggctcaccgt tacaccttggaatggataacgacgacaaaatcacgaccctagctcatgag ctcgttcatgctcgacatgtgttaggtggcagctccttagcggatggcgg agatcgctataatccacgtacgggatctggcaaagaggaacttagggccg ttggattagataagtaccgctattcacttacaaaaaaaccgtcagagaac tccatccgagctgaacacggcctgcctctgcgcatgaagtacagggcaca tcaatag
```

The HopPtoH protein encoded by this nucleic acid molecule has an amino acid sequence according to SEQ ID NO: 4 as follows:

```
MITPSRYPGIYIAPLSNEPTAAHTFKEQAEEALDHISAAPSGDKLLRKIS

TLASQKDRKVTLKEIEINNQCYTEAVLSRRQLEKYEPENFNENRHIASQL

SRKGTFTKGEGSNAIIGWSPDKASIRLNQNGSPLHLGMDNDDKITTLAHE

LVHARHVLGGSSLADGGDRYNPRTGSGKEELRAVGLDKYRYSLTKKPSEN

SIRAEHGLPLRMKYRAHQ
```

HopPtoH has been shown to be a protein that is secreted by DC3000. HopPtoH has significant homology (1e-114), as detected by BLAST search, to ORF3 from *Pseudomonas syringae* pv. *pisi* avrPpiC2 locus (Arnold et al., *Microbiology* 147:1171-1182 (2001); GenBank Accession No. CAC16702, each of which is hereby incorporated by reference in its entirety.

A third nucleic acid molecule encodes HopPtoE (ORF3) and has a nucleotide sequence according to SEQ ID NO: 5 as follows:

```
atgaatagagtttccggtagctcgtcagcgacttggcaggcagtcaacga tcttgtggagcaagtaagcgagagaaccacgttgtctacgacaggttatc agacggcaatgggccgcttgaacaaaccggaaaaatcagatgcggatgcg ctgatgactatgaggagggcgcaacagtacacggatagcgcgaagcgaac ttatatttcggaaacgctgatgaatctggcagatttgcagcaaaggaaaa tctatcgcaccaacagcgggaacttgcgtggcgcgattgagatgacgcct acgcaactcacagattgcgtacagaagtgccgcgaagaggggttctccaa ttgtgacatacaggcgctggaaatcggcttgcaccttcgacataagttag gaatctcagatttcaccatctacagcaaccgtaagttaagccataactat gtggtcatccaccccagcaatgcatttccgaaaggagcgattgtagactc ttggacgggacagggcgtggtggagctggacttcaagacccgattgaaat
```

```
tcaagcaccgggaagagaactacgcagtgaacgccaatatgcacgagtgg atcgagagatacgccaagcgcatgtgattgactga
```

The HopPtoE protein encoded by this nucleic acid molecule has an amino acid sequence according to SEQ ID NO: 6 as follows:

```
MNRVSGSSSATWQAVNDLVEQVSERTTLSTTGYQTAMGRLNKPEKSDADA

LMTMRRAQQYTDSAKRTYISETLMNLADLQQRKIYRTNSGNLRGAIEMTP

TQLTDCVQKCREEGFSNCDIQALEIGLHLRHKLGISDFTIYSNRKLSHNY

VVIHPSNAFPKGAIVDSWTGQGVVELDFKTRLKFKHREENYAVNANMHEW

IERYGQAHVID
```

HopPtoE has been shown to be a protein that is secreted by DC3000 as well as translocated in planta.

A fourth nucleic acid molecule encodes HopPtoG (ORF4) and has a nucleotide sequence according to SEQ ID NO: 7 as follows:

```
atgcaaataaagaacagtcatctctattcagcttcaagaatggtgcagaa tacttttaatgcctcgcctaagatggaagtaactaatgcaatagcaaaaa ataatgaacctgctgcgctgagcgctacgcaaactgcaaagacacacgaa ggcgattcaaaaggccaatccagcaataactctaaattgcccttccgcgc catgaggtacgctgcataccttgcaggcagcgcctacctctacgataaaa ctgccaataatttttttctttctaccacttctctgcatgatggcaaaggt ggttttaccagcgatgccaggcttaacgatgcacaagataaagcgcgaaa gcgctaccaaaacaaccatagcagcactcttgaaaataaaaactcgcttt taagcccgcttaggctttgcggagagaatcagttcttaacgatgattgat tatcgtgcagcaactaagatttacctctccgacctagttgacacggagca agcgcacacatcaattctgaagaatatatgtgcctgaaaggtgagctta ccaatgaagaggcaataaaaaaactcaacccggaaaaaacaccaaaagac tatgaccttacaaatagcgaagcctatataagcaagaacaaatattcttt gaccggcgttaaaaatgaggagacgggatctactggttatacatctcgtt ctatcacaaagccatttgtggaaaaggcctgaaacactttataaaagcg actcatggcgaaaaagctctcacgcccaagcagtgtatggaaactcttga taacttacttcgaaaaagtatcacgctcaacagtgattcccaattcgcag caggccaggcacttttggttttcagacaggtctatgcgggtgaagacgct tgggggatgcggaacgggtcatattgaaaagccattataatcggggcac tgtactccaagatgaagctgataaaatagaactaagtaggccgttctcag agcaagatttagcaaagaacatgtttaagaggaataccagcattgcaggg ccagtgctctaccacgcatatatttatatacaagaaaaaatcttcaagct acccccccgacaaaatagaagatttgaaacataaatcaatggcagacttga aaaacctgcctttgactcatgttaagcttagcaattccggtgtgggattt gaagacgcctcagggttaggagactcgtttacagctctcaacgcgacgtc ctgtgttaatcacgcaagaataatgagtggtgagcctccttgtcaaaag
```

```
atgatgttgtgattctgataggttgcctcaacgccgtatacgacaattcg agcggaataaggcattctctccgcgaaattgcacgagggtgctttgtggg tgctggttttacggtccaggacggtgacgacttctacaaacagatctgca aaaacgcctctaagcagttttacaacggctaa
```

The HopPtoG protein encoded by this nucleic acid molecule has an amino acid sequence according to SEQ ID NO: 8 as follows:

```
MQIKNSHLYSASRMVQNTFNASPKMEVTNAIAKNNEPAALSATQTAKTHE

GDSKGQSSNNSKLPFRAMRYAAYLAGSAYLYDKTANNFFLSTTSLHDGKG

GFTSDARLNDAQDKARKRYQNNHSSTLENKNSLLSPLRLCGENQFLTMID

YRAATKIYLSDLVDTEQAHTSILKNIMCLKGELTNEEAIKKLNPEKTPKD

YDLTNSEAYISKNKYSLTGVKNEETGSTGYTSRSITKPFVEKGLKHFIKA

THGEKALTPKQCMETLDNLLRKSITLNSDSQFAAGQALLVFRQVYAGEDA

WGDAERVILKSHYNRGTVLQDEADKIELSRPFSEQDLAKNMFKRNTSIAG

PVLYHAYIYIQEKIFKLPPDKIEDLKHKSMADLKNLPLTHVKLSNSGVGF

EDASGLGDSFTALNATSCVNHARIMSGEPPLSKDDVVILIGCLNAVYDNS

SGIRHSLREIARGCFVGAGFTVQDGDDFYKQICKNASKQFYNG
```

HopPtoG has been shown to be a protein that is secreted by DC3000 as well as translocated in planta by recombinant *Pseudomonas syringae* pv. *pisi*. Thus, HopPtoG appears to be a Hrp-injected effector protein. HopPtoG has significant homology, as detected by BLAST search (1e-137), to a hypothetical protein of *Ralstonia solanacearum* (see GenBank Accession No. NP_521884, which is hereby incorporated by reference in its entirety).

A fifth nucleic acid molecule encodes HopPtoS1 (ORF5) and has a nucleotide sequence according to SEQ ID NO: 9 as follows:

```
atgggtaatatttgtggtacttctggctccaatcatgtgtatagtccgcc tattagccctcaacatgcatctggttcgtccacaccagtgcccagtgctt ctgggacgatgctttctctcagtcatgaacaaatattaagccagaactat gctagcaatataaaggggaaatatcgcacgaaccccgaaaaggaccatc tcctaggctttctgatacgctgatgaagcaggcgctgtcttcagtgatca cacaagagaaaagcgacttaaaagtcaaccaagtcaatagcccaagat attcagcctccaaacagcatgatcaaaaatgcacttgatgaaaaagacag ccacccttttggtgattgcttttcagacgatgaatttcttgcgatccatc tctatacgagttgtctttacagaccgatcaaccatcatctgcggtatgcc ccgaaaaatgatgtcgcgcctgttgtcgaggcaatgaatagcggtttggc caaacttgctcaataccctgattatcaggtgtctggtcagctgcatagag gcatcaagcaaaagatggatgatggtgaagttatgagtcgcttcaagccg ggtaatacttatcgtgatgacgcgttcatgagcacatcgactagaatgga tgttacagaagaatttacttccgatgtcacgttacatctgcagtcctcat cagccgtcaatataggtcccttttcaaaaaacccatacgaggacgaagcg ctcatcccgccctgacgcctttcaaagtaaccggtctgcacaagcagga
```

```
cgataggtggcacgtccacttgaacgagatcgcagagagctctgacgagt ga
```

The HopPtoS1 protein encoded by this nucleic acid molecule has an amino acid sequence according to SEQ ID NO: 10 as follows:

```
MGNICGTSGSNHVYSPPISPQHASGSSTPVPSASGTMLSLSHEQILSQNY

ASNIKGKYRTNPRKGPSPRLSDTLMKQALSSVITQEKKRLKSQPKSIAQD

IQPPNSMIKNALDEKDSHPFGDCFSDDEFLAIHLYTSCLYREINHHLRYA

PKNDVAPVVEAMNSGLAKLAQYPDYQVSGQLHRGIKQKMDDGEVMSRFKP

GNTYRDDAFMSTSTRMDVTEEFTSDVTLHLQSSSAVNIGPFSKNPYEDEA

LIPPLTPFKVTGLHKQDDRWHVHLNEIAESSDE
```

HopPtoS1 has been shown to be a protein that is secreted by DC3000 as well as translocated in planta. HopPtoS1 has significant homology, as detected by BLAST search (1e-5), to a chicken ADP-ribosyltransferases (Tsuchiya, *J. Biol. Chem.* 269:27451-27457 (1994); GenBank Accession No. P55807, each of which is hereby incorporated by reference in its entirety), as well as significant homology to a type III-secreted ADP-ribosyltransferase from *P. aeruginosa* (Yahr et al., *Mol. Microbiol.* 22:991-1003 (1996), which is hereby incorporated by reference in its entirety). Further confirming its similarity to ADP-ribosyltransferases, HopPtoS1 has been determined to possess an ART domain (pfam1129).

A sixth nucleic acid molecule encodes ORF6 and has a nucleotide sequence according to SEQ ID NO: 11 as follows:

```
atgagcttatcgccgacgctgcaaaagctaactaatatattgggcccgac aaaaaatgccaagcctgtcacagaggctatccagtggcaggaaggcatgg atataacgctgcatgtcagcggcgacagccttaccttactagctaaaatc atagaactgcgtacagaccctaaagacgacattttattgcgcaagctgct tacccatacgtttccgggcctgcgtctgcgccgtggcgcgcttaccatca accctgatgaaagtgccctggttttctcttatgaacacgattttcaccttt ctggacaaagcccgttttgagagcctgctggccaactttgctgaaacggc gcaggagcttcgagacacagcgacacattttcgttttaactga
```

The protein encoded by this nucleic acid molecule has an amino acid sequence according to SEQ ID NO: 12 as follows:

```
MSLSPTLQKLTNILGPTKNAKPVTEAIQWQEGMDITLHVSGDSLTLLAKI

IELRTDPKDDILLRKLLTHTFPGLRLRRGALTINPDESALVFSYEHDFHL

LDKARFESLLANFAETAQELRDTATHFRFN
```

Although the protein of SEQ ID NO: 12 possesses N-terminal Hop features and features shared by type III chaperones, this protein was shown not to be secreted by DC3000. Because ORF6 is located directly upstream of ORF17 (described infra), it is believed that the protein of SEQ ID NO: 12 is a type III chaperone for the protein encoded by ORF17.

A seventh nucleic acid molecule encodes ORF7 and has a nucleotide sequence according to SEQ ID NO: 13 as follows:

```
atgaaacaacgagcgacagtcatctgcaaacgtgacggccaggtgcttta cgtacgcaaaccaaaatcccgctgggctttgccaggtggcaagattgaag ccggggaaacgcctttccaggctgccgtgcgcgagctttgcgaagaaacc ggtctggaaaatctcgatctgttgtacctggcggtgtacgagaaaggtga ggtcacgcactacgtgttcaccactcaggttcctgcctacagcgagcctt cgccccagaacgagatttctgcctgcaaatggcttgcgcccaaaaatctt ggcgaccttaaggccagcagcgcgaccaaggctatcgtcaagtcgtatgg ccgccaggctgaagacggtttactcagcgctaactag
```

The protein encoded by this nucleic acid molecule has an amino acid sequence according to SEQ ID NO: 14 as follows:

```
MKQRATVICKRDGQVLYVRKPKSRWALPGGKIEAGETPFQAAVRELCEET

GLENLDLLYLAVYEKGEVTHYVFTTQVPAYSEPSPQNEISACKWLAPKNL

GDLKASSATKAIVKSYGRQAEDGLLSAN
```

This protein shares significant homology, as detected by BLAST analysis (3e-7), to MutT mutator of *Mesorhizobium loti* (Genbank Accession No. NP_104556, which is hereby incorporated by reference in its entirety). The protein of SEQ ID NO: 12 was shown not to be secreted by DC3000. Although this protein is not secreted, it may still be an effector protein, because AvrB similarly is not secreted in culture although it is translocated in planta (see van Dijk et al., *J. Bacteriol.* 181:4790-4797 (1999); Gopalan et al., *Plant Cell* 8:1095-1105 (1996), each of which is hereby incorporated by reference in its entirety).

An eighth nucleic acid molecule encodes ORF8 and has a nucleotide sequence according to SEQ ID NO: 15 as follows:

```
gtgctcgcttttgcatacgtcagcctgattagagagcagaaattggacat caaaaaacgttggccttccagtgagcaggagttggtagaagtccgacggt ttaacaaaccctcgcccggctgccgcgtttccaggttcgcaatcgcctc acgccccgcttgattcaggcgctgctgcgggcggctcagattggtcgcgc gttgaaaccggtcaaacatgacctgcggattgaaacaaccatcgtcagca ccggtaacgtccctgtttcagtgcgaatcataaggcccaaaggcaaaccc aaaggcgtggtgtttgatattcacggcggcggtgggtgatcggcaacgc ccagatgaacgatgacctcaatatcggtatcgttaacgcgtgcaacgtgg cggtcgtgtccgttgattacagattggctttatcgaccccgtcgaaggg ctgatggatgactgcttttctgccgcatgctggctgctgggtagcgactg taaggagtttgccggcctgccggttattgtcgtcggtgagtccgcgggcg ggcatcttgccgcagccactttgctcaaattgaaagccaggcccgacttg ctcaagcgcgtagtcggcacggttctgtattacggcgtgtacgacctgac cgggacaaaaagcgttcgtaccgcaggcccggaaacgctggtgctcgacg gccgggcatggtcggcgcaatgcgcttgctcgccccggacagaaccgac gagaagcgccgcgagccgccgttatcgcccttgtatggcgacctcacgga tctgccgcccgccctgatgtttgtcggcgaactcgacccgctgctggacg acacgctggaaatggccgagcgatggaaaaactcggcagacgttgaaatg
```

-continued

```
catcttctgcccgagtctccacatgggttcatccacttcccgactgcctt ggcgcgcaaggtacttgcgcgcagccacgagtggataaacgcgaggatgg aaggacggccttaa
```

The protein encoded by this nucleic acid molecule has an amino acid sequence according to SEQ ID NO: 16 as follows:

```
VLAFAYVSLIREQKLDIKKRWPSSEQELVEVRRFNKTLARLPRFQVRNRL

TPRLIQALLRAAQIGRALKPVKHDLRIETTIVSTGNVPVSVRIIRPKGKP

KGVVFDIHGGGWVIGNAQMNDDLNIGIVNACNVAVVSVDYRLALSTPVEG

LMDDCFSAACWLLGSDCKEFAGLPVIVVGESAGGHLAAATLLKLKARPDL

LKRVVGTVLYYGVYDLTGTKSVRTAGPETLVLDGPGMVGAMRLLAPDRTD

EKRREPPLSPLYGDLTDLPPALMFVGELDPLLDDTLEMAERWKNSADVEM

HLLPESPHGFIHFPTALARKVLARSHEWINARMEGRP
```

This protein shares significant homology, as detected by BLAST analysis (1e-12), to a putative esterase/lipase of *Mesorhizobium loti* (Genbank Accession No. NP_105776, which is hereby incorporated by reference in its entirety). The protein of SEQ ID NO: 16 was shown not to be secreted by DC3000. Although this protein is not secreted, it may still be an effector protein, because AvrB similarly is not secreted in culture although it is translocated in planta (see van Dijk et al., *J. Bacteriol.* 181:4790-4797 (1999); Gopalan et al., *Plant Cell* 8:1095-1105 (1996), each of which is hereby incorporated by reference in its entirety).

A ninth nucleic acid molecule encodes ORF9 and has a nucleotide sequence according to SEQ ID NO: 17 as follows:

```
atgcaaacctatatacccta tccaaaaaaccctcccaccgttggtacagt tctgctgacttcctatggctcattcgcccatgaaaacgagatacctaaat cttgtgctgccgacgctttaagagtaggcaaagagctcgctgatggtttc gatggcgaggttcatcatctaggcgctctgatgctgatgatttccgactt tccagcagagccgctgctgaaagcatctgctgctaagaaaggttctttgc taggaattacttcgcttggctacctattatcctatggatctactggtgaa aaagcgaagcgaatcatcgaagcaggttgtggtatttttctcgtcagagt gagtggtgatattgaaaccctaaagcaaaaattgaagtttatagctctt ggtctgaataccagaagttccttgaaccatttttgaagacaggtgacttt tatccagtgaaaacgtcgtcgttttccgaataa
```

The protein encoded by this nucleic acid molecule has an amino acid sequence according to SEQ ID NO: 18 as follows:

```
MQTYIPYPKNPPTVGTVLLTSYGSFAHENEIPKSCAADALRVGKELADGF

DGEVHHLGALMLMISDFPAEPLLKASAAKKGSLLGITSLGYLLSYGSTGE

KAKRIIEAGCGIFLVRVSGDIENPKAKIEVYSSWSEYQKFLEPILKTGDF

YPVKTSSFSE
```

This protein shares significant homology, as detected by BLAST analysis (3e-50), to ORF4 of *Pseudomonas serioboryae* (Genbank Accession No. BAA87063, which is hereby incorporated by reference in its entirety).

A tenth nucleic acid molecule encodes ORF10 and has a nucleotide sequence according to SEQ ID NO: 19 as follows:

```
atgatcaacctcacccacattgcgtcttcattggcgcgggcagcgctcag cgattcgacaaagccgaagatggagcgcgcgataaacgtcgcgagccaca tcgctggcaaagtcgcgttgcaggtcaccagctcattactggagcagaaa ggtctgcttaacgagcgtcagcagaaagggctctcgatgattctgaaggc cttgagcggcaaggagccggtgaacaatgtcgagacgcacgaaggggag gccgattcaatctggcgcgagccgccttcgacgtggccagcgttgtctgg gagcgcgacaagtcgatgcataacgtgatgagctttctgggcgtcagcga cagcaagggcaagatgttgttctctctgggcaagaagctggcggatgcaa tggccaagcctgagcctggcaaggacaacagtgaggccacaaatgcgcgc catgcctatttctccagcaacttgaaactgaacaagttgatgaacgacct cactgaccaggttttcaacaagattcgccagtcgaacggtgatcgcgtgc gacgacccatgccagaaccattctggagaccttacggcgcccaacagcaa gcgcgcccgcaaacgcctcccggcactcgcccacaagccaacagcgcccc gccaccgccgccgaaagcagagccacgacctgcgtcgggccggcctgacg gcgcccaacagcaggcgcgcccggaaacgccgcctcgtactcgaccgcag gccaatagcactccgccaccgccgccgaaagcagagccacgacctgcgtc gggccggcctgacggcgcccagcagcaagcacgcccggaaacgcgccgc gcactcgcccgcaggcgaacagcacgccgccaccgccgcccaaggcagag ccacgacctgcgtccggccggcctgacggcgcccaacagcaagcacgccc ggaaacgccacctcgcactcgccccaagcgaacagcgcgccgcctccgc cgcccaaagcagagccacgacctgcgtccggccggcctgacggcacccaa cagcaagcacgcccggaaacgccacctcgcactcgccccaagcgaacag cgcgccgctccgccgcccaaagcagaacccagcgcaggcggcgaacggc cttcaacggcgcggcccaataacacatcggctgctgacgcatctgccagg gtgggcgattccgcacctgccaagccgcccgtcaagccgttgtacgagca cttgggcctcactgacatgtcggtagacttatccgccgttaaaaaggctt acagagatgccgcgatgaagaaccaccctgataaaaccgcggcaacgag gccgaggcggccgagcgcttcaaagtcatttcaaatgcgtacaagatttt gtccgaccggagttgcgcaaagcatacgacaacggccgtatcaatgagg ctggtaatagggcatga
```

The protein encoded by this nucleic acid molecule has an amino acid sequence according to SEQ ID NO: 20 as follows:

```
MINLTHIASSLARAALSDSTKPKMERAINVASHIAGKVALQVTSSLLEQK

GLLNERQQKGLSMILKALSGKEPVNNVETHEGGGRFNLARAAFDVASVVW

ERDKSMHNVMSFLGVSDSKGKMLFSLGKKLADAMAKPEPGKDNSEATNAR

HAYFSSNLKLNKLMNDLTDQVFNKIRQSNGDRVRRPMPEPFWRPYGAQQQ

ARPQTPPGTRPQANSAPPPPPKAEPRPASGRPDGAQQQARPETPPRTRPQ

ANSTPPPPPKAEPRPASGRPDGAQQQARPETPPRTRPQANSTPPPPPKAE
```

-continued
PRPASGRPDGAQQQARPETPPRTRPQANSAPPPPPKAEPRPASGRPDGTQ

QQARPETPPRTRPQANSAPPPPPKAEPSAGGERPSTARPNNTSAADASAR

VGDSAPAKPPVKPLYEHLGLTDMSVDLSAVKKAYRDAAMKNHPDKNRGNE

AEAAERFKVISNAYKILSDPELRKAYDNGRINEAGNRA.

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and shares significant homology, as detected by BLAST analysis (2e-11), to DnaJ protein (Genbank Accession No. BAB 17689, which is hereby incorporated by reference in its entirety).

An eleventh nucleic acid molecule encodes ORF11 and has a nucleotide sequence according to SEQ ID NO: 21 as follows:

```
atgaacattacgccgctcacgtcagccgcgggcaagggctcgtccgcaca
aggcacagacaaaatttccattcccaactccacgcgcatgatcaatgccg
cttcaatcaagtggttgaataaggtgcgtagcgccatcagtgaccacatc
cgcaccagcatcgagaaagggaaactgttcgagctcgcctccttgggcag
caacatgttcggtgtcccggctctttcagcgcgccctcgacgctccaac
ctgtgttggcgtttgaggctgaccccaatcacgacctgaaccttgtcagg
gtctatatgcaggacagcgccggcaagctcactcctgggacccgacgcc
caacgcggtcacgacgacgtcgaatccatcagagcctgatgcgcagagcg
atacggcttcgtcatcattacctcggcggcctcccgcaggctcggtgctg
agtttgctgggcattgcgctggatcacgcgcaacgccacagtcctcgcgc
ggacaggtctgccaagggacgacctggccgagaggagaggaacggggcaa
ggttcaatgccaagcaaacaaagccgacagaggctgaagcctacggtgat
catcagacacccaatcctgatttgcacaggcaaaaagagacagctcaacg
cgttgctgaaagcatcaacagcatgcgagagcagcaaaatggaatgcaac
gcgccgaagggcttctcagagccaaagaagcgttgcaagctcgggaagcc
gcgcgcaagcagcttctggacgtgctcgaggccatccaggctggccgtga
agactccaccgacaagaagatcagcgccactgaaaagaacgccacgggca
tcaactaccagtga
```

The protein encoded by this nucleic acid molecule has an amino acid sequence according to SEQ ID NO: 22 as follows:

MNITPLTSAAGKGSSAQGTDKISIPNSTRMINAASIKWLNKVRSAISDHI

RTSIEKGKLFELASLGSNMFGVPALSARPSTLQPVLAFEADPNHDLNLVR

VYMQDSAGKLTPWDPTPNAVTTTSNPSEPDAQSDTASSSLPRRPPAGSVL

SLLGIALDHAQRHSPRADRSAKGRPGREERNGARFNAKQTKPTEAEAYGD

HQTPNPDLHRQKETAQRVAESINSMREQQNGMQRAEGLLRAKEALQAREA

ARKQLLDVLEAIQAGREDSTDKKISATEKNATGINYQ

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis (5e-7), to a HrpA-like protein (Genbank Accession No. AAB00126.1, which is hereby incorporated by reference in its entirety).

A twelfth nucleic acid molecule encodes ORF13 and has a nucleotide sequence according to SEQ ID NO: 23 as follows:

```
atgcgcacatccgttaatggtctgcttgagcacagcctgaagaccctggg
ctttgatacttcggcattgcaggccttgcgcgacgacggttatttactgt
ggcaaggcaaggataagcaagccagtcttctggttccctctactgacggc
gacgcgcttttcgctatctgtaccttgagccgtgtcgatcccgagcacga
cggacgtctgctggcgcttgcattgcacctgaacctgtctcctgtccaca
cgatgagcgcatgtatagcacttgatgtcgagcaaaacacgttgtgtctt
cgctacacccatgaccttggcgggaacggggcagataccctgttgcttgc
gctcgaaaacgcccaagcgcttgctgaacagatcaagcaggtaatcgaaa
actttaggcacgatcagggacgccgatag
```

The protein encoded by this nucleic acid molecule has an amino acid sequence according to SEQ ID NO: 24 as follows:

MRTSVNGLLEHSLKTLGFDTSALQALRDDGYLLWQGKDKQASLLVPSTDG

DALFAICTLSRVDPEHDGRLLALALHLNLSPVHTMSACIALDVEQNTLCL

RYTHDLGGNGADTLLLALENAQALAEQIKQVIENFRHDQGRR

Because ORF13 shares features common to type III chaperones and is located directly upstream of hopPtoS1 (ORF5), it is believed that the protein of SEQ ID NO: 24 is a type III chaperone for HopPtoS1.

A thirteenth nucleic acid molecule encodes ORF14 and has a nucleotide sequence according to SEQ ID NO: 25 as follows:

```
atgatcgcgttcgcaaccggactgctagaacacagcctgaaacggcttgg
atacgacgccgcagatttgcaatcccttcgggatgaagggtatttgctgt
ggcacgggaaaaacggtcacaccagcctgttggtgcccgctgctggcggg
gatgcgcttttgtcatcagcaccctgagctacatcgatcctgaacagga
cgggcggctgctggcgcttgcgctgcatttgaacttgtcgccagcccaca
ctctgggcgccagtatcgcgctggatatcgagcaaaataccttgtgcctg
cgttacacgcacgacctcactgggcacggcacagacaatttgtcccgcgc
gcttgaaagcactcaggcacttgccgagcagatcaagcaggtcatcgaaa
ccttccgcagtgaattcggacgccgccaatgccgcccacacagcccga
cggccagatgccgtggcgctttag
```

The protein encoded by this nucleic acid molecule has an amino acid sequence according to SEQ ID NO: 26 as follows:

MIAFATGLLEHSLKRLGYDAADLQSLRDEGYLLWHGKNGHTSLLVPAAGG

DALFVISTLSYIDPEQDGRLLALALHLNLSPAHTLGASIALDIEQNTLCL

RYTHDLTGHGTDNLSRALESTQALAEQIKQVIETFRSEFGRPPMPAHTAR

RPDAVAL

ORF14 shares features common to type III chaperones and shares weak similarity with ORF8 of the DC3000 Conserved Effector Locus ("CEL") (U.S. patent application Ser. No. 09/825,414 to Collmer et al., filed Apr. 3, 2001, which is hereby incorporated by reference in its entirety), which is a candidate chaperone for the protein encoded by CEL ORF7. Thus, the protein of SEQ ID NO: 26 is likely a chaperone for the protein of SEQ ID NO: 28.

A fourteenth nucleic acid molecule encodes ORF15 and has a nucleotide sequence according to SEQ ID NO: 27 as follows:

gtgaaaaagtctggcgctggaactcaagcctatgcgttgttcgcctctgc gacgggaagctcgtcgaagggcgttctaagtaccattgccaggcacctga cgggatgttttgcacccaacaagactgcgcttcattcagcaacagccgtt tcgtatgagctattgccgggcaattattctgtcgccgccagtgtgcatgg cttgtcggttgatcaccgccagccggcgctgacacgactgagtaacgtgc tgttcaatcaggcactggcgctggacctggagcgttttgacgagggcgcg ccagccgacgaaatgttcaggccttcactgaaacgcgaaggtgcccatcc ccgattggccgactcactgggtggcgagcaactggctgtgcaaaccatgg agaagggccttaaacggctggcagaggatcctgcgcagtcctttgcgcga tgccattcatttttttacccgatcagtagtgataccacttcacctcaagc atcacttcattctgtggcgagctcatctggctga The protein encoded by this nucleic acid molecule has an amino acid sequence according to SEQ ID NO: 28 as follows:

VKKSGAGTQAYALFASATGSSSKGVLSTIARHLTGCFAPNKTALHSATAV

SYELLPGNYSVAASVHGLSVDHRQPALTRLSNVLFNQALALDLERFDEGA

PADEMFRPSLKREGAHPRLADSLGGEQLAVQTMEKGLKRLAEDPAQSFAR

CHSFFYPISSDTTSPQASLHSVASSSG

The protein of SEQ ID NO: 28 does not share all of the N-terminal features associated with known Hops, however, it is 34% identical with the product of ORF 26, which does.

A fifteenth nucleic acid molecule encodes HopPtoT1 (ORF16) and has a nucleotide sequence according to SEQ ID NO: 29 as follows:

atgaaaacagtcagcaatcactcgatacccagtacaaatctcgtcgtgga tgcgggaacggaaacttcggcgcagaaatcccagccggtttgcagcgaaa tccagcgtaacagcaagatcgaaaaagcagtcatcgaacacattgccgac cacccggcagcgaaatgacaataagcgcgctggttgacacgttgacaga cgttttgtcagggctcatggggaggttaaggggtgggccgaaatcgtcc aggcagtctctcgccctcatgacagtaatcgacacggcagtggagtgctc agcccgcgctttgatgtaatggggagtgttggttggaatgcggcagctat ccgggccaccagtcgcgtcgggacgcttcgagagaaaggtacactgttca ctaaccttatgctcagtaacaactttaaacatttgcttaaacgagtggtt aacgatccagccttgcagcaaaagctcgacggtgggttagacctcaacta tctgaaggcttgtgaaggcgatctttatgtcatgtcagggtgggctgcac gggctagcgaaagtcgtgaacaaattggcaaagcccggtatgaaacggca tcaaatcttagccagacgctgatcagtgcacgtgagttggcttttcatcg tcacaatccggttaatcatccgtctgcccaaacgaaagtgggcttcgata agggtttgcctgaggaatctgatctgcaggttctgagaggccatggcagc agtgtatggagtgtaaaaccgggcagcgatttcgcaaagcgtgctgaagt ttctggaaagcctattatcgccggcccgtccggtaccgcttcgcgcatgg tcgctgttgcgcgttttctggcaccggcttgtttgaaaagcctgggtatt gagagtgagcagaacctgaaagagcttgtgcggtatgcctgctatgccta tttcggtcaggacagccaccattcgatgcttgaagtgaatcttggtgtcg cttcccatggaatgccggaacaatgggacgacacgctttataacgagcct ttcagtaattcaattaaaggtcgcgggtttggtatagacaatctcgcgca taggcaagtcgtcaggcaggcggctcaaaagtcatga The protein encoded by this nucleic acid molecule has an amino acid sequence according to SEQ ID NO: 30 as follows:

MKTVSNHSIPSTNLVVDAGTETSAQKSQPVCSEIQRNSKIEKAVIEHIAD

HPAAKMTISALVDTLTDVFVRAHGEVKGWAEIVQAVSRPHDSNRHGSGVL

SPRFDVMGSVGWNAAAIRATSRVGTLREKGTLFTNLMLSNNFKHLLKRVV

NDPALQQKLDGGLDLNYLKACEGDLYVMSGWAARASESREQIGKARYETA

SNLSQTLISARELAFHRHNPVNHPSAQTKVGFDKGLPEESDLQVLRGHGS

SVWSVKPGSDFAKRAEVSGKPIIAGPSGTASRMVAVARFLAPACLKSLGI

ESEQNLKELVRYACYAYFGQDSHHSMLEVNLGVASHGMPEQWDDTLYNEP

FSNSIKGRGFGIDNLAHRQVVRQAAQKS

HopPtoT1 has been shown to be translocated by DC3000 in planta.

A sixteenth nucleic acid molecule encodes ORF17 and has a nucleotide sequence according to SEQ ID NO: 31 as follows:

atgcggtttgatgctgcccgaggccagaagcccaaagcccctatggatgc accgtcatcattacgtttgcgagcgatagcaggtggcatgcccagtgaag aagcaggaacgactgcacctgctgacgtgaatcagcctccacctgctgat gttcgtccagaaatgggtgtaggtcctgtgagactcttcgttaaactgat ggtaggaactctggcgctgtcgacaggagtccgttttgcaagataccag gtgatttcgcgaaggatccgggaggcagtgtatgggcagcaatcaatctg cagcatcgctcgagcgtcacacatcttgaacaaggcaataagacggttct tgagcgtttcggtgcacatattccaaaagacagtgcgtgtttcaaagctc gcgctgacgtcacacacgatgttccctcaggcgtggcagggcagtggaac cacaaaacccaacgggtaaaactgaaccctaacattcatttcgagagcca tccggcacaggtcgccggacatgagttcatacactgttacacgcatcctg agtttgtcgaacgccatataaaacatccgcactggaaagccctgaacgaa gggttgacgactcgtttgacagagaaactgccagaccctaagcgtctctt gcccattcccttggcaaaggatccctatcatggtttcaagctgtccaccg gggactcctggccggatgcggccaggcgaatcgaagacgaagttggcgaa -continued gatgtgttgttgaaagcgttctttggcggcgatgaccaggctattagtga agtagctaaagccgctgctcagatctaccccaagattgcctcacgtatta ccgagagggagttgtatcaagcgggcagcatgcgtggaggacaacagctg gccgagtgttacgtaggtgctttgctcaaaaacggtcagaaactgcctga cagttttacgaattatctgctacctgtatttagctattcagatataagcc ctggtcacgcgaaaaaaatacaggcgcaagcggaaaaaagtcaaaagcgg atgggaattgtgttcgatacagcgtttttttcacctgacctgaagaccca gagactggcacttggcatgctacgggaggacctgctgatgcactggaaaa aagttattccggatagaaagtaa The protein encoded by this nucleic acid molecule has an amino acid sequence according to SEQ ID NO: 32 as follows:

MRFDAARGQKPKAPMDAPSSLRLRAIAGGMPSEEAGTTAPADVNQPPPAD

VRPEMGVGPVRLFVKLMVGTLALSTGVRFARYPGDFAKDPGGSVWAAINL

QHRSSVTHLEQGNKTVLERFGAHIPKDSACFKARADVTHDVPSGVAGQWN

HKTQRVKLNPNIHFESHPAQVAGHEFIHCYTHPEFVERHIKHPHWKALNE

GLTTRLTEKLPDPKRLLPIPLAKDPYHGFKLSTGDSWPDAARRIEDEVGE

DVLLKAFFGGDDQAISEVAKAAAQIYPKIASRITERELYQAGSMRGGQQL

AECYVGALLKNGQKLPDSFTNYLLPVFSYSDISPGHAKKIQAQAEKSQKR

MGIVFDTAFFSPDLKTQRLALGMLREDLLMHWKKVIPDRK

While the protein of SEQ ID NO: 32 does not possess several N-terminal features associated with known Hops, ORF17 is preceded by a good candidate chaperone protein, encoded by ORF6. Furthermore, the protein of SEQ ID NO: 32 has been shown to be translocated by DC3000 in planta.

A seventeenth nucleic acid molecule encodes ORF18 and has a nucleotide sequence according to SEQ ID NO: 33 as follows:

atgaacaggcttcacaagaccagtctgctggcggctatattgaccgcatc cccctgcattatggcagctaacgctcatgctatgagttgtcctgtcccgc aaagcgtgaagtacgttaatggtatctatatcgcgccggaaacgtttgct ggttgggaggggaactgggtttctcaaccacacaagaaacactccattaa agagttttccactgctttatatctttcagtggataaaagtcagaagggag gaacattgactaactgtagttattcactaagcggagataatggcgtaata gatcttgagtatcgaaaatcaggaaatgagaatagactaaagacacttat cgtttccattgaaggtcagcacaattggattaaagagcgtggcgcggttg gaattcaaggatatgaatgtacaaagtcagcatctgagtgtcagttcgtt ccgctgcggctaaacgaggactga The protein encoded by this nucleic acid molecule has an amino acid sequence according to SEQ ID NO: 34 as follows:

MNRLHKTSLLAAILTASPCIMAANAHAMSCPVPQSVKYVNGIYIAPETFA

GWEGNWVSQPHKKHSIKEFSTALYLSVDKSQKGGTLTNCSYSLSGDNGVI

-continued

DLEYRKSGNENRLKTLIVSIEGQHNWIKERGAVGIQGYECTKSASECQFV

PLRLNED

This protein has significant homology, as detected by BLAST analysis (1e-6), to a putative *Yersinia pestis* exported protein (Genbank Accession No. NP_406993, which is hereby incorporated by reference in its entirety).

An eighteenth nucleic acid molecule encodes ORF19 and has a nucleotide sequence according to SEQ ID NO: 35 as follows:

atgcatcgtcctatcaccgcaggccataccacctcacgtctcatcctaga tcagtcaaaacaaatatcacgtaccccatcggaaagtagcgcgcaatcag cgctttctcagcaagcaagcatgagcagcccagttttggagcggtcgaaa agtgcgccagctttattgactgcggcacagcgcacgatgcttgcacaagt gggagcctgtaacgctcatctgacctcagatgaaaacatggccatcaacg aactgagatcacacaagccccttttacctaaggatacgtggtttttcact gatcctaacaaggacccagatgatgtcgtgacctacaccttgggcaagca attgcaggctgagggctttgtgcacatcacggatgtagtggcgacactgg gtgatgctgaagttcgctctcaacgtgccgagatggccaaaggcgtgttc aacaagcttgagttgcatgacgtgcatgtgtcgcgtggtcgggattacgc aatgaattcgcttcagtcgaaggaacatgccaaatttttactggaaggtc atgctttaagggctggacctggtgaaatacaccgcgacagcttgcaggac atgagcaggcgcctggcccgtgcgccacatggagtcggtattgtcgtaat tgcaggcatgagtgatatcaatgcgctcatcactacctgcccggatatgg tgcgcgaacgggttgatgacatcaccatcatgggcggcgtcgagccttta aaggacgcagatggttttgtacagcctgatgcacgcgcttacaacaatgc gaccgacatggacgctgcgcgcagtctttatcggaaagcgcaggagcttg gcattccacttcgtatagtgacaaaggaggcggcctataaaacggcggtt tcgccttcattttacgaagggatagcggggagcggacatccagtaggcca ctacctgagagacgttcagaagagtgcgttgaaaggcctctgggaaggta ttcaagctggattgcttcccgggttggatgactcatggttctttcggacg ttcatgccgaatgcacagattgaagcagcacaactggataaaaataaaga gagttcgtttgaagatatctggcctaaggtgacgaagctaaacctgtatg atcctctgacattactggcctcagtgccaggggcggcaaaactgctattt aaaccaaaagctatacacacagaaggatttggtgttgtagagcaagtagg tccagatgatgtgacgcatccagagaaagcaaagttattgatgtccgctt tagccaaatctgcgcttgtccagtcgacggtagccccagattga The protein encoded by this nucleic acid molecule has an amino acid sequence according to SEQ ID NO: 36 as follows:

MHRPITAGHTTSRLILDQSKQISRTPSESSAQSALSQQASMSSPVLERSK

SAPALLTAAQRTMLAQVGACNAHLTSDENMAINELRSHKPLLPKDTWFFT

DPNKDPDDVVTYTLGKQLQAEGFVHITDVVATLGDAEVRSQRAEMAKGVF

NKLELHDVHVSRGRDYAMNSLQSKEHAKFLLEGHALRAGPGEIHRDSLQD

MSRRLARAPHGVGIVVIAGMSDINALITTCPDMVRERVDDITIMGGVEPL

KDADGFVQPDARAYNNATDMDAARSLYRKAQELGIPLRIVTKEAAYKTAV

SPSFYEGIAGSGHPVGHYLRDVQKSALKGLWEGIQAGLLPGLDDSWFFRT

FMPNAQIEAAQLDKNKESSFEDIWPKVTKLNLYDPLTLLASVPGAAKLLF

KPKAIHTEGFGVVEQVGPDDVTHPEKAKLLMSALAKSALVQSTVAPD

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis (2e-92), to a putative protein of *Ralstonia solacearum* (Genbank Accession No. NP_518366, which is hereby incorporated by reference in its entirety). Furthermore, the protein of SEQ ID NO: 36 has been shown to be translocated by DC3000 in planta.

A nineteenth nucleic acid molecule encodes ORF20 and has a nucleotide sequence according to SEQ ID NO: 37 as follows:

gtgaaaatcaatctccccgcgctcagaacaacgtcttcacgcgtgcagat ctgcttgaccgcagtcctgctgtgcacaccgctgctgttttccgcgcatg cccaggcagccggcacggcttctgaacaagccaatgtggaagtgatgatt cgtcagctcaacgcgctcgaggccgtcgcccagcgcagtgtcgatcttcc acaagacccggcccaacgctatcacctggactatccccggttggtcagcg acatcgcgcgcatccgccagggcttgcaagactacctgtcgccgtcccgc gcacagccccgcgaccccgtggagctatcaggccattacaacgtcagcgg tgatcacacgccatga The protein encoded by this nucleic acid molecule has an amino acid sequence according to SEQ ID NO: 38 as follows:
VKINLPALRTTSSRVQICLTAVLLCT-PLLFSAHAQAAGTASEQANVEVMIRQL-NALEAVAQRSVDLPQD  PAQRYHLDYPRLVSDIAR-IRQGLQDYLSPSRAQPRDPVELSGHYNVSGDHTP This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A twentieth nucleic acid molecule encodes ORF21 and has a nucleotide sequence according to SEQ ID NO: 39 as follows:

atgcgttccagggttataactacatcgctggtagtcattatgctctcatg tgcatcagccgctccagcttgcttctccgcagacatgactcccagcgtgt cgaacgagagcacgtcggaggcggattttcagcaatggctggctactttc cgcagcaatgcaactactaagggcatcgacacagccacactcgatcttgc tttccaaaacatcacgcttgacccgactgtgcaccagttggatatggcgc aaccagagttcacgacggccatctgggattatttgtctgaacgtctgact ccgaagaatatccagcaagggcaggagcttctgcaaaaagagccagttct gaacgaggtagagcgtcactacggtgtggatgcgaagattatcgcggcca tctggtgtattgaaagcggctacggtaaggatattggtagtcgcgatgtg attcgttccttggccacgcttgcttacaagggccggcggatggattacgg ggctacacagttgatggccgcccttcatatcgtgcaaaacaaagacatcg cccgtgcgcaattgattggctcgtgggctggcgcgatggggcagacgcaa ttcatcccgacgacctatctcgactatgcagttgattttaaccacgacaa tcggcgcgacgtttggagttcccgggccgatgcgctggcctccactgcct cttatttacaacgcagcgcttggaactcgcgcgtctcttggggacaggag gtgcagttgcccgagaatttcgattacgctcaggctgacatgtcgatcaa gaagcccgttgccgaatggcaacggctcggggtgatgggaacgaagcaag cgattccgggcgagctcgcacaggagcaagcatcggtcctgctgcccgca ggttatcgcgggccagcatttatggtcctaagtaatttccgtagcatcct gcgctataacaactccactgcctatgcgctaacgatcgggctactagccg acagttatgctggcgggaccggcgtgtctcacccgtggccaactgataat cctcccttgggcagcattgcgcaggtaaccgatttgcagaaactgctgac tgctaagggctactccctgggtgctgctgacggtgttataggggcgatga cccgggcggccatccgggcttaccagaaggatcagcatttgccacccgac ggttacgccagcactgtactactggagagcctgcgccgatag The protein encoded by this nucleic acid molecule has an amino acid sequence according to SEQ ID NO: 40 as follows:

MRSRVITTSLVVIMLSCASAAPACFSADMTPSVSNESTSEADFQQWLATF

RSNATTKGIDTATLDLAFQNITLDPTVHQLDMAQPEFTTAIWDYLSERLT

PKNIQQGQELLQKEPVLNEVERHYGVDAKIIAAIWCIESGYGKDIGSRDV

IRSLATLAYKGRRMDYGATQLMAALHIVQNKDIARAQLIGSWAGAMGQTQ

FIPTTYLDYAVDFNHDNRRDVWSSRADALASTASYLQRSAWNSRVSWGQE

VQLPENFDYAQADMSIKKPVAEWQRLGVMGTKQAIPGELAQEQASVLLPA

GYRGPAFMVLSNFRSILRYNNSTAYALTIGLLADSYAGGTGVSHPWPTDN

PPLGSIAQVTDLQKLLTAKGYSLGAADGVIGAMTRAAIRAYQKDQHLPPD

GYASTVLLESLRR

This protein has significant homology, as detected by BLAST analysis (1e-106), to a putative transglycolase from *Pseudomonas aeruginosa* and *Ralstonia solanacearum* (respectively, Genbank Accession Nos. NP_252681 and NP_522801, each of which is hereby incorporated by reference in its entirety).

A twenty-first nucleic acid molecule encodes ORF22 and has a nucleotide sequence according to SEQ ID NO: 41 as follows:

atgcttgctcctgacggcgtagaaatcgatatcgtgctatcaggtatatg cggaactgatctggcggtattgtcgggccgtgaaggtggagaggtgggca ttatacgcgggcacgaagcagttggcattattatcgatgtaggtaaggat gtagtacacctacaaaaagggatgcgggtggtggttgatcccaacgaata ctgtggcgtttgcgaaccttgccgtcttgctaaaacgcacctatgcaatg gggggtgaacgctgggttggatatcgcaggtgtcaacaaacatggaact -continued
```
tttgccgagcgcttcgttactcgtgagcgttttgtgtatcaattgccaga cgatatgagctgggcagctggtgtgttggtgagcctgttgcctgcattc tgaataatatagaccaggcgttcattcgagcgggagagcgtgtgttgatc ctagggtctggccctatgagtctgattgcgcagatcgttctgcgctcaat gggagttgacacgctcgccactgatcgaaacacacatcgcatacagttcg gccgctcacaaagtcttgatgttatacatgccgatgatcttgagttgcag atgcagcaccaagaaaagtttgatgttgttatcgatactgtcggtaatca gatcgatacagcttcacgctacatcggtcgcggtgggagaattgtacttt ttggatttgatagtgactatcactacatgctgcctgtaaagtacttcctg gttaacgctatcagtattatttctgctggagaatacaatcagcactttcc tagagcaattcgtcttgtgcaaaaacttcctgagctagggcggctggtaa cgcatcgctacgtactagaaaatcactcggaggttttcgatgcacttctg aacgatgcttccgcccccaatataaaaagcgtattcacaccaaatctcgc ttatctttaa
```
The protein encoded by this nucleic acid molecule has an amino acid sequence according to SEQ ID NO: 42 as follows:

```
MLAPDGVEIDIVLSGICGTDLAVLSGREGGEVGIIRGHEAVGIIIDVGKD

VVHLQKGMRVVVDPNEYCGVCEPCRLAKTHLCNGGVNAGLDIAGVNKHGT

FAERFVTRERFVYQLPDDMSWAAGVLVEPVACILNNIDQAFIRAGERVLI

LGSGPMSLIAQIVLRSMGVDTLATDRNTHRIQFGRSQSLDVIHADDLELQ

MQHQEKFDVVIDTVGNQIDTASRYIGRGGRIVLFGFDSDYHYMLPVKYFL

VNAISIISAGEYNQHFPRAIRLVQKLPELGRLVTHRYVLENHSEVFDALL

NDASAPNIKSVFTPNLAYL
```
This protein has significant homology, as detected by BLAST analysis (2e-18), to a putative sorbitol dehydrogenase (Genbank Accession No. NP_389115, which is hereby incorporated by reference in its entirety).

A twenty-second nucleic acid molecule encodes ORF23 and has a nucleotide sequence according to SEQ ID NO: 43 as follows:

```
atgaaagttactgtattcagtcagatatcaattgatggcaagttgacgat gggcaaaggcgcatccagcaagccgttgtttcagaactttgatgatgatg acatgcgttttattcataagttccgcggcgaagtcgacgcaatcatggta gggcgcaatacaattgttactgacgatccacaattgaccaatcgctatga gtcgggtcgtaacccaatacgtatcattccaccacctccttagatctgc ctacttccgccagtattttcaaatcaccagagaaaactattatcgcaact agcgaacaggctcgtgatcatgaaatggtcaaacatatccgtgcttgtgg aaaggaggtgctctttgccggtgcaaagcatgtcgactttacacgacttt tccctatgctggaggcgcgcggaataaaccacatcatggttgagggcggt ggccacctgaactggcaggtattcaatctcgatctggtagatgaaattat actcatgcaggtgcctatcatcataggtggtgcggcaactgcaacgcttg ctgacggggtggggtatcgggatatcaacatggccaattcgtttacgctg catgctttagaagcacgcccccattacaatctcatgcacttcaagcgcga atcgaacaatcggagcccgtactga
```
The protein encoded by this nucleic acid molecule has an amino acid sequence according to SEQ ID NO: 44 as follows:

```
MKVTVFSQISIDGKLTMGKGASSKPLFQNFDDDDMRFIHKFRGEVDAIMV

GRNTIVTDDPQLTNRYESGRNPIRIIPTTSLDLPTSASIFKSPEKTIIAT

SEQARDHEMVKHIRACGKEVLFAGAKHVDFTRLFPMLEARGINHIMVEGG

GHLNWQVFNLDLVDEIILMQVPIIIGGAATATLADGVGYRDINMANSFTL

HALEARPHYNLMHFKRESNNRSPY
```
This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis (8e-38), to a riboflavin specific deaminase (Genbank Accession No. NP_213307, which is hereby incorporated by reference in its entirety).

A twenty-third nucleic acid molecule encodes ORF24 and has a nucleotide sequence according to SEQ ID NO: 45 as follows:

```
atggagcaggaaaagagttcctgtttgcgctacggcgtgacccttaatga aaaagatctgtcacgttttttgggaactacacagcactacatgtggagca cgattaaaaatgagtacgcgctcactgaatccatcgaccacttgatggca cagcatcaacagcaattaatgcgctcaatcagttttgaattgtttcaatc catgcctggcgtggaggcgcttctcaatttactggagcataccggagtgc cctgtgccgtagcctcttcgtctccacgtaatttggtcgagcttatattg aagaaaacgaaattgcgtcgatttttcaaagaggttatttgtggtactga tgttaaagagagtaaaccgaatccggagattttttcttacggcggccaagg gacttggagtgtcacctcgtgcatgtctggttattgaagactcccatcac ggtgttaccgctgcgaaggccgcccatatgttttgtataggtttgcgtca ttccagctcatttcagcaggatctgagcgctgctgatctgatcgccaata atcattatgacatcaagcaatggtttgcagaaaaatag
```
The protein encoded by this nucleic acid molecule has an amino acid sequence according to SEQ ID NO: 46 as follows:

```
MEQEKSSCLRYGVTLNEKDLSRFLGTTQHYMWSTIKNEYALTESIDHLMA

QHQQQLMRSISFELFQSMPGVEALLNLLEHTGVPCAVASSSPRNLVELIL

KKTKLRRFFKEVICGTDVKESKPNPEIFLTAAKGLGVSPRACLVIEDSHH

GVTAAKAAHMFCIGLRHSSSFQQDLSAADLIANNHYDIKQWFAEK
```
This protein has significant homology, as detected by BLAST analysis (5e-32), to a putative phosphatase from *Clostridium* (Genbank Accession No. NP_347269, which is hereby incorporated by reference in its entirety).

A twenty-fourth nucleic acid molecule encodes ORF25 and has a nucleotide sequence according to SEQ ID NO: 47 as follows:

```
atgaatgcgttcgcaaccggtcagcttgaatacagcctgaaaaagctggg atacgatgccgccgctttgcaggccctgcgcgaagaagggtacttgctgt ggaaagggaaaaacgaccagaccagcttgctggtgccctcggccgatctg gatgcacttttcgttatcaacacgttgagctacatcgaccccgagcatga cggacgtctgctggcgcttgcattgcaccttaacctgtccctgtccata cgatgagcgcctgcatagccctcgatgtcgagcaaaacacgttatgcctg cgctacacccatgaccttggcgggagcggggctgatacgctgttgcttgc gctcgaaaacgcccaggcgctggccgaacaggtcaggcaggtgatcgaaa ccttcaggcgtgaccaagggcgtccgtccgggcaaacgtctttgtcccgg caatccagtgctctgatgcgataa
```

The protein encoded by this nucleic acid molecule has an amino acid sequence according to SEQ ID NO: 48 as follows:

```
MNAFATGQLEYSLKKLGYDAAALQALREEGYLLWKGKNDQTSLLVPSADL

DALFVINTLSYIDPEHDGRLLALALHLNLSPVHTMSACIALDVEQNTLCL

RYTHDLGGSGADTLLLALENAQALAEQVRQVIETFRRDQGRPSGQTSLSR

QSSALMR
```

This protein shares features common to type III chaperones and is a putative chaperone for the product of ORF26 (described below).

A twenty-fifth nucleic acid molecule encodes ORF26 and has a nucleotide sequence according to SEQ ID NO: 49 as follows:

```
atgaaaatatccggctccacatcgcctgcacacacttcaacgaattccgc gcagaagtcctcttcaaaagggctgctgagtggtttggccaagcatttca aggggatgctcgtttctggcaacacttctggtcattcggcgctcgggcat tacgcgtcatccagcagcggctccaaaggcaaggcaccggtacgggacga ttacagcaacggaccgcaaacacgccttaacaacacacctctgaaacgag cactggcccgagagcttgatcgctttggctacggttcatcggcgaccgag tctttttgaccgctcattgcagcgtaaggataaaaatccagagcttgggaa ggtctga
```

The protein encoded by this nucleic acid molecule has an amino acid sequence according to SEQ ID NO: 50 as follows:

```
MKISGSTSPAHTSTNSAQKSSSKGLLSGLAKHFKGMLVSGNTSGHSALGH

YASSSSGSKGKAPVRDDYSNGPQTRLNNTPLKRALARELDRFGYGSSATE

SFDRSLQRKDKNPELGKV
```

The protein of SEQ ID NO: 50 has been shown to be translocated by DC3000 in planta.

A twenty-sixth nucleic acid molecule encodes ORF27 and has a nucleotide sequence according to SEQ ID NO: 51 as follows:

```
atgaaaaaatgtattgctctgctcctactctggtcgtctgcgaaggtgc attggcaggaacggcacgtgatgaacagaacatcacgtcttacatcgaca gtcacggcaccgaacagatcgcgttgcttgagaagctggtcaacatcaac agcgggacagacaacgttgagggtgtcgtcaaggtcggtaacctgatcaa gccggagctggaggcgttgggtttcgagaccgcctggcacgacctgccct cggcaatgaaccatgccggcagccttgtcgctgtgcatgacggcagcaag tctgcaaaacgtattctgctgataggccatctggatacggtcttttcctca aacaagccgctttcagacgttcgcttacctggacggcggcaaaaaagcca agggccccggcgtcattgatgacaaaggcggcgtggtcacgatgctttat gcattgcaggcgctcaagcacagcggcgcgctggaaaagatgaacatctc ggtagtcttgataggcgatgaagagctggcggccaaaccgaccgagattt ccagagagtggctgatcgccgaagccaaaagaagcgacattgcgctgggc ttcgaattcgccttgtcgcccaatcaactgatcaccgagcgaagagggct gagcgaatggttttttgaccagcaccggcatcgacaaacattcagcgacga tctttcagcctgagaccggttttggtgcgatgtacgagtcggcccgagtg cttgacgagattcgtcagaaactgtcgaacgagcagggcctgaccatcaa tccgggactcattctgggcggctcaacggctgtggaagatagcgccagtg ggcaaggcacggcttctggaagaaagacaacagttgcccggatcacgtcg gtgcatggtgatttgcgcttcagcagtgaagaccagagggcctctgcgga aacccgaatgaaggacatagccagtcacccgctgccgcagaccaacagcg acctgaaaataaaagccatcatgccggtcatggcggatcgcgaaagcaat cgccaactactggcagcctacagtcaggtcagccaggatctcgacggacc tgctttggagtcggcgccttcagcagaacgaggcggcgcagatatttcct atgtgaacaagtatgtgactgcgagcctggacggtcttggtgcgtggggg gcaggtgcgcacagtgaaaatgaaaccatcgagttgggctccttgcccgt ggtgacgaaacgggcggctattttcctgagccgctatggtaaccagtga
```

The protein encoded by this nucleic acid molecule has an amino acid sequence according to SEQ ID NO: 52 as follows:

```
MKKCIALLLTLVVCEGALAGTARDEQNITSYIDSHGTEQIALLEKLVNIN

SGTDNVEGVVKVGNLIKPELEALGFETAWHDLPSAMNHAGSLVAVHDGSK

SAKRILLIGHLDTVFPQTSRFQTFAYLDGGKKAKGPGVIDDKGGVVTMLY

ALQALKHSGALEKMNISVVLIGDEELAAKPTEISREWLIAEAKRSDIALG

FEFALSPNQLITERRGLSEWFLTSTGIDKHSATIFQPETGFGAMYESARV

LDEIRQKLSNEQGLTINPGLILGGSTAVEDSASGQGTASGRKTTVARITS

VHGDLRFSSEDQRASAETRMKDIASHPLPQTNSDLKIKAIMPVMADRESN

RQLLAAYSQVSQDLDGPALESAPSAERGGADISYVNKYVTASLDGLGAWG

AGAHSENETIELGSLPVVTKRAAIFLSRYGNQ
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted, and has significant homology, as detected by BLAST analysis, to a carboxypeptidase from *Bacillus* (4e-29) and a hydrolase from *Ralstonia* (5e-22) (Genbank Accession Nos. NP_241218 and NP_521834, respectively, each of which is hereby incorporated by reference in its entirety).

A twenty-seventh nucleic acid molecule encodes ORF28 and has a nucleotide sequence according to SEQ ID NO: 53 as follows:

```
atgaaccctataacacacagctttagtcatcttgggttttcaaacgctca
aagtacgtcagcgctggcgcccggcggtaataaagtgccgaactttgttt
cgcgagggcgaggcaaaggagtcccgcttgagcatttcaacaccgctgat
gagtatcgtttggcacgccagcagggcggcgtgctgaaatcaatagacgg
cagagagttcatgctactgctgcagaagtacacggccgccgaaacaagcg
acgaagaatttgcggatttgagggccgccataccgcgctattccattgac
ctggccgagccgggtcaaactaaagtgctttatcggggatatcgctgcc
ggagaagactgcggcgcgattactgaatatctcttggggttacgaaagtc
gcgaaatagcccatggtcttatccatggcttgcgggtagttaaggaaggt
ctgaagtag
```

The protein encoded by this nucleic acid molecule has an amino acid sequence according to SEQ ID NO: 54 as follows:

```
MNPITHSFSHLGFSNAQSTSALAPGGNKVPNFVSRGRGKGVPLEHFNTAD
EYRLARQQGGVLKSIDGREFMLLLQKYTAAETSDEEFADLRAAIPRYSID
LAEPGQTKVLYRGISLPEKTAARLLNISWGYESREIAHGLIHGLRVVKEG
LK
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. Furthermore, the protein of SEQ ID NO: 54 has been shown to be translocated by DC3000 in planta.

A twenty-eighth nucleic acid molecule encodes HopPtoL (ORF29) and has a nucleotide sequence according to SEQ ID NO: 55 as follows:

```
atgactactctgaccaccagacagatacaactcgcccacgcttggacatc
cgttcatacaggcgctggcctggccctggactgggtcgccgatgtggccg
aaaaggtcgaggaaatcgccaccaaggccgacgccctcagccgtgacttg
caccgcgcgcgcaacctgtcccgcagccttgggcgggtctcgacgacacc
catgggtatcggtttcttcggcttgtctcaggcaggcaagagctacctga
tttccgctctggcggcggacgagaaaggccagttgctgacccggctgggt
actcagcaactggacttcatcaagcacgtgaacccggtgggcggcggtaa
ggaggccaccggtctggtcacgcggttcacccgcaccgccgcgccaagtc
tggacccgcactttccggtggagctgcgtctgtttcgcgaggtcgagatc
gccatcattttggccaacgcctggtttgaggatttcgatcatcagcgctt
gaacagccaagtcaccgatgcgcagatcgatgcccttttgcagcgtttcg
aggggcaattggcagccgctccgacacctggcgtcagcagtgacgacgtg
gtgctgctatgggattacctggagcaccattacgctaacgccatgcgccc
gctgaacgcccgttattggccttgcgtggtcaaactggcgccgcgcttgt
cggcacgcgagcgcgctcaattgttcgagccgctgtggggcggcatcggc
```

```
aaaatgaccgaaacctatgagcaactggcctcggccctgcaccgcctggg
gctggcagagacagttttttgcgcccatcagcgcgctggtcaccgagcgcg
atgggcaactggtacaaagcaaaagcatcatcaacgtcgacattctcagc
cgtcttggcggcagcgcggactcggccatcgaggtacgtccggccagtga
aggcactttgcgccctgccgtgtcggtgaatcgggccgaactggcggcgc
tcaccaacgagttgattttttcgcctggataacgaaccggccaacgccatc
gtcaatagcgtcgatctgctcgacttcccgggctaccgcagccggcagaa
gctgatgagcatcaacgaggccagcgaagtcgacagcaatggcaccgcca
acaatccggtcgccaggctgttgctgcgcggcaaggtcgcttacttgttt
gagcgttacaccaacgagcaggaaatgaacgcgctggtgatgtgcaccag
caccttcaagcagagcgaagtggtgagcgtcggtccggtactcaagagct
ggatcgacaagacccaaggcaccagccccccagcagcgcgatggtcgggcc
agcggtctgatctgggcgttgaccatgtgtgacggctttatcggcggcgc
gctcaacggcgaggttgtgcagtttcccgaaggttgcgacaacatgctca
aactgaccatgatcgagcgattcggcaacgaagactggatgaaacaatgg
ggcagcacgcctttcaaaaacacctatctggtgcgcaagccgcgcttcaa
gaccagcttcatcgagttggcggcggacggtgaagaacgcgcttacaacg
actcatcgcactctgcgttacaggcattgcaacaagcgttcagcaacagt
gaactggtcaagcgccatgtggcagaaccgcaggacgcctggcaggcaat
gctgacactgaacgacggcggcatgactcgtttcagctcggcgttcagcc
cgattgccaacatcgacttcaagttacagcgtattgccgagcaactggac
gagttgatggtgcaattactgccgcgcctggagcagtactacgaagccgg
tggcgaagacgaacgggccaggaagaaggttatcgccaacctgattgccc
gcccgttcgcgaccacgccgcacggcaaacacgtgcttggcgaactgctc
ggttacatgtcgttgccggaacagcagttgcgcgaccttttacctgaacgg
tgatttcgccagccctgccagcgacgccactgcaccggtgcaggccgtcg
gcaagcctgaagtggaatacgacatattcggcgaggccatcgcagccact
gccacggtggaaatacccgcggcaccggccgtagcgccgcaataccagag
ccacgaacaccgtttcgcccgagcggccttcgacctgtgggcaacgcacc
tgcgcaacctcagccgtcgccagcacctgctggacctgttggagctgcct
gccgaggccatcgccctgctggtcaaggaactggtggtctgcgccgagcg
cctggacttgccattgcagctcagcaacgcgctgctcaagcgcgcccaga
gcggtgtgcgcaaagaaaacctggtgcagcgccaagtgctgaccgcgcaa
ctgctgctcaacgacttcgccgcctggttcgggcacaccgcccagccggc
gggtcagcggccaacgggcctgctgggtgccaaacaaccgctgtttgctt
tttatcaaaaggaaatgccagggcgcttcccgcacctcgcagcgcaagcc
gacgaccagagcgtgattttcgccgatgactggatttctggcattgccat
tcatacccagaaaaacgtcggccaccgcaagggcaaagaaatcactcctg
agcagaacgaggccatgggccgcgtcatccaggcgttcaaagcgagataa
```

The HopPtoL protein encoded by this nucleic acid molecule has an amino acid sequence according to SEQ ID NO: 56 as follows:

MTTLTTRQIQLAHAWTSVHTGAGLALDWVADVAEKVEEIATKADALSRDL

HRARNLSRSLGRVSTTPMGIGFFGLSQAGKSYLISALAADEKGQLLTRLG

TQQLDFIKHVNPVGGGKEATGLVTRFTRTAAPSLDPHFPVELRLFREVEI

AIILANAWFEDFDHQRLNSQVTDAQIDALLQRFEGQLAAAPTPGVSSDDV

VLLWDYLEHHYANAMRPLNARYWPCVVKLAPRLSARERAQLFEPLWGGIG

KMTETYEQLASALHRLGLAETVFAPISALVTERDGQLVQSKSIINVDILS

RLGGSADSAIEVRPASEGTLRPAVSVNRAELAALTNELIFRLDNEPANAI

VNSVDLLDFPGYRSRQKLMSINEASEVDSNGTANNPVARLLLRGKVAYLF

ERYTNEQEMNALVMCTSTFKQSEVVSVGPVLKSWIDKTQGTSPQQRDGRA

SGLIWALTMCDGFIGGALNGEVVQFPEGCDNMLKLTMIERFGNEDWMKQW

GSTPFKNTYLVRKPRFKTSFIELAADGEERAYNDSSHSALQALQQAFSNS

ELVKRHVAEPQDAWQAMLTLNDGGMTRFSSAFSPIANIDFKLQRIAEQLD

ELMVQLLPRLEQYYEAGGEDERARKKVIANLIARPFATTPHGKHVLGELL

GYMSLPEQQLRDLYLNGDFASPASDATAPVQAVGKPEVEYDIFGEAIAAT

ATVEIPAAPAVAPQYQSHEHRFARAAFDLWATHLRNLSRRQHLLDLLELP

AEAIALLVKELVVCAERLDLPLQLSNALLKRAQSGVRKENLVQRQVLTAQ

LLLNDFAAWFGHTAQPAGQRPTGLLGAKQPLFAFYQKEMPGRFPHLAAQA

DDQSVIFADDWISGIAIHTQKNVGHRKGKEITPEQNEAMGRVIQAFKAR

HopPtoL has been shown to be a protein that is secreted by DC3000. HopPtoL has significant homology, as detected by BLAST search (1e-21), to an SPI-2 regulated SrfC (see Worley et al., *Mol. Microbiol.* 36:749-761 (2000); GenBank Accession No. AAF74575, each of which is hereby incorporated by reference in its entirety).

A twenty-ninth nucleic acid molecule encodes HopPtoS2 (ORF30) and has a nucleotide sequence according to SEQ ID NO: 57 as follows:

atgaatataaatcgacaactgcctgtatcaggctcggagcgattgttgac tcccgacgtgggcgtatctcgccaggcttgttccgaaaggcattattcta ctggacaggatcggcatgattttttaccgttttgctgccaggctacatgtg gatgcgcagtgttttggtctgtcaatagacgatttgatggataagttttc tgacaagcacttcagggctgagcatcctgaatacagggatgtctatccgg aggaatgttctgccatttatatgcataccgctcaagactattctagtcac ctcgtaagggggaaataggaacgccgctgtaccgagaggtcaataatta tcttcgacttcaacatgagaattctgggcgagaagctgaaattgataatc acgacgaaaagctatcgcctcacataaaaatgctttcatctgcgcttaat cgtttaatggatgtcgccgcttttagaggaacggtttatagaggcattcg cggtgatttagataccattgctcggctctaccatctattcgatacgggcg gccggtacgtagagcccgctttcatgagtacaactcgaataaaggacagt gcccaggtgtttgagccaggcacgccaaacaatagctttccagataag cctaaaaagaggcgccgacatttcgggatcttcccaagcgccctcagagg aagaaatcatgctacccatgatgagtgagttcgtcattgaacatgcatcc gctctttccgaaggaaagcatttatttgtattaagtcagatttga The HopPtoS2 protein encoded by this nucleic acid molecule has an amino acid sequence according to SEQ ID NO: 58 as follows:

MNINRQLPVSGSERLLTPDVGVSRQACSERHYSTGQDRHDFYRFAARLHV

DAQCFGLSIDDLMDKFSDKHFRAEHPEYRDVYPEECSAIYMHTAQDYSSH

LVRGEIGTPLYREVNNYLRLQHENSGREAEIDNHDEKLSPHIKMLSSALN

RLMDVAAFRGTVYRGIRGDLDTIARLYHLFDTGGRYVEPAFMSTTRIKDS

AQVFEPGTPNNIAFQISLKRGADISGSSQAPSEEEIMLPMMSEFVIEHAS

ALSEGKHLFVLSQI

HopPtoS2 has been shown to be a protein that is secreted by DC3000. HopPtoS2 has significant homology, as detected by BLAST search (1e-5), to *Clostridium* exoenzyme C3 ADP-ribosyltransferase, (Nolling et al., *J. Bacteriol.* 183:4823-4838 (2001); GenBank Accession No. NP_346979, each of which is hereby incorporated by reference in its entirety). Further confirming that HopPtoS2 has similarity to ADP-ribosyltransferases, it was determined to possess an ART domain (pfam1129). In addition, HopPtoS2 has 20.5% identity to the HopPtoS1 as determined using EMBOSS software.

A thirtieth nucleic acid molecule encodes HopPtoS3 (ORF31) and has a nucleotide sequence according to SEQ ID NO: 59 as follows:

atgaatatcagtcctgtatcgggtgcccacggtagcagctaccttcagc tcaatccacagcatcgacggcatcgaaaggtccctctggatccttctca aacagctcggcggctgttttcaccctgcctgggtagcagctctactggg gccatactttctcccgctcatgagcaggtattgagccacacctattccag caatattaaaggaaagttgcgcacgacgcccccaaaaggaccgtcgccca ggttgtctgacacacctatgaagcaggcgcttcttcaatgatcgtacag gagcgaaaacggcttaaaagtcaacccaagtcattggcctcggatataga acgtccagacagtatgatcaaaaaagcgcttgatgaaaaagacggccacc cgtttggcgagcgcttttcagacgacgaatttcttgcgattcatctctat acgagctgtctttataggccgatcaatcatcatctgcggtatgccccgaa caatgatgttgcaccggttgtcgaggcactgaaaagtggtttggcaaagc ttgctcaagaccctgattatcaagtgtctagccagcttcatagaggcatc aagcaaaagatgagtgatggcgaggtcatgagtcgtttcaaaccgggtaa gacctatcgtgatgaagcgttcatgagcacatcaactcatatgcaggttt cagaagagtttacctccgacgttacgttgcacctgcggtcctcatcagct gtcaatataggccccttttcgaaaaatccatacgaggacgaagcgcttat ctcgcccctgacgcctttcaaagtaaccggtctgcgcaagcaggacgata agtggcacgtcgatttgaacgagatagcagataattcagacgagtga HopPtoS3 has an amino acid sequence according to SEQ ID NO: 60 as follows:

MNISPVSGAHGSSYPSAQSTASTASKGPSGSFLKQLGGCFSPCLGSSSTG

AILSPAHEQVLSHTYSSNIKGKLRTTPPKGPSPRLSDTPMKQALSSMIVQ

ERKRLKSQPKSLASDIERPDSMIKKALDEKDGHPFGERFSDDEFLAIHLY

-continued

```
TSCLYRPINHHLRYAPNNDVAPVVEALKSGLAKLAQDPDYQVSSQLHRGI

KQKMSDGEVMSRFKPGKTYRDEAFMSTSTHMQVSEEFTSDVTLHLRSSSA

VNIGPFSKNPYEDEALISPLTPFKVTGLRKQDDKWHVDLNEIADNSDE
```

HopPtoS3 has significant homology, as detected by BLAST analysis (5e-3), to chicken ADP-ribosyltransferase (Tsuchiya et al., *J. Biol. Chem.* 269:27451-27457 (1994); Genbank Accession No. P55807, each of which is hereby incorporated by reference in its entirety). Further confirming that HopPtoS3 is an ADP-ribosyltransferase, it was determined to possess an ART domain (pfam1129). In addition, HopPtoS3 has 71.7% identity to HopPtoS1 as determined using EMBOSS software.

A thirty-first nucleic acid molecule encodes ORF32 and has a nucleotide sequence according to SEQ ID NO: 61 as follows:

```
atgaatattaacccttccctgggcgctcatggcagcgcctactcgtcgcc tcaaagtgatacttcgaaggccactggaaaagcacctgcgccttcttttt tcaaacagttgggcggctgttttttcgccgtgccttggttcccatgcgtca agcagccaacaactgtccgccagtcatgcgcagacgctcagtcagaatta ctccagcaacattcaggggacgagccgcacacgccagccgagagcaccct cgccacgcctgtcagatacgcccatgaagcaggcgctttcctcaatgatc gaacgcgagcgtttgcggcttcaaggtctttcgggaggaatgttctcggg cattgactccgccgatgccatgattggtcgagcgctcacgaagaaggatt caaacccaaaggctgcgcgttttagtgatgatgagtttctcgccgttcac ctctacacaacttgcctctacagacctatcaatcatcatcttcggtatca acactag
```

The protein encoded by this nucleic acid molecule has an amino acid sequence according to SEQ ID NO: 62 as follows:

```
MNINPSLGAHGSAYSSPQSDTSKATGKAPAPSFFKQLGGCFSPCLGSHAS

SSQQLSASHAQTLSQNYSSNIQGTSRTRQPRAPSPRLSDTPMKQALSSMI

ERERLRLQGLSGGMFSGIDSADAMIGRALTKKDSNPKAARFSDDEFLAVH

LYTTCLYRPINHHLRYQH
```

This protein has significant homology, as detected by BLAST analysis (5e-3), to chicken ADP-ribosyltransferase (Tsuchiya et al., *J. Biol. Chem.* 269:27451-27457 (1994); Genbank Accession No. P55807, each of which is hereby incorporated by reference in its entirety). Further confirming that protein of SEQ ID NO: 62 is an ADP-ribosyltransferase, it was determined to possess an ART domain (pfam1129). In addition, this protein has 51.3% identity to HopPtoS1 as determined using EMBOSS software.

A thirty-second nucleic acid molecule encodes ORF33 and has a nucleotide sequence according to SEQ ID NO: 63 as follows:

```
atgagctcgatcacgcacaccaacacgccgcaattggcggtcagcgattc acggggtctgccggtacgcagtgtgcagttctatcgtggcgctgatggtc
```

-continued

```
agcctgttgacgcgagggtgacgcagcactatttcgacaaggccgggcga ctgatcgccagtcgcgatccacgttttccagtcgtttgaaatacggtgt ctgtgcgcctgtgaacctgatgcaaatcgtcagcttgtccggggctttgc tgttatcgaaaagtgtcgattcaggttggcgggtgagcctgaacggcgaa gcggggcagttagtcgacagctgtgacggacgtgacaacccgcgccagat cgaatacgacgggctgttgcgccctttggcgatcaacgaatcaggccgaa tgaccgagcgcttcacttatggcgggcctgccactgctgagcataaccag tgcaatcaactgattcgccatgacgatacggcaggctcgcgcttgctgcg ggactatggactgtcgggtagggcgttgagcgaaaaaaggtacttcctgc agtcgcccgacagcccggactggccacttgccgagcctgatcgtgatgca ctgctcgagccggtcggcctgcagacgcgctgggctttcaacgcgcaggg cgaggacctggcgcagactgacgcaaacggtaatgtccagcgtttcagtc acggtgtggctgggcaactgcacgctgttgaactgaccctggccaatacg gcacagcggcaaacgctggtcagtgcaattcactacgacgcgttcaatca ggccgagcaggagacggcaggaaatggtgtggtcagtcgctatgtgtatg atcaacaggacggtcggctgactgagctcagtgcgctatctgccgacggc tcagtgttgcaaaaactgaactacagctatgacccggcaggtaacgttct actcatcaacgatgcctcgcaaccagaccggtattgcggcaatcagcgta tcgagccgataaaccgttactgttacgacacgttgtatcagttgatcgaa gccacggggcgggaggtcagaaacggggccagccatggtccggcgctacc cggtctgcaacctctgccgacgctcgatccttgccaggtcagcaactaca cacagcgttacagctacgacgctgcgggtaacctgctgcaaatgcgccac gaaggcgcgcacaacttcacccgcaacatgcacgttgatcccgacagcaa tcgcagcctgcccgacaatgacaggtatgtggatttcgccacgagttttg atgccaacggcaatctgctgcaactcgtgcgtgggcagaccatgagctgg gatgtgcgtaatcagttgcggcaaatcactaccgtgcaacgtgaagacgc accgaatgatgaagagcgctatgtatacgacggccagggccagcgctgcc gcaagatcagcaccgcgcaggcatcaggtcgcacactgaccaatgaagtt cgctacctgccgggactggaagttcggaccacggccgatggagaaactct tcacgtcgttacggctcaggcgggtcgcaacagcgtgcgggtgttgcact gggaagccggaaaaccaggcgctattgcgaacgatcaggtgcgttacagc ctgggtgatcatctgggctcgagcacgctggagcttgatcagcaaggcgg cctgatcagccaggaaagttattaccccttggcggcacggcctggtggg cggcgcgtagtgcagtggaggccaagtacaaaacagtgcgttattcgggt aaagagcgcgatgccagcgggctttattattacggggttcaggtattacgc gccgtggttgcagcggtggatcaatcctgacccggcgggggatgtggatg ggttgaatctgtacaggatggtcagaaataatccgcttgtttacgttgat gcgaagggccagcaacctgaacctgttccaaaaactattcaccagatctg gataggtgaaaacaagaatgccttgagagctcaggttagcaatatcaaca gaaccgttgaaatggcttgggggtataaagtgaagttgcatctggaaacg aggacgccggaagcttattcggaaatcgaaaaggatctgagatccgaagt
```

-continued

```
ggttctgcttcctgattcccaggtttttcaaaacttcaaggagaagccgc tttatgcggcctatgaagatttccgaagaaacaatcagaattacgctttc gcggtagacgttttacgtatgcataccgttcatgagttgggcgggattta ttcagatgtcgatgacgtttatgcaggtgcggagactggcggaatgacgc agttgggggataatccgctgtttgcagaacctgatgaggttttgacgctg gatcctgttcatgtcccttgggagcccagaattctgttgaaagttttat ggtcaataacagctcatttgccgctcattcaggtgcaggcgtcttacttg acatgatggggaaggagcgaaacgatatgatgaagccgttgagggcgga agttatccggatccgacgggcatgaacggtataggtctaagtctgctctg gaatcctaacccggcagtaagagttcgaacgttatcgaatgtagtaggcc ccggcttgtttacagacacactgcacgcttcggacacagcatacggtgag cttttagtaatctgaaaggcgtcgtctttcaaaaacagccgttcacgtt tgccgaccaaatggccaggaagatgccgctgcatcggcatataaaaagcg gcgcggcgcaaacctggcgctga
```

The protein encoded by this nucleic acid molecule has an amino acid sequence according to SEQ ID NO: 64 as follows:

```
MSSITHTNTPQLAVSDSRGLPVRSVQFYRGADGQPVDARVTQHYFDKAGR
LIASRDPRFSSRLKYGVCAPVNLMQIVSLSGALLLSKSVDSGWRVSLNGE
AGQLVDSCDGRDNPRQIEYDGLLRPLAINESGRMTERFTYGGPATAEHNQ
CNQLIRHDDTAGSRLLRDYGLSGRALSEKRYFLQSPDSPDWPLAEPDRDA
LLEPVGLQTRWAFNAQGEDLAQTDANGNVQRFSHGVAGQLHAVELTLANT
AQRQTLVSAIHYDAFNQAEQETAGNGVVSRYVYDQQDGRLTELSALSADG
SVLQKLNYSYDPAGNVLLINDASQPDRYCGNQRIEPINRYCYDTLYQLIE
ATGREVRNGASHGPALPGLQPLPTLDPCQVSNYTQRYSYDAAGNLLQMRH
EGAHNFTRNMHVDPDSNRSLPDNDRYVDFATSFDANGNLLQLVRGQTMSW
DVRNQLRQITTVQREDAPNDEERYVYDGQGQRCRKISTAQASGRTLTNEV
RYLPGLEVRTTADGETLHVVTAQAGRNSVRVLHWEAGKPGAIANDQVRYS
LGDHLGSSTLELDQQGGLISQESYYPFGGTAWWAARSAVEAKYKTVRYSG
KERDASGLYYYGFRYYAPWLQRWINPDPAGDVDGLNLYRMVRNNPLVYVD
AKGQQPEPVPKTIHQIWIGENKNALRAQVSNINRTVEMAWGYKVKLHLET
RTPEAYSEIEKDLRSEVVLLPDSQVFQNFKEKPLYAAYEDFRRNNQNYAF
AVDVLRMHTVHELGGIYSDVDDVYAGAETGGMTQLGDNPLFAEPDEVLTL
DPVHVPWEPQNSVESFMVNNSSFAAHSGAGVLLDMMGEGAKRYDEAVEGG
SYPDPTGMNGIGLSLLWNPNPAVRVRTLSNVVGPGLFTDTLHASDTAYGE
LFSNLKGVVFQKQPFTFADQMARKMPLHRHIKSGAAQTWR
```

This protein has significant homology, as detected by BLAST analysis (1e-128), to SepC insecticidal toxin (Hurst et al., *J. Bacteriol.* 182:5127-5138 (2000); Genbank Accession No. NP_065279, each of which is hereby incorporated by reference in its entirety). This protein also has significant homology (2e-128), as detected by BLAST search, to putative insecticidal toxin from *Yersinia pestis* (Parkhill et al., *Nature* 413:523-527 (2001); GenBank Accession NC_003143.1, each of which is hereby incorporated by reference in its entirety).

A thirty-third nucleic acid molecule encodes ORF34 and has a nucleotide sequence according to SEQ ID NO: 65 as follows:

```
atgccgatcaccgcgcagcagttgctgcagatactcccgagcgctggcca gaaagccggcgttttgcacccgtcctgaacacagcgatgagcaagcacc agatcttgacgccgctgcgcatcgcggctttcatcgcccaggtcggtcat gagtccggccaactgcgctacgtccgcgagatttggggccgactccgca gcagctgggttatgaaggccgcaaggacctcggcaataccgtggcgggtg atggttcgaagtaccgcgggcgcggcctgatccagatcaccggccgggcc aactatgccgaatgcggcgaggcgctgggcctagacctgatccatcaccc ggaactgctcgagcagccggagcacgccacaatgtcggcagcgtggtact ggagcagccgtggcctgaactcgctggccgacaaaggggactttcttcaa attcccgaagaatcaacggaggcaccaatggactggcggatcggcaggc gctgtacgaccgggcgctgaaggtgctggcgtga
```

The protein encoded by this nucleic acid molecule has an amino acid sequence according to SEQ ID NO: 66 as follows:

```
MPITAQQLLQILPSAGQKAGVFAPVLNTAMSKHQILTPLRIAAFIAQVGH
ESGQLRYVREIWGPTPQQLGYEGRKDLGNTVAGDGSKYRGRGLIQITGRA
NYAECGEALGLDLIHHPELLEQPEHATMSAAWYWSSRGLNSLADKGDFLQ
ITRRINGGTNGLADRQALYDRALKVLA
```

This protein has significant homology, as detected by BLAST analysis (3e-36), to a lytic enzyme (Nakayama et al., *Mol. Microbiol.* 38:213-231 (2000); Genbank Accession No. BAA83137, each of which is hereby incorporated by reference in its entirety).

A thirty-fourth nucleic acid molecule encodes ORF35 and has a nucleotide sequence according to SEQ ID NO: 67 as follows:

```
atgaatctaacagctttaggttcaaagctgtctcggtatcgcaagcagct tgcgatgagcgaggaagaagtgtgtgcggtcaccacatcccccttgagc gcctgcagtcagttgaagccggctctcaggcgcctacgggtgatgaagtg cttatcctggccgatctctaccactgcaacttcaaattcttcatctcgaa cgagccgctcgccccctttgagcagaccgaaatcctgtatcgcaggcacg gagctgagttcatcaaggaggatcgtagagccgtccaagaattcctgtac ctctgcgaaacagaggacttcctgatgagtgagttgaaggctatgaagct cgaatttccgctgccgcaggcttctgggaattttaagaatgatggaatcc gagcggctgaagcctttcgccttttcaatcagcaccccacaaacgccgtg cctcggatgtgtatcaggagattcgccaaaccggagtgcatgtgttccg tagaaagcttggtaactctaacatttcggggcttttcctggctcacccca cggctgggaagtgcattctggtcaactacagcgaagacgtataccggcag cggtttagcgctgcgcatgaatttgctcacgctcttttcgatgcgcaggg
```

-continued tggcccagtattacctactcccgtacgactaaggctgacctagtcgaag tgagagcaaacacctttgcctcccggtatctgatgccttcagaaatcctc cgacagctgcccaaccctgagcaatggacacaggaaaatacccagtattg ggctcatgagttgcgagtcagctgcgttgccttgggcataggtctgaagt ccgagggcttaattagcgagcaagcattccagaggataaagtcgtaccgc gttcctcgtgaactgaagattgacccagaattgccggcccaattgacgac gcaacagcgtgagcgaaaggctaagttactggaaaaggggttatctgaca gctacgtcgcactgtgcctagacgctcagagccgtggcatcatcactcaa ggtcgattggctgaagccttgcttagtgacttgggaggccttcaagagct gctcagcctttatggaagatcgcgcaatggccattga The protein encoded by this nucleic acid molecule has an amino acid sequence according to SEQ ID NO: 68 as follows:

MNLTALGSKLSRYRKQLAMSEEEVCAVTHIPLERLQSVEAGSQAPTGDEV

LILADLYHCNFKFFISNEPLAPFEQTEILYRRHGAEFIKEDRRAVQEFLY

LCETEDFLMSELKAMKLEFPLPQASGNFKNDGIRAAEAFRLFNQHPTNAV

PRDVYQEIRQTGVHVFRRKLGNSNISGLFLAHPTAGKCILVNYSEDVYRQ

RFSAAHEFAHALFDAQGGPSITYSRTTKADLVEVRANTFASRYLMPSEIL

RQLPNPEQWTQENTQYWAHELRVSCVALGIGLKSEGLISEQAFQRIKSYR

VPRELKIDPELPAQLTTQQRERKAKLLEKGLSDSYVALCLDAQSRGIITQ

GRLAEALLSDLGGLQELLSLYGRSRNGH

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-fifth nucleic acid molecule encodes ORF36 and has a nucleotide sequence according to SEQ ID NO: 69 as follows:

atgaatatcaacccttggcttcttcattacagaatcaacagcgcactct cttaggcccgccccccctcaattcatctgctgctctgccgatcaagatcc ctgtggcgcatgataaagcgcgtgaccctaacgctgaattctataccacc gaggaaacgccctggtttgccggctacaaaaagtcggaggcaggacgcgc tattttagagaaaatgtctgagaaggaagcaaaagatatccgaggcgagt atctgggaaactacatgaaagcctttgacgaaccatatgtcgtatgtac gacaattttcacgatttcaaacagcagcttttttaccttaatacggagct gtcaaaaaagcatttcggcttcacgctgggctttaatcaggacattcagg tgaccgacccggacgaggtactcacccccggcagagttcacgtacctgacc gagaagctgaacgaacgccaacaactgaaagaggatctgcgtgcgcacgc aaaaattgtgatgacgctgctcgaccattacaccgaaaaattcgataacc ggcacacctcaatctggagagttacagcaaggtcatcgactacggacag atcttcagccgcaatcatattggcaatttcatggacacgattatctacca -continued gatcgagcgcaatgcgccgaagcgtgaggaagaaccaaaacctctggttg atgtgcacgcttga The protein encoded by this nucleic acid molecule has an amino acid sequence according to SEQ ID NO: 70 as follows:

MNINPLASSLQNQQRTLLGPPPLNSSAALPIKIPVAHDKARDPNAEFYTT

EETPWFAGYKKSEAGRAILEKMSEKEAKDIRGEYLGNYMKAFDETICRMY

DNFHDFKQQLFYLNTELSKKHFGFTLGFNQDIQVTDPDEVLTPAEFTYLT

EKLNERQQLKEDLRAHAKIVMTLLDHYTEKFDNRHTLNLESYSKVIDYGQ

IFSRNHIGNFMDTIIYQIERNAPKREEEPKPLVDVHA

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-sixth nucleic acid molecule encodes ORF37 and has a nucleotide sequence according to SEQ ID NO: 71 as follows:

atgggcctgatcggcgtcaaacagaacaaaccgcaacaggcgcagaccta cctgacgcgcctgcaagcgctgtcgccagcgccctggcaggcggtgcagc tggagcaggacattgccctcggccagccgcaaaatcaggcgctgctggat gatgcccgacgcctggccgacgccggtgagcgtgacaaggcgaccggggt gtttcgccagttgttcaacgccgtttgcctcaaggcactgtcggccgcg agtactacaccaacctgggcttcaacaatgcggactggcccgaggcgcgc aagggttttgaacgcctgatgcggcagaaccctgacgactcgattctggc gctgttctttgccaagcacctggcccgccgcgaagacagccgcgccgaag gcatcgccgctctggcgcgcctgagcactcatccggacatcgccggcgat gccgatcagagctggcgcatggcgctggtctggatcggcccgcctgcggc tgcgcaagtgccactgttcgacgcgtttctcaaggttcatcccgacgatc aggaaatccgcgaccagttgaacaagggtcgccagcagcatgccagcggc gctgcctcaggctggcagcaagacccgctggtggcgcgcggcttgaaggc gctggaaaaaatgatcatgtggcggccgaagaagcctttgccgcccgcc tgaaaatcaaggcggacgatgccaacgtgcttggcgcctgggcgtggtg cgtcagcagcagaaccggttgcctgaagccgaacaattgctgacccgcgc cacgcgccagcagggcggtgcgcgctggaaaaacgcgctggaaaacgtac agctctggacctcgctgcaagaggcccgtgacctgcaggccaaagggcag accggcaaggctcaagcgttgctggctcaggcgcagcggcaaaaccctga caatatcgacgtgcgtttgaccctggccgacgtgcaggtgcaggccgggc aactggacgccgcgcaagcgggctatcgtcaggtactggcgacccagcgc ggtaatccgcaggcaatccgcgggctgatcaacgtgctggcccagcgtgg tcaggctgatgaagcgttgcgcctgctcgacacattgtcgccaggcgaac aggccaaactgggcgacagcggtcgcttcaaggcgctgcgctccacccag gtgcgcggctggccgagcagcgtggcgatgttcgcgctgcccaggtggc cttgaaagacgcggtgaagaacgacccggacaatgtctggacgcgttttg

```
atctggcgcgcctgtacctcaagaccgacgaagcgcccaaggcccgcgcg
ctgatcgacgagctgctcaaggctcagcccaacaatatcgatgcgctcta
caccagcgcgctgctgtcagtggaaatgggccagtggcaggacgcgcaga
ccacgtttacgcgcatcccggttgatcagcgcacgccggacatgaaagcg
cttgctgacgaagtcaccatgaccgtgcagatcaatctggccatcggcat
cgcccggcgcggtcagcgccaggaagcgttggcgctgctcgatcgcttgc
aaccggtcgccagcggcagcccggagcgtcaactcacgctggccagcgct
tacatcgatgcgggcgagcccgcgcgcggtcgggaaatggccgtgcggc
catcgctcaggcccctttgccgtcggccgacctgatgctgcaatacgccg
gtctgctgctcgcagcgggcgatgacgtgcaggtcaatgcgatcctgcgc
aacgtgcagggtcagccgatgagcgtgcagacccgcaaacgttttgatga
cctttgtaccgctaccgcattcgtcaggccgatctgctgcgtgaaggcg
gtgatctggcgggcgctacgacacgctggcacctgctttggcgcagcgc
ccggacgacattcaggcggtgtcggccttcgcccgcatgtacaccgccaa
tggcgacagcgcccgagcgttcgagctgtacaagcctttgttgcagcgcc
agcccaatgacccgcaagtgttgctgggcgcagccgatgcggcggtcaaa
gcgcatgattatggctttgccgaaaaagccctgagccagttccgcaaact
ggagcgtaacgacccgcagaccctgacggaggccgcacgtatctaccaaa
gcatggggcagaccggcgcggccaccgagttgctgcgcaaggccgtggcc
atcgaacagagtgaaaaacagcgcgcgatggctgtgcaggctgtgtcgac
cagcaccacgtcgtccaacccgtttgcgacgggcggctcacgtagcctgg
cggcggcttcggctattccggctccggctcaggtgtcgctcagcggtggg
agagcgcttgaaacaaacagtgcgcctgaaatatctgccccgcgtgacac
cgcttatcccggccagatcgccgcaccacaaccgctgtctgccgcacgta
cgcaaagtgtgcgcggcaatccgttcatggcagccaccgaccgcgatcag
gccagcagcgcacagcaggcgctcaatcgcattcttgagcagcgcagtgg
cttcgtcagtcagggcctggccgtgcgcagcaataacagcgagtcgggtc
tgagcaaactgaccgtggtcgagacccgctagaggtcaatttgcctgcc
ggtgataaccgggtggccgtgcgcgtcacgccggtgtcgctgaatgctgg
cagcttgaagtcagatgcaggtgcccgttttggcggtggcaccagcggtg
ctgccggttcgcagagcgacaagggtgtcggtctggcggtggcgttcgag
cgccccgaagaaggcctcaaggccgatatcggcaccacgccgatgggttt
caaatacaccacggttgccggcggcgcgagtgtcgaccggccgttgggta
acaacccggacctgcgctacggcctcaacgtgtcacggcgtccggtgacg
gacagcgtgacttcgtttgccggttccacagacgagcgcagcggcctgtc
ctggggcggcgtcacggccaacggcggcgcggtcagctcagctatgacg
accagaccatcggcggttatggctacggctcgtggcacaaactggttggc
aacaacgtgaaatccaacaccgaggcgaagtgggtggcggcgttactg
gtacctgcgcaatgccgaggacgcaaactgaccgcaggcctgagcctga
tgggcatgagctatgacaatgaccagagctacttcacgtacggccacggt
ggctatttcagcccgcagagcttctatgccatcggcgtgccggtgatgtg
```
```
ggcacagcgcaccgagcgtttcagctatcaggtcaagagctcggtcgggg
tccagcacttcaagcaggacggcgccgaattcttccccgacgacagcacg
ctacaggccgcttccgcccagcgctacacagggcaaagcaaaaccggaat
tggctacaacctgagcgcggcaggcgagtacaagctcgattccagcctgt
tcatgggggccagtctgggcctggacaatgcccgggactatcgccagttc
agcggcgcgctttacctgcgttacatgttcgaggacataaccggcccgat
ggcactgccggtcagcccttaccgttcaccttattccaactga
```

The protein encoded by this nucleic acid molecule has an amino acid sequence according to SEQ ID NO: 72 as follows:

```
MGLIGVKQNKPQQAQTYLTRLQALSPAPWQAVQLEQDIALGQPQNQALLD
DARRLADAGERDKATGVFRQLFNGRLPQGTVGREYYTNLGFNNADWPEAR
KGFERLMRQNPDDSILALFFAKHLARREDSRAEGIAALARLSTHPDIAGD
ADQSWRMALVWIGPPAAAQVPLFDAFLKVHPDDQEIRDQLNKGRQQHASG
AASGWQQDPLVARGLKALEKNDHVAAEEAFAARLKIKADDANVLGGLGVV
RQQQNRLPEAEQLLTRATRQQGGARWKNALENVQLWTSLQEARDLQAKGQ
TGKAQALLAQAQRQNPDNIDVRLTLADVQVQAGQLDAAQAGYRQVLATQR
GNPQAIRGLINVLAQRGQADEALRLLDTLSPGEQAKLGDSGRFKALRSTQ
VARLAEQRGDVRAAQVALKDAVKNDPDNVWTRFDLARLYLKTDEAPKARA
LIDELLKAQPNNIDALYTSALLSVEMGQWQDAQTTFTRIPVDQRTPDMKA
LADEVTMTVQINLAIGIARRGQRQEALALLDRLQPVASGSPERQLTLASA
YIDAGEPARGREMARAAIAQAPLPSADLMLQYAGLLLAAGDDVQVNAILR
NVQGQPMSVQTRKRFDDLLYRYRIRQADLLREGGDLAGAYDTLAPALAQR
PDDIQAVSAFARMYTANGDSARAFELYKPLLQRQPNDPQVLLGAADAAVK
AHDYGFAEKALSQFRKLERNDPQTLTEAARIYQSMGQTGAATELLRKAVA
IEQSEKQRAMAVQAVSTSTTSSNPFATGGSRSLAAASAIPAPAQVSLSGG
RALETNSAPEISAPRDTAYPGQIAAPQPLSAARTQSVRGNPFMAATDRDQ
ASSAQQQALNRILEQRSGFVSQGLAVRSNNSESGLSKLTVVETPLEVNLPA
GDNRVAVRVTPVSLNAGSLKSDAGARFGGGTSGAAGSQSDKGVGLAVAFE
RPEEGLKADIGTTPMGFKYTTVAGGASVDRPLGNNPDLRYGLNVSRRPVT
DSVTSFAGSTDERSGLSWGGVTANGGRGQLSYDDQTIGGYGYGSWHKLVG
NNVKSNTRGEVGGGVYWYLRNAEDSKLTAGLSLMGMSYDNDQSYFTYGHG
GYFSPQSFYAIGVPVMWAQRTERFSYQVKSSVGVQHFKQDGAEFFPDDST
LQAASAQRYTGQSKTGIGYNLSAAGEYKLDSSLFMGASLGLDNARDYRQF
SGALYLRYMFEDITGPMALPVSPYRSPYSN
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (e=0), as detected by BLAST search, to cellulose synthase from *Pseudomonas fluorescens* (Spiers et al., *Genetics* 161:33-46 (2002); GenBank Accession P58937, each of which is hereby incorporated by reference in its entirety).

A thirty-seventh nucleic acid molecule encodes ORF38 and has a nucleotide sequence according to SEQ ID NO: 73 as follows:

```
atgaaactgatacgacagatccgctcgcagggtcgtcagtcgcccttgtt
cgaggaccttgcccagctcgaggggcgaagcgtcaatggctggccgagc
gcgccgtgcagttcgcactgggcttgcacggccgccggccagaggtcgat
aaccccttcaaaggcaaactgcgtgaagacctgtgctgcatcatgttcga
tgacctgtcgctgcacaccctggtcgagcgttacgcggccagtgaagccc
tgcgacgacacgacagcgagtacttcagcaaactgatcgccacgacacga
aataccgtggaacggcgcatcgtctttcacgggctgctggaacacttcga
caggctgttgcctatcgaaaagagcatctaccaactcaactaccgcagcg
ttcaatacgcgcacctggagcaggaagaagccctgtacggcaaactgata
atggaacaacccattagtgcactgctggaagtgcacacgcctgagtggct
tcttgagaatctgtcttcgtttgagttttcgattgattga
```

The protein encoded by this nucleic acid molecule has an amino acid sequence according to SEQ ID NO: 74 as follows:

```
MKLIRQIRSQGRQSPLFEDLAQLEGRKRQWLAERAVQFALGLHGRRPEVD
NPFKGKLREDLCCIMFDDLSLHTLVERYAASEALRRHDSEYFSKLIATTR
NTVERRIVFHGLLEHFDRLLPIEKSIYQLNYRSVQYAHLEQEEALYGKLI
MEQPISALLEVHTPEWLLENLSSFEFSID
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-eighth nucleic acid molecule encodes ORF39 and has a nucleotide sequence according to SEQ ID NO: 75 as follows:

```
atgcgactgactactaaaggccgatacgctgtgacagccatgcttgacct
ggcgttacatgcgcagaacgggccagtgtctctggccgacatctccgagc
ggcagggcatttccctgtcttatctcgaacagttgttcgccaaactgcgt
cgcggcaatctggtttccagtgttcgtggtccgggcggcggttatcagct
gtctcgtgacatgaaaggcatccaggtcgcccaagtcgtcgacgcggtca
atgaatcggtcgatgccacgcgttgtcaggggctgggtgattgccacgct
ggcgatacctgcctgacccaccacttgtggtgcgatctgagccagcagat
tcacgaatttctaagcggtatcagcttggcggatcttgtcactcgccgtg
aggtacaagaagtcgctcagcgccaggatatgcgccgtggtcataaccac
acgtcgcaactgggtaagatcgaaacgtccgccgtcgaatga
```

The protein encoded by this nucleic acid molecule has an amino acid sequence according to SEQ ID NO: 76 as follows:

```
MRLTTKGRYAVTAMLDLALHAQNGPVSLADISERQGISLSYLEQLFAKLR
RGNLVSSVRGPGGGYQLSRDMKGIQVAQVVDAVNESVDATRCQGLGDCHA
GDTCLTHHLWCDLSQQIHEFLSGISLADLVTRREVQEVAQRQDMRRGHNH
TSQLGKIFTSAVE
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A thirty-ninth nucleic acid molecule encodes ORF40 and has a nucleotide sequence according to SEQ ID NO: 77 as follows:

```
atgaataccgtcagaaaacccataacaccacggatgctcagcatgaccga
taaaaacggcacccatcgacaacgacgtgctgcactgttccccaaaaccc
cggcgaccgccaccagcctgtgcccttcagagggcctaatatcgccatc
gtcccggtgcgctatgcgctggatcgctcgcgctatgacgctgaccccgc
gcaactgaagccactgcccaaagacggccaatgggcccacctgccgacgc
tgaaaactcgcagttacaccttacgccaactgtacgacggctacgtttac
gtgttcgacgaaacggccggcacgttgcacgaatacgcagcctcagccag
cgacggccatctgagccgcatcgtctggaccgatgcacacatcggtaacg
accagcgaagcggtgccggtgaagggcaacccctttgtgcttacccgcgt
gaccaccgcctgcacatcgccttttctcccctgcaatggacatggcgaat
gtgcgagcacatgcgctcccacgcccaagccgcgcgttgtggatgaagg
cgctggacctggccagctactgcctcaccatggccgaaccggacaccctg
ccgctggatcgcatcgccgaggccgtggcggatatcgacaaagactgtgt
tgtggaagatggccgttttgcagattcggcgattcccagtgttcgcccgc
catcagaaggtgcagaaccctatccgttatgggcaccgctgggcgccgat
gtcttctggcagggcagcgtctacgatcaggacagctctctggtcattgc
cctcaatgacccgctcgccgttttcaacgacttgggcatgcagctggcgg
ccgatcaggcggcttttcgggaatggcaaagcgcccacgaacacaagatc
cagattgcccagaccgtcgccacgctgtgcggtgcagagagcgaagcaga
gaagctgccagcatcggtgcgcggtgatgcgctgcgcacgcatcagtacc
tgagcgaggtcgaagcctactttgaacaatgcattcttgaagaagcacag
atcagcagtagcaacgttcctggagattttctgctgctgccggacatgtt
caagagcctggacatgcgcaaatcgatcgaaacacgttatggcagcgcgc
cgaccgatgagggcgcgcaggcctggaaagatcgccacaaatggcggcgc
gaggtcgatctgagcagtgcgcgtcagtacctttttgcagcacctgccgac
cggagacaaacgcctgcaacaggtgcgtgacacgcaaagcgatttccagc
actgggcggcacatataggcaccgaaccgctcaagctgttcatcgacacc
acacacccgaaaacctgctgtatttgcagacgatcatgctcaatctgca
gatcatctatgcgcaggacagcgccgcaaatgcctggctcgccgagcagg
aagccaacaccagcagcctgtttggcaccctgcgttatggttttcgcca
gcgctcaagcacgccctgcatcaggaagccgacgcactgctgaacggcct
cggcgacgtcactaatctggccacgcgcatcggtgaactcaatggcgtgc
tcaaccatcaggtttttgccgacaagccgtggatgaaggcgctgaaacag
cctgttcaagacaccttcaaagccctcggcgaactggccagcggtgccgg
```

```
caaagccaggttttgaaagtgtattactggcatgggtgcccatcgacagcc
gcatggcccttggcaagcagcagaacatcgttgcgttgcttcgcaccctg
ctgatcggccagatattgctcgactcgacagcacgcgtcgcgatcaatga
gcagacagtgaccaagctcaaacagtgggtaagtgagtggcaagtcctca
acaagcaaatcagcgagctggtgcgcagttggcaatacccgaacgcctac
aacacgcgccaaagcaccgctcgcaaattgcaggcccataaacacaaact
gcgcgttcacgaactgagcatccctgccctgctcgactttcagaacaacg
aatacgccaagctattgcaggacgagattcgtcagtacttccagtctggc
aaaaccctcgccacggactggctcgcccgcgccaaaggctggaccgaccg
actgggcggcgttgctggcacgatcacctggggcgtggtcatgcttaacc
tgatcaataccgccttcctctatcgggaccttacccgggacggggatttc
agtaccaaggacattggcaaggtgacgtatggattgggtacagcttcaa
tctgttgatggcggtgtttgtggacgcgccgtggagcatcataagggacg
caacgccagcgctgatcgatggcaagaatgtggccattctggacaggtcc
agtgcgtactggaaagccaagggaaatgcagcgtggggtgatgcgatacg
tgggttcagggtttcgatggtggcgatgggtgggtttggcttgcggcgg
ttacgcttgaattatttgatgttacagatgattttcacgcagctaaaaca
tcagaagaaacatatggaattggcatcaagggggttttccgtagtggtgat
gggattgggtgctgcggcccagctaatggcaggcatttctcccgctggcg
tttttacgattatcgcaatgagtccgtggttcagcgtagcgctactggca
gcaggcttgatttatcttttgctacgatggcccttaattacttcaagca
agacagtgtcggctggtggctacgcaagtgctgttggtccataacccaag
actatcgctatgctgagactgcggaaggtaagcatgacgaagtgcgcgcg
ctgatggaaataaaattatctccgcaggtccatgtaaaaagcaccgtgaa
ttatgaaaaccgttatcttggcaaaaacgatcactacagcgtagcggtac
aaaatggcgcggggtacaagtgcgcttgccgaatcttctacgcgggctg
tccgtgcatttcaatatcgttagtagcaagagaccatggggcgtgctgcc
cgtagaaaaaatagatcagccgatacatgaagcttttctggaccacgggc
aattcaggaaagtcgaacagttcgggatgtttaccaacaagcctgctggc
aaggcgagtgaagactatacctaccccgcatgccacctgaaaacgaaga
cctcatctgggaaacctgggtgccgctcgacaaggacgcaacgtatcttg
agttgcaaatctggtacccggccaatcttttaaatcctggcggagacgat
agaagctatctgtttcagatggagcttggcacaaaaggcgataccgctat
tgacggcctggctgcagtggaactcgaggtaaaggcatcaagcaggattg
gcgctctgaccctagaagtcgcagagggcacacctgtatga
```

The protein encoded by this nucleic acid molecule has an amino acid sequence according to SEQ ID NO: 78 as follows:

```
MNTVRKPITPRMLSMTDKNGTHRQRRAALFPKTPATATSLCPFRGPNIAI
VPVRYALDRSRYDADPAQLKPLPKDGQWAHLPTLKTRSYTLRQLYDGYVY
VFDETAGTLHEYAASASDGHLSRIVWTDAHIGNDQRSGAGEGQPFVLYPR
DHRLHIAFSPLQWTWRMCEHMRSHAPSRALWMKALDLASYCLTMAEPDTL
PLDRIAEAVADIDKDCVVEDGRFADSAIPSVRPPSEGAEPYPLWAPLGAD
VFWQGSVYDQDSSLVIALNDPLAVFNDLGMQLAADQAAFREWQSAHEHKI
QIAQTVATLCGAESEAEKLPASVRGDALRTHQYLSEVEAYFEQCILEEAQ
ISSSNVPGDFLLLPDMFKSLDMRKSIETRYGSAPTDEGAQAWKDRHKWRR
EVDLSSARQYLLQHLPTGDKRLQQVRDTQSDFQHWAAHIGTEPLKLFIDT
THPKTLLYLQTIMLNLQIIYAQDSAANAWLAEQEANTSSLFGTLRYGFSP
ALKHALHQEADALLNGLGDVTNLATRIGELNGVLNHQGFADKPWMKALKQ
PVQDTFKALGELASGAGKARFESVLLAWVPIDSRMALGKQQNIVALLRTL
LIGQILLDSTARVAINEQTVTKLKQWVSEWQVLNKQISELVRSWQYPNAY
NTRQSTARKLQAHKHKLRVHELSIPALLDFQNNEYAKLLQDEIRQYFQSG
KTLATDWLARAKGWTDRLGGVAGTITWGVVMLNLINTAFLYRDLTRDGDF
STKDIGKVTYGLGYSFNLLMAVFVDAPWSIIRDATPALIDGKNVAILDRS
SAYWKAKGNAAWGDAIRGFRVSMVAMGGFGLAAVTLELFDVTDDFHAAKT
SEETYGIGIKGFSVVVMGLGAAAQLMAGISPAGVFTIIAMSPWFSVALLA
AGLIYLFATMALNYFKQDSVGWWLRKCCWSITQDYRYAETAEGKHDEVRA
LMEIKLSPQVHVKSTVNYENRYLGKNDHYSVAVQNGAGVQVRLPNLLRGL
SVHFNIVSSKRPWGVLPVEKIDQPIHEAFLDHGQFRKVEQFGMFTNKPAG
KASEDYTYPRMPPENEDLIWETWVPLDKDATYLELQIWYPANLLNPGGDD
RSYLFQMELGTKGDTAIDGLAAVELEVKASSRIGALTLEVAEGTPV.
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fortieth nucleic acid molecule encodes ORF41 and has a nucleotide sequence according to SEQ ID NO: 79 as follows:

```
atgtgcctggtggcgagcctgtcggtgctggcaggcatgaccgatgccat
cggcttcatggccaccggcgatttcgtctcgttcatgagcggcaacacca
cgcgccttgcggtggcgatcagtgatggcgatttgagcgtcacactccgt
ctggccctggccatctttgcgtttattgccggcaatgcactgggcgttgt
cgttgcgcgcctgggcaaccggcgcgccctgcccttactgctggctatcg
ccacgctgttgtgccgctgcgcgtggccgttggcgaacaatatgctt
gccctgatctgggcgattctggcgatgggcatgctcaacgccgctgtcga
gcaggtcaacgggctgccggtgggcctgacctacgtgaccggcgcgctgt
cgcgactggggcgcggtctgggccgctggatgctcggcaacgccgggat
ggctggcgcattcaactggtcccgtgggccgggatgttcattggcgcagt
gatcggcgcgttgcttgaacatcgtctggggctcaatgccttgctggtca
gcgccagcctgtcagcgttaatggcgctggtgtcgctgaaaatcccgcat
cgctggcaacgtcagtacatgccgcgctga
```

The protein encoded by this nucleic acid molecule has an amino acid sequence according to SEQ ID NO: 80 as follows:

```
MCLVASLSVLAGMTDAIGFMATGDFVSFMSGNTTRLAVAISDGDLSVTLR

LALAIFAFIAGNALGVVVARLGNRRALPLLLAIATLLCAAAAWPLANNML

ALIWAILAMGMLNAAVEQVNGLPVGLTYVTGALSRLGRGLGRWMLGERRD

GWRIQLVPWAGMFIGAVIGALLEHRLGLNALLVSASLSALMALVSLKIPH

RWQRQYMPR
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-first nucleic acid molecule encodes ORF42 and has a nucleotide sequence according to SEQ ID NO: 81 as follows:

```
atgagagggcttggtgttctgagcatgaaccaccagtttcagggcaatac cctgttcaaagaaataagcggtaccagcttttccgcgccctacatcaccc atcttgcgggccgtctccttaacgagcacccagaggcatcggcgaacctc ttgcgcgctatgctggtgaatcatgcgtcattgtctagcgaggtcgagac gactttctccgacgacatgaggaagggctacaaagctaataaggcgaccc acaaccgtgaaatatcgcgcgatgtgagtggttacggccaagtgaatgag gcagacctgtttcggtcttccgaccattgcgttgtgctgatgtgtgaaga gtccattgagaaggactcgtgccagttctacgaactgcctttgcccactt cgtttcttcgcagggctagaggggcaaggcacctgagcgtcacgctggct tattctcctgccgtcaggacaactcggttggactatctggcaactcagat cagttatcgcctagtgaaaggttcgtcgcttgaggaagtccaggcctcgt ttaactacgacaagcaggacgaaacgaagacccgtggagatgacgctgag cagaatcgagacatcactgctcagttgagaagccgcgggaccgtccagtc ctcgcggtggacgttcaagaagcgaaatccagaagaaaaatggtttgtag ttgtgatccgccaggatcgggaatggaatcatcccgacgtgctggatcga gaatcttacgccctggtggtaacagttgctgatcgtgacaacgaacacgc gcagttgtatgccgaaattcaagccaagctgacgcttcaaaatcaggtgc gtgaagaggcaaggcagcgggctgttctgtaa
```

The protein encoded by this nucleic acid molecule has an amino acid sequence according to SEQ ID NO: 82 as follows:

```
MRGLGVLSMNHQFQGNTLFKEISGTSFSAPYITHLAGRLLNEHPEASANL

LRAMLVNHASLSSEVETTFSDDMRKGYKANKATHNREISRDVSGYGQVNE

ADLFRSSDHCVVLMCEESIEKDSCQFYELPLPTSFLRRARGARHLSVTLA

YSPAVRTTRLDYLATQISYRLVKGSSLEEVQASFNYDKQDETKTRGDDAE

QNRDITAQLRSRGTVQSSRWTFKKRNPEEKWFVVVIRQDREWNHPDVLDR

ESYALVVTVADRDNEHAQLYAEIQAKLTLQNQVREEARQRAVL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-second nucleic acid molecule encodes ORF43 and has a nucleotide sequence according to SEQ ID NO: 83 as follows:

```
atgggcattggcggtttgcttaaacctttggtcgattttttaccgaagtt gccgaccttacgcaccaagatttcctcgccttccatcagctacgcgcgtt tgcaaagcgatgcgtcccaggtacgcagtaaattgggattgggtgagcgc agcgtgctgggttatgaagcgctgatcgccgagttcaaggcgtgcgggc ggttctggtgcccgttctttggggacaaaagcagcaacacaagaatgcgt tgcacattctattgccggcgtcagatgtcacctttgtcttcgtcaacctg gataccaagctggaagacttcaagttttggatggcccacgagttagcgca tgtctacactcctgagcttgcgggtagtgacgaggggaggattttgcgg atgcctttgccggtgccctgctgtttcctgaggcttgcgtgcagctagcg tatgccgaggcggcgaagcgcctagcgcagctggggaggtgagtgtcct tcagcagcatgcccggcatcaccaaatttcactgaacacggtgttccagc aggcgcagggatatgcggcggaaaacaatctgccatccttacgggtaccg gaaaggacaattcacgcggtgcgcaacagctccacgccgcagttggtcag tacgatcctgtttgatccgactccacccaaaccggcgcaatacattgccg cagcgtcgaatgtgtttcagtctgagttcttcctggcgctgaaacgcatg attcgcgagcacgggacgggcccgtcgtatgttcagcaaatcatggatgt atcactcagtgatgcctccgcgctttacggcgagctcgcgcgttga
```

The protein encoded by this nucleic acid molecule has an amino acid sequence according to SEQ ID NO: 84 as follows:

```
MGIGGLLKPLVDFLPKLPTLRTKISSPSISYARLQSDASQVRSKLGLGER

SVLGYEALIAEFKACGAVLVPVLWGQKQQHKNALHILLPASDVTFVFVNL

DTKLEDFKFWMAHELAHVYTPELAGSDEGEDFADAFAGALLFPEACVQLA

YAEAAQAPSAAGEVSVLQQHARHHQISLNTVFQQAQGYAAENNLPSLRVP

ERTIHAVRNSSTPQLVSTILFDPTPPKPAQYIAAASNVFQSEFFLALKRM

IREHGTGPSYVQQIMDVSLSDASALYGELAR
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-third nucleic acid molecule encodes ORF44 and has a nucleotide sequence according to SEQ ID NO: 85 as follows:

```
atgaagcagctcgcggcaggcagcaatgtgcatgttcttgaaatgagtc tttccagatagataaggtgcgcttttggggccacagcttggacagatt tcgcaacaggtgaaagcgtgtaccaagcgtcccaggaggcaaggcgaggc atgaatgactttcgcttgatccgtgcaggcgagggttaccgcgcattgag catcagtgatgtgatcagtcgaaatcatcgaacttacgagtggctcaagg aagagctcgccatggagttcgatggtcagaccattgtcatcactcatcat tgcccgttggtcaattactgtgcccagagcagggctcaccgctaatgcc tgcttattcaaatgattggccagaactcgttcgtcaggctgatgtgtggg tcttttgggcacacgcacagtcatgtcgatgtcatggtggaaggatgccga
```

-continued ctcattagtaaccctagaggttatccaggtgagagttgcggctttgccaa tgactttgtggtcgatattaactag The protein encoded by this nucleic acid molecule has an amino acid sequence according to SEQ ID NO: 86 as follows:

MKQLAAGSNVHVLENESFQIDKVRFLGATAWTDFATGESVYQASQEARRG

MNDFRLIRAGEGYRALSISDVISRNHRTYEWLKEELAMEFDGQTIVITHH

CPLVNYCGPEQGSPLMPAYSNDWPELVRQADVWVFGHTHSHVDVMVEGCR

LISNPRGYPGESCGFANDFVVDIN.

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-fourth nucleic acid molecule encodes ORF45 and has a nucleotide sequence according to SEQ ID NO: 87 as follows:

atgacgctgacgcagcgtcaggcatggcatcgcgaggcacagcggtttgg cgagcaggtggtgaacatgcgcaaagccagcaaggagcacttcggccagg cggaaaatgacagccgcacctatccggcgcgctttatcgaccagcaactg gctcaactgctgaaccggctatccatcgctgcaacggcgcaacagatcaa tatttcactgacctacaggacgggcaccgaagtgctcgaaattcccggcg cgcctgtattgccagaaaccgagaccgagaacgtttcactcaggcaactg gtgcatacccaggccctgcgcaccaaggccaaggatgccgtgcttctacg cgctgtcgacgccgaaggcgtcccccttgcgcacttggacaagcaggccg taaccgagctgattgccacgctggaagatcaccgatacctcagtgattac cttgacctgcacctgaaaacctcggcgtatgcacagcagctcaagcggtc agaaaaagccatgttgcaagctcagatgaagatggcgctgctggagatcg agcaacaggcttttgcaccagccggtcgcgagtggatcaaggctgtgctg gattcgccagcccccaaggacgtcgaaccatggcaggggaaagcattga agtccgttttttcagcgtcaaccaattcaagatgaccaatgtcatgctga ttgctccagccggtaaattcgagaaggggccgctggtgctttgcacgctg gatgcttccgacggtgtggttttccgctggtttaacagcatgtatcacct gaccaccagctttctggaagaggcacccttccagcagtatctgattcagc aaataccggtttccaggcgtcttgagacgctgcatgccatgcagtacgaa aaggaagccaagcattggcgtccgccagaagtattcacccaactgacgct gctaccgatcccgtcaaggctgctgcgcccagtcgtgtttgtcagccaga gcaaagacatttacgaggaaaatcacgagaccaagatcaaccatctgatc aacgaagccaaacggcagatgagcctgtccaccggtacagggcaatcggg tcggggcttcgatctgatcgcgagcattgcgattctgtttctgcctggcg cgatcatgatgcctgtctcgctgggcgctggccttaacaaaacctggagc gcttttcgaaaatcgatgaaaacgacctggaaggtgccgccgaggagtt tctgagcgccctcagctatcttgccattaccttggtcggccatttggcgc -continued tggccttgaaaccggcaggaagcgccgcaaaaacggtgagacgtccgcac ctggtacgcagagtcggtcgtgatgggcaggcacagatcggctacctcct gtcgcattcaaaagcgccgcgtttcccagactcgaaattgatcgctgcaa tggaccccaaacgcttcgtcgccattgaggtagaaggccagacctgctta ataagccggcgggccaacctgttcggccactcacgcctttatcgggtaaa cccgatggatgcaacgcaactggtgcacgagcaggagtttgccttgcgca gcaccaacggcacctggaaaatcgtgggcaaacagatcctgcgcatgagt cagtccgcaatccgcaatgcccaggctcaactgaccagcctgacaaatct ctggccggcgtctctggaggaagcaagtagcgccgaacgcttgagcttcg agaccgactacctggcgctggcccagacatccaacgcagaaaactattcc gaaatagtcgcctacgtggaaagcggttcaacagacatcaacccgctgct gcgaagcggcgtgcgcaacgccaccacgcgcagattttacgtcagttcc ataaactcaatgcgtgggaaggcactgcctttcgcgccacctatgtgtcc agcgacggggtggcatgccttgagcgcgaagtgggttcggtgttcaccga caacggcgtgcagtctgcatcggtgtcgcgagccaatgcctccagatgga gccaggacgggttcgtgagcagcaacgccaatgccgcaaaccacccggtg ttcttcatctttgcaccgggagtgcccaagaagaacatgttcaccggctt tcttggcgatcacgtggcaatcccgccaggcacgtgcgtgcaactgggtg cgaccaagcggataaacggacagctgtttgcctggttcgatgcgcccgaa caaatggtcgatcagacctacgatctctatacaggagaacaggaactctg ggtctga The protein encoded by this nucleic acid molecule has an amino acid sequence according to SEQ ID NO: 88 as follows:

MTLTQRQAWHREAQRFGEQVVNMRKASKEHFGQAENDSRTYPARFIDQQL

AQLLNRLSIAATAQQINISLTYRTGTEVLEIPGAPVLPETETENVSLRQL

VHTQALRTKAKDAVLLRAVDAEGVPLAHLDKQAVTELIATLEDHRYLSDY

LDLHLKTSAYAQQLKRSEKAMLQAQMKMALLEIEQQAFAPAGREWIKAVL

DSPAPQRRTMAGESIEVRFFSVNQFKMTNVMLIAPAGKFEKGPLVLCTLD

ASDGVVFRWFNSMYHLTTSFLEEAPFQQYLIQQIPVSRRLETLHAMQYEK

EAKHWRPPEVFTQLTLLPIPSRLLRPVVFVSQSKDIYEENHETKINHLIN

EAKRQMSLSTGTGQSGRGFDLIASIAILFLPGAIMMPVSLGAGLYKTWSA

FSKIDENDLEGAAEEFLSALSYLAITLVGHLALALKPAGSAAKTVRRPHL

VRRVGRDGQAQIGYLLSHSKAPRFPDSKLIAAMDPKRFVAIEVEGQTCLI

SRRANLFGHSRLYRVNPMDATQLVHEQEFALRSTNGTWKIVGKQILRMSQ

SAIRNAQAQLTSLTNLWPASLEEASSAERLSFETDYLALAQTSNAENYSE

IVAYVESGSTDINPLLRSGVRNATTRRFLRQFHKLNAWEGTAFRATYVSS

DGVACLEREVGSVFTDNGVQSASVSRANASRWSQDGFVSSNANAANHPVF

FIFAPGVPKKNMFTGFLGDHVAIPPGTCVQLGATKRINGQLFAWFDAPEQ

MVDQTYDLYTGEQELWV

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-fifth nucleic acid molecule encodes ORF46 and has a nucleotide sequence according to SEQ ID NO: 89 as follows:

```
atgactcagctaaaccctgcgggacaaccgcccgcagaaccgacccgaat
cgtcaaagctcacattgacctcatggatcctgccgaaagcgctgactacg
aggcgacccgaatggcattgctcgcagcgatgcaaagcggcaatgccgcg
atcaacctgaacagattcggctcaagcccgacccagcgtccgggttcgg
cgaatactgcgctgagaaagctgcgctacctcacccggtccaggccgaaa
accaggaactcccgtttcagatagacagcgatggcagcgtcagtctggca
ttgatgctgcgctataactacgggttgtcgctgccgcaatcgcctgacga
aacagcgatcaaaaccctgctcaatacgctggcagaacttcgcaccagtc
aagaactggggcttattgatcagttcgacatcaaggccatgctgaccatg
caaaatctgcaggatctgaagcgagcctgcattgagtaccttggcaccga
cggtggcacgctgctaggcaagctgggtgctgaaataattgcctcctgcc
cactggcagatgtgcagaactccccggtgacggttattgccggattctc
agatcggaaccggcaagggcattggggcaaacgctgctggcacagcttgg
tcggcctgaagaagaaacggacgcgtccctgacaacactcgtggaccgga
ttttatggtatgccatcagtagcgatcttcatgatccagaaaaccggaag
ccaggagaaattgccggctatccattcacccaggccgaaaaccagggacg
ccgccacgctgacatcctgaacgatattcacaaccacctgatcaccacgg
gcaaggctgagtctgtcaacgaagcaataattgcctgcttcatacttgca
ctcgatgactgcccggaatggctggtcagcagtgttcccgatgatctgcc
atacggctgtacagaggtgtgggtcaactttcaacatggggtcacacttg
cggaagtcatcgagtttggctcgtcacgctggatgaactttgaagacctg
atcgagctgccggtgattttcaacaaaaagatggacaccgaagagcagca
agtcgcctatgtcgcaacgcgcatgcccattcttctgacttgggcccagg
ccaacggttacattcgtacccagagcgacctgccttactccgaacaagag
atagaacaggccgccagcgcgtttgaacactccgagaaacaatcccttga
agctgcgaacgccttgatccggaaagcgccagaacgcaaagccatggcta
tcagtgccatgaaagaagcgcggaggacgcctgaaatagaaaaaatactt
gagcaggaagattactggtttccgcccatcgatctcggcatcaggctggc
ggtgctacgcaaaaatcacacgcctgtctatcgcgatcaccaaggcacgc
tctcaccgtcaaatctgccatacgaccctacggcataaaacacaaggcg
tcgtcgttgctggagatctacatggcaggtgaaaacattgatgactggag
actgccggggcgcaacagcaacgagggcctgcttcccatcaaccgtgaaa
tgcagttgttgtacaaggcgctgccagacatcaatcaaaggttcgagagt
gaatttcaggcttatctggcagatgcccgtaaggcgtatgcgacgattat
cagaaagttgctgactcacctgccgctcaagcaccgcatggcgatcgaaa
atggtgaggtgtcgctacactcactcagattgccgaccaaggacgtgctg
gcggcgacagagagcgaaaaacatcgggagccgttgcgagggcgcacggg
```

-continued

```
ctttgtcatcaaagctgtctacgagggcaaaaccacgttttacgaggtgt
ttccgttatcgatgattgtacgctatcgccctgatctggaggcccttctc
aagaacggtgtggtcggtatagattttgggacattctgcctcccacccg
tataccggtagcggtttataacggaatcacaatgccatttgatcagggag
cctatttgaacggtcagctacctgagcctggggcaagcgctgtgatgatt
gcagaaaccattggtgaacgatttgattcttcaagtgcagaggtcgggca
acaccagcctccgacctcgttttcaaaacgctctactggcattgccgaga
ccatcacaacatcgcttttctacgtcaacgaagatgcactctttgcacac
tgcaaaagcctcacgcaggtagaaatagataacggtgccccaggtgcgct
cgaagaggtgtccagcttctgatacacctgacgccctggccggaaatcg
aaaacattctgtccggagagaaagcgcttatgaggggaggagcaatcggt
ctggcgctttacatgattccctatgtgggacccgcgggcaagttgctcgc
aggcacggcaaaagtcgttacccgcctgggcaaaagcctcataaccagcg
gtagcaaagtccaggtctcgaaattgctcatcacggccggcaccaccctg
aaagacgccccgctgatcatgatcagacaggcccctgacatgaccagtaa
agcaatgactggcgtttcgcaattcgtcgtgaaacacgtcacctggaaat
ttctggcgatacgtataggtattggtttaagccgcaggcttgtagccatc
atgagcaggcagcaggcccaggccgcaaagcaagaggccacgtaa
```

The protein encoded by this nucleic acid molecule has an amino acid sequence according to SEQ ID NO: 90 as follows:

```
MTQLNPAGQPPAEPTRIVKAHIDLMDPAESADYEATRMALLAAMQSGNAA
INLEQIRLKPDPASGFGEYCAEKAALPHPVQAENQELPFQIDSDGSVSLA
LMLRYNYGLSLPQSPDETAIKTLLNTLAELRTSQELGLIDQFDIKAMLTM
QNLQDLKRACIEYLGTDGGTLLGKLGAEIIASCPLADVQNSPVTVIARIL
RSEPARALGQTLLAQLGRPEEETDASLTTLVDRILWYAISSDLHDPENRK
PGEIAGYPFTQAENQGRRHADILNDIHNHLITTGKAESVNEAIIACFILA
LDDCPEWLVSSVPDDLPYGCTEVWVNFQHGVTLAEVIEFGSSRWMNFEDL
IELPVIFNKKMDTEEQQVAYVATRMPILLTWAQANGYIRTQSDLPYSEQE
IEQAASAFEHSEKQSLEAANALIRKAPERKAMAISAMKEARRTPEIEKIL
EQEDYWFPPIDLGIRLAVLRKNHTPVYRDHQGTLSPSNLPYDPYGIKHKA
SSLLEIYMAGENIDDWRLPGRNSNEGLLPINREMQLLYKALPDINQRFES
EFQAYLADARKAYATIIRKLLTHLPLKHRMAIENGEVSLHSLRLPTKDVL
AATESEKHREPLRGRTGFVIKAVYEGKTTFYEVFPLSMIVRYRPDLEALL
KNGVVGIDFWDILPPTRIPVAVYNGITMPFDQGAYLNGQLPEPGASAVMI
AETIGERFDSSSAEVGQHQPPTSFSKRSTGIAETITTSLFYVNEDALFAH
CKSLTQVEIDNGAPGALEEVSSFLIHLTPWPEIENILSGEKALMRGGAIG
LALYMIPYVGPAGKLLAGTAKVVTRLGKSLITSGSKVQVSKLLITAGTTL
KDAPLIMIRQAPDMTSKAMTGVSQFVVKHVTWKFLAIRIGIGLSRRLVAI
MSRQQAQAAKQEAT
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-sixth nucleic acid molecule encodes ORF47 and has a nucleotide sequence according to SEQ ID NO: 91 as follows:

atgtctgttacttcatctgtcctgcgactgtcgcgcctgagcgtgtcgtt
atcacttttgggcatgctgtcgtctgcactgtttgccggcgcggcattcg
ccagcgacgagacgcaactgatcgaatccctcaacgcctaccgtggccag
gcgcagcgctgtggcgagcaggtgtccatggaactgccgccgctgagcac
cgacccgcgtctggtgctgcccgccagtggcaacctgaacctgcaacagt
cgctgacccgcgcgtcttatccgatggtcaccgtgcaggcgatcagtctg
tccggaccgcgagatgcggcgtcggcgttgaaggcggtgcaggagagttt
ctgccgcgtggtgctggacccgcagttcgtcgatatcggggtcagccggg
acgggcgcgactggcgcatcgtgctggcgcgctcgctggtggcatcacgt
ctgggtgactggcaagcagaaggtcagaaaattctggagatgatcaacac
cgcccgtacccaggcgcgtcagtgcggttcgcaatccttcgcggccacta
caccgttgagctggaatcaggtattggggacggccgcacaaggacactcg
caggcaatggccaatcagaacttctttgaccacaaggggcgcgacggccg
cacgcccgggacagggccgagcttgccggctatctgggccagcagatcg
gtgagaatattgccgcaggccaggacactgcccgcaaggtggtggacggc
tggctggtcagcccgggccactgcgcaaacctgatgaccccggttttcg
cgagctgggagccgcctacgcgatggaccccaaaagtgacgcggggattt
actggacagccatgttcggcacgcagcaatag The protein encoded by this nucleic acid molecule has an amino acid sequence according to SEQ ID NO: 92 as follows:

MSVTSSVLRLSRLSVSLSLLGMLSSALFAGAAFASDETQLIESLNAYRGQ
AQRCGEQVSMELPPLSTDPRLVLPASGNLNLQQSLTRASYPMVTVQAISL
SGPRDAASALKAVQESFCRVVLDPQFVDIGVSRDGRDWRIVLARSLVASR
LGDWQAEGQKILEMINTARTQARQCGSQSFAATTPLSWNQVLGTAAQGHS
QAMANQNFFDHKGRDGRTPGDRAELAGYLGQQIGENIAAGQDTARKVVDG
WLVSPGHCANLMTPGFRELGAAYAMDEKSDAGIYWTAMFGTQQ

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A forty-seventh nucleic acid molecule encodes ORF48 and has a nucleotide sequence according to SEQ ID NO: 93 as follows:

atgccgttattaaactggtccagacacatggttcatttaacagccatcgg
ccttatcagcattccggctgcctatgcagcggacaccctgacccgcgaca
atggcgcagcggtcggcgacaaccagaactctcagactgcaggcgcccaa
gggcctgtcctgctgcaagacgtacagctgctgcagaagctgcagcgttt
tgatcgcgagcgtatcccggagcgtgtggtccacgcacgcggcactggcg
tgaaaggcgaattcacagcgtccgccgacatcagcgacctgagcaaggcg
accgtcttcaaatcgggtgagaagacccggtattcgtacgttttcttc
cgtggtccacggcaaccactcgccagaaaccctgcgcgacccgcatggct
tcgccaccaagttctacaccgctgatggcaactgggacctggtaggcaac
aacttcccgacgttcttcatccgcgacgccatcaagttcccggacatggt
gcacgccttcaagcctgacccgcgtaccaacctggacaacgactcgcgcc
gcttcgacttcttctcgcatgtaccggaagccacgcgcacgctgaccctg
ctgtactccaacgaaggcacaccgaccggctatcgcttcatggacggcaa
cggcgttcacgcctacaaactggtcaacgccaaaggcgaagtgcactacg
tcaagttccactggaagacgctgcaaggcatcaagaacctcgaccctaaa
gaagtcgctcaggttcagtccaaggactacagccacctgaccaacgacct
ggtcggcgccatcaagaagggtgacttcccgaaatgggacctgtacatcc
aggtgctgaaacctgaagacctggccaagttcgacttcgacccgctggac
gccaccaaaatctggcctgatgtgccagagaagaaaatcggccagatggt
cctgaacaagaacgtcgacaacttcttccaggaaaccgagcaggtcgcca
tggcacccgccaacctggtccctggtatcgagccttccgaagaccgtctg
ctgcaaggtcgagtgttctcctatgccgacacgcaaatgtatcgcctggg
tgccaacggcctgagcctgccggtcaaccagccaaaggttgcagtgaaca
acggcaatcaggatggcgcgatgaacagcggcaaaaccaccagcggcgtg
aactacgagcctagccgtctggaacccgtcctgccgatgagaaagcacg
ttacagcgagctgccaatcagcggcactacccagcaggcgaagatcacgc
gtgagcagaacttcaagcaggcgggtgatctgtatcgctcttacaacgcg
aaagagcagaccgacctggtgcagagcttcggtgaatcgctggccgacac
tgacaccgaaagcaagaacatcatgctgtcgttcctctacaaggcagacc
ccacctatggcactcgggtaaccgaagcggccaaaggcgatctggccaag
gtcaagtcactggctgccagcctgaaagactga The protein encoded by this nucleic acid molecule has an amino acid sequence according to SEQ ID NO: 94 as follows:

MPLLNWSRHMVHLTAIGLISIPAAYAADTLTRDNGAAVGDNQNSQTAGAQ
GPVLLQDVQLLQKLQRFDRERIPERVVHARGTGVKGEFTASADISDLSKA
TVFKSGEKTPVFVRFSSVVHGNHSPETLRDPHGFATKFYTADGNWDLVGN
NFPTFFIRDAIKFPDMVHAFKPDPRTNLDNDSRRFDFFSHVPEATRTLTL
LYSNEGTPTGYRFMDGNGVHAYKLVNAKGEVHYVKFHWKTLQGIKNLDPK
EVAQVQSKDYSHLTNDLVGAIKKGDFPKWDLYIQVLKPEDLAKFDFDPLD
ATKIWPDVPEKKIGQMVLNKNVDNFFQETEQVAMAPANLVPGIEPSEDRL
LQGRVFSYADTQMYRLGANGLSLPVNQPKVAVNNGNQDGAMNSGKTTSGV
NYEPSRLEPRPADEKARYSELPISGTTQQAKITREQNFKQAGDLYRSYNA
KEQTDLVQSFGESLADTDTESKNIMLSFLYKADPTYGTRVTEAAKGDLAK
VKSLAASLKD.

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (e=0), as detected by BLAST search, to catalase isozyme catalytic subunit CatF from *Pseudomonas syringae* pv. *syringae* (GenBank Accession AAC61659, which is hereby incorporated by reference in its entirety).

A forty-eighth nucleic acid molecule encodes ORF49 and has a nucleotide sequence according to SEQ ID NO: 95 as follows:

```
atggggtttcgagctgcggcaaaagtgccgtcggtgcagaaatcgcccg
taacagcggcggtcgcctgatcgaaggcgatgcgttccatcccaggcca
acatcgacaagatgagcgccggcaccccctcaccgacgaagaccgtgcc
ggctggctgacccgtctgggtgaagaactggccgcagcccttgccaaggg
cgaacatccggtgctgacctgttcggcactcaagctcatttatcgtgaac
gcctgcgtgcggcggtgccgggcctggttttgtctttctcgaactgagc
aaagagctggccaccgagcgttgcgccaaccggacccgggcatttcatgcc
tgcgagtctggtcgatagccagttcgcgaccctggaaccaccgatcggcg
agccactgaccctggtggtcgatgccagcaagcctatcgatgtaattggt
gaacaagccgcggcatggtggaaaggctctcacgcctga
```

The protein encoded by this nucleic acid molecule has an amino acid sequence according to SEQ ID NO: 96 as follows:

```
MGVSSCGKSAVGAEIARNSGGRLIEGDAFHPQANIDKMSAGTPLTDEDRA
GWLTRLGEELAAALAKGEHPVLTCSALKLIYRERLRAAVPGLGFVFLELS
KELATERCANRTGHFMPASLVDSQFATLEPPIGEPLTLVVDASKPIDVIG
EQAAAWWKGSHA
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (1.1e-52), as detected by BLAST search, to gluconokinase from *Pseudomonas aeruginosa* (Stover et al., *Nature* 406:959-964 (2000); GenBank Accession AAG05709, each of which is hereby incorporated by reference in its entirety).

A forty-ninth nucleic acid molecule encodes ORF50 and has a nucleotide sequence according to SEQ ID NO: 97 as follows:

```
atgcgaccggtgtctatgttttccctgcgttccatttgtgctgccgcact
gtttgcgctttgcctgtctatcttcccggcgctggccgccgagccgccca
cccgcgatgccgtgcagcaaagcctcgacaagattgccgaccgcaagctg
ccggatgccgatcagaaggccttgcagcaggtgcttgagcagacgctggc
gtttctcaacagcaaagacgacagcgagcaaaagctgaccgcgctcaagc
agcagctggctcaagcgccaaaacagacctcggacaaccagcgcgagctg
gcccggttgaaagaaagcaaagtcgttgccgttgcacagcgctacgtgg
cctcgatgtgccgcaactggagcaactgctcagccagcgcagcacccagc
aaagtgatctgcaaagcgagcttaacgacgccaacagcctggccatcacc
gcgcaaacccggccggagcgggcgcagactgaaatcagcgccaatcagac
acgcatccagcagatcaatgccatcctcaagaatggcaaagacaacggca
agaccctgagtgccgatcagcgcaatctgctcaatgcggaactggcctcg
atcaacgcgctgaacctgctgcgccgtcaggaactggccggcaacagcca
gttacaggacctgggcaacagccagcacgacttgctgaccgaaaaagtcg
cccgccaggagcaggaaattcaggacctgcaaaccctgatcaacgacaag
cgccgagcccagtcgcagaaaaccgtggcggacctgtctctggaagcgca
gaaatccggtggcagcagcctcctggcgaccgagagcgccgccaacctca
agctgtccgattacctgctgcgcggcaccgaccgtctcaacgagctgacc
cagcaaaacctcaagaccaagcagcaactggacaacctgacgcagaccga
tcaagccctcagcgagcagatcaacgtgctgagcggcagcctgctgctgt
ccaagattctctacaagcaaaaacagtcgttgccgcacctggaactggac
aaaggcctggctgacgaaatcgccaacatccgcctttatcagttcgacat
caatcagcaacgcgagcagatgagcacaccgaccgcttacgtcgaacgac
tgctcgccacccagcccccggaaaatatcaccccgcaactgcgcaggacg
ctgcttgatctggccatcacccgcagcgacctgctcgaacgcctgaaccg
cgagctgagcgcgttgctcaacgagtccatcacgctgcaattgaaccaga
agcagttgaccagtaccgccgtcggcctgcgctccacgctggacgagcag
atgttctggatccccagcaacaagccgctggatctggagtggttccagaa
catctggccgcgcctgcaaaaacaggtcgcgaccctgccctggacgtcca
gcctcagcgagctgtcggacggcttgacacaacgcccgctgctgtttctg
ccattgttactgctgatcggtgtactgacctggaggcgcaaggcgcttta
ccagaagctcaaccggctgcacgccgacatcggccacttcaaacgcgaca
gtcagtggaaaacccgttggcgctgctgatcaacgtgctgctggccatg
ccggtcgcattggggctggcgctgtgcggctacgccttgcaaatcgatgc
gcgcgggcaaaacgccaaccttggcgaggccttgctgcagatcgcgctgg
cctggctagtgttctacaccgcctaccgcgtgctggcccgtccggcgtt
gcgcaactgcactttcgctgggaaccggcgcaggtcgcgttcttgcgcgg
ctgggtcgtcgcctggggttggtggtgctggcgctggtcgccgtggtgg
cggtcgccgagcatcaaccggccgcgctggccgacgacgtgctgggtatc
ggcgtggtgctgacctgttacgcgctgatgacctggctgctgggccgatt
gctgctctccagccctacgcaccacaacgcgtcgctgttccgcaagacgc
tgggtgtggcgttcacggcattgccggtcgcgctgtttctggcggtgtgc
ttcggctactactacaccgcactcaagctcagcgaccgtctgatcgacac
gctgtacctgatgatgatctggctgatggtcgaggccaccttcgttcgtg
gtctgggcgttgccgcgcggcgactggcctaccagcgtgcgctggccaaa
cgtcaggctgcgcgagaaacggtgacagcgacatcccgtcgaagaacc
gaaactggacatcgaacaggtcaaccagcagtcgctgcgcctgattcgtc
tggccttgctggctggtttcgtcggcgcgttgtacctggtctgggccgag
ctgatcacggtgttcgcctacctggacaacatcatcctctacgaatacac
aagcggcacaggcgccaacatgagcatggtgccgatcagcctgagcgact
```

```
tcctcggtgccggggtcatcatcgtcattacctttgtgctggcgggcaac ctgcccggcttgctcgaggtgctggttctgtcacgcatgaacctggcgca aggcagcgcctatgcgaccaccacgctgctctcctacaccatcgccggca tcggctttgtgaccacgctgtccacattaggcgtgagctgggacaagctg cagtggctggtcgcagcgctgtcggtgggcctggggttcggcatgcagga gatcttcgccaacttcatttccggcatcatgatcctcttcgagcgcccgg tacggatcggcgacaccatcaccatcggcgccctgtcgggtacggtcagc aagatccgcatccgcgccacgaccatcaccgacttcgaccgcaaggacat tatcgtcccgaacaagaccttcatcaccggccagctcatcaactggtcac tgactgacaccgtcacccgcgtaacgctcaagctgggtgtggattacggc tcggacctggacctcgtgcgctccctgctgctgcaagccgcacgggaaaa ccctcggtgctcaaggagccagagcccattgtctacttcctgaacttcg gcgaaagcaccctcgaccacgaactgcgcatgcacgttcgcgacctgggc gaccgcaacccggtactcgacgagatcaaccgcttcatcaaccgcgagtt caagaaacagcacatcaacatctcgttccgccagatggagatctacctca aaacacccagggcctggaatacaaactggtgcccgccgaaccaggcgaa aagcacggcgcaccggctgggcaaaccacgctgcaaccggtaaacaccaa agtagccccggcaaccaaagatgcgccagagccgccggagttgaggctgg actga
```

The protein encoded by this nucleic acid molecule has an amino acid sequence according to SEQ ID NO: 98 as follows:

```
MRPVSMFSLRSICAAALFALCLSIFPALAAEPPTRDAVQQSLDKIADRKL

PDADQKALQQVLEQTLAFLNSKDDSEQKLTALKQQLAQAPKQTSDNQREL

ARLKESKVVAVAQRYGGLDVPQLEQLLSQRSTQQSDLQSELNDANSLAIT

AQTRPERAQTEISANQTRIQQINAILKNGKDNGKTLSADQRNLLNAELAS

INALNLLRRQELAGNSQLQDLGNSQHDLLTEKVARQEQEIQDLQTLINDK

RRAQSQKTVADLSLEAQKSGGSSLLATESAANLKLSDYLLRGTDRLNELT

QQNLKTKQQLDNLTQTDQALSEQINVLSGSLLLSKILYKQKQSLPHLELD

KGLADEIANIRLYQFDINQQREQMSTPTAYVERLLATQPPENITPQLRRT

LLDLAITRSDLLERLNRELSALLNESITLQLNQKQLTSTAVGLRSTLDEQ

MFWIPSNKPLDLEWFQNIWPRLQKQVATLPWTSSLSELSDGLTQRPLLFL

PLLLLIGVLTWRRKALYQKLNRLHADIGHFKRDSQWKTPLALLINVLLAM

PVALGLALCGYALQIDARGQNANLGEALLQIALAWLVFYTAYRVLAPSGV

AQLHFRWEPAQVAFLRGWVRRLGLVVLALVAVVAVAEHQPAALADDVLGI

GVVLTCYALMTWLLGRLLLSSPTHHNASLFRKTLGVAFTALPVALFLAVC

FGYYYTALKLSDRLIDTLYLMMIWLMVEATFVRGLGVAARRLAYQRALAK

RQAARENGDSDIPVEEPKLDIEQVNQQSLRLIRLALLAGFVGALYLVWAE

LITVFAYLDNIILYEYTSGTGANMSMVPISLSDFLGAGVIIVITFVLAGN

LPGLLEVLVLSRMNLAQGSAYATTTLLSYTIAGIGFVTTLSTLGVSWDKL

QWLVAALSVGLGFGMQEIFANFISGIMILFERPVRIGDTITIGALSGTVS

KIRIRATTITDFDRKDIIVPNKTFITGQLINWSLTDTVTRVTLKLGVDYG

SDLDLVRSLLLQAARENPRVLKEPEPIVYFLNFGESTLDHELRMHVRDLG

DRNPVLDEINRFINREFKKQHINISFRQMEIYLKNTQGLEYKLVPAEPGE

KHGAPAGQTTLQPVNTKVAPATKDAPEPPELRLD
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. This protein also has significant homology (e=0), as detected by BLAST search, to putative potassium efflux system from *Yersinia pestis* (Parkhill et al., *Nature* 413:523-527 (2001); GenBank Accession No. NP_406604, each of which is hereby incorporated by reference in its entirety).

A fiftieth nucleic acid molecule encodes ORF51 and has a nucleotide sequence according to SEQ ID NO: 99 as follows:

```
atgtcaacgttgaatcatacgtctgctgtaaattgccgcgtcagttttga tggtgaccgttgctatgtagacacccccatccagatcatgccgggtgagc gatgggctgtaaatatcgtacctaacgatttagtcacaatccactacgag gccgccagcaatcacgactaccctttgctgctggccagcataaaaaatct gtttaccgatgagcgttgtgtcgtgctaaagcccggccttacacagcaag cttttgaacatgtattttttcagaggttaacagccttaaacctaacgcgact catgttcgcttgttgcatcgagcgcagcgtattttctagaaaacatgat ccgtagcgtacagataacctcgcaaggtatcagcgtcactttcgcaaccg ccgaattcaaaaattataactaccagctaaaggtggataaatatacttt gcaaggcttgacaaggggtaccctctctattcggagctggttgaaaacac ctggataacgaaattatccgtagcccataatattctgtattccatctctg tgagcctggaccactcaagcacaccttatacactttttcaggaaccctc gcggaagacaatatagtccagccgatacgggcgcttttcaccgacaacac catgactcaactcacctccttggccgatcagaaaaccgtggatgccttgt atacgacggtcaatggcaacccggttatcagcatcaaaaaacgcgcagat tatcggtcttatctgaacatcgcacagaagttactgcttccaagaaccta caccaaagtagtacggacagtgagcagcctgtctgtgcattttacggggg aggcgtacaaacaattcaactacaagatgcttgtcaacaatgcttatgca tccgagatcacccgagggaaggcttattactccagcgtgagcaatggggt gtggaccacttccggtacgcatgacagcgacgacaactgcaaagtcactt gtgattacaagggcgcaacctacgtcctgtacgagagtaatgcggcagat agacgcactgaaacctgggcacaagacccgtacgttactcattgcgaccc gagagacctgtaa
```

The protein encoded by this nucleic acid molecule has an amino acid sequence according to SEQ ID NO: 100 as follows:

```
MSTLNHTSAVNCRVSFDGDRCYVDTPIQIMPGERWAVNIVPNDLVTIHYE

AASNHDYPLLLASIKNLFTDERCVVLKPGLTQQALNMYFSEVNSLKPNAT
```

HVRLLHRAQRIFLENMIRSVQITSQGISVTFATAEFKNYNYQLKVDKYTF

ARLDKGYPLYSELVENTWITKLSVAHNILYSISVSLDHSSTPYTLFSGTL

AEDNIVQPIRALFTDNTMTQLTSLADQKTVDALYTTVNGNPVISIKKRAD

YRSYLNIAQKLLLPRTYTKVVRTVSSLSVHFTGEAYKQFNYKMLVNNAYA

SEITRGKAYYSSVSNGVWTTSGTHDSDDNCKVTCDYKGATYVLYESNAAD

RRTFTWAQDPYVTHCDPRDL

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-first nucleic acid molecule encodes ORF52 and has a nucleotide sequence according to SEQ ID NO: 101 as follows:

atgcgcctgatcgcgcagattctgcccggcctgccggaaaacaccactta cagcgccgcgctgcgtccaacaccctggcgcgggccatgcccaacgcca ttcgcaatgcgctgggcaccctggggctggtggctgcgcgcacccagcca agcatctttccgttgccgtcgcgcaacgtcagcggtggcgaaaaagagga cgacctggagattctgctcaaactcgcggccgccgctgtttcgcgcctgc aaagccaccagttgggcggcctggagcagacccgtaccaatgccgatggc actcaggtgactacatggcaactggaagtgccgatgcgcaacgcccatga catcgtgccgttgcaggtcaaggtgcagcgcgaagacaagcctgatcagg acgccaccgaagaccgcgacgatatcgagatcaaggaaacccgtgaaaaa ctctggaaagtcgatctggctttcgacctggagccgcttggcccatgca ggtgcatgcgcaactgctgcgcggcacgctgtccagccagttatgggccg agcgcccggatagcgcaacactgatcgaacatgaactggggcatttgcgc gagcgcctgattgcctgcgcctgccgtcggggaactggcgtgcagcca tggcgttccgccgcaagggccgcgcaccgccctcgaacaacgctggatcg acgagaacgcctga The protein encoded by this nucleic acid molecule has an amino acid sequence according to SEQ ID NO: 102 as follows:

MRLIAQILPGLPENTTYSAAAASNTLARAMPNAIRNALGTLGLVAARTQP

SIFPLPSRNVSGGEKEDDLEILLKLAAAAVSRLQSHQLGGLEQTRTNADG

TQVTTWQLEVPMRNAHDIVPLQVKVQREDKPDQDATEDRDDIEIKETREK

LWKVDLAFDLEPLGPMQVHAQLLRGTLSSQLWAERPDSATLIEHELGHLR

ERLIACGLAVGELACSHGVPPQGPRTALEQRWIDENA

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-second nucleic acid molecule encodes ORF53 and has a nucleotide sequence according to SEQ ID NO: 103 as follows:

atgagtagcgtcgcagcactgatcaccatatcgactggacagacgcagtt cgttaaagtcgcgcggacgtcattttctgtgctacgaatcccctcgccg gcagatgtcgtgtccgggatcagttgaccactacaataaagacagagcag aaacccataaaaataggggaagagacgtgagcctaaatgatcacttgaa aaaagcattgaattctgattccagcgacgagcttgatgaaatcaccgacc tttatgtgacgttgcctgcagaggtcttcagttgcttgaccatttcactc gaagggaattggaaggaaattgatagcgtctggtctgctcggttagacgc agcagattcaaagaataatacaaaatgtcacgtccatatcgccaaaacca agcatcgatcctcaaaaagcaaacaggtttcttggaacagtgatggtagc cggcatgataaaaaaacattcgatgtaacgctgggacagagcagaaaggc ccaggcgatagctaggaaattttttaggccttggcgagtccataagccttg aaagcaaagattccaagcagatggttgaaagacctctactcagcactgct acatccttttcgaatgatggaaaagaggtgaaggtcgagttctacgtgga agaatccaccgcccaccttcccgcatggttacgatggtag The protein encoded by this nucleic acid molecule has an amino acid sequence according to SEQ ID NO: 104 as follows:

MSSVAALITISTGQTQFVKVARTSFSVLRIPLAGRCRVRDQLTTTIKTEQ

KPIKIGGRDVSLNDHLKKALNSDSSDELDEITDLYVTLPAEVFSCLTISL

EGNWKEIDSVWSARLDAADSKNNTKCHVHIAKTKHRSSKSKQVSWNSDGS

RHDKKTFDVTLGQSRKAQAIARKFLGLGESISLESKDSKQMVERPLLSTA

TSFSNDGKEVKVEFYVEESTAHLPAWLRW

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-third nucleic acid molecule encodes ORF54 and has a nucleotide sequence according to SEQ ID NO: 105 as follows:

atgaagccaatccatactgcccgatacaacgcctggaatcagttggagca ggagaccgcccatgactggctgggggccaaacccttggccagcagcaccc ttggctaccgctacgatgactggaaccagcgatgctgcaccacgaccgat gacaacgtacagacttatgagtattcagacccgatcggcagcgacgtaca taaaggcccaatccagaaaacctggaaacagagtggcgaccggagggcc gcatcagtggccgcagcgaaacctggctgaatctgttcggcaaaccggac cggatccggacgctgaccgctggtaaaacgggtcgcagccgcacgcacag catgagccgcagccggaacctgaccacgactgagcaggaactgagcaggc agacctttctgtacgacgggctgggacgctgcaccgagcagcgcgatgca ctccagcaaagcaccctgttcagctacgacaactggtcacgcatggtctc ctccacgcttgcagacggcagcgtcatcaaccggagttatgcgccgcaaa gcagcagtgagctggcaacgatgctcgaggtcgtgcaccagaacggcacc accagaaccgtggcaggtacacagaaatttgacgggcttgagcgtgtgac gcagaccaaaacaggtgaccgcgtcgaacagttcaactacgacgccggtg

```
agatgcagcccaggtcgcgcacaacagccgggctggacaacatcaacttt
acctacactcgggcgctcactgatcagatttttccagcacggctccgga
tgaaacggccaaattcgattatgacaagaccagtgcccgcctcatcgaag
cgacgaacccgcaaggcacgcgcacttaccgctatgacgtgcacaatcaa
ctgacgggagagacttgggacaatctgctgggtcaggcttgggaaacccg
acaccaatcatcgctgctgggtcggccgatcaagcgcaccgatctcaaaa
aaggcgaggcggcgggcgcagagacccgttacgactacgacacgctcggc
agaatcaggtttatcaaccagagcaacctgcgcaccacaatcgactatga
cgtgctgggccagctctgcaaggtggccaccgaggacctgcaggccggaa
ctggcgtgatcatcgacatggaatacgacgaccagggacaggaaattctc
agaacccagaccgcaagcaaccaagcggcgttgaccttgactcaaacgtg
ggcagtggacgggcttttgaaaacccgcgacctgcaacaggcgggtagcc
ccctgctgcacgaaacgtttagctacgaccccagaggccgcctgacactg
gtgaattacctgggtagcagcttgccgagagacgaactgcaaaggagat
gaccagacaaatattcagcttcgacgagctggacaacattacgctatgcc
agaccaggtttaccgatggcacctctgagcgagcagcttcaaatacggc
agccccggcgacgataagcataaagaccgctgccagcttttgagtattgc
ctacacgccgcccagaaaaacaccggacccgacattcagttacgacgcca
acggtaaccagcttaaagacgagcatggcaacagtctgcattacgatagc
cagagccgcctgctgcaggtcgcagaaaccggcggtgcccctatcagcca
ataccgttatgacggccacaatcaactggtcgccaccagggatggcaatg
aaagcgagattttgcggttctatgagggtcatcaactgagcagcacggtg
caggaagatcaacgcactcagtacctgcatctcggcaacagccgctggg
ccagcagattgtggacgacgccgagcaaaccctgttgctactgactgacg
caaaccagagcgttatgggtgaatttcaacaaggccagctgcgcaaggcg
gtctacagtgcctacggggagcgccacagcgaggaggcgctgctgagcac
tgccgggtttaacggtgaagtacgcgaagccgccaacggctggtatctgt
tgggcaatggctaccgggcctacaaccctctcctgatgcgcttccacagc
ccggattttctcagcccttcgccgaaggcggcgtcaaccctacacta
ctgcctgggcaaccccatcgccctgcgcgacccgacaggacatgatgcca
gcggtcagactggccggttgagacggcccgatgaggggctttgccaatg
caacaaggtggcggagatatcatgggttgggtgggtgtaggaataggcgt
tgttttcaccgtattgggcgttgccgctaccatagccacgttaggaacag
ccacaccggttaccggcccggtaactgtcctgggcatttccatgaccgcc
agcgctgccgcggccgtttcgacagtctcgaccggtgcgttgatcgtcgg
tacggcattgacagcggcttcaactacggccaatacagttgccattgtaa
ataacgatcagacggccggagaagtcggcggctggttgggtattgccgct
gtgcccgttggcttggtaggggtttggcgcggggggctgtggtggcgagggc
agttgcggctgcggctaaagttgcggctgccaacgctggtacgatcggtg
tccgcagcgtcagcagaataggcctcgctgctgctggtgcccgcagaacc
```

```
atttccagcgctgccagcagcgctcggcgccaaatcagcaacatgttagg
cagaatcttaccccgtgctctaaacaggactgctgctactgcacgccgga
ttccaagcgttacaagtggcggatcaggaccagggccatcattatttaca
cagactaccttaacgaatcgattgggatgacgcagaccactattttttc
aacgaatgcgagcggaatcccaccggccacgcaggtaactcgaatctag
```

The protein encoded by this nucleic acid molecule has an amino acid sequence according to SEQ ID NO: 106 as follows:

```
MKPIHTARYNAWNQLEQETAHDWLGAKPLASSTLGYRYDDWNQRCCTTTD
DNVQTYEYSDPIGSDVHKGPIQKTWKQSGDPEGRISGRSETWLNLFGKPD
RIRTLTAGKTGRSRTHSMSRSRNLTTTEQELSRQTFLYDGLGRCTEQRDA
LQQSTLFSYDNWSRMVSSTLADGSVINRSYAPQSSSELATMLEVVHQNGT
TRTVAGTQKFDGLERVTQTKTGDRVEQFNYDAGEMQPRSRTTAGLDNINF
TYTRALTDQIFSSTAPDETAKFDYDKTSARLIEATNPQGTRTYRYDVHNQ
LTGETWDNLLGQAWETRHQSSLLGRPIKRTDLKKGEAAGAETRYDYDTLG
RIRFINQSNLRTTIDYDVLGQLCKVATEDLQAGTGVIIDMEYDDQGQEIL
RTQTASNQAALTLTQTWAVDGLLKTRDLQQAGSPLLHETFSYDPRGRLTL
VNYLGSSLPRDELQREMTRQIFSFDELDNITLCQTRFTDGTSERAAFKYG
SPGDDKHKDRCQLLSIAYTPPRKTPDPTFSYDANGNQLKDEHGNSLHYDS
QSRLLQVAETGGAPISQYRYDGHNQLVATRDGNESEILRFYEGHQLSSTV
QEDQRTQYLHLGEQPLGQQIVDDAEQTLLLLTDANQSVMGEFQQGQLRKA
VYSAYGERHSEEALLSTAGFNGEVREAANGWYLLGNGYRAYNPLLMRFHS
PDFLSPFAEGGVNPYTYCLGNPIALRDPTGHDASGQTGRLRRPDEGALPM
QQGGGDIMGWVGVGIGVVFTVLGVAATIATLGTATPVTGPVTVLGISMTA
SAAAAVSTVSTGALIVGTALTAASTTANTVAIVNNDQTAGEVGGWLGIAA
VPVGLVGFGAGAVVARAVAAAAKVAAANAGTIGVRSVSRIGLAAAGARRT
ISSAASSARRQISNMLGRILPRALNRTAATARRIPSVTSGGSGPGPSLFT
QTTFNESIGMTQTTIFSTNASGIPPATQVTRI
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-fourth nucleic acid molecule encodes ORF55 and has a nucleotide sequence according to SEQ ID NO: 107 as follows:

```
atgcggtgtgtgaggcgatcaagaaggttctttaagctgcaagctgcaag
ctgcaagaaaaagcaggaccgctttagcttagctgacgctccactgagta
ctttccatcgaacgatccgaaaaaccctgcctcgaaagcttgtcagaccc
ttttctgaatcagctatcgaggtagtcatgtccatcgaaccccaacgtca
gaaagaacagccaccggccagcacacgccagcggatcagggcccggatc
gcaatgatccggccatcgagccgcaggtttcggacgtagagccggagact
gaaaaaggtgacggccagacgcaaggccagacccctgccccagccaaag
```

-continued
```
ccagtcacaaagtcagaatcagagccagcagtccaacggcagcgcttacg tgcctgactatgagccgcaggaaaaaaaggaagaccagcgcaatcatcag cccactcaaggcactgatgctgatatcgacaccaatgcgggctga
```

The protein encoded by this nucleic acid molecule has an amino acid sequence according to SEQ ID NO: 108 as follows:

```
MRCVRRSRRFFKLQAASCKKKQDRFSLADAPLSTFHRTIRKTLPRKLVRP

FSESAIEVVMSIEPQRQKEQPPGQHTPADQGPDRNDPAIEPQVSDVEPET

EKGDGQTQGQTPAPSQSQSQSQNQSQQSNGSAYVPDYEPQEKKEDQRNHQ

PTQGTDADIDTNAG
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-fifth nucleic acid molecule encodes ORF56 and has a nucleotide sequence according to SEQ ID NO: 109 as follows:

```
atgcccgtcactggtgcaggctttatcaagcgtttgacgcaattgtccct ctgcgccggcatggcgctggtcccggtggccgtacaggcagccgaaagcg atccttgggaaggcatcaaccgttccattttcagcttcaacgataccctt gacgcttatacgctcaagccgctggcaaagggttatcagtacatcgctcc gcagtttgtcgaagacggtattcataacttcttcagcaatatcggcgatg tcggcaatctggcgaacaacgtcttgcaggccaaacctgaagcggccggt gtagataccgcacgccttatcgtcaacactacgttcggtctgctgggctt cattgacgtcggcacccgcatgggcctgcaacgcagtgatgaagacttcg gccagacactgggctactggggtgtgccaagcggcccgttcgtggtgatt ccgctgctgggcccaagcacggtgcgtgacgccattgccaagtacccgga cacctacacctccccgtaccgctatattgatcacgtacccacccgcaaca cggcgttgggcgtcaatctggtcgacacgcgtgccagcctgctgtccgcc gagcgcctggtcagtggtgatcgctacaccttcatccgcaacgcttactt gcagaaccgcgaattcaaggtcaaggacgggcaggtcgaagacgatttt aa
```

The protein encoded by this nucleic acid molecule has an amino acid sequence according to SEQ ID NO: 110 as follows:

```
MPVTGAGFIKRLTQLSLCAGMALVPVAVQAAESDPWEGINRSIFSFNDTL

DAYTLKPLAKGYQYIAPQFVEDGIHNFFSNIGDVGNLANNVLQAKPEAAG

VDTARLIVNTTFGLLGFIDVGTRMGLQRSDEDFGQTLGYWGVPSGPFVVI

PLLGPSTVRDAIAKYPDTYTSPYRYIDHVPTRNTALGVNLVDTRASLLSA

ERLVSGDRYTFIRNAYLQNREFKVKDGQVEDDF
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-sixth nucleic acid molecule encodes ORF57 and has a nucleotide sequence according to SEQ ID NO: 111 as follows:

```
atgacactttcaaccctgcgccctaccccgcgccagcagtatgaatcgcc cgagtcagccgaggatttcacccagcggctggccgacctgacccgcacgc tggccgaaacagccgagcagtacgacatcagcgcgcagttccctcacgcc aacttccgcttgctgcacagccacggactgctcggcctgaccgtgcctgc cgaactgggcggcggcgctgccgacctgtcgcgggcgcagcaggtcatca gcgcagtggccagaggcgagccttcgacagcgctgattctggtcatgcag tacctgcagcattccaggctgcaggacaaccgcaactggccgagccacct gcgcgaacaggtggccaaagacgccgtgcacgagggcgcgctgatcaacg cgctgcgtgtcgaacccgacctgggcacacctgcgcgtggcggcttgccg ggcaccatcgcccggcgcagcgccgaaggctggcgcatcagcggcagcaa gatctactccaccggcagccatggcctgacctggttcgccgtgtgggcgc gcagcgatgacgaggacccgctggtcggcagttggctggtgcacaaggac acgcccgggatcagcatcgtcgaggactgggaccatctgggcatgcgcgc cacctgcagccacgaggtcaggttcgacaacgtgcgagtgccgctcgaac acgcggtcagcgtcagtccgtggagcgccccgcaatccgagcttgatggt gccggcatgctgtggatgtcggtgctgctgtcgtcggtctacgatggcat cgctcaatctgcccgcgactggctggtgcactggctggaacagcgcacgc cttccaacctgggcgccgcgctgtcgaccctgccgcgctttcaggaaaca gtcgggcagatcgacacactgctgttcgccaaccgcagcctgctggagtc cgccgcccaagggcacacacccgcacagcatgccgcgcagatcaaatacc tggtgaccggcaatgccatccgcgcagtggaactggccattgaggcctcg ggcaatcccgggctttcacgcactaacccgctgcagcgtcattaccgcaa cgtgctatgcggccgggtgcatacgccgcagaacgacgccgtgttgatgg gcgtgggcaaagcggtatttgcggcacgcaagcagagccagtaa
```

The protein encoded by this nucleic acid molecule has an amino acid sequence according to SEQ ID NO: 112 as follows:

```
MTLSTLRPTPRQQYESPESAEDFTQRLADLTRTLAETAEQYDISAQFPHA

NFRLLHSHGLLGLTVPAELGGGAADLSRAQQVISAVARGEPSTALILVMQ

YLQHSRLQDNRNWPSHLREQVAKDAVHEGALINALRVEPDLGTPARGGLP

GTIARRSAEGWRISGSKIYSTGSHGLTWFAVWARSDDEDPLVGSWLVHKD

TPGISIVEDWDHLGMRATCSHEVRFDNVRVPLEHAVSVSPWSAPQSELDG

AGMLWMSVLLSSVYDGIAQSARDWLVHWLEQRTPSNLGAALSTLPRFQET

VGQIDTLLFANRSLLESAAQGHTPAQHAAQIKYLVTGNAIRAVELAIEAS

GNPGLSRTNPLQRHYRNVLCGRVHTPQNDAVLMGVGKAVFAARKQSQ
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-seventh nucleic acid molecule encodes ORF58 and has a nucleotide sequence according to SEQ ID NO: 113 as follows:

atgaatctcacaacacttcctcttgcgctcagcattgcttgcgctgcgg
catcacacctgccttcgcgggcacaagcgtctctgaggcttcacacaaag
tgaatgtgcagcaagttcgtaacgcgacggtaaagatctcctacggcggc
acgacctttctgatcgacccgatgctggccaaaaagggaacctacccagg
gtttgaaaatacctatcgaagcaatctgcgcaatccactggttgatctga
ccgaatcgcccaccgaagtgatcgccggtatcgacgcagttatcgtcact
catacgcaccttgaccattgggacgatgctgcacaaaaagtgctgcctaa
agacatccctctgttcacccagcatgaaaaagacgcgcagctgattcgct
ctcaaggtttcaagaacgtacgcgtattgactgatgaagccgaattcggc
ggcgtcaaaattaccaagaccggtgggcagcatggcaccgacgaaatgta
tgccgtgccagccctcgcgaagcctctgggtgaagcaatgggcgttgtat
ttcaagccccgggctacaagaccctctacctcgctggtgacactgtctgg
cgtaaagaggtcgatcaggctatcgagaactattgtcccgaagtcatcgt
actcaatgccggcaaagcaaaaatgacggggtatgaggggggcgatcatca
tgggggaagaggatgtactgcgcgcttcacaggtcgcgaagaacgcgaaa
atcgtcgctgtacacatgaatgcaatcaaccatatgtccctgacccgtga
gcaattgcgcgcttacgtcaagcagcagggtatcgaaagtcgtgtagaca
taccggaagatggcgcttcactggagttctga The protein encoded by this nucleic acid molecule has an amino acid sequence according to SEQ ID NO: 114 as follows:

MNLTTLPLALSIACAAAITPAFAGTSVSEASHKVNVQQVRNATVKISYGG
TTFLIDPMLAKKGTYPGFENTYRSNLRNPLVDLTESPTEVIAGIDAVIVT
HTHLDHWDDAAQKVLPKDIPLFTQHEKDAQLIRSQGFKNVRVLTDEAEFG
GVKITKTGGQHGTDEMYAVPALAKPLGEAMGVVFQAPGYKTLYLAGDTVW
RKEVDQAIENYCPEVIVLNAGKAKMTGYEGAIIMGEEDVLRASQVAKNAK
IVAVHMNAINHMSLTREQLRAYVKQQGIESRVDIPEDGASLEF

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-eighth nucleic acid molecule encodes ORF59 and has a nucleotide sequence according to SEQ ID NO: 115 as follows:

atgcatctgttgccgtttgcgcgttacccccttatcacctgcagaaacacc
taaacccaaggtgaccatgaaggttggagatttcagggcttacgacaccg
ctccagcacccggagtgaccactgcgtcctgcggacaactggcaatcggc
accaagttagaaatcatcgagaccgccgagaatggcgaacttacttatgc
caagggtaagattctatctggcagcgtgaagcaggggcaaccaaaaaac
gggtcgagggggcggaggtctggttcgcttatttgaaaaacggcgaaccc
tacaaaaactcagtccctaagcgcatctggctcgctgacgatgtgcctga
gcgagcaagacccaattactggcagggtaaggtcaaagcctcagtagtga
ataagttgccgctgtacgatgatcctgccagccctacaaatggccagcct
gcaggcgcccgaaggggactctggagctggtcatgaacagcgtcatcga
gtttaactcttcggaagtcgtcaacctggcgctggatggcaagctgcatc
ggatggccaagtgcacgatgctgagtggcggcctgcggggtcatggtgcg
gttcccccagcttttgggcatgtgttgaaaatgaccctgctaataaagt
attgaaatgggactcggtaacgccgaccagttttgatacggtcgttatga
cgagcaccggagtgaaggcgggcgatccaattggctatcttggacaaacc
gaaaatctcaccggtgaaaatggcggcgtcagcagcaaataccaggttca
cgtcgaattttcacagccgatgctgaggttaaagacttcctcaagaaca
ccgcgggtttgaagattgggaagcaatacctgcaccttgcaagcggggct
gtactcaagcaaaaagcgcccgcgaccggcaccacagcactcaagcaaga
ccatgcggttgacttggctaaagccacaattgtcaaagaaggcaccgatg
actggtatgaggtcagcgtgatcgaggacgatcagcctgtagccggcctg
ataaaaaaagccactgcgctagtcatcacacagcacgattgggaaaaatt
gggctttcagatcgtagaggagaacaacgcagcagccgatggtttcttgg
acccggatgcaatgccacagttcttcaaagacctattcgcgaagatcgac
aagaaccacgatggtgaggtggagcctgctgaactggctgaggctcttaa
gaaaccggaaaccagaacccagtgggccaggcttgttgcccatcacccta
cggagtggaaagataaggcaggctcccccaagtggagcaagttggataaa
ctgctggaaacgtcgccgaagatgttgaaacatgaaaaagaacgcattga
taaatatgtattttgggatgagttgtcagggaaagctaagatgacctcaa
gttttaatatggcattttcatccggtagaattcatttcaacatttagcgca
aaaaagtctgcgcttgcaacgccatagttaaggctactcgctgggtttc
ttccagtaagacgcactatggcccattgcatacgggtgataaagagcttg
ggagtgcacctcagtgggatgacctggtctcagaaggaaaaataacggaa
gaggagaaaaaattattgttgtaatgtctggaaacgaggcaaaaattaa
cggagtacaaagttatgatagcgaaataattactgccggcgcgatgcaga
aaacaattaacttgtccggtggcggtgagctgccactacaagttaagaag
tttaaaaatcagcatcccgaggcgtacatcgaatactttgattctcaagg
ctggaagttggatgagacaggtgattcggcgaaatgtattatcaagggc
cggctcgagctagtggcgcaaagctggaaggaaaggcgctgaaggataat
ttaaaaattggttgcagtgaatcgacatttgggaaggtggttgactgtca
acctgtttcagtgatggcctgcgctatcgcaagtccgttatatatccaga
tacaaataatggatttatagaaaggttacgtagttctttaacgaagaag
cccacaggctataactttactgctgggggattttcaagacctctctcgg
aaaagctgtggttttggatcacgatataaatcgacccgggtatgtgaagg
atgacttgggatctgctcttgacacttttttttgctcaaaatccaacagtc
agccgggatattgatacatggggcgcagcatatagcgttaatgagcgaaa

```
agttttagacctgtatggcgctcgaagaagaatgaccaatgcattgcttc gatacaatcacttgaaggcggagttataa
```

The protein encoded by this nucleic acid molecule has an amino acid sequence according to SEQ ID NO: 116 as follows:

```
MHLLPFARYPLSPAETPKPKVTMKVGDFRAYDTAPAPGVTTASCGQLAIG

TKLEIIETAENGELTYAKGKILSGSVKQGATKKRVEGAEVWFAYLKNGEP

YKNSVPKRIWLADDVPERARPNYWQGKVKASVVNKLPLYDDPASPTNGQP

AGARKGTLELVMNSVIEFNSSEVVNLALDGKLHRMAKCTMLSGGLRGHGA

VPPSFWACVENDPANKVLKWDSVTPTSFDTVVMTSTGVKAGDPIGYLGQT

ENLTGENGGVSSKYQVHVEIFTADAEVKDFLKNTAGLKIGKQYLHLASGA

VLKQKAPATGTTALKQDHAVDLAKATIVKEGTDDWYEVSVIEDDQPVAGL

IKKATALVITQHDWEKLGFQIVEENNAAADGFLDPDAMPQFFKDLFAKID

KNHDGEVEPAELAEALKKPETRTQWARLVAHHPTEWKDKAGSPKWSKLDK

LLETSPKMLKHEKERIDKYVFWDELSGKAKMTSSLIWHFHPVEFISTFSA

KKVCACNAIVKATRWVSSSKTHYGPLHTGDKELGSAPQWDDLVSEGKITE

EEKKIIVVMSGNEAKINGVQSYDSEIITAGAMQKTINLSGGGELPLQVKK

FKNQHPEAYIEYFDSQGWKLDETGDSAKMYYQGPARASGAKLEGKALKDN

LKIGCSESTFGKVVDCQPVSVMACAIASPLYIQIQIMDFIERLRSSLTKK

PTGYNFTAGGFFKTSLGKAVVLDHDINRPGYVKDDLGSALDTFFAQNPTV

SRDIDTWGAAYSVNERKVLDLYGARRRMTNALLRYNHLKAEL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A fifty-ninth nucleic acid molecule encodes ORF60 and has a nucleotide sequence according to SEQ ID NO: 117 as follows:

```
atgcggccgttgcctgcgttcagtattttgcagtttgatccgttgaaacg ttcgggtcctgcgctgacggtcgaacgtgatacaccggtcgatagcaagc ctattaatgacgtgcgttgtcgcttccgtacgtgctacccgaccgaagtt caggcgctggatctgaccgcgctgaattactcggtgaaaggcggtggttc gttgctcagcctgcgcctggagatgagcgctgaaggtcacttgggtgagc ttgaactgagccgcctgcgtctgcactttgcaggcgagcgctatatcagc cagatgctgtacctctgcctgctacgcaatctcgagggtatcgagctgat ccctctggacgctgccggcaagcccatcgacggtgtcaatggcgcgccaa tggcgttcaagatgccgggcgaccgtgtacagccggtagggtttgccgaa gaagaggcgttgatcccgtatccgctgaacacgttccgcggttatcgcta cctgcaggagtacttcgcgtttcaggacaagttcctgttcgtcgacatca acggtctggatctgctcaacgcactgccagaagagacactcaaacaagtg cgcggccttgagttgcgctttgatattcgcaagagcggcattcagcgtct tcgtcccaccctggataacgtaaagctgtattgcacgccgatcgtcaact
```

```
tgttcaagcacgacgccttgccgattcgccttgatggcaagcaggacgag tacctgctgctgcccgccgaatatggcctggaaacctgtggtgtgttttc ggttgaaaccgtgaccggttggaagccgggaggtcttggctatcaggatt atgtgccgttcgaatcctttgagcacgacccccagtttcgacgtgcccaac agccgtccgcattacagcattcgccagcgttcttctttgctccatgaagg cctcgacacttatctgagtttcggcattcgccatacagaagcgcacgaaa ccctgtcgatcgagttgatgtgcaccaatcagaacctgccacgcaaactc aaactgggcgaaatcaacgtggcctgcgaagatacgccggagttttgag tttccgcaatatcacaccggctacctccagtttcgcgccccgctgaacc gtgacttcctgtggaagttgatcagcaatatgtcgctcaattacttgtct ctggctgacgtcaatgcgctgaaggtgattctggaaacctacgatttgcc ccgttactacgaccagcacgcggaaaaagtcagcaagcgcctgttgggcg gtttgaaatcgatcaagcatcaacacgtggacagattgcaccgagggtta ccggtacgcggattgcgcactgagctgaccatcgacccggaagggtatat cggcgaaggcgacatgtttgtattcgcttcggttctcaacgagttttcg cgctttacgccagtctcaattcgtaccacgagctgcgggtaaaaagcaca cagggagaggtgtaccaatggacaccacgtatgggcctccagcccctgct ttaa
```

The protein encoded by this nucleic acid molecule has an amino acid sequence according to SEQ ID NO: 118 as follows:

```
MRPLPAFSILQFDPLKRSGPALTVERDTPVDSKPINDVRCRFRTCYPTEV

QALDLTALNYSVKGGGSLLSLRLEMSAEGHLGELELSRLRLHFAGERYIS

QMLYLCLLRNLEGIELIPLDAAGKPIDGVNGAPMAFKMPGDRVQPVGFAE

EEALIPYPLNTFRGYRYLQEYFAFQDKFLFVDINGLDLLNALPEETLKQV

RGLELRFDIRKSGIQRLRPTLDNVKLYCTPIVNLFKHDALPIRLDGKQDE

YLLLPAEYGLETCGVFSVETVTGWKPGGLGYQDYVPFESFEHDPSFDVPN

SRPHYSIRQRSSLLHEGLDTYLSFGIRHTEAHETLSIELMCTNQNLPRKL

KLGEINVACEDTPEFLSFRNITPATSSFAPPLNRDFLWKLISNMSLNYLS

LADVNALKVILETYDLPRYYDQHAEKVSKRLLGGLKSIKHQHVDRLHRGL

PVRGLRTELTIDPEGYIGEGDMFVFASVLNEFFALYASLNSYHELRVKST

QGEVYQWTPRMGLQPLL
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A sixtieth nucleic acid molecule encodes ORF61 and has a nucleotide sequence according to SEQ ID NO: 119 as follows:

```
atggtcaaggttacctcttccggatttactgccaaccctctctctcatca tgcggacagtgttccccgcgaacagtcccctcagttaccggagcctg tgcatctggttgatttaagcgagtcgtcccgcaagggcggcatgcgaaat
```

-continued cggccgcatgccagtttgaacagtcaggtgctcgaactgcaagcggtgcc
gtcgcaacgtggaaagcatgttcgtgtcagaagtcatgccgatggcgaga
gtgtcattaatgcctggctggcaaagcgccctcggttcaaagcgaaacc
agtcttgataacgatggcaaactggtgcgttacaccccgtgaatcatga
gccgctggcgccgcgcaatgaggcgttttcacctcggtgccggggatgt
tgatggccgttttgacggtccaccccgagatggaacatggcatcagcggg
gacataactgctgatgctgtggctgccggcttgccgaaccgccaatagg
gttgctaaccggaatctggcagtcttcccatgatcgagcctatctggagc
gtggcggtgtggtgcataccgccaatatggaagagcgctgggcgccgttg
acgctgccaggcatcaatcccgagagcccctgcgaatggccggtttgca
ggccgatggtggagtctatctgcataacgcagccaactgtggcgcttga
ccgaaactgccgccgagtccgtgaccaccgaaaaccttcctgaaggtgcg
gcggtacgcattggcgccggtggcgaggtgcatgggctgcatgaaggcgc
gcttcattcgaatggcatttcccgtccaatcgagctttggcggccaaaag
ctggcgcgccggggcgcagcagagtccggcgcgcccgttgatttgctg
ccgttaccgggtggcaccgctgcactgatccttgatgacaagggacgtat
ttatcacgctgatctgaaaggcacaggcgctgttgaagcccaccggctga
aattacctgctgactttgcgcagggtaaaggttgggccgtgaccgccatg
ggattgtcccgagacgacactgttcatctgatgctgcaggatcagaacgg
gcgtcgcatgagcttgcagcgagcaccgggcgaggcgctgtttcgtcctg
cgtacctgctggatcgcccgttgctgctgctctataccgaagggctgcat
gttccgtcggaggccgcggtgcagtcgcacgttcagcttgatggtcatgc
tcaactggggcatatcgatggcgtgctgcattataaagcggctcccgatc
agtcatgggaacggctaaagcagtcgggcggcgaaccgctgacgggtttg
actgctcttattccagcccgctgggatttatcgacaggaaaccggtttt
cgctttagtggggatgcccggcaggtggtcgagttgaaactggaggggc
gtacatcctggttgccgagcgatgccgagcttccgcgtcaccctgcgggc
gggcctttggcggtgataccggatacggtagcgttacgcaccagcccgat
cgcgcagtttgacgagcctgtacaggcgctggcggttcacggtaatcgcc
gggtcgtcgcgctgacggattcggggcgattaatggctgccgatgcggac
accccagcccgccgacttcccacgttgcagcgccccatcgccatcgccgt
agggctcaacgatcagttactggtgctgcatcatccccatagccagcgcc
cccagttgaaacggttgagtgcgaaagatgactgggagccggtgccgata
attctgccgggtattgttcacccttcaagtcttcgcgctactcgcacggg
gcaaatacaagtgcagctgggagaaaactggcatacgttgctgccatcaa
tgacgtcgcacgataatcagcgcttacctgcccgcgtaaaacctgaacca
gaggggatgaggcgccgtcggcgaatttcctggcgggtagcaacgccct
cgccaatcagcagcaagccagtcgtatcagcacaccgcatcatgacgcat
cggtggttacgacgctggcggggacaacagccaacaaccgttgacgatg
gcgtcgagcctacaggcagtggttgatacgacccgcgctcaggtaggcgc
gttggcgagagatgtagtgggcgcagcggcgaacagcacgatgcgggcaa -continued tggcgcataccttgggtgttgtactgccgccaacgcctcaggagaagcgc
ctggccagtttccataatgaggcgaaacaggcttatacatcaggaaaaat
actgtttgagcatctgccgtcactcgcgcaagtgcgcgtcgcttcagccg
tagggccgtcggacggagaaagattcgggctgtcacatcagcaaacgcaa
cgcttgttgacgctgcgagaggggaagctggaagcgctgttacgcgactt
gcgcaagatcggctttcatgaaggggtgatcatgggcgatatgggcgaca
gcgacagtgcgcacggtcttgtttcgacgacatcgacaccaacgttccgg
ctggccgagctatggcgacggcagcattcgcgagtggataaggcgctgtc
ttccgctggattatccagatcggaagatatttttccggacttgaacctaa
gtatcaacgcgttggctggcggcgcggcgctgaatgcggatcgtatgagc
gaacgtgaagctgagttgttgagcgttttgtgcgaggtcagcgaaaaaat
gatgcgcgctggcgtacgcttgccggcagatgatggaagcgttgacagcg
cccacagccaggcgccatacggcttgagaacagcaggattgattgcaggt
ctggtggactatgatgcgctgttgagcagtaccgacgcgcaggcgctgga
aatggcggagcgacttcagcaagatgccaggcttgctgcattgtgcaaac
tcggtctgtcttcgtggggtcaattagcggccttcgatgatgtggtgacg
acgtttcgcgaacagatatcgttaccgggctcggcacgccgcacccagtt
gctcaaaaatcttggcttgccacccgatgccgcgccggacgaaatggcgg
cgcgcatgtccgacttactcctggatctgttcaaccggagcaccttcttt
tcgacgcagtcgcgtggtctggaactgcgcggttcgttgggatcggctga
ctggaaacatctcaatgcgttcagcgtcggcgtgactggcgaggcgcttc
aagtgctcggcgtagagcgcatcggcgatggcaaggacggcgatgccggg
ttggtcgcgttttttgtgcgccacgccaaagcctctgtatctgcgacgtc
agggatcggaatcgatttcaagccaggccccggcactggcggccgtgtta
ttgattcgcgaccgggtcgctcgatgaactcgacgtggggaggctctacc
aacctgggtatttccggcgcgtaccagcatggtcagggcgccgccgtgat
catcgcaccgtcgacgatctccgatttcgtgcggctgttattcgatgtca
accatcccgataccacccaaatcctgcgcaccggtgtgaacggtggttcg
attggtcttgatctgtttgaaaccaatgtgaatgcctctgtgggggcgaa
cgtcagcgtatcgccattcagcctgagccagaaatatgggccacagaaac
cgacggcagatgcggccgtctctggcccagacaatcggcgcagcaccgcg
tcagggtcgttgtcggtaggcgggacggctcaggctggcgcgcactgggg
gcaaatggagttgcacctggatcacgcctgggccgatattatcggtctgg
aatttcagggccgcacggatttcaatcttgaattcaatagcggcctgaat
ctgggaggcgcgctgtcttccgcgctgggcgataaccccaaaagttgat
aaatgcgtccactggaaacggcaatctgcaactcgccggcatccgcgtcg
cgtcaagcgatgtgcagttgccgaccgatgctgtggttgacgacaagcgc
cgtggccccttcctgtcgacggccagctataaacgcaccttcgataccga
agttgccaagcctgttacggccggggagtggagccagatgcgccagcgcc
ttgccaaagcctttcctgacaatatcgcagagttgggcgcgctcgattac

```
cccaccaggcccggtgagcgtatcgcgaccatcaaacaggtgattgaccg
catacaaggtgcgaaggcgcgtagcgtggaagccgtcggtgcaatggacg
gaaaggcattgcaccgtcagcgtttcgatgccgcgagagaaatgtcgaac
gccggcaacagcgtatggcgggcgagttccgaaattgagcgcgcctcgat
cgtggagatgctgcatcagttgcgtcagcaggaacaaagcgccgtccaga
atcacgcccgagccattccggcgcgcgtgtggaattcaacctgttcggt
cgtgaatcgctggaaacggtggtcttcacgccatcggtcatctggggct
tggcagcaagctgaacgatctggcggagctgcgtcgcaaggtgccgggtc
tcgatcaggtcatgctgagtttccagtcgttgcccaaggtcaatcaggtg
cgctacgtttttgagatgcgccctcaggcgaggttcgccatcaatgacgc
gctactggcgcgcgagcagcaggcatcggcacgtgcgctcggtttgcagg
gaccctcgggaagtgaattgaattggcgcggcgttctggacaagatcaaa
accacgcctgacctttatcggctggcggcgatcgccgtacataacaccga
tgaaaaccccgtgacctcaagaatagggctgccgctgctgaatgtgtcgg
ccacaggcgcgcacatcgcatcagttgttcgaggcggaaatccagttcga
tacggtctgtatgacggtctgcaaggggttgagttgctggaggccggaaa
cagggcattgcagtcgccgttacgggcattacagcaatccggtattcagg
ccctggggcagagaacccaggccggggaggttgcgtatggcccccttcg
ccgcgcaaagagtcgccgttgcgcaccgcagtggatgctgctgcgctgac
aacgagtgacatcgcgcgacaacttgaggttaaagtccagcgcatgaata
ccgcgcatgagcgtgaggcgaatgctatcagttcgttccagcaggcttat
gggatcgcgtccgcgcatctagacaggctgcttttgcgcattcctgaatt
gccattacctgaaattgatgaccgcgacgtcgatggaggacgtgtgcgcg
gtacatttgcgtcgctccagcgacatcatcaggcgctggatgacgctata
agtgccatgcatcaggccagcgaaaaggtgtacacgatacctggcaagca
ggccactcaagagcaagacccggcgctggctcaactgctctctgttgaaa
aacgtcggcgttcgctcgggcatgccttggaaacactggcgggcagaggg
gtggaagcgggcacggccacagggcttgaacttaacagggtctcatcgca
agtgaatgatctggtcgctcgccgggacgcgctgctaaggcagcgtgaaa
gcggtgttcaggagggcggtctggatagcgaagagctggaaatggaactt
caattgaccacctcagtgctgcagcggttgcgcgccgatttgctcggcga
gcggcaggcgatggaggctaccgccaaacgcctggatcaggcgagccgcg
ctgccctcgaaggtgagcgcagcttcagcgacgccgtgcgtgacagggcg
tgggggcgaactcgataacgtgtag
```

The protein encoded by this nucleic acid molecule has an amino acid sequence according to SEQ ID NO: 120 as follows:

```
MVKVTSSGFTANPLSHHADSVSPANSPPQLPEPVHLVDLSESSRKGGMRN
RPHASLNSQVLELQAVPSQRGKHVRVRSHADGESVINAWLAKRPSVQSET
SLDNDGKLVRYTPVNHEPLAPRNEAFFTSVPGMLMAVLTVHPEMEHGISG
DITADAVAARLAEPPIGLLTGIWQSSHDRAYLERGGVVHTANMEERWAPL
TLPGINPREPLRMAGLQADGGVYLHNGSQLWRLTETAAESVTTENLPEGA
AVRIGAGGEVHGLHEGALHSNGISRPIELWRPKAGAPGREQSPARPVDLL
PLPGGTAALILDDKGRIYHADLKGTGAVEAHRLKLPADFAQGKGWAVTAM
GLSRDDTVHLMLQDQNGRRMSLQRAPGEALFRPAYLLDRPLLLLYTEGLH
VPSEAAVQSHVQLDGHAQLGHIDGVLHYKAAPDQSWERLKQSGGEPLTGL
TALYSSPLGFIDRKPVFALVGDARQVVELKLEGRTSWLPSDAELPRHPAG
GPLAVIPDTVALRTSPIAQFDEPVQALAVHGNRRVVALTDSGRLMAADAD
TPARRLPTLQRPIAIAVGLNDQLLVLHHPHSQRPQLKRLSAKDDWEPVPI
ILPGIVHPSSLRATRTGQIQVQLGENWHTLLPSMTSHDNQRLPARVKPEP
EGDEAPSANFLAGSNALANQQQASRISTPHHDASVVTTLAGTTANNPLTM
ASSLQAVVDTTRAQVGALARDVVGAAANSTMRAMAHTLGVVLPPTPQEKR
LASFHNEAKQAYTSGKILFEHLPSLAQVRVASAVGPSDGERFGLSHQQTQ
RLLTLREGKLEALLRDLRKIGFHEGVIMGDMGDSDSAHGLVSTTSTPTFR
LAELWRRQHSRVDKALSSAGLSRSEDIFPDLNLSINALAGGAALNADRMS
EREAELLSVLCEVSEKMMRAGVRLPADDGSVDSAHSQAPYGLRTAGLIAG
LVDYDALLSSTDAQALEMAERLQQDARLAALCKLGLSSWGQLAAFDDVVT
TFREQISLPGSARRTQLLKNLGLPPDAAPDEMAARMSDLLLDLFNRSTFF
STQSRGLELRGSLGSADWKHLNAFSVGVTGEALQVLGVERIGDGKDGDAG
LVAFFVRHAKASVSATSGIGIDFKPGPGTGGRVIDSRPGRSMNSTWGGST
NLGISGAYQHGQGAAVIIAPSTISDFVRLLFDVNHPDTTQILRTGVNGGS
IGLDLFETNVNASVGANVSVSPFSLSQKYGPQKPTADAAVSGPDNRRSTA
SGSLSVGGTAQAGAHWGQMELHLDHAWADIIGLEFQGRTDFNLEFNSGLN
LGGALSSALGDNPQKLINASTGNGNLQLAGIRVASSDVQLPTDAVVDDKR
RGPFLSTASYKRTFDTEVAKPVTAGEWSQMRQRLAKAFPDNIAELGALDY
PTRPGERIATIKQVIDRIQGAKARSVEAVGAMDGKALHRQRFDAAREMSN
AGNSVWRASSEIERASIVEMLHQLRQQEQSAVQNHARAIPGARVEFNLFG
RESLETVVFHAIGHLGLGSKLNDLAELRRKVPGLDQVMLSFQSLPKVNQV
RYVFEMRPQARFAINDALLAREQQASARALGLQGPSGSELNWRGVLDKIK
TTPDLYRLAAIAVHNTDENPVTSRIGLPLLNVSATGATSHQLFEAEIQFR
YGLYDGLQGVELLEAGNRALQSPLRALQQSGIQALGQRTQAGEVAYGPPS
PRKESPLRTAVDAAALTTSDIARQLEVKVQRMNTAHEREANAISSFQQAY
GIASAHLDRLLLRIPELPLPEIDDRDVDGGRVRGTFASLQRHHQALDDAI
SAMHQASEKVYTIPGKQATQEQDPALAQLLSVEKRRRSLGHALETLAGRG
VEAGTATGLELNRVSSQVNDLVARRDALLRQRESGVQEGGLDSEELEMEL
QLTTSVLQRLRADLLGERQAMEATAKRLDQASRAALEGERSFSDAVRDRA
WGELDNV
```

This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A sixty-first nucleic acid molecule encodes a HrpA-related protein and has a nucleotide sequence according to SEQ ID NO: 121 as follows:

```
atgaacattacgccgctcacgtcagccgcgggcaagggctcgtccgcaca aggcacagacaaaatttccattcccaactccacgcgcatgatcaatgccg cttcaatcaagtggttgaataaggtgcgtagcgccatcagtgaccacatc cgcaccagcatcgagaaagggaaactgttcgagctcgcctccttgggcag caacatgttcggtgtcccggctctttcagcgcgcccctcgacgctccaac ctgtgttggcgtttgaggctgaccccaatcacgacctgaaccttgtcagg gtctatatgcaggacagcgccggcaagctcactccctgggacccgacgcc caacgcggtcacgacgacgtcgaatccatcagagcctgatgcgcagagcg atacggcttcgtcatcattacctcggcggcctcccgcaggctcggtgctg agtttgctgggcattgcgctggatcacgcgcaacgccacagtcctcgcgc ggacaggtctgccaagggacgacctggccgagaggagaggaacggggcaa ggttcaatgccaagcaaacaaagccgacagaggctgaagcctacggtgat catcagacacccaatcctgatttgcacaggcaaaagagacagctcaacg cgttgctgaaagcatcaacagcatgcgagagcagcaaaatggaatgcaac gcgccgaagggcttctcagagccaaagaagcgttgcaagctcgggaagcc gcgcgcaagcagcttctggacgtgctcgaggccatccaggctggccgtga agactccaccgacaagaagatcagcgccactgaaaagaacgccacgggca tcaactaccagtga
```

The Hrp-A related protein has an amino acid sequence according to SEQ ID NO: 122 as follows:

```
MNITPLTSAAGKGSSAQGTDKISIPNSTRMINAASIKWLNKVRSAISDHI

RTSIEKGKLFELASLGSNMFGVPALSARPSTLQPVLAFEADPNHDLNLVR

VYMQDSAGKLTPWDPTPNAVTTTSNPSEPDAQSDTASSSLPRRPPAGSVL

SLLGIALDHAQRHSPRADRSAKGRPGREERNGARFNAKQTKPTEAEAYGD

HQTPNPDLHRQKETAQRVAESINSMREQQNGMQRAEGLLRAKEALQAREA

ARKQLLDVLEAIQAGREDSTDKKISATEKNATGINYQ
```

The HrpA-related protein, has significant homology, as detected by BLAST analysis (5e-07), to the C-terminal 43 amino acids of HrpA (GenBank Accession AF232004; Alfano et al., *Proc. Natl. Acad. Sci. USA* 97:4856-4861 (2000), each of which is hereby incorporated by reference in its entirety). Expression of the hrpA-related gene is activated by HrpL, as indicated by miniTn5gus mutagenesis. This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted. HrpA is the Hrp pilus subunit protein (Roine et al., *Proc. Natl. Acad. Sci. USA* 94:3459-3464 (1997), which is hereby incorporated by reference in its entirety).

A sixty-second nucleic acid encodes ORF01152 and has a nucleotide sequence according to SEQ ID NO: 123 as follows:

```
atgaccttaagaatcaatactcgttctgctaccccggttgtacctctgga aacaggctctacatcgcagccgacaccaccgccggtcacggcaagagcga ctgagcctcccccgtcgccaatcctgcggcgcctaaatcagcgccaggt gttcagcaagcacacgggctgaagacgcgcatcgctggcaagctttccga acgtcagaccaatttcagtctcgggattcccggcactggtcgtactctca accggcccttgcgcagcgggattccggaggaaggtgagcaggtatcgaac gaggagagtcatgatccgttgctcaaggaagcgcatgaactgcagcgtat ggtggagtcggcgctgacccatctgaaggcggcaccgacgtctctctggg agcgtcccgcccttcaacggtaaggcgtattaccaccaagattttccg tggctaaagcctgccccgctgcgcgaagtcgcaagcaatggcagcaacgc caagaccaagatcaagatcaactcacagcaaagccctgaaaccatcgcag cggcggtgaaagagctgagcacccggctcgatcaccagagcaaggtgctc gccacagccacccacgcactggtcgctgcgcgtgagcatcttgaatcgct cgaacaggccaccccgccctcgtcgaccgaaccactggaccatgccaggg ctcgcgttcaacaagccgactccaccacccgcctggccagtcagcaactt cgtgagctgattcagggtacagacgtgttgcaactgggcgcgctgagtga agggcaggatcaggttgaacagaaagccgagttttct
```

The protein encoded by the nucleic acid molecule has an amino acid sequence according to SEQ ID NO: 124 as follows:

```
MTLRINTRSATPVVPLETGSTSQPTPPPVTARATEPPPVANPAAPKSAPG

VQQAHGLKTRIAGKLSERQTNFSLGIPGTGRTLNRPLRSGIPEEGEQVSN

EESHDPLLKEAHELQRMVESALTHLKAAPTSLWERPAPSTVRRITTKIFP

WLKPAPLREVASNGSNAKTKIKINSQQSPETIAAAVKELSTRLDHQSKVL

ATATHALVAAREHLESLEQATPPSSTEPLDHARARVQQADSTTRLASQQL

RELIQGTDVLQLGALSEGQDQVEQKAEFS
```

Expression of ORF01152 is activated by HrpL, as indicated by miniTn5gus mutagenesis (Fouts et al., *Proc. Natl. Acad. Sci. USA* 99(4):2275-2280 (2001), which is hereby incorporated by reference in its entirety). This protein possesses N-terminal Hop features (see U.S. patent application Ser. No. 10/341,180 to Collmer et al., filed Jan. 13, 2003, which is hereby incorporated by reference in its entirety), suggesting that it is likely to be secreted.

A sixty-third nucleic acid molecule encodes HopPtoF (formerly AvrPphF$_{Pto}$ ORF2) and has a nucleotide sequence according to SEQ ID NO: 125 as follows:

```
ataggtaatatttgcggcacctcgggctcacgtcatgtgtatagcccatc ccatacacaacgaataacttcagctccctctacatccactcatgttggtg gagatacactgacatccattcatcagctttcgcatagtcagagagagcag tttctgaacatgcatgatccaatgagagtaatgggacttgaccatgatac cgagcttttcagaacgacggatagtcgctatataaaaaacgataaactcg cgggcaatccacaatccatggcgagtatccttatgcatgaagaactgcgc cccaatcgttttgccagccatacaggtgcccaaccacacgaagcaaggc gtacgttccgaaaagaataaaagccaccgatctaggagttccatcactga acgtaatgactggctcgctagcgcgagacggaattagagcttatgatcac
```

```
atgagtgataatcaggtctctgtcaaaatgcgactgggagattttctcga aaggggtggcaaggtctatgccgacgcttcgtctgtagctgacgatgggg aaacatcacaagctctgattgtcacattgcccaaaggacagaaagtgccg gtcgaaagggtctga
```

HopPtoF has an amino acid sequence according to SEQ ID NO: 126 as follows:

```
MGNICGTSGSRHVYSPSHTQRITSAPSTSTHVGGDTLTSIHQLSHSQREQ

FLNMHDPMRVMGLDHDTELFRTTDSRYIKNDKLAGNPQSMASILMHEELR

PNRFASHTGAQPHEARAYVPKRIKATDLGVPSLNVMTGSLARDGIRAYDH

MSDNQVSVKMRLGDFLERGGKVYADASSVADDGETSQALIVTLPKGQKVP

VERV
```

Contrary to the previously identified sequence of hopPtoF (see U.S. patent application Ser. No. 10/114,828 to Collmer et al., filed Apr. 2, 2002, which is hereby incorporated by reference in its entirety), hopPtoF possesses a rare ATA start codon, which is believed to be involved in regulating protein synthesis in DC3000. HopPtoF has been shown to be expressed by DC3000 and it has been shown to be translocated in planta, where it is localized to the plant plasma membrane and has a role in virulence. HopPtoF has also been shown to cause a hypersensitive response in *Arabidopsis* Col-0. The homologous *Pseudomonas syringae* pv. *phaseolicola* AvrPphF effector protein has been shown to play a role in both development of the hypersensitive response and virulence in several plants (Tsiamis et al., "Cultivar-specific avirulence and virulence functions assigned to avrPphF in *Pseudomonas syringae* pv. *phaseolicola*, the cause of bean halo-blight disease," *EMBO J.* 19(13):3204-3214 (2000), which is hereby incorporated by reference in its entirety). Finally, HopPtoF has since been shown to be cytotoxic to eukaryotic cells, specifically cultured mammalian CHO and HEK293 cell lines.

A sixty-fourth nucleic acid molecule encodes IaaL$_{Pto}$ and has a nucleic acid sequence according to SEQ ID NO: 208 as follows:

```
atgactgcctacgatgtagaaaaggaatggagcagaatttccaatactgc cgctaaaactcaccagaacaacgattttgaaggtttcacctaccaggact tcagaacccacgtaccgatcatggacaaggaaggcttcgcggcacaaacc gaacgctgccttgagcgcaacgagcgcaactgcctgatcggctttaccag tggcaccagcggcaacctcaaacgctgttattactactacgactgtgaag tcgatgaagacagttcccgctccaacgtcttccgcagcaatggtttcatt caacccggtgatcgctgcgccaacctgttcaccatcaacctgttttctgc cctgaacaacatcaccaccatgatggccggtaactgcggtgcgcatgtgg tgtccgtaggcgatatcaccctgctgaccaagagtcacttcgaggcgctc aactcgatcaagctcaacgtactgctcggcgtacccgtcgaccatcctgca gttcatcgatgccatgcagcagcacggtgtgcacatcgatatcgaaaagg tcgtcttcaatggcgagggcctgaaaacctttcagaagaaaatcatcagg gaagcctttggcgaacaggtctccatcgtcggcgtatatggcagttccga
```

```
gggcggcattctgggtttcaccaacagcccttgccacaccgaatacgagt ttctttccgacaaatacttcatcgagaaagaaggcgacagcatcctcatc acctcgttgacccgcgagaacttcacaccgctgctccggtatcgcctggg agacaccgcaacgctttcgctgaaaggcgacaagctctatttgactgaca tccagcgggaggacatgagcttcaacttcatgggcaacctcattggtctg ggcatcattcaacaagcgatcaaacagacactgggccgcacgctggaaat ccaggttcacctgtcagtgactgatgcgcgcaaagaactggtgaccgttt tcgttcaggcctcggaagtcaacgaagatgaacgcgccagaatcgaaaca gccatcgccgatattccggacatcaacgaggcctatcagaaagaccaggg cagcgtgctggttgtgcgcaaggatgccagagactacgccgtctcggagc gaggcaaaatgctctacatcattgaccgcaggaat
```

IaaL$_{Pto}$ has an amino acid sequence according to SEQ ID NO: 209 as follows:

```
MTAYDVEKEWSRISNTAAKTHQNNDFEGFTYQDFRTHVPIMDKEGFAAQT

ERCLERNERNCLIGFTSGTSGNLKRCYYYYDCEVDEDSSRSNVFRSNGFI

QPGDRCANLFTINLFSALNNITTMMAGNCGAHVVSVGDITLLTKSHFEAL

NSIKLNVLLGVPSTILQFIDAMQQHGVHIDIEKVVFNGEGLKTFQKKIIR

EAFGEQVSIVGVYGSSEGGILGFTNSPCHTEYEFLSDKYFIEKEGDSILI

TSLTRENFTPLLRYRLGDTATLSLKGDKLYLTDIQREDMSFNFMGNLIGL

GIIQQAIKQTLGRTLEIQVHLSVTDARKELVTVFVQASEVNEDERARIET

AIADIPDINEAYQKDQGSVLVVRKDARDYAVSERGKMLYIIDRRN
```

IaaL$_{Pto}$ has significant homology, as detected by BLAST analysis (0), to IAA-lysine synthetase (GenBank accession M35373; Roberto et al., *Proc. Natl. Acad. Sci. USA* 87: 5797-5801 (1990), each of which is hereby incorporated by reference in its entirety).

Fragments of the above-identified proteins or polypeptides as well as fragments of full length proteins can also be used according to the present invention.

Suitable fragments can be produced by several means. Subclones of the gene encoding a known protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for activity, e.g., as a product required for pathogen virulence.

In another approach, based on knowledge of the primary structure of the protein, fragments of the protein-coding gene may be synthesized using the PCR technique together with specific sets of primers chosen to represent particular portions of the protein. Erlich, H. A., et al., "Recent Advances in the Polymerase Chain Reaction," *Science* 252:1643-51 (1991), which is hereby incorporated by reference. These can then be cloned into an appropriate vector for expression of a truncated protein or polypeptide from bacterial cells as described above.

As an alternative, fragments of a protein can be produced by digestion of a full-length protein with proteolytic enzymes like chymotrypsin or *Staphylococcus* proteinase A, or trypsin. Different proteolytic enzymes are likely to cleave different proteins at different sites based on the amino acid sequence of the particular protein. Some of the fragments that result from proteolysis may be active virulence proteins or polypeptides.

Chemical synthesis can also be used to make suitable fragments. Such a synthesis is carried out using known amino acid sequences for the polypeptide being produced. Alternatively, subjecting a full length protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The proteins or polypeptides used in accordance with the present invention are preferably produced in purified form (preferably at least about 80%, more preferably 90%, pure) by conventional techniques. Typically, the protein or polypeptide of the present invention is secreted into the growth medium of recombinant host cells (discussed infra). Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the protein or polypeptide of interest is subjected to gel filtration in an appropriately sized dextran or polyacrylamide column to separate the proteins. If necessary, the protein fraction may be further purified by HPLC.

Other DNA molecules encoding other effector proteins or polypeptides can also be identified by determining whether such DNA molecules hybridize under stringent conditions to a nucleic acid molecule as identified above. An example of suitable stringency conditions is when hybridization is carried out for about 8 to about 20 hours at a temperature of about 37° C. using a hybridization medium that includes 0.9× sodium citrate ("SSC") buffer, followed by washing for about 5 minutes to about 1 hour with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. up to and including about 65° C. (inclusive of all temperature in such range) for about 8 up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 µg/ml *E. coli* DNA, followed by washing for about 5 minutes to about 1 hour, at about 42° C. up to and including about 65° C. (inclusive of all temperatures in such range) in a 0.2×SSC buffer. Such hybridizing nucleic acid molecules preferably hybridize over substantially over their entire length. Moreover, such hybridizing nucleic acid molecules does not include previously reported nucleic acid molecules that encode effector proteins.

The delivery of effector proteins or polypeptides can be achieved in several ways: (1) as a stable transgene; (2) transiently expressed via *Agrobacterium* or viral vectors; (3) delivered by the type III secretion systems of disarmed pathogens or recombinant nonpathogenic bacteria which express a functional, heterologous type III secretion system; or (4) delivered via topical application followed by TAT protein transduction domain-mediated spontaneous uptake into cells. Each of these is discussed infra.

The DNA molecule encoding the protein or polypeptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," Gene Expression Technology vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

Because it is desirable for recombinant host cells to secrete the encoded protein or polypeptide, it is preferable that the host cell also possess a functional type III secretion system. The type III secretion system can be heterologous to host cell (Ham et al., "A Cloned *Erwinia chrysanthemi* Hrp (Type III Protein Secretion) System Functions in *Escherichia coli* to Deliver *Pseudomonas syringae* Avr Signals to Plant Cells and Secrete Avr Proteins in Culture," *Microbiol.* 95:10206-10211 (1998), which is hereby incorporated by reference in its entirety) or the host cell can naturally possess a type III secretion system. Host cells which naturally contain a type III secretion system include many pathogenic Gram-negative bacterium, such as numerous *Erwinia* species, *Pseudomonas* species, *Xanthomonas* species, etc. Other type III secretion systems are known and still others are continually being identified. Pathogenic bacteria that can be utilized to deliver effector proteins or polypeptides are preferably disarmed according to known techniques, i.e., as described above. Alternatively, isolation of the effector protein or polypeptide from the host cell or growth medium can be carried out as described above.

Another aspect of the present invention relates to a transgenic plant which express a protein or polypeptide of the present invention and methods of making the same.

In order to express the DNA molecule in isolated plant cells or tissue or whole plants, a plant expressible promoter is needed. Any plant-expressible promoter can be utilized regardless of its origin, i.e., viral, bacterial, plant, etc. Without limitation, two suitable promoters include the nopaline synthase promoter (Fraley et al., *Proc. Natl. Acad. Sci. USA* 80:4803-4807 (1983), which is hereby incorporated by reference in its entirety) and the cauliflower mosaic virus 35S promoter (O'Dell et al., "Identification of DNA Sequences Required for Activity of the Cauliflower Mosaic Virus 35S Promoter," *Nature*, 313(6005):810-812 (1985), which is hereby incorporated by reference in its entirety). Both of these promoters yield constitutive expression of coding sequences under their regulatory control.

While constitutive expression is generally suitable for expression of the DNA molecule, it should be apparent to those of skill in the art that temporally or tissue regulated expression may also be desirable, in which case any regulated promoter can be selected to achieve the desired expression. Typically, the temporally or tissue regulated promoters will be used in connection with the DNA molecule that are expressed at only certain stages of development or only in certain tissues.

In some plants, it may also be desirable to use promoters which are responsive to pathogen infiltration or stress. For example, it may be desirable to limit expression of the protein or polypeptide in response to infection by a particular pathogen of the plant. One example of a pathogen-inducible promoter is the gst1 promoter from potato, which is described in U.S. Pat. Nos. 5,750,874 and 5,723,760 to Strittmayer et al., each of which is hereby incorporated by reference in its entirety.

Expression of the DNA molecule in isolated plant cells or tissue or whole plants also requires appropriate transcription termination and polyadenylation of mRNA. Any 3' regulatory region suitable for use in plant cells or tissue can be operably linked to the first and second DNA molecules. A number of 3' regulatory regions are known to be operable in plants. Exemplary 3' regulatory regions include, without limitation, the nopaline synthase 3' regulatory region (Fraley et al., *Proc. Nat'l. Acad. Sci. USA,* 80:4803-4807 (1983), which is hereby incorporated by reference in its entirety) and the cauliflower mosaic virus 3' regulatory region (Odell, et al., *Nature,* 313 (6005):810-812 (1985), which is hereby incorporated by reference in its entirety).

The promoter and a 3' regulatory region can readily be ligated to the DNA molecule using well known molecular cloning techniques described in Sambrook et al., *Molecular Cloning: A Laboratory Manual,* Second Edition, Cold Spring Harbor Press, NY (1989), which is hereby incorporated by reference in its entirety.

One approach to transforming plant cells with a DNA molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., each of which is hereby incorporated by reference in its entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the DNA molecule into plant cells is fusion of protoplasts with other entities, either minicells, cells, lysosomes, or other fusible lipid-surfaced bodies that contain the DNA molecule. Fraley et al., *Proc. Natl. Acad. Sci. USA,* 79:1859-63 (1982), which is hereby incorporated by reference in its entirety.

The DNA molecule may also be introduced into the plant cells by electroporation. Fromm, et al., *Proc. Natl. Acad. Sci. USA* 82:5824 (1985), which is hereby incorporated by reference in its entirety. In this technique, plant protoplasts are electroporated in the presence of plasmids containing the DNA molecule. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *Agrobacterium rhizogenes* previously transformed with the DNA molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA molecule of the present invention can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. Schell, *Science,* 237: 1176-83 (1987), which is hereby incorporated by reference in its entirety.

Plant tissue suitable for transformation include leaf tissue, root tissue, meristems, zygotic and somatic embryos, and anthers.

After transformation, the transformed plant cells can be selected and regenerated.

Preferably, transformed cells are first identified using, e.g., a selection marker simultaneously introduced into the host cells along with the DNA molecule of the present invention. Suitable selection markers include, without limitation, markers coding for antibiotic resistance, such as kanamycin resistance (Fraley et al., *Proc. Natl. Acad. Sci. USA,* 80:4803-4807 (1983), which is hereby incorporated by reference in its entirety). A number of antibiotic-resistance markers are known in the art and other are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow.

Once a recombinant plant cell or tissue has been obtained, it is possible to regenerate a full-grown plant therefrom. Thus, another aspect of the present invention relates to a transgenic plant that includes a DNA molecule of the present invention, wherein the promoter induces transcription of the first DNA molecule in response to infection of the plant by an oomycete. Preferably, the DNA molecule is stably inserted into the genome of the transgenic plant of the present invention.

Plant regeneration from cultured protoplasts is described in Evans, et al., *Handbook of Plant Cell Cultures, Vol.* 1: (Mac-Millan Publishing Co., New York, 1983); and Vasil I. R. (ed.), *Cell Culture and Somatic Cell Genetics of Plants,* Acad. Press, Orlando, Vol. I, 1984, and Vol. III (1986), each of which is hereby incorporated by reference in their entirety.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA molecule is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Diseases caused by the vast majority of bacterial pathogens result in limited lesions. That is, even when everything is working in the pathogen's favor (e.g., no triggering of the hypersensitive response because of R-gene detection of one of the effectors), the parasitic process still triggers defenses after a couple of days, which then stops the infection from spreading. Thus, the very same effectors that enable parasitism to proceed must also eventually trigger defenses. Therefore, premature expression of these effectors is believed to "turn on" plant defenses earlier (i.e., prior to infection) and make the plant resistant to either the specific bacteria from which the effector protein was obtained or many pathogens. An advantage of this approach is that it involves natural products and plants seem highly sensitive to pathogen effector proteins.

According to one embodiment, a transgenic plant is provided that contains a heterologous DNA molecule of the present invention. When the heterologous DNA molecule is expressed in the transgenic plant, plant defenses are activated, imparting disease resistance to the transgenic plant. The transgenic plant can also contain an R-gene whose product is activated by the protein or polypeptide product of the heterologous DNA molecule. The R gene can be naturally occurring in the plant or heterologously inserted therein. By disease resistance, it is believed that the effector proteins of the present invention can impart to plants resistance against bacterial, viral, and/or fungal diseases.

In addition to imparting disease resistance, it is believed that stimulation of plant defenses in transgenic plants of the present invention will also result in a simultaneous enhancement in growth and resistance to insects.

Alternative to transgenic expression is topical application of the effector proteins to plants. The embodiments of the present invention where the effector polypeptide or protein is applied to the plant can be carried out in a number of ways, including: 1) application of an isolated protein (or composition containing the same) or 2) application of bacteria which do not cause disease and are transformed with a gene encoding the effector protein of the present invention. In the latter embodiment, the effector protein can be applied to plants by applying bacteria containing the DNA molecule encoding the effector protein. Such bacteria are preferably capable of secreting or exporting the protein so that the protein can contact plant cells. In these embodiments, the protein is produced by the bacteria in planta.

Such topical application can be carried out using an effector-TAT protein, which will afford transduction domain-mediated spontaneous uptake of the effector protein into cells. Basically, this is carried out by fusing an 11-amino acid peptide (YGRKKRRQRRR, SEQ ID No: 127) by standard rDNA techniques to the N-terminus of the effector protein, and the resulting tagged protein is taken up into animal cells by a poorly understood process. This peptide is the protein transduction domain (PTD) of the human immunodeficiency virus (HIV) TAT protein (Schwarze et al., "Protein transduction: unrestricted delivery into all cells?" *Trends Cell Biol.* 10:290-295 (2000), which is hereby incorporated by reference in its entirety). Other PTDs are known and can be used for this purpose (Prochiantz, "Messenger proteins: homeoproteins, TAT and others," *Curr. Opin. Cell Biol.* 12:400-406 (2000), which is hereby incorporated by reference in its entirety). See PCT Application Publication No. WO 01/19393 to Collmer et al., which is hereby incorporated by reference in its entirety.

When the effector protein is topically applied to plants, it can be applied as a composition, which includes a carrier in the form, e.g., of water, aqueous solutions, slurries, or dry powders. In this embodiment, the composition contains greater than about 5 nM of the protein of the present invention.

Although not required, this composition may contain additional additives including fertilizer, insecticide, fungicide, nematicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and, in some instances, abrading agents. These materials can be used to facilitate the process of the present invention.

According to one embodiment, a transgenic plant including a heterologous DNA molecule of the present invention expresses one or more effector proteins, wherein the transgenic plant is capable of supporting growth of compatible nonpathogenic bacteria. The compatible nonpathogenic bacteria can be naturally occurring or it can be recombinant. Preferably, the nonpathogenic bacteria is recombinant and expresses one or more useful products. Thus, the transgenic plant becomes a green factory for producing desirable products. Desirable products include, without limitation, products that can enhance the nutritional quality of the plant or products that are desirable in isolated form. If desired in isolated form, the product can be isolated from plant tissues. To prevent competition between the non-pathogenic bacteria which express the desired product and those that do not, it is possible to tailor the needs of recombinant, non-pathogenic bacteria so that only they are capable if living in plant tissues expressing a particular effector protein or polypeptide of the present invention.

The effector proteins or polypeptides of the present invention are believed to alter the plant physiology by shifting metabolic pathways to benefit the parasite and by activating or suppressing cell death pathways. Thus, they may also provide useful tools for efficiently altering the nutrient content of plants and delaying or triggering senescence. There are agricultural applications for all of these possible effects.

Thus, a further aspect of the present invention relates more generally to a method of modifying a metabolic pathway in a cell by introducing into the cell an effector protein or polypeptide of the present invention which interacts with a native cellular protein involved in a metabolic pathway of the cell. As a result of introducing the protein or polypeptide into the cell, the protein or polypeptide modifies the metabolic pathway through its interaction with the native cellular protein. By way of example, it is believed that HopPtoD2 is a tyrosine phosphatase that interacts with MAPK.

Yet another aspect of the present invention relates to a method of causing eukaryotic cell death which is carried out by introducing into a eukaryotic cell a protein which is cytotoxic and causes cell death. The eukaryotic cell which is treated can be either in vitro or in vivo. When treating eukaryotic cells in vivo, a number of different protein- or DNA-delivery systems can be employed to introduce the effector protein into the target eukaryotic cell.

Another aspect of the present invention relates to a method of inhibiting programmed cell death which is carried out by introducing into a eukaryotic cell susceptible to programmed cell death, a protein that is a hypersensitive response suppressor, where the introduction thereof is performed under conditions effective to inhibit programmed cell death of the eukaryotic cell. By inhibiting programmed cell death, it is intended that such inhibition includes both delaying the occurrence of programmed cell death as well as preventing programmed cell death. The eukaryotic cell which is treated can be either in vitro or in vivo. When treating eukaryotic cells in vivo, a number of different protein- or DNA-delivery systems can be employed to introduce the effector protein into the target eukaryotic cell. By way of example, hypersensitive response suppressor proteins include, without limitation, AvrPphE$_{Pto}$, AvrPpiB1$_{Pto}$, AvrPtoB, HopPtoD1, HopPtoE, HopPtoF (previously designated AvrPphF$_{Pto}$ ORF2), and HopPtoK.

Because programmed cell death (including apoptosis) is involved in the pathogenesis of a variety of diseases, the HR suppressor proteins of the present invention can be used in the regulation thereof and, thus, as therapeutic agents in the intervention of a wide array of disease processes or maladies (see Rudin & Thompson, *Ann. Rev. Med.* 48:267-81 (1997), which is hereby incorporated by reference in its entirety).

The protein- or DNA-delivery systems can be provided in the form of pharmaceutical compositions which include the delivery system in a pharmaceutically acceptable carrier, which may include suitable excipients or stabilizers. The dosage can be in solid or liquid form, such as powders, solutions, suspensions, or emulsions. Typically, the composition will contain from about 0.01 to 99 percent, preferably from about 20 to 75 percent of active compound(s), together with the carrier, excipient, stabilizer, etc.

The compositions of the present invention are preferably administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Alternatively, the effector proteins can also be delivered via solution or suspension packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art.

One approach for delivering an effector protein into cells involves the use of liposomes. Basically, this involves providing a liposome which includes that effector protein to be delivered, and then contacting the target cell with the liposome under conditions effective for delivery of the effector protein into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), each of which is hereby incorporated by reference in their entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in their entirety.

An alternative approach for delivery of effector proteins involves the conjugation of the desired effector protein to a polymer that is stabilized to avoid enzymatic degradation of the conjugated effector protein. Conjugated proteins or polypeptides of this type are described in U.S. Pat. No. 5,681,811 to Ekwuribe, which is hereby incorporated by reference in its entirety.

Yet another approach for delivery of proteins or polypeptides involves preparation of chimeric proteins according to U.S. Pat. No. 5,817,789 to Heartlein et al., which is hereby incorporated by reference in its entirety. The chimeric protein can include a ligand domain and, e.g., an effector protein of the present invention. The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein, which allows the effector protein to de-stabilize the cell checkpoint control mechanism, affording its cytotoxic effects.

When it is desirable to achieve heterologous expression of an effector protein of the present invention in a target cell, DNA molecules encoding the desired effector protein can be delivered into the cell. Basically, this includes providing a nucleic acid molecule encoding the effector protein and then introducing the nucleic acid molecule into the cell under conditions effective to express the effector protein in the cell. Preferably, this is achieved by inserting the nucleic acid molecule into an expression vector before it is introduced into the cell.

When transforming mammalian cells for heterologous expression of an effector protein, an adenovirus vector can be employed. Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in their entirety. Adeno-associated viral gene delivery vehicles can be constructed and used to deliver a gene to cells. The use of adeno-associated viral gene delivery vehicles in vitro is described in Chatterjee et al., *Science* 258:1485-1488 (1992); Walsh et al., *Proc. Nat'l. Acad. Sci.* 89:7257-7261 (1992); Walsh et al., *J. Clin Invest.* 94:1440-1448 (1994); Flotte et al., *J. Biol. Chem.* 268:3781-3790 (1993); Ponnazhagan et al., *J. Exp. Med.* 179:733-738 (1994); Miller et al., *Proc. Nat'l. Acad. Sci.* 91:10183-10187 (1994); Einerhand et al., *Gene Ther.* 2:336-343 (1995); Luo et al., *Exp. Hematol.* 23:1261-1267 (1995); and Zhou et al., *Gene Ther.* 3:223-229 (1996), each of which is hereby incorporated by reference in their entirety. In vivo use of these vehicles is described in Flotte et al., *Proc. Nat'l. Acad. Sci.* 90:10613-10617 (1993); and Kaplitt et al., *Nature Genet.* 8:148-153 (1994), each of which is hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; and U.S. Pat. No. 5,885,808 to Spooner et al.; and U.S. Pat. No. 5,871,727 to Curiel, each of which is hereby incorporated by reference in their entirety).

Retroviral vectors which have been modified to form infective transformation systems can also be used to deliver nucleic acid encoding a desired effector protein into a target cell. One such type of retroviral vector is disclosed in U.S. Pat. No. 5,849,586 to Kriegler et al., which is hereby incorporated by reference in its entirety.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired effector protein, thereby causing cytotoxic effects.

Particularly preferred is use of the effector proteins of the present invention to treat a cancerous condition (i.e., the eukaryotic cell which is affected is a cancer cell). This can be carried out by introducing or administering to a patient, a cytotoxic *Pseudomonas* protein under conditions effective to inhibit cancer cell division, thereby treating the cancer condition.

By introducing, it is intended that the effector protein is administered to the patient, preferably in the form of a composition which will target delivery to the cancer cells. Alternatively, when using DNA-based therapies, it is intended that the introducing be carried out by administering a targeted DNA delivery system to the patient such that the cancer cells are targeted and the effector protein is expressed therein. A number of targeted delivery systems are known in the art and can be employed herewith.

EXAMPLES

The following Examples are intended to be illustrative and in no way are intended to limit the scope of the present invention.

Materials & Methods for Example 1-2

Strains and Media:

*Escherichia coli* strain DH5α was used for cloning experiments, and *P. s. tomato* DC3000 or derivatives and *P. s. phaseolicola* 3121 were used for secretion or translocation assays, respectively. Routine culture conditions for bacteria are similar to those described (van Dijk et al., *J. Bacteriol.* 181:4790-4797 (1999), which is hereby incorporated by reference in its entirety). Antibiotics were used at the following concentrations: 100 µg/ml ampicillin, 20 µg/ml chloramphenicol, 10 µg/ml gentamicin, 100 µg/ml rifampicin, 10 µg/ml kanamycin, and 20 µg/ml tetracycline.

Secretion Assays:

All of the secretion assays used *P. s. tomato* DC3000 strains carrying a pML123 derivative containing a PCR-cloned ORF (encoding a candidate Hrp-secreted protein) fused to nucleotide sequences that encoded either the hemagglutinin or FLAG epitopes along with their native ribosome binding sites (Labes et al., *Gene* 89:37-46 (1990), which is hereby incorporated by reference in its entirety). Details about the primers and the constructs are provided below.

HopPtoE: The hopPtoE gene was cloned using forward primer (agtaggatccatagaaaaataccataggggtgca, SEQ ID No: 128) containing a BamHI site and reverse primer (agtatctagatcacttgtcatcgtcgtccttgtagtcgtcaatcacatgcgcttg, SEQ ID No: 129) containing an XbaI site and FLAG epitope codons. The hopPtoC gene was cloned into plasmid vector pLN162.

HopPtoG: The hopPtoG gene was cloned using forward primer (atgcggatcccgtatgaccttgtaaaat, SEQ ID No: 130) containing a BamHI site and reverse primer (atgctctagatcaagcgtaatctggaacatcgtatgggtagccgttgtaaaactgctt, SEQ ID No: 131) containing an XbaI site and HA epitope codons. The hopPtoG gene was cloned into plasmid vector pLN131.

HopPtoH: The hopPtoH gene was cloned using forward primer (agtcggatccgataatcctggatgatccattg, SEQ ID No: 132) containing a BamHI site and reverse primer (agtcctcgagtcacttgtcatcgtcgtccttgtagtcttgatgtgccctgtactt, SEQ ID No: 133) containing an XhoI site and FLAG epitope codons. The hopPtoH gene was cloned into plasmid vector pLN150.

HopPtoI: The hopPtoI gene was cloned using forward primer (agtaaagcttacgggcaggtattgcaag, SEQ ID No: 134) containing a BamHI site and reverse primer (agtatctagatcacttgtcatcgtcgtccttgtagtcttttttgggcagccagcg, SEQ ID No: 135) containing an XbaI site and FLAG epitope codons. The hopPtoC gene was cloned into plasmid vector pLN165.

HopPtoL: The hopPtoL gene was cloned using forward primer (agtaggatcctgcctccaactattggct, SEQ ID No: 136) containing a BamHI site and reverse primer (agtatctagatcacttgtcatcgtcgtccttgtagtctctcgctttgaacgcctg, SEQ ID No: 137) containing an XbaI site and FLAG epitope codons. The hopPtoL gene was cloned into plasmid vector pLN224.

HopPtoS1: The hopPtoS1 gene was cloned using forward primer (ataggatcccgagaacggcgcggacgtg, SEQ ID No: 138) containing a BamHI site and reverse primer (atatctagatcatttatcatcatcatctttataatcctcgtcagagctctctgc, SEQ ID No: 139) containing an XbaI site and FLAG epitope codons. The hopPtoC gene was cloned into plasmid vector pLN142.

HopPtoS2: The hopPtoS2 gene was cloned using forward primer (gatggatccacgcacataacaacggtg, SEQ ID No: 140) containing a BamHI site and reverse primer (atatctagatcatttatcatcatcatctttataatcaatctgacttaatac, SEQ ID No: 141) containing an XbaI site and FLAG epitope codons. The hopPtoC gene was cloned into plasmid vector pLN223.

Constructs carrying different epitope-tagged ORFs were electroporated into DC3000 and a DC3000 hrcC mutant and grown in Hrp-inducing conditions (Yuan & He, *J. Bacteriol.* 178:6399-6402 (1996), which is hereby incorporated by reference in its entirety). Additionally, all of the DC3000 strains also carried pCPP2318, a construct that contains blaM lacking signal peptide sequences (Charkowski et al., *J. Bacteriol.* 179:3866-3874 (1997), which is hereby incorporated by reference in its entirety). DC3000 cultures were separated into cell-bound and supernatant fractions as described (van Dijk et al., *J. Bacteriol.* 181:4790-4797 (1999), which is hereby incorporated by reference in its entirety). Proteins were separated with SDS/PAGE by standard procedures (Sambrook et al., *Molecular Cloning: A Laboratory Manual*, Cold Spring Harbor Lab Press, Plainview, N.Y. (1989), which is hereby incorporated by reference in its entirety), transferred to polyvinylidene difluoride membranes, and immunoblotted by using anti-FLAG (Sigma), anti-hemagglutinin (Roche Molecular Biochemicals), or anti-β-lactamase (5 Prime→3 Prime) as primary antibodies. Primary antibodies were recognized by goat anti-rabbit IgG-alkaline phosphatase conjugate (Sigma), which were visualized by chemiluminescence by using a Western-Light chemiluminescence detection system (Tropix, Bedford, Mass.) and X-Omat x-ray film.

Plant Materials and Translocation Assays:

*Arabidopsis thaliana* accession Columbia (Col-0) and rps2-201 (Kunkel et al., *Plant Cell* 5:865-875 (1993), which is hereby incorporated by reference in its entirety) mutant plants were grown in a growth chamber with 12 h of light at 24° C. (22° C. at night) and 70% relative humidity. Details about the primers and constructs described below.

AvrRpt2: The avrRpt2 gene was cloned using forward primer (attggtacctctagaggatccaaccttcaatctgaa, SEQ ID NO: 142) containing KpnI, XbaI, and BamHI sites and reverse primer (atgtcgacttagcggtagagcattgcg, SEQ ID No: 143) containing an SalI site.

The avrRpt2 gene was cloned into plasmid vector pNavrRpt2.

HopPtoG-AvrRpt2: The chimeric gene was cloned using forward primer (gcgaattcgttagttgattttgtctagcg, SEQ ID NO: 144) containing an EcoRI site, and reverse primer (gaggatccgccgttgtaaaactgcttaga, SEQ ID NO: 145) containing a BamHI site. The chimeric gene was cloned into plasmid vector phopPtoGNavrRpt2.

The partial avrRpt2 gene with the N-terminal 40 codons deleted was amplified by using standard PCR procedures and cloned into pMOD (Epicentre Technologies, Madison, Wis.). After confirmation by sequence analysis, it was cloned into the KpnI and SalI sites of the broad-host-plasmid pLK, resulting in pΔavrRpt2. DNA fragments spanning 200 bp upstream of the Hrp boxes and the complete ORF for hopPtoG was cloned into pΔavrRpt2 to produce phopPtoG-ΔavrRpt2. The construct was introduced in *P. s. phaseolicola* 3121 by electroporation. Bacterial strains in 10 mM $MgCl_2$ at a cell density of $10^8$ colony-forming units/ml were infiltrated into *A. thaliana* Col-0 and Col-0 rps2-201 plants with a needleless syringe.

Identification of Putative Effector Protein ORFs:

Several approaches were employed for the identification of putative effector proteins, including the use of a Hidden Markov Model to analyze regions upstream of ORFs for hrp-related promoters (Fouts et al., *Proc. Natl. Acad. Sci. USA* 99(4):2275-2280 (2001), which is hereby incorporated by reference in its entirety), a miniTn5gus transposon-based assay which identifies HrpL-activated insertions, via insertions downstream of Hrp boxes (Fouts et al., *Proc. Natl. Acad. Sci. USA* 99(4):2275-2280 (2001), which is hereby incorporated by reference in its entirety), and computer search for candidate Hrp-secreted proteins based on an algorithm that identifies compliance or non-compliance with export signal rules of known effector proteins (N-terminal 50 amino acids) (Petnicki-Ocwieja et al., *Proc. Natl. Acad. Sci. USA* 99:7652-7657 (2002); U.S. patent application Ser. No. 10/341,180 to Collmer et al., filed Jan. 13, 2003, each of which is hereby incorporated by reference in its entirety).

Materials & Methods for Example 3-8

Bacterial Strains, Plasmids, and Media:

*Escherichia coli* strains DH5α and DB3.1 (Invitrogen) were used for general cloning and Gateway technology manipulations, respectively. *P. s.* pv. *tomato* DC3000 and *P. fluorescens* strains were grown in King's B (KB) broth at 30° C. (King et al., *J. Lab. Med.* 22:301-307 (1954), which is hereby incorporated by reference in its entirety). *E. coli* and *Agrobacterium tumefaciens* C58C1 were grown in LB broth at 37° C. or 30° C., respectively. Unless otherwise noted, constructs used were made by PCR and Table 1 below includes a list of nucleotide primer sequences that were used. The pHIR11 derivative, pLN18, which lacks shcA and hopPsyA was generated as described previously (van Dijk et al., *Mol. Microbiol.* 44:1469-1481 (2002), which is hereby incorporated by reference in its entirety). Briefly, 2 kb regions upstream and downstream of shcA and hopPsyA were PCR cloned into pBluescript-II KS on either side of an nptII antibiotic marker. When transformed into the *E. coli* strain C2110 (Kahn and Hanawalt, *J. Mol. Biol.* 128:501-525 (1979), which is hereby incorporated by reference in its entirety) containing pHIR11, this construct recombined into pHIR11 because ColE1 plasmids, such as pBluescript-II KS, cannot replicate in this polA mutant at 42° C. When this strain was grown at 30° C., the ColE1 replicon replicated, forcing it to recombine out of pHIR11. pHIR11 derivatives that lacked shcA and hopPsyA were identified with PCR. Antibiotics were used at the following concentrations (μg/ml): rifampicin, 100; ampicillin, 100; gentamicin, 10; kanamycin, 50; tetracycline, 20; nalidixic acid, 20; and spectinomycin 50.

TABLE 1

Additional information on plasmid constructions

| Gene Name | Primer Nucleotide Sequences (5'→3') and Other Relevant Features | SEQ ID NO: | Parent Plasmid | Plasmid Construct |
|---|---|---|---|---|
| shcA and hopPsyA | P21: gtaaaacgacggccagt<br>P23: atgagaattcgcatctccatgcatctt (Eco RI)<br>P227: cggactcgagctcagggcgcgaaactga (Xho I)<br>P228: gtatggtaccccgacctggcaaccgcag (Kpn I) | 146<br>147<br>148<br>149 | pHIR11 | pLN18 |
| avrPto | P792: agtcctcgagactaaagagggtatacgaatgggaaatata (Xho I)<br>P793: agtcgatatctcattgccagttacggtacgggc (Eco RV) | 150<br>151 | pBBR1 MCS2 | pLN526 |
| hopPtoT | P582: gatggatccaagtaaccggtctgcaca (Bam HI)<br>P583: atatctagatcatttatcatcatcatctttatatgacttttgagccgcctg (Xba I) | 152<br>153 | pML123 | pLN256 |
| mouse α-Bax | P0942: ggcctcgagatggacgggtccggggagcagctt (Xho I)<br>P0943: ggcactagttcagcccatcttcttccagatggtg (Spe I) | 154<br>155 | pTA7002 | pLN555 |
| avrPphE$_{Pto}$ | P683: cacctatttaattcgttgagaaacaatgaaaata<br>P684: gacatctcgtctcgccaagcc | 156<br>157 | Gateway entry | pCPP5057 |
| avrPpiB1$_{Pto}$ | P685: caccaagcaacgtctggaggcaacaatgca<br>P686: gtcgcctaggaaattatttagttcccatga | 158<br>159 | Gateway entry | pCPP5052 |
| avrPtoB | P693: caccaagatcggagaggatcagaatatggcg<br>P694: ggggactattctaaaagcatacttggc | 160<br>161 | Gateway entry | pLN323 |
| hopPsyA | P787: caccttagcgtaaggagctaacaatgaaccc<br>P788: gttcgcgccctgagcgc | 162<br>163 | Gateway entry | pLN458 |
| hopPtoE | P695: cacccataggggtgcaataacaatgaataga<br>P696: gtcaatcacatgcgcttggcc | 164<br>165 | Gateway entry | pLN324 |
| hopPtoF | P900: aaaaagcaggcttcgaaggagatagaaccatgtatagcccatcc<br>P901: agaaagctgggtaacagaccctttcgac | 166<br>167 | Gateway entry | pCPP5070 |
| hopPtoG | P0904: cacccacataggatatgtaaacaatgcaaataaagaac<br>P0905: gccgttgtaaaactgcttagaggc | 168<br>169 | Gateway entry | pLN520 |
| hopPtoK | P940: caccacaaagaggttttcaaacaatgaatc<br>P941: gcagtagagcgtgtcgcgac | 170<br>171 | Gateway entry | pCPPS 100 |
| avrPphE$_{Pto}$ | Gateway recombination | | pML1123<br>pPZP212 | pCPP5068<br>pLN535 |
| avrPpiB1$_{Pto}$ | Gateway recombination | | pML1123<br>pPZP212 | pCPP5063<br>pLN503 |
| avrPtoB | Gateway recombination | | pML1123<br>pPZP212 | pLN347<br>pLN502 |
| hopPsyA | Gateway recombination | | pPZP212 | pLN474 |
| hopPtoE | Gateway recombination | | pPZP212 | pLN524 |
| hopPtoF | Gateway recombination | | pML1123<br>pPZP212 | pCPP5070<br>pLN525 |
| hopPtoG | Gateway recombination | | pPZP212 | pLN530 |
| hopPtoK | Gateway recombination | | pML123 | pCPP5100 |
| avrPPhE$_{Pto}$ | P166: atacataacgctggccta<br>P167: cggatccatgacaatcgt | 172<br>173 | pKnockout- | pLN15 |
| avrPpiB1$_{Pto}$ | P168: gcaaatcctttaagctct<br>P169: tgtttcgctaagccactg | 174<br>175 | pKnockout- | pLN16 |
| avrPtoB | P304: tcgcgccaaaccagggag<br>P305: tcccacattctgcaacgc | 176<br>177 | pKnockout- | pLN42 |
| hopPsyA$_{Pto}$ | P188: aaccccattcagtcacgc<br>P189: tttgccatgcgtgattgc | 178<br>179 | pKnockout- | pLN23 |

TABLE 1-continued

Additional information on plasmid constructions

| Gene Name | Primer Nucleotide Sequences (5'→3') and Other Relevant Features | SEQ ID NO: | Parent Plasmid | Plasmid Construct |
|---|---|---|---|---|
| hopPtoD1 | P160: cctctacgatctattcaa<br>P161: ggcaatgctcgcggcctg | 180<br>181 | pKnockout- | pLN4 |
| hopPtoE | P913: tccggtagctcgtcagcg<br>P914: gtggatgaccacatagttatg | 182<br>183 | pKnockout- | pLNS43 |
| hopPtoF | P179: agcccatcccatacacaa<br>P180: cactttctgtcctttggg | 184<br>185 | pKnockout- | pLN7 |
| hopPtoG | P256: tattcagcttcaagaatg<br>P257: acccgcatagacctgtct | 186<br>187 | pKnockout- | pLN29 |
| hopPtoH | P194: atcactccgtctcgatatc<br>P195: tgccctgtacttcatgcg | 188<br>189 | pKnockout- | pLN27 |
| hopPtoJ | P173: ctatgtatttcaaaacac<br>P174: atcaccctctgtaattccc | 190<br>191 | pKnockout- | pLN8 |
| hopPtoK | P171: cgcatttcaaccagctca<br>P172: cagcaccggaagcccttc | 192<br>193 | pKnockout- | pLN9 |
| hopPtoS1 | P190: ggtaatatttgtggtacttc<br>P191: cagatgtaacgtgacatc | 194<br>195 | pKnockout- | pLN41 |
| hopPtoT | P192: acagtcagcaatcactcg<br>P193: tacactccatacactgctg | 196<br>197 | pKnockout- | pLN25 |
| avrPphE$_{Pto}$ | P854: ttgaattcatgaaaatacataacgctgg (Eco RI)<br>P855: ttctcgagtcagacatctcgtctcgc (Xho I) | 198<br>199 | pGilda | pLN508 |
| avrPpiB1$_{Pto}$ | P860: ttggatccgtatgcacgcaaatcctttaagctc (Bam HI)<br>P861: ttctcgagtcagtcgcctaggaaattatttagttcc (Xho I) | 200<br>201 | pGilda | pLN507 |
| hopPtoE | P858: ttgaattcatgaatagagtttccggtagctc (Eco RI)<br>P859: ttctcgagtcagtcaatcacatgcgcttgg (Xho I) | 202<br>203 | pGilda | pLN504 |
| hopPtoF | P856: ttgaattcatgggtaatatttgcggcacctc (Eco RI)<br>P857: ttctcgagtcagacccttttcgaccgg (Xho I) | 204<br>205 | pGilda | pLN505 |
| hopPtoG | P862: ttgaattcatgcaaataaagaacagtcatctc (Eco RI)<br>P863: ttctcgagtcagccgttgtaaaactgcttagag (Xho I) | 206<br>207 | pGilda | pLN506 |

Hypersensitive Response Assays:

The broad-host-range vector pML123 was used to express effector genes in Pseudomonas strains (Labes et al., Gene 89:37-46 (1990), which is hereby incorporated by reference in its entirety). The pML123 constructs containing hopPtoC, hopPtoD1, hopPtoD2, and hopPtoJ are described in U.S. patent application Ser. No. 10/114,828 to Collmer et al., filed Apr. 2, 2002, which is hereby incorporated by reference in its entirety; and pML123 constructs containing hopPtoE, hopPtoG, hopPtoH, hopPtoI, hopPtoL, hopPtoS1, and hopPtoS2 are described above. A pML123 construct containing hopPtoB was similarly prepared. pML123 constructs containing hopPtoF, hopPtoK, hopPtoT, avrPtoB, avrPphEPto, avrPpiB1Pto, and avrPto are detailed in Table 1. P. fluorescens(pHIR11) carrying pML123 constructs with effector genes or vector controls with an OD600 of 0.2 (ca. $10^8$ cells/ml) in 5 mM MES (pH 5.6) and infiltrated into Nicotiana tabacum cv. Xanthi, N. benthamiana, or A. thaliana Ws-0 leaves. For bacterial mixing experiments involving two different P. fluorescens strains, P. fluorescens(pLN18) and a pML123 effector construct were infiltrated 2 h before P. fluorescens(pHIR11). The plants were scored for the production of an HR after 24 h. DC3000 strains were tested for their ability to elicit an HR on Nicotiana tabacum cv. xanthi by infiltrating strains with an OD600 of 0.2 along with 10-fold serially diluted samples with a needleless syringe.

Type III Secretion Assays, SDS-PAGE, and Immunoblot Analysis:

DC3000 and DC3000 hrcC mutant (Yuan and He, J. Bacteriol. 178:6399-6402 (1996), which is hereby incorporated by reference in its entirety) carrying the plasmids pLN162, pLN526, pCPP2318, which encode for HopPtoE-FLAG, AvrPto, and β-lactamase, respectively, were grown in type III-inducing minimal medium (Huynh et al., Science 245: 1374-1377 (1989), which is hereby incorporated by reference in its entirety). Cells were adjusted to an initial OD600 of 0.3 and grown for 6 h and separated into cell-bound and supernatant fractions by centrifugation at 4° C. Protein samples from bacterial cultures were prepared similarly as described (van Dijk et al., J. Bacteriol. 181:4790-4797 (1999), which is hereby incorporated by reference in its entirety). Cell and supernatant fractions were analyzed by SDS-PAGE (Sambrook and Russell, Molecular Cloning: A Laboratory Manual, Cold Spring Harbor Laboratory Press, Cold Spring Harbor, N.Y. (2001), which is hereby incorporated by reference in its entirety), transferred to polyvinylidene difluoride membranes, and immunoblotted using anti-AvrPto, -β-lactamase, or -FLAG as primary antibodies. Generation of anti-AvrPto antibodies has been described (van Dijk et al., *J. Bacteriol.* 181:4790-4797 (1999), which is hereby incorporated by reference in its entirety). The anti-β-lactamase antibodies were purchased from Chemicon International and the anti-FLAG antibodies were purchased from Sigma Chemical Co. Primary antibodies were recognized by goat anti-immunoglobulin G-alkaline phosphatase conjugate (Sigma Chemical Co.), and visualized by chemiluminescence using a chemilumincescence detection system and X-Omat X-ray film.

*Agrobacterium*-Mediated Transient Assays:

The avr gene hopPsyA was recombined into a derivative of pPZP212 (Hajdukiewicz et al., *Plant Mol. Biol.* 25:989-994 (1994), which is hereby incorporated by reference in its entirety), pLN462, which was modified to be a Gateway Destination vector, resulting in pLN474. The bax gene was PCR-cloned into pTA7002, creating pLN531, and expression of bax was induced with dexamethasome as previously described (Aoyama and Chua, *Plant Journal* 11:605-612 (1997), which is hereby incorporated by reference in its entirety). The effector genes carried on Gateway entry vectors avrPphEPto, avrPpiB1Pto, avrPtoB, hopPtoE, hopPtoF, and hopPtoG were recombined into pLN462 (which fused each gene to a hemagglutinin epitope) creating constructs pLN535, pLN503, pLN502, pLN524, pLN525, and pLN530, respectively. *Agrobacterium*-mediated transient expression experiments were done by infiltrating *A. tumefaciens* C58C1 (van Larebeke et al., *Nature* 252:169-170 (1974), which is hereby incorporated by reference in its entirety) harboring the disabled Ti plasmid pMP90 (Koncz and Schell, *Mol. Gen. Genet.* 204:383-396 (1986), which is hereby incorporated by reference in its entirety) at an OD600 of 0.4 into *N. benthamiana* and *N. tabacum* cv. *xanthi* plants using a needleless syringe as described (van den Ackerveken et al., *Cell* 87:1307-1316 (1996), which is hereby incorporated by reference in its entirety). For co-expression experiments, *Agrobacterium* strains carrying pPZP212 binary plasmids with different effector genes were infiltrated 4 h prior to infiltration of strains expressing either Bax or HopPsyA. Evidence of production of effectors from transient assays was acquired by harvesting 1 cm diameter leaf disks from infiltrated zones, grinding leaf tissue with a mortar and pestle in the presence of liquid nitrogen, and resuspending plant material in 50 µl of 1×SDS-PAGE tracking buffer. SDS-PAGE and immunoblot analysis were performed as described above using high affinity anti-hemagglutinin antibodies (Roche).

Construction of DC3000 Effector Mutants:

In-frame internal fragments of the effector genes were PCR cloned into XcmI digested pKnockout-. (Windgassen et al., *FEMS Microbiol. Lett.* 193:201-205 (2000), which is hereby incorporated by reference in its entirety) using the primer sets listed in Table 1 above. The resulting constructs were conjugated separately into DC3000 by triparental mating using spectinomycin as selection for the plasmid marker. The following effector mutants were confirmed with primers that flanked each coding region: hopPtoD1, UNL104; hopPtoC, UNL106; hopPtoE, UNL139; hopPtoK, UNL107; hopPtoJ, UNL108; hopPtoF, UNL109; avrPhEPto, UNL113; avrPpiB1Pto, UNL114; hopPtoH, UNL118; hopPtoT, UNL122; hopPtoG, UNL124; hopPtoS1, UNL126; and avrPtoB, UNL127.

Yeast Viability Assays:

To determine whether type III effector-encoding plasmids rescued yeast from Bax-induced lethality, the effector genes avrPphEPto, avrPpiB1Pto, hopPtoG, hopPtoF, and hopPtoE were PCR-cloned into the yeast expression vector pGilda (Clontech, Palo Alto, Calif.) resulting in constructs pLN508, pLN507, pLN506, pLN505, and pLN504, respectively. Table 1 above contains information for the nucleotide primers used to make these constructs. *S. cerevisiae* EGY48 strain containing pJG4-5-Bax (kindly provided by J. C. Reed, Burnham Institute, La Jolla, Calif.) and various pGilda plasmids containing effector genes were grown in SC-U-L/glucose media overnight. The chicken Bcl-xL cloned in pGilda was kindly provided by C. Thompson (University of Chicago, Chicago, Ill.), which acted as a positive control for PCD suppression in these experiments. The yeast cultures were then serial 10-fold diluted into SC medium, and 5 µl of each dilution was dropped onto SC-U-L/Galactose or SC-UL/Glucose plates. Cells were incubated at 30oC for 5 days, and photographed. For oxidative stress experiments, EGY48 strains containing pGilda effector constructs were grown in SC-U media overnight and treated as described in Abramovitch et al. (Abramovitch et al., *EMBO* 22:60-69 (2003), which is hereby incorporated by reference in its entirety).

Example 1

Demonstration of *Pseudomonas syringae* pv. *tomato* DC3000 Protein Secretion

From the hidden Markov model analysis, 28 candidate effector ORFs were identified that were not homologs of known Avr proteins/Hops or of any proteins unlikely to be secreted, and whose low G+C % content and association with mobile genetic elements suggested horizontal acquisition. Several of the predicted proteins shared amino acid identity with proteins likely to be effectors. For example, HopPtoS1 (ORF5) yields several ADP-ribosyltransferases in BLASTP searches (highest BLAST E value 1 e-5), including a type III-secreted ADP-ribosyltransferase from *Pseudomonas aeruginosa* (Yahr et al., *Mol. Microbiol.* 22:991-1003 (1996)), and HopPtoH (ORF2) is homologous to an ORF adjacent to the avrPpiC2 avr gene of *P. s. pisi* (Arnold et al., *Microbiology* 147:1171-1182 (2001), which is hereby incorporated by reference in its entirety) (see Table 2 below).

To test whether these proteins travel the Hrp pathway, the ORFs were cloned into a broad-host-range vector fused to either the hemagglutinin or FLAG epitope. DC3000 wild-type and Hrp mutant cultures carrying these constructs were separated into supernatant and cell fractions and analyzed with SDS/PAGE and immunoblots. Five of the eight proteins tested were secreted via the DC3000 Hrp system (FIG. 1A) and consequently were designated as HopPtoE, HopPtoG, HopPtoH, HopPtoI, and HopPtoS1, respectively. Although three ORFs (ORF6, ORF 7, and ORF8) were not detectably secreted in culture, they may still be effectors because AvrB similarly is not secreted in culture although translocated in planta (van Dijk et al., *J. Bacteriol.* 181:4790-4797 (1999); Gopalan et al., *Plant Cell* 8:1095-1105 (1996), each of which is hereby incorporated by reference in its entirety).

TABLE 2

ORFs with 5' Hrp Promoter Sequences and Encoding Proteins Demonstrated to be Secreted by the *P. syringae* Hrp System

| Initial designation | New designation | Size (bp) | % G + C | Homolog (BLASTP E value) | GenBank Accession[∓] |
|---|---|---|---|---|---|
| ORF1 | HopPtoI | 1,899 | 48.9 | None | NA |
| ORF2[†] | HopPtoH | 657 | 47.2 | ORF3 from *P. s. pisi* avrPpiC2 locus (1e−114) | CAC16702 |
| ORF3 | HopPtoE | 636 | 50.7 | None | NA |
| ORF4 | HopPtoG | 1,482 | 43.7 | Hypothetical protein from *R. solanacearum* (1e−137) | NP_521884 |
| ORF5[‡] | HopPtoS1 | 852 | 46.5 | Chicken ADP-ribosyltransferase (1e−5) | P55807 |

[∓]Each of the listed Genbank Accessions is hereby incorporated by reference in its entirety.
[†]ORF2: homolog described in Arnold et al., Microbiology 147: 1171–1182 (2001), which is hereby incorporated by reference in its entirety.
[‡]ORF5: homolog described in Tsuchiya et al., J. Biol. Chem. 269: 27451–27457 (1994), which is hereby incorporated by reference in its entirety. Determined to possess an ART domain (pfam1129), further confirming its similarity to ADP-ribosyltransferases.

To determine whether the export signal-based search had identified any novel Hrp-secreted proteins, secretion assays were also performed on ORF29 and ORF30, both of which seemed to be particularly promising candidates. The products encoded by ORF29 and ORF30 share similarity with a putative type III effector from *S. enterica*, SrfC, and ADP-ribosyltransferases, respectively. Both ORFs were PCR-cloned into a broad-host-range vector fused to the FLAG epitope, and each construct was introduced into DC3000 wild-type and Hrp mutant strains. The epitope-tagged ORF29 and ORF30 proteins were secreted by DC3000 in a Hrp-dependent manner without leakage of a cytoplasmic marker protein (FIG. 1B), and consequently they were designated as HopPtoL and HopPtoS2, respectively (see Table 3 below).

pathway encoded by SPI2 of *S. enterica* (Worley et al., Mol. Microbiol. 36:749-761 (2000), which is hereby incorporated by reference in its entirety). A further indicator of the efficacy of the search was the finding of three additional ADP-ribosyltransferases, ORF 30, 31, and 32, all with significant amino acid sequence identity to HopPtoS1 (Table 3).

Example 2

AvrRpt2 Translocation Assay Indicates that at Least One of the Additional Hops is Translocated into Plant Cells HopPtoG was selected to test for translocation into plant cells because it shared no similarities with any sequences in

TABLE 3

Selected ORFs Encoding Candidate Effector Proteins That Were Identified by the Genomewide Search Based on Export-Signal Patterns

| Designation | New Designation | Size (bp) | % G + C | Hrp promoter[∓] | Mobile DNA[†] | Homolog (BLASTP E value) | GenBank Accession[‡] |
|---|---|---|---|---|---|---|---|
| ORF29[§] | HopPtoL | 2700 | 61.0 | n | n | SPI-2 regulated SrfC (1e−21) | AAF74575 |
| ORF30[Θ,¶] | HopPtoS2 | 795 | 46.5 | y | n | Clostridium exoenzyme C3 ADP ribosyltransferase (1e−5) | NP_346979 |
| ORF31[⁊,¶] | NA | 897 | 49.8 | y | y | Chicken ADP ribosyltransferase (5e−3) | P55807 |
| ORF32[⁊,¶] | NA | 507 | 54.2 | y | y | Chicken ADP ribosyltransferase (5e−3) | P55807 |
| ORF33[⊖] | NA | 2823 | 55.2 | n | y | SepC insecticidal toxin (1e−128) | NP_065279 |
| ORF34* | NA | 534 | 63.5 | y | n | Lytic enzyme (3e−36) | BAA83137 |

[∓]Indicates that the ORF is within 10 kb of a HrpL-responsive Hrp promoter identified in Fouts
[†]Indicates that a transposon, plasmid, or a phage-related sequence is within 10 kb.
[‡]Each of the listed Genbank Accessions is hereby incorporated by reference in its entirety.
[¶]ORF was determined to possess an ART domain (pfam1129), further confirming its similarity to ADP-ribosyltransferases.
[§]Homolog identified in Worley et al, Mol. Microbiol. 36: 749–761 (2000), which is hereby incorporated by reference in its entirety.
[Θ]Homolog identified in Nolling et al., J. Bacteriol 183: 4823–4838 (2001), which is hereby incorporated by reference in its entirety.
[⁊]Homolog identified in Tsuchiya et al., J. Biol. Chem. 269: 27451–27457 (1994), which is hereby incorporated by reference in its entirety.
[⊖]Homolog identified in Hurst et al., J. Bacteriol. 182: 5127–5138 (2000), which is hereby incorporated by reference in its entirety.
*Homolog identified in Nakayama et al., Mol. Microbiol. 38: 213–231 (2000), which is hereby incorporated by reference in its entirety.

Interestingly, the export signal-based search found a putative effector, SrfC, that is predicted to travel the type III the databases and was shown to be secreted (FIG. 1B). *P. s. phaseolicola* carrying a plasmid expressing hopPtoG-Δavr- Rpt2 elicited an RPS2-dependent hypersensitive response in *A. thaliana* Col-0 (FIG. 1C), indicating that targeting information in HopPtoG directed translocation of the AvrRpt2 fusion protein into plant cells. Thus, HopPtoG appears to be a Hrp-injected effector protein.

Discussion of Examples 1-2

One demonstration of the selectivity of the export signal rules is that only the chicken ADP-ribosyltransferase NRT2$_{CHK}$ shows major violations of the rules even though this protein is more similar to HopPtoS1 and S2 than either of the type III-secreted ADP-ribosyltransferases from *P. aeruginosa*, ExoS and ExoT (see Petnicki-Ocwieja et al., *Proc. Natl. Acad. Sci. USA* 99:7652-7657 (2002); U.S. patent application Ser. No. 10/341,180 to Collmer et al., filed Jan. 13, 2003, each of which is hereby incorporated by reference in its entirety).

HopPtoS1 and HopPtoS2 share sequence similarity with ADP-ribosyltransferases, proteins that have long been implicated in bacterial pathogenesis in animals through the modification of host signal transduction pathways (Finlay & Falkow, *Microbiol. Mol. Biol. Rev.* 61:136-169 (1997), which is hereby incorporated by reference in its entirety), but until now have not been implicated in the bacterial pathogenesis of plants. The DC3000 genomic studies described in Fouts et al. (*Proc. Natl. Acad. Sci. USA* 99:2275-2280 (2002), which is hereby incorporated by reference in its entirety) clearly show that several of the effectors in DC3000 are redundant. By using the pattern-based export prediction, three ADP-ribosyltransferase genes (in addition to hopPtoS1) that have N-termini putative export signals were identified in the genome of DC3000. One of these, ORF32, appears to be truncated. The other two, HopPtoS2 and ORF31, are full-length genes based on sequence alignments. HopPtoS2 is secreted by the Hrp system (FIG. 1B) and ORF31 shares high amino acid sequence identity with the Hrp-secreted HopPtoS1. Interestingly, HopPtoS1 contains putative myristoylation and palmitoylation sites at its N terminus, whereas the other two do not, indicating that HopPtoS1 may be localized to the plasma membrane. Thus, there appear to be at least three Hrp-secreted ADP-ribosyltransferases and these may localize to different regions of the plant cell. The existence of these proteins in *Pseudomonas syringae* is particularly noteworthy given that ADP-ribosyltransferase genes have not been identified in the bacterial plant pathogen genomes that have been published thus far (Simpson et al., *Nature* 406:151-159 (2000); Wood et al., *Science* 294:2317-2323 (2001); Goodner et al., *Science* 294:2323-2328 (2001); Salanoubat et al., *Nature* 415:497-502 (2002), each of which is hereby incorporated by reference in its entirety). Significantly, the genomewide search for export signals yielded a homolog of the *S. enterica* candidate effector SrfC, further adding to the growing list of effectors shared between plant and animal pathogens. It is also noteworthy that one of the ORFs found by the genomewide search (ORF48) is a homolog of a bacterial catalase (BLASTP 1e-126), and another (ORF49) is a glucokinase homolog (BLASTP 3e-42). These putative effectors likely have a role in oxidative stress and regulation of sugar metabolism, respectively.

Example 3

HopPtoE Suppresses the Hypersensitive Response in Tobacco and a DC3000 HopPtoE Mutant Possesses an Enhanced Hypersensitive Response Phenotype In the course of experiments with confirmed DC3000 type III effectors, the effector HopPtoD2 was observed capable of suppressing the HR elicited by *P. s. phaseolicola* on *Nicotiana benthamiana* plants. These results prompted the screening other effector proteins for HR suppressor activity (Collmer et al., *Trends Microbiol.* 10:462-470 (2002)). To do this, the pHIR11 system was used, allowing nonpathogens such as *E. coli* and *P. fluorescens* to elicit the HR and secrete effectors in culture via the TTSS. This tool allowed for testing whether individual effectors were capable of suppressing the HopPsyA-dependent HR as depicted in FIG. 2A. *P. fluorescens*(pHIR11) strains carrying a number of different effector constructs were infiltrated into tobacco (*N. tabacum* cv. *xanthi*). Interestingly, HopPtoD2, the effector that suppressed an HR elicited by *P. phaseolicola*, did not suppress the HopPsyA-dependent HR (FIG. 4A). The first identified effector to suppress or block the HR elicited by *P. fluorescens* (pHIR11) was HopPtoE (FIG. 2B). To detect a potential phenotype consistent with HopPtoE acting as an HR suppressor, a DC3000 mutant defective in HopPtoE was constructed. Both DC3000 and the hopPtoE mutant, UNL139, elicited an HR in tobacco when infiltrated into leaf panels at high inoculum (FIG. 2C).

Based on this result, it is likely that effectors have functionally redundant roles, which may partially mask a phenotype. Therefore, a more sensitive HR assay was performed, where 10-fold serially diluted bacterial strains were infiltrated into tobacco leaf panels to detect any subtle difference in the 5 ability of different strains of bacteria to elicit an HR. When UNL139 was tested in this assay, it was more effective than DC3000 at HR elicitation at lower cell density (FIG. 2C). Interestingly, when hopPtoE was provided in trans to UNL139, the mutant strain was less effective at HR elicitation than DC3000 (FIG. 2C). Thus, the enhanced HR phenotype of the hopPtoE mutant was complemented by hopPtoE. These observations are consistent with HopPtoE acting as an HR suppressor and suggest that HopPtoE contributes incrementally to the ability of the pathogen to suppress the HR.

Example 4

HopPtoE does not Block the DC3000 Type III Secretion System

Figure 3B:
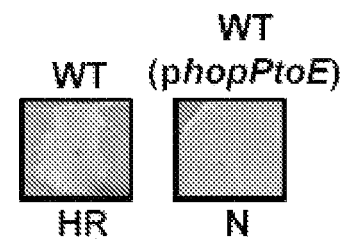

One possible explanation for the observed phenotypes was that HopPtoE was blocking the type III secretion of other type III substrates, including Avr proteins. There is actually a precedent for type III substrates, such as HrpZ and HrpW, to block the type III secretion of proteins from *P. syringae* (Alfano et al., *Mol. Microbiol.* 19:715-728 (1996); Charkowski et al., *J. Bacteriol.* 180:5211-5217 (1998), each of which is hereby incorporated by reference in its entirety) and it was crucial to consider this alternative. To test this, DC3000 and a DC3000 hrcC mutant defective in the TTSS, both carrying plasmids that contained avrPto and hopPtoE, were grown in a medium that induced type III secretion. These cultures were separated into supernatant and cell fractions, and analyzed them by SDS-PAGE and immunoblots with either anti-FLAG or -AvrPto antibodies. Both AvrPto and HopPtoE were secreted in culture via the TTSS (FIG. 3B), indicating that, at least in culture, over-expression of hopPtoE did not block type III secretion. It was next determined whether expression of hopPtoE in DC3000 altered its HR-eliciting ability. Because DC3000 contains a native copy of hopPtoE in its genome, these experiments actually tested whether over-expression of HopPtoE altered the HR phenotype. DC3000 strains, with and without plasmid-encoded hopPtoE, were infiltrated into tobacco at high inoculum levels ($10^8$ cells/ml). After 24 hours, DC3000 elicited an HR on tobacco, whereas DC3000 with a plasmid containing hopPtoE did not (FIG.

3B), indicating that over-expression of HopPtoE suppressed the HR. However, after approximately 3 h, DC3000 with hopPtoE in trans also elicited an HR. Thus, hopPtoE in trans in DC3000 only delayed the ability of this pathogen to elicit an HR. When these experiments were repeated in *N. benthamiana*, the HR delay was greater than 24 h, indicating that the suppression ability of HopPtoE depended to a certain extent on the test plant. To eliminate the possibility that HopPtoE affected the ability of *P. fuorescens*(pHIR11) to deliver the Avr protein HopPsyA into plant cells, a different bacterial strain was used to deliver HopPsyA (as compared to the strain used to deliver HopPtoE) into plant cells. To accomplish this, a pHIR11 derivative, pLN18, was constructed so as to lack hopPsyA and shcA, a gene that encodes a chaperone for HopPsyA (van Dijk et al., *Mol. Microbiol.* 44:1469-148 (2002), which is hereby incorporated by reference in its entirety). *P. fluorescens*(pLN18) does not elicit an HR on tobacco because it lacks HopPsyA (FIG. 3C), while maintaining the ability to secrete proteins via its functional TTSS.

Figure 3C:
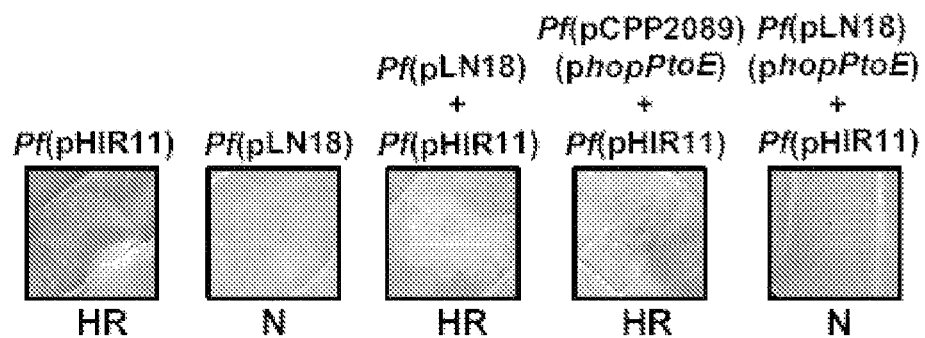

In planta mixed-inoculum experiments were performed by first infiltrating into tobacco *P. fluorescens*(pLN18) with hopPtoE contained in a broad-host-range plasmid and, after 2 h, *P. fluorescens*(pHIR11). *P. fluorescens*(pHIR11) was infiltrated at an OD600 sufficient to cause HR elicitation. FIG. 3C shows that *P. fuorescens*(pLN18) retained the ability to suppress the pHIR11-dependent HR. This indicates that the HR suppression activity does not occur in the bacterial cell.

Example 5 pHIR11 Assays Identify Seven Effectors Capable of Suppressing the HopPsyA-Dependent Hypersensitive Response Nineteen confirmed effector genes were cloned into a broad-host-range plasmid and tested to determine whether the encoded effectors were able to suppress the HR elicited by *P. fluorescens*(pHIR11) (see FIG. 4A for a list of the effectors tested). Each candidate suppressor gene was expressed in *P. fluorescens*(pHIR11) and these strains were infiltrated into tobacco and *Arabidopsis thaliana* ecotype Ws-0, two plants that produce an HR in response to pHIR11-containing bacteria.

Surprisingly, seven of the nineteen effectors tested were able to suppress the pHIR11-dependent HR on both *A. thaliana* and tobacco (FIGS. 4B-C). In planta mixed-inoculum experiments similar to those describe in FIG. 3C demonstrated that all of the identified suppressors were able to inhibit the pHIR11-dependent HR. These results indicate that the site of suppressor activity was outside of the bacteria. Two of the identified suppressors, HopPtoF and AvrPtoB, were homologs of AvrPphF and VirPphA, respectively, two Avr proteins able to "block" the HR produced by *P. s. phaseolicola* (Jackson et al., *Proc. Natl. Acad. Sci. USA* 96:10875-10880 (1999); Tsiamis et al., *EMBO J.* 19:3204-3214 (2000), each of which is hereby incorporated by reference in its entirety). The VirPphA homolog, AvrPtoB, was recently reported to suppress the HR elicited by AvrPto (Abramovitch et al., *EMBO J.* 22:60-69 (2003), which is hereby incorporated by reference in its entirety). Thus, these findings demonstrate that AvrPtoB and HopPtoF are HR suppressors. The other HR suppressors identified were AvrPphE$_{Pto}$, AvrPpiB1$_{Pto}$, HopPtoD1, and HopPtoK. The HR suppression observed for HopPtoD1 and HopPtoK was not complete (i.e., the HR was present, although much reduced).

Example 6

Figure 5A:
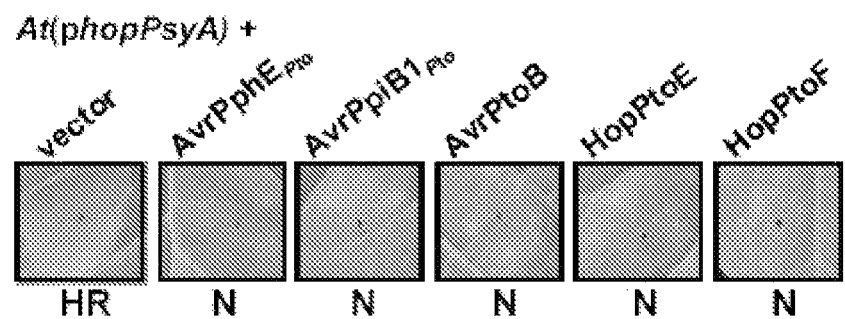
FIGS. 5A-B illustrate that the HR elicited by HopPsyA can be suppressed via *Agrobacterium* transient expression of effectors.
Figure 5B:
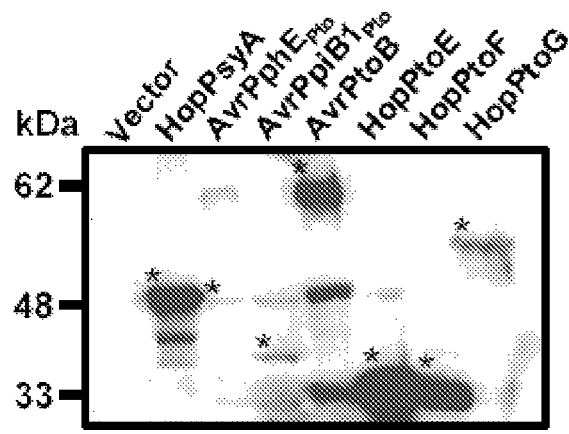

*Agrobacterium* Transient Assays that Co-Deliver HopPsyA and Individual Hypersensitive Response Suppressors Confirm that Each Effector Alone Suppresses the HopPsyA-Dependent Hypersensitive Response Inside Plant Cells To determine if the HR suppression is due solely to the suppressor proteins, both HopPsyA and individual HR suppressor effectors were transiently co-delivered using *Agrobacterium*-mediated transient assays (agroinfitrations) (van den Ackerveken et al., *Cell* 87:1307-1316 (1996), which is hereby incorporated by reference in its entirety). In each case, the effector suppressed the HopPsyA-dependent HR (FIG. 5A). Protein expression was confirmed with immunoblots that showed the agroinfiltrations produced both HopPsyA and the specific suppressor tested (FIG. 5B). These data complement the bacteria-delivered suppressor data shown above, because agroinfiltrations demonstrate that the suppressor activity is dependent only on the suppressor and that the suppressor acts within plant cells, whereas the experiments where *P. fluorescens*(pHIR11) deliver each suppressor resemble what happens in nature and protein levels are closer to the levels that the pathogen "inject" into plant cells.

Example 7

Figure 6:
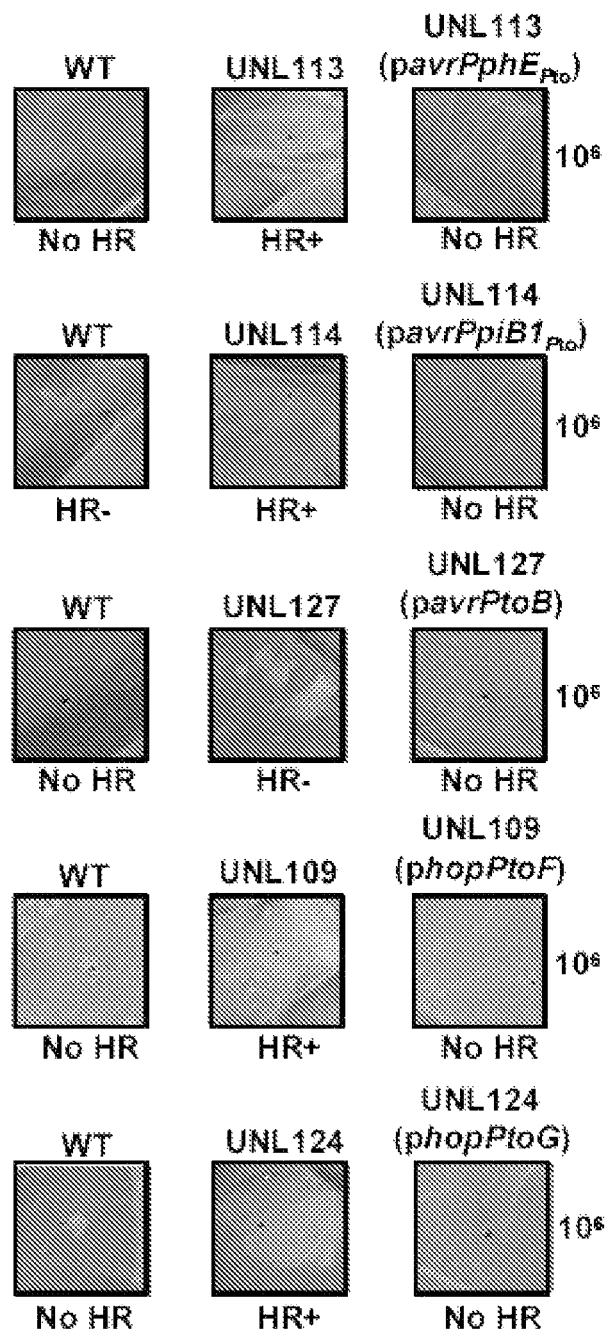
FIG. 6 is an image showing that *Pseudomonas syringae* pv. *tomato* DC3000 suppressor mutants display an enhanced ability to elicit the HR. *N. tabacum* cv. *xanthi* leaves were infiltrated with *P. syringae* strains that were 10-fold serially diluted from $10^8$ cells/ml. The last dilution ($10^6$ cells/ml) that resulted in an HR is shown. In all cases, the mutants exhibit more HR at this dilution than the wild type, and this phenotype was complemented when the suppressors were provided in trans. The following strains were infiltrated: DC3000 wild type, WT; avrPphEPto mutant, UNL113; avrPpiB1Pto mutant, UNL114; avrPtoB mutant, UNL127; hopPtoF mutant, UNL109; hopPtoG mutant, UNL124. HR was scored for each sample: spotty HR(HR−); strong HR(HR+); or no HR.
Figure 7A:
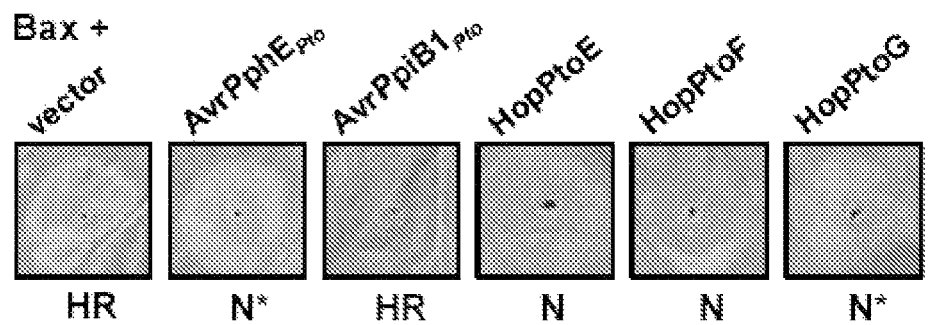
FIGS. 7A-B illustrate that *Pseudomonas syringae* pv. *tomato* DC3000 HR suppressors inhibit the PCD initiated by Bax in plants and yeast.
Figure 7B:
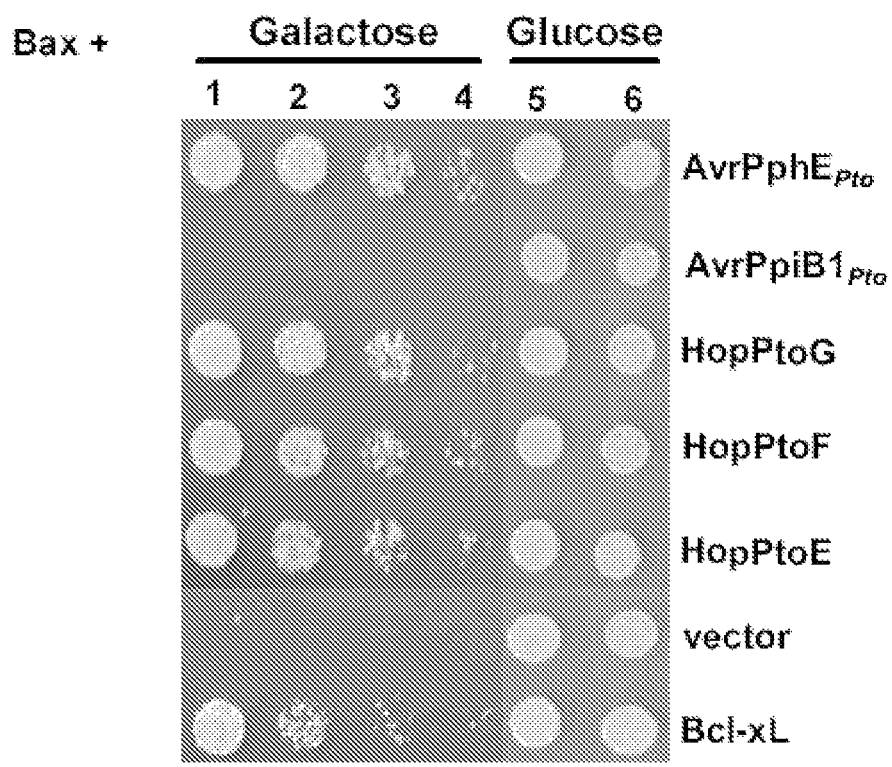

DC3000 Suppressor Mutants Display an Enhanced Ability to Elicit a Hypersensitive Response on Nonhost Plants, Consistent with Loss of Hypersensitive Response Suppression Activity in the Pathogen Based on the above findings, it was recognized that a pathogen may encode multiple HR suppressors, each contributing, perhaps incrementally, to the suppression of the HR and/or plant defenses. To analyze these proteins in more detail, mutants defective in each gene corresponding to the effectors listed in FIG. 4A were made. The ability of DC3000 and the suppressor mutants to induce defense responses on non-host plants were tested, similar to the experiments described in FIG. 2C. Tobacco leaves were infiltrated with different dilutions of DC3000 or each mutant, and then their ability to elicit an HR was analyzed. Interestingly, all the mutants were more effective at eliciting an HR at lower concentrations, generally producing an HR at 10-fold higher dilution than wild type DC3000 (FIG. 6). As an example, UNL105 caused a confluent HR at a titer of $10^6$ cells/ml, whereas DC3000 only produced a spotty HR or no HR at this titer. It is important to note that DC3000 produced a typical HR at dilutions of $10^6$ cells/ml or higher. This enhanced HR phenotype produced by each suppressor mutant resulted from the absence of the effector, because when each was supplied in trans the HR-eliciting ability returned to a DC3000-like HR (FIG. 6).

Although HopPtoG was not identified as an HR suppressor in the assays with *P. fuorescens*(pHIR11), the hopPtoG mutant UNL124 caused an enhanced HR phenotype. Moreover, additional assays shown below suggest that HopPtoG does function as a suppressor. Thus, these findings demonstrate that the phenotype of potential suppressor mutants on non-host plants is consistent with and complements HR suppression data. Therefore, the HR titration assays should be useful in the identification of other HR suppressors in bacterial plant pathogens.

Example 8

*Pseudomonas syringae* Hypersensitive Response Suppressors Inhibit Programmed Cell Death Induced by the Pro-apoptotic Protein Bax in Both Plants and Yeast The pro-apoptotic mouse protein Bax has been shown to induce PCD in plants that resembles the HR (Kawai-Yamada et al., *Proc. Natl. Acad. Sci. USA* 98:12295-12300 (2001); Lacomme and Santa Cruz, *Proc. Natl. Acad. Sci. USA* 96:7956-7961 (1999), each of which is hereby incorporated by reference in its entirety). Bax is a member of the Bcl-2 family of pro-apoptotic proteins and is thought to initiate programmed cell death ("PCD") by localizing to the mitochondria and causing the release of pro-apoptotic factors, including cytochrome c (Jurgensmeier et al., *Proc. Natl. Acad. Sci. USA* 95:4997-5002 (1998), which is hereby incorporated by reference in its entirety). Recently, Abramovitch et al. (*EMBO J.* 22:60-69 (2003), which is hereby incorporated by reference in its entirety) reported that AvrPtoB suppresses Bax-induced PCD in plants. The suppressors identified in Examples 3-7 were tested in their ability to suppress Bax-induced PCD in plants. With the exception of AvrPpiB1$_{Pto}$, all of them suppressed Bax-induced cell death in plants (FIG. 7A). Interestingly, AvrPphE, HopPtoG, HopPtoF, and HopPtoE also suppressed Bax-induced PCD in yeast (FIG. 7B). The fact that AvrPtoB was unable to suppress Bax-induced PCD in yeast highlights a difference between the activity of these suppressors. Moreover, AvrPphE, HopPtoG, HopPtoF, and HopPtoE were unable to suppress the PCD initiated in yeast by $H_2O_2$, while AvrPtoB did suppress PCD in this assay (Abramovitch et al., *EMBO J.* 22:60-69 (2003), which is hereby incorporated by reference in its entirety). This further demonstrates that the PCD suppressors display different PCD suppressing characteristics.

Discussion of Examples 3-8

Effectors delivered by the Hrp TTSS appear central to *P. syringae* pathogenesis, but the anti-host functions of these proteins remain obscure. The above Examples identify a founding inventory of Hrp effectors from *P. s. tomato* DC3000 using several novel bioassays and provide evidence that many of these proteins appear to suppress one or more broadly conserved eukaryote PCD pathways. To understand these results, it is useful to consider the collection of effectors that were assayed, the utility and limitations of the bioassays, and the role of plant cell death in disease and defense. The nineteen effectors considered here were recently identified in DC3000 on the basis of their homology with known effectors and/or their ability to be secreted and/or translocated by the Hrp TTSS. In general, *P. syringae* TTSS effectors identified on the basis of avirulence phenotypes are designated Avrs, whereas those identified through secretion assays are designated Hops. However, the working assumption is that all of the "Avrs" are injected into plant cells by the Hrp system and many of the "Hops" will confer avirulence phenotypes to bacteria if tested in hosts that happen to carry a corresponding R gene; that is, effectors, Avrs, and Hops are synonymous terms.

It must be noted that the effector described herein do not represent the entire inventory of DC3000 effectors. Effectors encoded within the Hrp pathogenicity island are described elsewhere (Alfano et al., *Proc. Natl. Acad. Sci. USA* 97:4856-4861 (2000), which is hereby incorporated by reference in its entirety. Additional candidate effectors in DC3000 have also been identified (Collmer et al., *Trends Microbiol.* 10:462-470 (2002), which is hereby incorporated by reference in its entirety).

However, the set of effectors analyzed here suggests that many DC3000 effectors have HR suppression activity. The bioassays used herein were designed to efficiently detect HR suppressor activity, determine whether suppressor action occurs in plant cells rather than in bacteria, and determine if the test effectors could also suppress PCD in other plants and the model eukaryote, yeast. The primary screen, based on suppression of the HR elicited by *P. fluorescens*(pHIR11) in tobacco, proved to be simple and effective (FIG. 2). Although there is the formal possibility that suppressors identified with this bioassay could be merely interfering with the delivery of HopPsyA, multiple lines of evidence indicate that they act after delivery into plant cells. For example, HopPtoE overexpression had no effect on the secretion of AvrPto (FIG. 3A), a representative type III substrate, and HopPtoE suppressed HopPsyA-dependent HR elicitation when delivered by a functional TTSS in a different strain (FIG. 3C) or when transiently expressed in plant cells following inoculation with *A. tumefaciens* (FIG. 5A). It is also noteworthy that the suppressors identified herein functioned when delivered via the TTSS, a natural route that is thought to yield relatively low levels of effectors within plant cells. *Agrobacterium*-mediated transient expression, in contrast, can produce far higher levels of effectors within plant cells potentially leading to artifactual responses. It should also be noted that HopPtoD1 and HopPtoK appear to exhibit limited suppressor activity.

In an attempt to identify plant targets or sites of action of the suppressors in plants, HopPtoE, AvrPphE$_{Pto}$, AvrPiB1$_{Pto}$, AvrPtoB, HopPtoF, and HopPtoG were subjected to cursory bioinformatic analyses. BLASTP and PSI-BLAST searches (Altschul et al., *Nucleic Acids Res.* 25: 3389-3402 (1997), which is hereby incorporated by reference in its entirety) did not identify any proteins (other than clear Avr homologs) that shared significant similarity with any of the suppressors. However, 3D-PSSM analyses, a method that uses protein fold recognition to identify proteins with similar folding patterns (Kelley et al., *J. Mol. Biol.* 299:499-520 (2000), which is hereby incorporated by reference in its entirety), indicated that AvrPtoB had similarity to heme-dependent peroxidases (above 90% certainty; PSSM E value 0.0895). Moreover, when AvrPtoB was aligned with a lignin peroxidase, a representative heme-dependent peroxidase (Welinder, *Eur. J. Biochem.* 151:497-504 (1985), which is hereby incorporated by reference in its entirety), the amino acids within the peroxidase active site were present similarly spaced in AvrPtoB. This result is intriguing because of the clear involvement of reactive oxygen species (ROS) in plant defense (Mittler, *Trends Plant Sci.* 7:405-410 (2002), which is hereby incorporated by reference in its entirety) and the potential of peroxidases to modulate ROS. Moreover, there have been reports of peroxidases rescuing Bax-induced cell death in yeasts (Kampranis et al., *J. Biol. Chem.* 275:29207-29216 (2000); Moon et al., *Biochem. Biophys. Res. Commun.* 290:457-462 (2002), each of which is hereby incorporated by reference in its entirety) and transgenic antisense tobacco plants with reduced amounts of ascorbate peroxidase were "hyperresponsive" to *P. syringae* (Mittler et al., *Proc. Natl. Acad. Sci. USA* 96:14165-14170 (1999), which is hereby incorporated by reference in its entirety), producing a phenotype reminiscent of the enhanced HR phenotypes produced by the suppressor mutants reported here. However, Abramovitch et al. (*EMBO J.* 22:60-69 (2003), which is hereby incorporated by reference in its entirety) reported that AvrPtoB possessed predicted structural features similar to domains within Bcl-2 family members, an equally intriguing finding due to the involvement of these proteins in PCD regulation. Yeast has emerged as model for studying PCD and has proven particularly useful for the analysis of cell death inducers and suppressors obtained from multicellular eukaryotes with more complex PCD pathways (Madeo et al., *Curr. Genet.* 41:208-216 (2002), which is hereby incorporated by reference in its entirety). An example of the utility of the yeast system to plant PCD research is found in the induction of yeast PCD by the plant defense protein osmotin (Narasimhan et al., *Mol. Cell.* 8:921-930 (2001), which is hereby incorporated by reference in its entirety). A particularly fruitful use of the yeast system involves heterologous expression of the mammalian Bax protein, which induces PCD in yeast. Yeast expressing Bax can be screened, as done here, for heterologously expressed genes that block Bax-induced PCD. This system has been used to identify the *Arabidopsis* ethylene-responsive element binding protein (AtEBP) as a suppressor of PCD (Pan et al., *FEBS Lett.* 508:375-378 (2001), which is hereby incorporated by reference in its entirety) and its relevance to plant biology is further indicated by observations that Bax expression in tobacco can induce an apparent HR and that Bcl-2 (an anti-aptototic gene of the Bax/Bcl-2 family) expression in tobacco strongly alters plant-pathogen interactions (Dickman et al., *Proc. Natl. Acad. Sci. USA* 98:6957-6962 (2001); Lacomme and Santa Cruz, *Proc. Natl. Acad. Sci. USA* 96:7956-7961 (1999), each of which is hereby incorporated by reference in its entirety).

Four of the five effectors tested (AvrPphE$_{Pto}$, HopPtoG, HopPtoF, and HopPtoE) suppress Bax-induced yeast PCD, indicating that the targets are likely to be broadly conserved and not unique to plants. Interestingly, AvrPpiB1$_{Pto}$ and AvrPtoB failed to do so, even though both suppressed the HR elicited by *P. fluorescens*(pHIR11) in both tobacco and *Arabidopsis*, and DC3000 avrPtoB and avrPpiB1Pto mutants produced enhanced HRs. It is also puzzling that HopPtoG failed to suppress the HR elicited by *P. fluorescens*(pHIR11) although a DC3000 hopPtoG mutant had enhanced HR activity and HopPtoG suppressed Bax-induced yeast PCD. Moreover, it is also noteworthy that HopPtoD2, an effector that was recently identified to suppresses an HR elicited by avirulent *P. syrinage* strains did not suppress the HR elicited by *P. fluorescens*(pHIR11). These exceptions suggest that multiple bioassays will be required to identify all of the DC3000 effectors with some ability to suppress PCD.

While the suppressors described here were identified due to their ability to suppress PCD, it is possible they suppress other more general plant defenses as well. Indeed, HopPtoD2 has been found to be an active protein tyrosine phosphatase that appears to modulate a mitogen-activated protein kinase (MAPK) pathway in tobacco. An analogous MAPK pathway in *Arabidopsis* is part of the plant innate immune system activated in response to bacterial flagellin (Asal et al., *Nature* 415:977-983 (2002); Felix et al., *Plant J.* 18:265-276 (1999), each of which is hereby incorporated by reference in its entirety). The innate immune systems of mammals, insects, and plants have the capacity to recognize common markings on microorganisms, such as flagellin or LPS (Boller, *Annu. Rev. Plant Physiol. Plant Mol. Biol.* 46:189-214 (1995); Medzhitov and Janeway, *Trends Microbiol.* 8:452-456 (2000), each of which is hereby incorporated by reference in its entirety). These common components have been referred to as pathogen-associated molecular patterns (PAMPs) and they are not known to elicit the HR in plants. Thus, the assays used herein would not detect the activity of suppressors that specifically targeted PAMP-induced defense pathways unless the target was at convergence points of PCD pathways and PAMP-induced innate immunity pathways. Future research will determine whether these PCD suppressors specifically target Avr-induced PCD pathways or also suppress other plant defenses generally grouped into a broad category of defenses typically referred to as non-host resistance (Heath, *Curr. Opin. Plant Biol.* 3:315-319 (2000), which is hereby incorporated by reference in its entirety).

A general model of suppressor function must also reconcile several behaviors of bacterium-plant interactions that involve multiple effectors. Expression in *P. syringae* of a heterologous effector typically results in HR elicitation in test plants that carry a corresponding R gene despite the presence of resident suppressor effectors. For example, DC3000 heterologously expressing avrRpt2 or avrRps4 elicits the HR in *Arabidopsis* plants carrying the corresponding R genes (Hinsch and Staskawicz, *Mol. Plant-Microbe Interact.* 9:55-61 (1996); Kunkel et al., *Plant Cell* 5:865-875 (1993), which is hereby incorporated by reference in its entirety). On the other hand, suppressors can block HR elicitation by resident effectors, as revealed by the original discovery of suppressors like VirPphA and effectors with masked avirulence activity in *P. s. phaseolicola* (Jackson et al., *Proc. Natl. Acad. Sci. USA* 96:10875-10880 (1999), which is hereby incorporated by reference in its entirety) and by the observations presented here that several effectors can block HR elicitation by HopPsyA in the heterologous *P. fluorescens*(pHIR11) system. Perhaps the simplest explanation is that there is a hierarchy in the delivery of effectors by wild-type strains. Such a hierarchy in delivery has been proposed to explain the deployment of effectors with conflicting activities, such as the *Salmonella* SopE and SptP proteins, in animal pathogens (Cornelis and van Gijsegem, *Annu. Rev. Microbiol.* 54:734-774 (2000); Galan and Zhou, *Proc. Natl. Acad. Sci. USA* 97:8754-8761 (2000), each of which is hereby incorporated by reference in its entirety). The global identification of a set of suppressors in *P. s. tomato* DC3000 should facilitate systematic investigation of the underlying functions of TTSS effectors in *P. syringae* pathogenesis.

A final aspect of PCD and pathogenesis is that the ability to elicit host cell death appears to be a general characteristic of TTSS-dependent pathogens like *P. syringae* despite the fact that these bacteria typically rely upon living host cells as sites of multiplication (Alfano and Collmer, *J. Bacteriol.* 179: 5655-5662 (1997); Knodler and Finlay, *Microbes Infect.* 3:1321-1326 (2001), each of which is hereby incorporated by reference in its entirety). This is particularly puzzling with *P. syringae* because late-stage infections with most strains produce necrotic lesions, but the symptomless growth of *P. s. syringae* gacS mutants suggests that such cell killing may be gratuitous (Willis et al., *Mol. Plant-Microbe Interact.* 3:149-156 (1990), which is hereby incorporated by reference in its entirety). Similarly puzzling are recent observations suggesting that plants compromised in PCD pathways are unexpectedly more resistant to *P. syringae* (Lincoln et al., *Proc. Natl. Acad. Sci. USA* 99:15217-15221 (2002); Stone et al., *Plant Cell* 12:1811-1822 (2000); Richael et al., *Physiol. Mol. Plant. Pathol.* 59:213-221 (2001), each of which is hereby incorporated by reference in its entirety). Thus, rapid and delayed host cell death are associated with defense and disease, respectively, and pathogen manipulation of cell death pathways may be a central process in pathogenesis.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. An expression system comprising a vector into which is inserted a DNA molecule comprising a nucleotide sequence which
   (i) encodes a polypeptide having the amino acid sequence of SEQ ID NO: 58, or
   (ii) hybridizes, under stringency conditions comprising 1M Na$^+$ at 65° C. followed by wash conditions comprising 0.2× sodium citrate at 65° C., to a DNA molecule complementary to SEQ ID NO: 57, wherein the nucleotide sequence encodes a polypeptide that has ADP-ribosyl transferase activity; or
   (iii) is complementary to the nucleic acid molecules of (i) or (ii).

2. The expression system according to claim 1, wherein the DNA molecule is inserted in sense orientation relative to a promoter sequence.

3. The expression system according to claim 1, wherein the DNA molecule hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

4. The expression system according to claim 1, wherein the DNA molecule comprises a nucleotide sequence which (i) encodes a polypeptide having the amino acid sequence of SEQ ID NO: 58 or (ii) hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

5. A host cell comprising the expression system of claim 1, or (ii).

6. The host cell according to claim 5, wherein the host cell is a bacterial cell or a plant cell.

7. The host cell according to claim 6, wherein the bacterial cell is *Agrobacterium*.

8. The host cell according to claim 5, wherein the DNA molecule hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

9. The host cell according to claim 5, wherein the DNA molecule comprises a nucleotide sequence which (i) encodes a polypeptide having the amino acid sequence of SEQ ID NO: 58 or (ii) hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

10. A transgenic plant comprising a DNA molecule comprising a nucleotide sequence which
    (i) encodes a polypeptide having the amino acid sequence of SEQ ID NO: 58, or
    (ii) hybridizes, under stringency conditions comprising 1M Na$^+$ at 65° C. followed by wash conditions comprising 0.2× sodium citrate at 65° C., to a DNA molecule complementary to SEQ ID NO: 57, wherein the nucleotide sequence encodes a polypeptide that has ADP-ribosyl transferase activity; or
    (iii) is complementary to the nucleic acid molecules of (i) or (ii).

11. The transgenic plant according to claim 10, wherein the DNA molecule hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

12. The transgenic plant according to claim 10, wherein the DNA molecule comprises a nucleotide sequence which (i) encodes a polypeptide having the amino acid sequence of SEQ ID NO: 58 or (ii) hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

13. A method of making a transgenic plant cell, said method comprising:
    providing a DNA molecule comprising a nucleotide sequence which
    (i) encodes a polypeptide having the amino acid sequence of SEQ ID NO: 58, or
    (ii) hybridizes, under stringency conditions comprising 1M Na$^+$ at 65° C. followed by wash conditions comprising 0.2× sodium citrate at 65° C., to a DNA molecule complementary to SEQ ID NO: 57, wherein the nucleotide sequence encodes a polypeptide that has ADP-ribosyl transferase activity; or (iii) is complementary to the nucleic acid molecules of (i) or (ii); and transforming a plant cell with the DNA molecule under conditions effective to yield transcription of the DNA molecule.

14. The method according to claim 13, wherein the DNA molecule hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

15. The method according to claim 13, wherein the DNA molecule comprises a nucleotide sequence which (i) encodes a polypeptide having the amino acid sequence of SEQ ID NO: 58 or (ii) hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

16. A method of making a transgenic plant, said method comprising:

transforming a plant cell under conditions effective to yield transcription of a DNA molecule comprising a nucleotide sequence which (i) encodes a polypeptide having the amino acid sequence of SEQ ID NO: 58, or (ii) hybridizes, under stringency conditions comprising 1M Na$^+$ at 65° C. followed by wash conditions comprising 0.2× sodium citrate at 65° C., to a DNA molecule complementary to SEQ ID NO: 57, wherein the nucleotide sequence encodes a polypeptide that has ADP-ribosyl transferase activity; or (iii) is complementary to the nucleic acid molecules of (i) or (ii); and regenerating a transgenic plant from the transformed plant cell.

17. The method according to claim 16, wherein the DNA molecule hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

18. The method according to claim 16, wherein the DNA molecule comprises a nucleotide sequence which (i) encodes a polypeptide having the amino acid sequence of SEQ ID NO: 58 or (ii) hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

19. A method of inhibiting programmed cell death, said method comprising introducing into a plant cell the expression system according to claim 1, wherein the expression system delivers the DNA molecule into the plant cell and a hypersensitive response suppressor protein is expressed in the plant cell under conditions effective to inhibit programmed cell death of the plant cell.

20. The method according to claim 19, wherein the plant cell is in vitro.

21. The method according to claim 19, wherein the plant cell is in vivo.

22. A transgene comprising:

a DNA molecule comprising a nucleotide sequence which (i) encodes a polypeptide having the amino acid sequence of SEQ ID NO: 58, or (ii) hybridizes, under stringency conditions comprising 1M Na$^+$ at 65° C. followed by wash conditions comprising 0.2× sodium citrate at 65° C., to a DNA molecule complementary to SEQ ID NO: 57, wherein the nucleotide sequence encodes a polypeptide that has ADP-ribosyl transferase activity; or (iii) is complementary to the nucleic acid molecules of (i) or (ii);

a promoter sequence not native to the DNA molecule; and a termination sequence not native to the DNA molecule.

23. The transgene according to claim 22, wherein the DNA molecule hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

24. The transgene according to claim 22, wherein the DNA molecule comprises a nucleotide sequence which (i) encodes a polypeptide having the amino acid sequence of SEQ ID NO: 58 or (ii) hybridizes, under stringency conditions comprising 1M Na$^+$ at 65° C. followed by wash conditions comprising 0.2× sodium citrate at 65° C., to a DNA molecule complementary to SEQ ID NO: 57 and encodes a polypeptide that has ADP-ribosyl transferase activity.

\* \* \* \* \*